(12) United States Patent
Takami et al.

(10) Patent No.: US 7,217,722 B2
(45) Date of Patent: May 15, 2007

(54) NITROGEN-CONTAINING COMPOUNDS HAVING KINASE INHIBITORY ACTIVITY AND DRUGS CONTAINING THE SAME

(75) Inventors: Atsuya Takami, Takasaki (JP); Hiroshi Iijima, Takasaki (JP); Masayuki Iwakubo, Takasaki (JP); Yuji Okada, Takasaki (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 156 days.

(21) Appl. No.: 10/181,943

(22) PCT Filed: Jan. 2, 2001

(86) PCT No.: PCT/JP01/00721

§ 371 (c)(1),
(2), (4) Date: May 19, 2003

(87) PCT Pub. No.: WO01/56988

PCT Pub. Date: Aug. 9, 2001

(65) Prior Publication Data

US 2004/0102437 A1 May 27, 2004

(30) Foreign Application Priority Data

Feb. 1, 2000 (JP) .............................. 2000-24292

(51) Int. Cl.
*C07D 213/75* (2006.01)
*A61K 31/47* (2006.01)

(52) U.S. Cl. ....................................... 514/307; 546/139

(58) Field of Classification Search ................ 546/139; 514/307

See application file for complete search history.

(56) References Cited

U.S. PATENT DOCUMENTS

| 4,022,900 A | 5/1977 | Mathison |
| 5,955,496 A | 9/1999 | Hammock et al. |

FOREIGN PATENT DOCUMENTS

| EP | 0 168 005 A2 | 1/1986 |
| EP | 0 277 791 A2 | 8/1988 |
| EP | 616807 A1 * | 11/1994 |
| EP | 0 656 353 A1 | 6/1995 |
| GB | 2 009 155 A | 6/1979 |
| GB | 2020280 * | 11/1979 |
| JP | 10-147585 A | 6/1998 |
| JP | 11-139969 A | 5/1999 |
| WO | WO 88/08424 A1 | 11/1988 |
| WO | WO 91/17748 A1 | 11/1991 |
| WO | WO 92/12961 A1 | 8/1992 |
| WO | WO 94/21613 A1 | 9/1994 |
| WO | WO 95/04045 A1 | 2/1995 |
| WO | WO 95/07075 A1 | 3/1995 |
| WO | WO 95/07891 A1 | 3/1995 |
| WO | WO 95/20578 A1 | 8/1995 |
| WO | WO 96/04266 A2 | 2/1996 |
| WO | WO 96/24586 A1 | 8/1996 |
| WO | WO 96/37473 A1 | 11/1996 |
| WO | WO 97/03967 A1 | 2/1997 |
| WO | WO 97/20833 A1 | 6/1997 |
| WO | WO 97/44036 A1 | 11/1997 |
| WO | WO 97/44337 A1 | 11/1997 |
| WO | WO 97/48697 A1 | 12/1997 |
| WO | WO 97/49399 A1 | 12/1997 |
| WO | WO 98/06433 A1 | 2/1998 |
| WO | WO 98/09961 A1 | 3/1998 |
| WO | WO 98/22455 A1 | 5/1998 |
| WO | WO 99/00357 A1 | 1/1999 |
| WO | WO 99/16768 A1 | 4/1999 |
| WO | WO 99/21836 A1 | 5/1999 |
| WO | WO 99/37640 A1 | 7/1999 |
| WO | WO 99/38867 A1 | 8/1999 |
| WO | WO 99/64423 A1 | 12/1999 |
| WO | WO 00/26208 A1 | 5/2000 |
| WO | WO 00/48998 A1 | 8/2000 |
| WO | WO 01/15677 A2 | 3/2001 |

OTHER PUBLICATIONS

Sanchez et al, Heterocyles, vol. 31, No. 11, pp. 2003-2010, 1990.*
Llama et al, J. Pharm. Pharmacol, vol. 43, pp. 68-69, 1991.*
J.R. Bagley et al., "New 4-(Heteroanilido)piperidines, Structurally Related to the Pure Opioid Agonist Fentanyl, with Agonist and/or Antagonist Properties," J. Med. Chem. (1989) 32:663-671, American Chemical Society.
T. Singh et al., "Antimalarials. 7-Chloro-4-(substituted amino)quinolines," Journal of Medicinal Chemistry (1971) 14(4):283-286.

* cited by examiner

*Primary Examiner*—Zinna N. Davis
(74) *Attorney, Agent, or Firm*—Foley & Lardner LLP

(57) ABSTRACT

An objective of the present invention is to provide compounds having Rho kinase inhibitory activity. The compounds according to the present invention are those represented by formula (I) or pharmaceutically acceptable salts or solvates thereof:

$$\text{Het}-\text{X}-\text{Z} \qquad (I)$$

wherein Het represents a monocyclic or bicyclic heterocyclic group containing at least one nitrogen atom, for example, pyridyl or phthalimide; X represents group (i) —NH—C(=O)—NH—Q1-, group (ii) —NH—C(=O)—Q2-, wherein Q1 and Q2 represent a bond, alkylene, or alkenylene, or the like; and Z represents hydrogen, halogen, a monocyclic, bicyclic, or tricyclic carbocyclic group, a heterocyclic group or the like, for example, optionally substituted phenyl.

17 Claims, No Drawings

NITROGEN-CONTAINING COMPOUNDS HAVING KINASE INHIBITORY ACTIVITY AND DRUGS CONTAINING THE SAME

BACKGROUND OF THE INVENTION

1. Field of the Invention

The present invention relates to compounds having Rho kinase inhibitory activity and more particularly to compounds usable for the therapy of diseases mediated by Rho kinase.

2. Related Art

It has been clarified that Rho is activated upon the receipt of signals from various cell membrane receptors, and the activated Rho functions, through ROCK/Rho kinase and, further, actomyosin system, as a molecular switch of a wide variety of cellular phenomena such as smooth muscle contraction, cell movement, cell adhesion, change in character of cells (formation of actin stressed fibers), control of cell division (sthenia of cytokinesis or activation of gene transcription), platelet aggregation, leukocyte aggregation, cell proliferation, sthenia of carcinogenesis and invasion of cancer and the like.

The contraction of smooth muscle is deeply involved in the pathology of hypertension, angina pectoris, vasospasm, for example, cardiovascular contraction and cerebrovascular contraction, asthma, peripheral circulatory disorder, threatened premature birth, glaucoma, constriction of visual field, pollakiuria, impotence and the like. Cell movement plays an important role in invasion/metastasis of cancer, arteriosclerosis, retinopathy, immune response and the like. Cell adhesion is deeply involved in metastasis of cancer, inflammation, and autoimmune diseases. The alteration of morphology of cells is deeply involved in cerebral dysfunction, osteoporosis, microbism and the like. Cell proliferation is deeply involved in cancer, arteriosclerosis and the like. Thus, Rho is deeply involved in various diseases.

ROCK or ROCK I (Japanese Patent Laid-Open No. 135683/1997; and T. Ishizaki et al., EMBO J., Vol. 15, No. 8, pp 1885–1893 (1996)) and Rho kinase or ROCK II (Japanese Patent Laid-Open No. 113187/1998; and T. Matsui et al., EMBO J., Vol. 15, No. 9, pp 2208–2216 (1996)) are reported as serine/threonine kinase which is activated upon the activation of Rho. They have been proven to be isozymes (O. Nakagawa et al., FEBS Lett., Vol. 392, No. 2, pp 189–193 (1996)).

Compounds having ROCK/Rho kinase inhibitory activity include trans-4-amino(alkyl)-1-pyridylcarbamoylcyclohexane compounds (WO 90/05723), benzamide compounds (WO 95/28387), Y-27632 (Uehata, M., Ishizaki, T. et al.: Nature, 389: 990–994, 1997), and fasudil hydrochloride commercially available as cerebrovascular contraction inhibitor (HA-1077, Asahi Kasei kogyo K. K.) (Ono-Saito, N., Niki, I., Hidaka, H.: Pharmacol. Ther., 123–131, 1999). Further, WO 98/06433 discloses ROCK/Rho kinase inhibitors.

SUMMARY OF THE INVENTION

The present inventors have found that certain nitrogen-containing compounds have Rho kinase inhibitory activity (Pharmacological Test Example 1).

The present inventors have further found that certain nitrogen-containing compounds have leukocyte migration inhibitory activity (Pharmacological Test Example 2).

The present inventors have further found that certain nitrogen-containing compounds have albuminuria amelioration activity in anti-GBM model rats (Pharmacological Test Examples 3 and 4).

The present inventors have further found that certain nitrogen-containing compounds have blood antihypertensive activity in spontaneously hypertensive rats (Pharmacological Test Example 5).

An object of the present invention is to provide compounds having Rho kinase inhibitory activity.

Another object of the present invention is to provide a pharmaceutical composition for use in the treatment of diseases mediated by Rho kinase.

According to the present invention, there is provided a compound represented by formula (I) or a pharmaceutically acceptable salt or solvate thereof:

$$\text{Het—X—Z} \quad (I)$$

wherein

Het represents a five- to seven-membered monocyclic saturated or unsaturated heterocyclic group containing at least one nitrogen atom, or a nine- to twelve-membered bicyclic saturated or unsaturated heterocyclic group containing at least one nitrogen atom and the carbocyclic and heterocyclic groups are optionally substituted by a halogen atom, an oxygen atom, hydroxyl, or $C_{1-4}$ alkylcarbonyl, X represents a group selected from the group consisting of groups (i) to (ix):

$$\text{—NH—C(=O)—NH—Q1-} \quad (i)$$

wherein

Q1 represents a bond, alkylene having 1 to 4 carbon atoms, or alkenylene having 2 to 4 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$\text{—NH—C(=O)—Q2-} \quad (ii)$$

wherein

Q2 represents a bond, alkylene having 1 to 5 carbon atoms, or alkenylene having 2 to 5 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$\text{—NH—C(=O)—Q3-Q4-Q5-} \quad (iii)$$

wherein
Q3 represents
alkylene having 1 to 4 carbon atoms or
alkenylene having 2 to 4 carbon atoms,
Q4 represents —O—, —NH—, or —S(=O)m- wherein m is an integer of 0 to 2,
Q5 represents
a bond,
alkylene having 1 to 3 carbon atoms, or
alkenylene having 2 or 3 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$—N(—R^1)—Q6-Q7- \quad (iv)$$

wherein
$R^1$ represents a hydrogen atom or $C_{1-4}$ alkylcarbonyl,
Q6 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl,
Q7 represents
a bond, $$—(CH_2)n1-CR^{2a}R^{2b}—(CH_2)n2-$$

wherein
n1 and n2 are each an integer of 0 to 3,
when n2 is 2 or 3, —CH$_2$—CH$_2$— in —(CH$_2$)n2- may represent —CH=CH— or —C≡C—,
$R^{2a}$ and $R^{2b}$, which may be the same or different, represent
a hydrogen atom,
a halogen atom,
$C_{1-6}$ alkyl optionally substituted by hydroxyl, carboxyl, $C_{1-4}$ alkoxycarbonyl,
cyano,
—(C=O)—N(—R$^{2c}$)(—R$^{2d}$) wherein $R^{2c}$ and $R^{2d}$, which may be the same or different, represent a hydrogen atom; $C_{1-4}$ alkyl optionally substituted by a halogen atom; $C_{1-4}$ alkoxy optionally substituted by a halogen atom; cyclopropyl; or benzyl of which the phenyl portion is optionally substituted by one or two $C_{1-4}$ alkoxys, or
phenyl optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy,
—(CH$_2$)p-NR$^3$— wherein p is an integer of 0 to 2, $R^3$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; $C_{1-4}$ alkylcarbonyloxy of which the alkyl portion is optionally substituted by a halogen atom; or benzyloxy,
—NH—(CH$_2$)q1-CR$^{4a}$R$^{4b}$—(CH$_2$)q2- wherein q1 and q2 are each an integer of 0 to 2 and $R^{4a}$ and $R^{4b}$ each independently represent a hydrogen atom, $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy,
—(C=O)—O—CR$^{4a}$R$^{4b}$—CH$_2$— wherein $R^{4a}$ and $R^{4b}$ are as defined above,
—NH—(CH$_2$)i-NH— wherein i is an integer of 1 to 4, or
—S(=O)j- wherein j is 0, 1, or 2, $$—NH—Q8-Q9-Q10- \quad (v)$$

wherein
Q8 represents
alkylene having 1 to 5 carbon atoms or
alkenylene having 2 to 5 carbon atoms,
Q9 represents —O—, —NH—, or —S(=O)r- wherein r is an integer of 0 to 2,
Q10 represents
a bond,
alkylene having 1 to 3 carbon atoms, or
alkenylene having 2 or 3 carbon atoms, wherein the alkylene and alkenylene are optionally substituted by $C_{1-4}$ alkyl or phenyl optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$—O—Q11-Q12- \quad (vi)$$

wherein
Q11 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl,
Q12 represents
a bond,
—(CH$_2$)s-CHR$^5$— wherein s is an integer of 0 to 2 and $R^5$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy,
—(CH$_2$)t-NR$^6$— wherein t is an integer of 0 to 2 and $R^6$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, or —NH—$(CH_2)$u-$CHR^7$— wherein u is an integer of 0 or 1 and $R^7$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —Q13-Q14-  (vii)

wherein

Q13 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl, Q14 represents a bond, —$(CH_2)$v-$CHR^8$— wherein v represents an integer of 0 to 2 and $R^8$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —$(CH_2)$w-$NR^9$— wherein w represents an integer of 0 to 2 and $R^9$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, or —NH—$(CH_2)$x-$CHR^{10}$— wherein x is an integer of 0 or 1 and $R^{10}$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —C(=O)—Q15-$(CH_2)$y-  (viii)

wherein Q15 represents a five- to seven-membered saturated or unsaturated heterocyclic group and this heterocyclic group is optionally substituted by an oxygen atom, hydroxyl, or $C_{1-4}$ alkyl and y is an integer of 0 to 4, and —C(=O)—$NR^1$—Q16-$(CH_2)$z-  (ix)

wherein $R^1$ is as defined above, Q16 represents a five- to seven-membered saturated or unsaturated carbocyclic or heterocyclic group and the carbocyclic and heterocyclic groups are optionally substituted by an oxygen atom, hydroxyl, or $C_{1-4}$ alkyl, and z represents an integer of 0 to 4, Z represents a hydrogen atom, a halogen atom, a three- to seven-membered saturated or unsaturated monocyclic carbocyclic or heterocyclic group, a nine- to twelve-membered bicyclic saturated or unsaturated carbocyclic or heterocyclic group, or a thirteen- to fifteen-membered tricyclic saturated or unsaturated carbocyclic or heterocyclic group, wherein the carbocyclic and heterocyclic groups are optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy of which the phenyl portion is optionally substituted by a halogen atom, provided that when X represents group (i) wherein Q1 represents a bond and Z represents 2-ethoxycarbonyl-phenyl, 2-methoxy-phenyl, 2-nitro-phenyl, or 4-nitro-phenyl, Het does not represent 4-pyridyl, and when X represents group (iv) wherein $R^1$ represents a hydrogen atom, Q6 represents formula

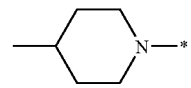

wherein the bond with ★ represents a bond to Q7, and Q7 represents —$CH_2$—$CH_2$—, and Z represents an unsubstituted phenyl, Het does not represent 1-piperidinyl, 4-morpholinyl, 3-pyridinyl, 4-pyridinyl, 2-chloro-3-pyridinyl, 2-chloro-5-pyridinyl, 5-indolyl, 5-indazolyl, 3-quinolinyl, or 2,1,3-benzothiadiazol-4-yl.

The compounds according to the present invention are useful for the treatment of diseases mediated by Rho kinase.

According to the present invention, there is provided a pharmaceutical composition comprising a compound represented by formula (Ia) or a pharmaceutically acceptable salt or solvate thereof, for use in the therapy of diseases mediated by Rho kinase:

Het—X—Z  (Ia)

wherein

Het represents a five- to seven-membered monocyclic saturated or unsaturated heterocyclic group containing at least one nitrogen atom, or a nine- to twelve-membered bicyclic saturated or unsaturated heterocyclic group containing at least one nitrogen atom and the carbocyclic and heterocyclic groups are optionally substituted by a halogen atom, an oxygen atom, hydroxyl, or $C_{1-4}$ alkylcarbonyl, X represents a group selected from the group consisting of groups (i) to (ix):

—NH—C(=O)—NH—Q1-  (i)

wherein

Q1 represents a bond, alkylene having 1 to 4 carbon atoms, or alkenylene having 2 to 4 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally susbituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —NH—C(=O)—Q2-  (ii)

wherein

Q2 represents a bond, alkylene having 1 to 5 carbon atoms, or alkenylene having 2 to 5 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —NH—C(=O)—Q3-Q4-Q5-  (iii)

wherein

Q3 represents alkylene having 1 to 4 carbon atoms or alkenylene having 2 to 4 carbon atoms, Q4 represents —O—, —NH—, or —S(=O)m- wherein m is an integer of 0 to 2, Q5 represents a bond, alkylene having 1 to 3 carbon atoms, or alkenylene having 2 or 3 carbon atoms, wherein the alkylene and alkenylene are optionally substituted by $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —N(—R$^1$)—Q6-Q7-  (iv)

wherein $R^1$ represents a hydrogen atom or $C_{1-4}$ alkylcarbonyl,

Q6 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl, Q7 represents a bond, —(CH$_2$)n1-CR$^{2a}$R$^{2b}$—(CH$_2$)n2- wherein n1 and n2 are each an integer of 0 to 3, when n2 is 2 or 3, —CH$_2$—CH$_2$— in —(CH$_2$)n2- may represent —CH=CH— or —C≡C—, $R^{2a}$ and $R^{2b}$, which may be the same or different, represent a hydrogen atom, a halogen atom, $C_{1-6}$ alkyl optionally substituted by hydroxyl, carboxyl, $C_{1-4}$ alkoxycarbonyl, cyano, —(C=O)—N(—R$^{2c}$)(—R$^{2d}$) wherein $R^{2c}$ and $R^{2d}$, which may be the same or different, represent a hydrogen atom; $C_{1-4}$ alkyl optionally substituted by a halogen atom; $C_{1-4}$ alkoxy optionally substituted by a halogen atom; cyclopropyl; or benzyl of which the phenyl portion is optionally substituted by one or two $C_{1-4}$ alkoxys, or phenyl optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —(CH$_2$)p-NR$^3$— wherein p is an integer of 0 to 2, $R^3$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —NH—(CH$_2$)q1-CR$^{4a}$R$^{4b}$—(CH$_2$)q2- wherein q1 and q2 are each an integer of 0 to 2 and $R^{4a}$ and $R^{4b}$ each independently represent a hydrogen atom, $C_{1-4}$ alkyl or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, —(C=O)—O—CR$^{4a}$R$^{4b}$—CH$_2$— wherein $R^{4a}$ and $R^{4b}$ are as defined above, —NH—(CH$_2$)i-NH— wherein i is an integer of 1 to 4, or —S(=O)j- wherein j is 0, 1, or 2, —NH—Q8-Q9-Q10-  (v)

wherein

Q8 represents alkylene having 1 to 5 carbon atoms or alkenylene having 2 to 5 carbon atoms, Q9 represents —O—, —NH—, or —S(=O)r- wherein r is an integer of 0 to 2, Q10 represents a bond, alkylene having 1 to 3 carbon atoms, or alkenylene having 2 or 3 carbon atoms, wherein the alkylene and alkenylene are optionally substituted by $C_{1-4}$ alkyl or phenyl optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$—O—Q11\text{-}Q12\text{-} \qquad \text{(vi)}$$

wherein

Q11 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl, Q12 represents a bond, $—(CH_2)s\text{-}CHR^5—$ wherein s is an integer of 0 to 2 and $R^5$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $—(CH_2)t\text{-}NR^6—$ wherein t is an integer of 0 to 2 and $R^6$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, or $—NH—(CH_2)u\text{-}CHR^7—$ wherein u is an integer of 0 or 1 and $R^7$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$—Q13\text{-}Q14\text{-} \qquad \text{(viii)}$$

wherein

Q13 represents a bond or a five- to seven-membered saturated or unsaturated carbocyclic or heterocyclic group and the carbocyclic and heterocyclic groups are optionally substituted by an oxygen atom, hydroxyl, or $C_{1-4}$ alkyl, Q14 represents a bond, $—(CH_2)v\text{-}CHR^8—$ wherein v represents an integer of 0 to 2 and $R^8$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $—(CH_2)w\text{-}NR^9—$ wherein w represents an integer of 0 to 2 and $R^9$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, or $—NH—(CH_2)x\text{-}CHR^{10}—$ wherein x is an integer of 0 or 1 and $R^{10}$ represents a hydrogen atom, $C_{1-4}$ alkyl, or phenyl which is optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy, $$—C(=O)—Q15\text{-}(CH_2)y\text{-} \qquad \text{(viii)}$$

wherein Q15 represents a five- to seven-membered saturated or unsaturated heterocyclic group and this heterocyclic group is optionally substituted by an oxygen atom, hydroxyl, or $C_{1-4}$ alkyl and y is an integer of 0 to 4, and $$\text{(ix)}—C(=O)—NR^1—Q16\text{-}(CH_2)z\text{-} \qquad \text{(ix)}$$

wherein $R^1$ is as defined above, Q16 represents a five- to seven-membered saturated or unsaturated carbocyclic or heterocyclic group and the carbocyclic and heterocyclic groups are optionally substituted by an oxygen atom, hydroxyl, or $C_{1-4}$ alkyl, and z represents an integer of 0 to 4, Z represents a hydrogen atom, a halogen atom, a three- to seven-membered saturated or unsaturated monocyclic carbocyclic or heterocyclic group, a nine- to twelve-membered bicyclic saturated or unsaturated carbocyclic or heterocyclic group, or a thirteen- to fifteen-membered tricyclic saturated or unsaturated carbocyclic or heterocyclic group, wherein the carbocyclic and heterocyclic groups are optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy of which the phenyl portion is optionally substituted by a halogen atom.

DETAILED DESCRIPTION OF THE INVENTION

Compound

The terms "alkyl," "alkoxy," "alkenyl," "alkylene," and "alkenylene" as used herein as a group or a part of a group respectively mean straight chain or branched chain alkyl, alkoxy, alkenyl, alkylene, and alkenylene.

Examples of $C_{1-4}$ alkyl include methyl, ethyl, n-propyl, isopropyl, n-butyl, i-butyl, s-butyl, and t-butyl.

Examples of $C_{1-4}$ alkoxy include methoxy, ethoxy, n-propoxy, i-propoxy, n-butoxy, i-butoxy, s-butoxy, and t-butoxy.

The expression "alkyl optionally substituted by" as used herein means alkyl, on which one or more hydrogen atoms are optionally substituted by one or more substituents which may be the same or different. It will be apparent to a person skilled in the art that the maximum number of the substituents can be determined depending upon the number of substitutable hydrogen atoms on the alkyl group. This can apply to groups having substituents other than alkyl.

The term "halogen atom" as used herein means a fluorine, chlorine, bromine, or iodine atom.

Examples of the saturated or unsaturated monocyclic three- to seven-membered carbocyclic group include cyclopropyl, cyclopentyl, cyclohexyl, and phenyl.

The saturated or unsaturated monocyclic five- to seven-membered heterocyclic ring may contain one or more hetero-atoms selected from oxygen, nitrogen, and sulfur atoms.

Examples of the saturated or unsaturated monocyclic five- to seven-membered heterocyclic group include pyridyl, furanyl, piperidyl, pyrimidyl, imidazolyl, thienyl, thiophenyl, isoxazoyl, isothiazoyl, 1,2,3-oxadiazoyl, furazanyl, 1,2,3-triazoyl, 1,2,4-triazoyl, pyridazyl, pyrrolinyl, pyronyl, morphonyl, and triazinyl.

Examples of the saturated or unsaturated bicyclic nine- to twelve-membered carbocyclic group include naphthalenyl, naphthyl, and indenyl.

Examples of saturated or unsaturated bicyclic nine- to twelve-membered, preferably nine- or ten-membered, heterocyclic group include indolyl, quinolinyl, quinazolinyl, 1,3-benzodioxole, isoindolyl, indazolyl, 1H-pyrazolo[3,4-d]pyrimidyl, benzotriazolyl, isoquinolinyl, sinolinyl, phthalazinyl, pteredinyl, naphthyridinyl, benzimidazolinyl, benzothiazolinyl, benzoxazolinyl, 3,4-methylenedioxyphenyl, and benzo[6]furanyl.

Examples of the saturated or unsaturated tricyclic thirteen- to fifteen-membered carbocyclic or heterocyclic group include fluorenyl, carbazolyl, phenothiazinyl, and phenoxazinyl.

In formulae (I) and (Ia), Het may be a five- to seven-membered monocyclic saturated or unsaturated heterocyclic group containing at least one, preferably 1 to 3, nitrogen atoms, preferably a heterocyclic group containing only a nitrogen atom as the hetero-atom.

In formulae (I) and (Ia), the monocyclic heterocyclic group represented by Het preferably represents formula (IIa), (IIb), or (IIc):

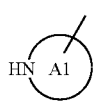
(IIa)

(IIb)

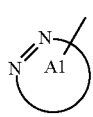
(IIc)

wherein A1 represents a five- to seven-membered monocyclic saturated or unsaturated heterocyclic group having at least one nitrogen atom.

In formulae (I) and (Ia), more preferably, the monocyclic heterocyclic group represented by Het represents 1,2,3-triazoyl, 1,2,4-triazoyl, and pyrrolinyl represented by formula (IIa), pyridyl, pyrimidyl, isoxazoyl, isothiazoyl, furazanyl, and triazinyl represented by formula (IIb), and 1,2,3-oxadiazoyl and pyridazyl represented by formula (IIc).

In formulae (I) and (Ia), Het may represent a nine- to twelve-membered bicyclic saturated or unsaturated heterocyclic group containing at least one, preferably 1 to 3, nitrogen atoms, preferably a heterocyclic group containing only a nitrogen atom as the hetero-atom.

In formulae (I) and (Ia), the bicyclic heterocyclic group represented by Het preferably represents formula (IIIa), (IIIb), (IIIc), (IIId), (IIIe), (IIIf), (IIIg), (IIIh), (IIIi), or (IIIj):

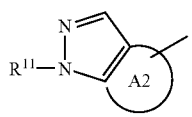
(IIIa)

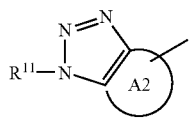
(IIIb)

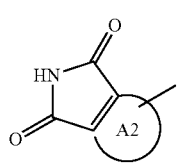
(IIIc)

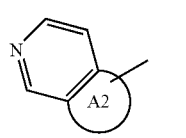
(IIId)

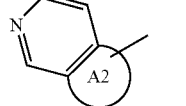
(IIIe)

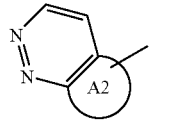
(IIIf)

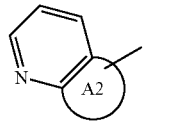
(IIIg)

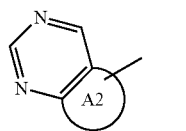
(IIIh)

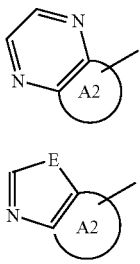

wherein A2 represents phenyl optionally substituted by a halogen atom, or an unsaturated six-membered heterocyclic ring which is optionally substituted by a halogen atom and contains one or two nitrogen atoms; $R^{11}$ represents a hydrogen atom or $C_{1-4}$ alkylcarbonyl; and E represents —NH—, —O—, or —S—.

Preferably, the A2 portion represents a group selected from the group consisting of the following groups:

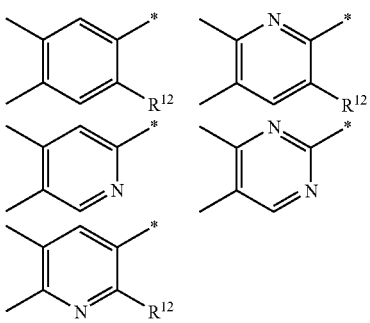

wherein $R^{12}$ represents a hydrogen atom or a halogen atom; and a bond with ★ represents a bond to group X with the remaining two bonds each representing a bond to the heterocyclic group.

In formulae (I) and (Ia), more preferred examples of the bicyclic heterocyclic group represented by Het include:

1H-5-indazolyl, 1-acetyl-1H-5-indazolyl and 1H-pyrazolo[3,4-d]pyrimidin-4-yl represented by formula (IIIa);

1H-5-benzotriazolyl represented by formula (IIIb);

1,3-dioxy-2,3-dihydro-1H-5-isoindolyl and 6-chloro-1,3-dioxy-2,3-dihydro-1H-5-isoindolyl represented by formula (IIIc);

isoquinolinyl represented by formula (IIId);
sinolinyl represented by formula (IIIe);
quinolinyl and naphthyridinyl represented by formula (IIIf);
quinazolinyl represented by formula (IIIg);
phthalazinyl represented by formula (IIIh);
pteredinyl represented by formula (IIIi); and
benzimidazolinyl, benzothiazolinyl and benzoxazolinyl represented by formula (IIIj).

In formulae (I) and (Ia), an example of preferred group (i) represented by X is that Q1 represents a bond, alkylene having 1 to 3 carbon atoms, or alkenylene having 2 or 3 carbon atoms and the alkylene and alkenylene are optionally substituted by $C_{1-4}$ alkyl or optionally substituted phenyl.

In formulae (I) and (Ia), an example of preferred group (ii) represented by X is that Q2 represents a bond, alkylene having 1 to 3 carbon atoms, or alkenylene having 2 or 3 carbon atoms and the alkylene and alkenylene are optionally substituted by $C_{1-4}$ alkyl or optionally substituted phenyl.

In formulae (I) and (Ia), an example of preferred group (iii) represented by X is that Q3 represents alkylene having 1 or 2 carbon atoms or alkenylene having 2 carbon atoms; Q4 represents —O—, —NH—, or —S(=O)m- wherein m is an integer of 0 to 2; and Q5 represents a bond, alkylene having 1 or 2 carbon atoms, or alkenylene having 2 carbon atoms and the alkylene and alkenylene represented by Q5 represent $C_{1-4}$ alkyl or optionally substituted phenyl.

In formulae (I) and (Ia), an example of preferred group (iv) represented by X is that $R^1$ represents a hydrogen atom or $C_{1-4}$ alkylcarbonyl; Q6 represents a bond, a five- to seven-membered saturated carbocyclic group or a five- to seven-membered saturated heterocyclic group containing one nitrogen atom and the carbocyclic and heterocyclic groups are optionally substituted by an oxygen atom; and Q7 represents a bond, —(CH$_2$)n1-CR$^{2a}$R$^{2b}$—(CH$_2$)n2-, wherein n1 is an integer of 0 or 1, n2 is 0, $R^{2a}$ represents a hydrogen atom, and $R^{2b}$ represents a hydrogen atom, $C_{1-4}$ alkyl, or optionally substituted phenyl, —(CH$_2$)p-NR$^3$—, wherein p is an integer of 0 or 1 and $R^3$ represents a hydrogen atom, $C_{1-4}$ alkyl, or optionally substituted phenyl, or —NH—(CH$_2$)q1-CR$^{4a}$R$^{4b}$—(CH$_2$)q2- wherein q1 is 0 or 1, q2 is 0, $R^{4a}$ represents a hydrogen atom, and $R^{4b}$ represents a hydrogen atom, $C_{1-4}$ alkyl or optionally substituted phenyl.

Another example of preferred group (iv) represented by X is, that $R^1$ represents a hydrogen atom or $C_{1-4}$ alkylcarbonyl; Q6 represents a bond, a five- to seven-membered saturated carbocyclic group or a five- to seven-membered saturated heterocyclic group containing one nitrogen atom and the carbocyclic and heterocyclic groups are optionally substituted by an oxygen atom; and Q7 represents a bond, —(CH$_2$)n1-CR$^{2a}$R$^{2b}$—(CH$_2$)n2-, wherein n1 and n2 are each an integer of 0 to 3, $R^{2a}$ represents a hydrogen atom, and $R^{2b}$ represents a hydrogen atom, optionally substituted $C_{1-6}$ alkyl, carboxyl, $C_{1-4}$ alkoxycarbonyl, cyano, —(C=O)—N(—R$^{2c}$)(—R$^{2d}$), wherein $R^{2c}$ and $R^{2d}$, which may be the same or different, represent a hydrogen atom, optionally substituted $C_{1-4}$ alkyl, optionally substituted $C_{1-4}$ alkoxy, cyclopropyl, or optionally substituted benzyl, or optionally substituted phenyl, —(CH$_2$)p-NR$^3$—, wherein p is an integer of 0 or 1, $R^3$ represents a hydrogen atom, $C_{1-4}$ alkyl, or optionally substituted phenyl, —NH—(CH2)q1-CR$^{4a}$R$^{4b}$—(CH2)q2-, wherein q1 and q2 are each an integer of 0 to 2, $R^{4a}$ represents a hydrogen atom, and $R^{4b}$ represents a hydrogen atom, $C_{1-4}$ alkyl, or optionally substituted phenyl, —(C=O)—O—CR$^{4a}$R$^{4b}$—CH$_2$—, wherein $R^{4a}$ represents a hydrogen atom and $R^{4b}$ represents a hydrogen atom, optionally substituted $C_{1-6}$ alkyl, or optionally substituted phenyl, —NH—(CH$_2$)i-NH—, wherein i is an integer of 1 to 4, or —S(=O)j- wherein j is 0, 1, or 2.

In formulae (I) and (Ia), an example of more preferred group (iv) represented by X is that $R^1$ represents a hydrogen atom; Q6 represents a five- to seven-membered saturated carbocyclic group optionally substituted by an oxygen atom; and Q7 represents —(CH$_2$)p-NR$^3$—, wherein p is an integer of 0 or 1 and $R^3$ represents a hydrogen atom, $C_{1-4}$ alkyl, or optionally substituted phenyl, or —NH—(CH$_2$)q1-CR$^{4a}$R$^{4b}$—(CH$_2$)q2-, wherein q1 is 0 or 1, q2 is 0, $R^{4a}$ represents a hydrogen atom, and $R^{4b}$ represents a hydrogen atom, $C_{1-4}$ alkyl, or optionally substituted phenyl.

Another example of more preferred group (iv) represented by X is that $R^1$ represents a hydrogen atom; Q6 represents a five- to seven-membered saturated heterocyclic group which is optionally substituted by an oxygen atom and contains one nitrogen atom; and Q7 represents —(CH$_2$)n1-CR$^{2a}$R$^{2b}$—(CH$_2$)n2- wherein n1 is an integer of 0 or 1, n2 is 0, R$^2$a represents a hydrogen atom, and R$^{2b}$ represents a hydrogen atom, C$_{1-4}$ alkyl, or optionally substituted phenyl.

Still another example of more preferred group (iv) represented by X is that R$^1$ represents a hydrogen atom; Q6 represents a five- to seven-membered saturated carbocyclic group or a five- to seven-membered saturated heterocyclic group containing one nitrogen atom and the carbocyclic and heterocyclic groups are optionally substituted by an oxygen atom; and Q7 represents —(CH$_2$)n1-CR$^{2a}$R$^{2b}$—(CH$_2$)n2- wherein n1 and n2, which may be the same or different, are each an integer of 0 to 3, R$^{2a}$ represents a hydrogen atom, and R$^{2b}$ represents a hydrogen atom or optionally substituted C$_{1-4}$ alkyl.

A further example of more preferred group (iv) represented by X is that R$^1$ represents a hydrogen atom; Q6 represents a five- to seven-membered saturated carbocyclic group or a five- to seven-membered saturated heterocyclic group containing one nitrogen atom and the carbocyclic and heterocyclic groups are optionally substituted by an oxygen atom; and Q7 represents —(CH$_2$)n1-CR$^{2a}$R$^{2b}$—(CH$_2$)n2- wherein n1 and n2 are each 0, R$^{2a}$ represents a hydrogen atom, and R$^{2b}$ represents optionally substituted C$_{1-6}$ alkyl, carboxyl, C$_{1-4}$ alkoxycarbonyl, cyano, —(C=O)—N(—R$^{2c}$)(—R$^{2d}$) wherein R$^{2c}$ and R$^{2d}$ are as defined in formula (I), or optionally substituted phenyl.

A still further example of more preferred group (iv) represented by X is that R$^1$ represents a hydrogen atom; Q6 represents a five- to seven-membered saturated carbocyclic group or a five- to seven-membered saturated heterocyclic group containing one nitrogen atom and the carbocyclic and heterocyclic groups are optionally substituted by an oxygen atom; and Q7 represents —(CH$_2$)n1-CR$^{2a}$R$^{2b}$—(CH$_2$)n2- wherein n1 is an integer of 0 to 3, n2 is 0, and R$^{2a}$ and R$^{2b}$ represent a halogen atom.

Another example of more preferred group (iv) represented by X is that R$^1$ represents a hydrogen atom; Q6 represents a five- to seven-membered saturated carbocyclic group or a five- to seven-membered saturated heterocyclic group containing one nitrogen atom and the carbocyclic and heterocyclic groups are optionally substituted by an oxygen atom; and Q7 represents —NH—(CH$_2$)q1-CR$^{4a}$R$^{4b}$—(CH$_2$)q2- wherein q1 and q2 are each an integer of 0 to 2, R$^{4a}$ represents a hydrogen atom, and R$^{4b}$ represents a hydrogen atom, C$_{1-4}$ alkyl, or optionally substituted phenyl.

Still another example of more preferred group (iv) represented by X is that R$^1$ represents a hydrogen atom, Q6 represents a bond, and Q7 represents a bond.

In formulae (I) and (Ia), an example of preferred group (v) represented by X is that Q8 represents alkylene having 1 to 3 carbon atoms or alkenylene having 2 or 3 carbon atoms; Q9 represents —O—, —NH—, or —S(=O)r- wherein r is an integer of 0 to 2; and Q10 represents a bond, alkylene having 1 or 2 carbon atoms or alkenylene having 2 carbon atoms and the alkylene and alkenylene represented by Q10 are optionally substituted by C$_{1-4}$ alkyl or optionally substituted phenyl.

In formulae (I) and (Ia), an example of preferred group (vi) represented by X is that Q11 represents a bond, a five- to seven-membered saturated carbocyclic group optionally substituted by an oxygen atom, or a five- to seven-membered saturated heterocyclic group containing one nitrogen atom; and Q12 represents a bond, —(CH$_2$)s-CHR$^5$—, wherein s is an integer of 0 or 1, R$^5$ represents a hydrogen atom, C$_{1-4}$ alkyl, or optionally substituted phenyl, —(CH$_2$)t-NR$^6$—, wherein t is an integer of 0 or 1, R$^6$ represents a hydrogen atom, C$_{1-4}$ alkyl, or optionally substituted phenyl, or —NH—(CH$_2$)u-CHR$^7$— wherein u is an integer of 0 or 1, and R$^7$ represents a hydrogen atom, C$_{1-4}$ alkyl, or optionally substituted phenyl.

In formulae (I) and (Ia), an example of preferred group (vii) represented by X is that Q13 represents a bond, a saturated carbocyclic group optionally substituted by an oxygen atom, or a five- to seven-membered saturated heterocyclic group containing one nitrogen atom; Q14 represents a bond, —(CH$_2$)v-CHR$^8$—, wherein v is an integer of 0 or 1, R$^8$ represents a hydrogen atom, C$_{1-4}$ alkyl, or optionally substituted phenyl, —(CH$_2$)w-NR$^9$—, wherein w is an integer of 0 or 1, R$^9$ represents a hydrogen atom, C$_{1-4}$ alkyl, or optionally substituted phenyl, or —NH—(CH$_2$)x-CHR$^{10}$— wherein x is an integer of 0 or 1 and R$^{10}$ represents a hydrogen atom, C$_{1-4}$ alkyl, or optionally substituted phenyl.

In formulae (I) and (Ia), an example of preferred group (viii) represented by X is that Q15 represents a five- to seven-membered saturated heterocyclic group which is optionally substituted by an oxygen atom and contains two nitrogen atoms, more preferably a piperazine ring or a homopiperazine ring; and y is 1 or 2.

In formulae (I) and (Ia), an example of preferred group (ix) represented by X is that Q16 represents a five- to seven-membered saturated carbocyclic group optionally substituted by an oxygen atom, or a five- to seven-membered saturated heterocyclic group containing one nitrogen atom; and z is 1 or 2.

In formulae (I) and (Ia), preferably, "five- to seven-membered saturated heterocyclic group" represented by Q6 in group (iv), Q11 in group (vi), Q13 in group (vii), Q15 in group (viii), and Q16 in group (ix) represent any one of the following groups:

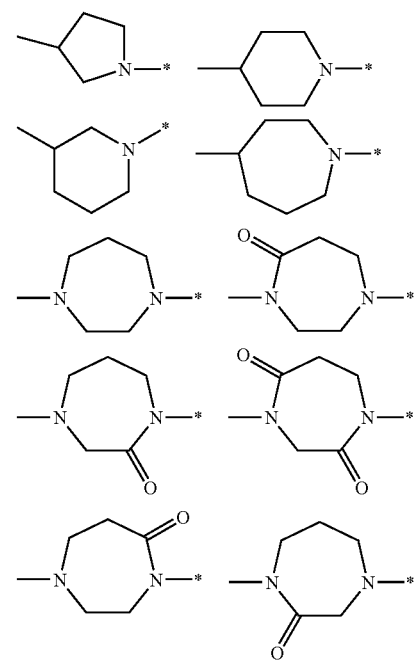

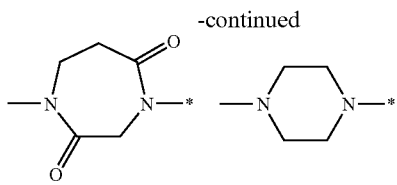

-continued

When Q6 in group (iv) represents the above group, the bond with ★ represents a bond to Q7 and the bond without ★ represents a bond to group —N(—R¹)—.

When Q11 in group (vi) represents the above group, the bond with ★ represents a bond to Q12, and the bond without ★ represents a bond to group —O—.

When Q13 in group (vii) represents the above group, the bond with ★ represents a bond to Q14, and the bond without ★ represents a bond to group Het.

When Q15 in group (viii) represents the above group, the bond with ★ represents a bond to —(CH$_2$)y-, and the bond without ★ represents a bond to —C(=O)—.

When Q16 in group (ix) represents the above group, the bond with ★ represents a bond to —(CH$_2$)z-, and the bond without ★ represents a bond to —N(—R¹)—.

In formulae (I) and (Ia), the five- to seven-membered monocyclic saturated or unsaturated carbocyclic group represented by Z is preferably phenyl, cyclohexyl, norpyranyl, or norbornanyl.

In formulae (I) and (Ia), phenyl represented by z is preferably substituted at the 2- and 6-positions, at the 3- and 4-positions, or at the 2-, 4-, and 6- positions.

In formulae (I) and (Ia), the five- to seven-membered saturated or unsaturated monocyclic carbocyclic or heterocyclic group represented by Z is preferably a five- to seven-membered saturated or unsaturated heterocyclic group containing one nitrogen atom and/or one oxygen atom, more preferably furanyl, pyridyl, piperidyl, pyrrolidinyl, pyronyl, isoxazoyl, morphonyl, or imidazolyl.

In formulae (I) and (Ia), the five- to seven-membered saturated or unsaturated monocyclic carbocyclic or heterocyclic group represented by Z is preferably a five- to seven-membered saturated or unsaturated heterocyclic group containing two nitrogen atoms, more preferably imidazolyl.

In formulae (I) and (Ia), the five- to seven-membered saturated or unsaturated monocyclic carbocyclic or heterocyclic group represented by Z is preferably a five- to seven-membered saturated or unsaturated heterocyclic group containing one sulfur atom, more preferably thienyl.

In formulae (I) and (Ia), the nine- to twelve-membered bicyclic saturated or unsaturated carbocyclic group represented by Z is preferably a nine- to ten-membered bicyclic unsaturated carbocyclic group, more preferably naphthyl, naphthalenyl, or indenyl.

In formulae (I) and (Ia), the nine- to twelve-membered bicyclic saturated or unsaturated heterocyclic group represented by Z is preferably a nine- to ten-membered unsaturated bicyclic heterocyclic group containing one nitrogen atom and/or one or two oxygen atoms, more preferably indolyl, 1,3-benzodioxole, quinolyl, quinazolyl, isoquinolyl, 3,4-methylenedioxyphenyl, benzo[6]furanyl, sinolyl, indazolyl, benzimidazolyl, benzotriazolyl, or phthalazinyl.

In formulae (I) and (Ia), the thirteen- to fifteen-membered tricyclic saturated or unsaturated carbocyclic or heterocyclic group represented by Z is preferably fluorenyl, phenothiazinyl, carbazolyl, or phenoxazinyl.

Examples of preferred compounds represented by formula (I) and preferred compounds represented by formula (Ia) according to the present invention include:

(1) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3- dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (i) wherein Q1 represents a bond, alkylene having 1 to 3 carbon atoms, or alkenylene having 2 or 3 carbon atoms and the alkylene and alkenylene are optionally substituted by $C_{1-4}$ alkyl or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(2) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (ii) wherein Q2 represents a bond, alkylene having 1 to 3 carbon atoms, or alkenylene having 2 or 3 carbon atoms and the alkylene and alkenylene are optionally substituted by $C_{1-4}$ alkyl or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(3) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iii) wherein Q3 represents alkylene having 1 or 2 carbon atoms or alkenylene having 2 carbon atoms, Q4 represents —O—, —NH—, or —S(=O)m- wherein m is an integer of 0 to 2, and Q5 represents a bond, alkylene having 1 or 2 carbon atoms, or alkenylene having 2 carbon atoms and the alkylene and alkenylene represented by Q5 represents $C_{1-4}$ alkyl or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(4) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein $R^1$ represents a hydrogen atom or $C_{1-4}$ alkylcarbonyl, Q6 represents a bond, a five- to seven-membered saturated carbocyclic group or a five- to seven-membered saturated heterocyclic group containing one nitrogen atom and the carbocyclic and heterocyclic groups are optionally substituted by an oxygen atom, and Q7 represents a bond; —$(CH_2)n1$-$CR^{2a}R^{2b}$—$(CH_2)n2$- wherein n1 is an integer of 0 or 1, n2 is 0, $R^{2a}$ represents a hydrogen atom, and $R^{2b}$ represents a hydrogen atom, $C_{1-4}$ alkyl, or optionally substituted phenyl; $(CH_2)p$-$NR^3$- wherein p is an integer of 0 or 1 and $R^3$ represents a hydrogen atom, $C_{1-4}$ alkyl, or optionally substituted phenyl; or —NH—$(CH_2)q1$-$CR^{4a}R^{4b}$—$(CH2)q2$- wherein q1 is 0 or 1, q2 is 0, $R^{4a}$ represents a hydrogen atom, and $R^{4b}$ represents a hydrogen atom, $C_{1-4}$ alkyl, or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted; (4') compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein $R^1$ represents a hydrogen atom or $C_{1-4}$ alkylcarbonyl, Q6 represents a bond, a five- to seven-membered saturated carbocyclic group or a five- to seven-membered saturated heterocyclic group containing one nitrogen atom and the carbocyclic and heterocyclic groups are optionally substituted by an oxygen atom, and Q7 represents a bond; —$(CH_2)n1$-$CR^{2a}R^{2b}$—$(CH_2)n2$- wherein n1 and n2 are each an integer of 0 to 3, $R^{2a}$ represents a hydrogen atom, and $R^{2b}$ represents a hydrogen atom, optionally substituted $C_{1-6}$ alkyl, carboxyl, $C_{1-4}$ alkoxycarbonyl, cyano, —(C=O)—N(—$R^{2c}$)(—$R^{2d}$), wherein $R^{2c}$ and $R^{2d}$, which may be the same or different, represent a hydrogen atom, optionally substituted $C_{1-4}$ alkyl, optionally substituted $C_{1-4}$ alkoxy, cyclopropyl, or optionally substituted benzyl, or optionally substituted phenyl; —$(CH_2)p$-$NR^3$— wherein p is an integer of 0 or 1 and $R^3$ represents a hydrogen atom, $C_{1-4}$ alkyl, or optionally substituted phenyl; —NH—$(CH_2)q1$-$CR^{4a}R^{4b}$—$(CH_2)q2$- wherein q1 and q2 are each an integer of 0 to 2, $R^{4a}$ represents a hydrogen atom, and $R^{4b}$ represents a hydrogen atom, $C_{1-4}$ alkyl or optionally substituted phenyl; —(C=O)—O—$CR^{4a}R^{4b}$—$CH_2$- wherein $R^{4a}$ represents a hydrogen atom and $R^{4b}$ represents a hydrogen atom, optionally substituted $C_{1-6}$ alkyl, or optionally substituted phenyl; —NH—$(CH_2)i$-NH—0 wherein i is an integer of 1 to 4; or —S(=O)j- wherein j is 0, 1, or 2, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(5) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (v) wherein Q8 represents alkylene having 1 to 3 carbon atoms or alkenylene having 2 or 3 carbon atoms, Q9 represents —O—, —NH—, or —S(=O)r- wherein r is an integer of 0 to 2, and Q10 represents a bond, alkylene having 1 or 2 carbon atoms, or alkenylene having 2 carbon atoms and the alkylene and alkenylene represented by Q10 are optionally substituted by $C_{1-4}$ alkyl or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(6) compound wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (vi) wherein Q11 represents a bond, a five- to seven-membered saturated carbocyclic group optionally substituted by an oxygen atom, or a five- to seven-membered saturated heterocyclic group containing one nitrogen atom, and Q12 represents a bond; —$(CH_2)s$-$CHR^5$— wherein s is an integer of 0 or 1 and $R^5$ represents a hydrogen atom, $C_{1-4}$ alkyl, or optionally substituted phenyl; —$(CH_2)t$-$NR^6$— wherein t is an integer of 0 or 1 and $R^6$ represents a hydrogen atom, $C_{1-4}$ alkyl, or optionally substituted phenyl; or —NH—$(CH_2)u$-$CHR^7$— wherein u is an integer of 0 or 1 and $R^7$ represents a hydrogen atom, $C_{1-4}$ alkyl, or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(7) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (vii) wherein Q13 represents a bond, a five- to seven-membered saturated carbocyclic group optionally substituted by an oxygen atom, or a five- to seven-membered saturated heterocyclic group containing one nitrogen atom, and Q14 represents a bond; —$(CH_2)v$-

CHR$^8$— wherein v is an integer of 0 or 1 and R$^8$ represents a hydrogen atom, C$_{1-4}$ alkyl, or optionally substituted phenyl; —(CH$_2$)w-NR$^9$— wherein w is an integer of 0 or 1 and R$^9$ represents a hydrogen atom, C$_{1-4}$ alkyl, or optionally substituted phenyl; or —NH—(CH$_2$)x-CHR$^{10}$— wherein x is an integer of 0 or 1 and R$^{10}$ represents a hydrogen atom, C$_{1-4}$ alkyl, or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(8) compounds wherein Het represents a monocyclic heterocyclic group represented by formula (IIa), (IIb), or (IIc), or alternatively Het represents a bicyclic heterocyclic group represented by formula (IIIa), (IIIb), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (viii) wherein Q15 represents a five- to seven-membered saturated heterocyclic group which is optionally substituted by an oxygen atom and contains two nitrogen atoms, more preferably a piperazine ring or a homopiperazine ring, and y is 1 or 2, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted; and (9) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (ix) wherein Q16 represents a five- to seven-membered saturated carbocyclic group optionally substituted by an oxygen atom or a five- to seven-membered saturated heterocyclic group containing one nitrogen atom and z is 1 or 2, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted.

Further examples of preferred compounds represented by formula (I) and preferred compounds represented by formula (Ia) according to the present invention include:

(10) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R$^1$ represents a hydrogen atom, Q6 represents a five- to seven-membered saturated carbocyclic group optionally substituted by an oxygen atom, and Q7 represents —(CH$_2$)p-NR$^3$— wherein p is an integer of 0 or 1 and R$^3$ represents a hydrogen atom, C$_{1-4}$ alkyl, or optionally substituted phenyl; or —NH—(CH$_2$)q1-CR$^{4a}$R$^{4b}$—(CH$_2$)q2- wherein q1 is 0 or 1, q2 is 0, R$^{4a}$ represents a hydrogen atom, and R$^{4b}$ represents a hydrogen atom, C$_{1-4}$ alkyl, or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(11) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R$^1$ represents a hydrogen atom, Q6 represents a five- to seven-membered saturated heterocyclic group which is optionally substituted by an oxygen atom and contains one nitrogen atom, and Q7 represents —(CH$_2$)n1-CR$^{2a}$R$^{2b}$—(CH$_2$)n2- wherein n1 is an integer of 0 or 1, n2 is 0, R$^{2a}$ represents a hydrogen atom, and R$^{2b}$ represents a hydrogen atom, C$_{1-4}$ alkyl, or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(12) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R$^1$ represents a hydrogen atom, Q6 represents a five- to seven-membered saturated carbocyclic group or a five- to seven-membered saturated heterocyclic group containing one nitrogen atom and the carbocyclic and heterocyclic groups are optionally substituted by an oxygen atom, and Q7 represents —(CH$_2$)n1-CR$^{2a}$R$^{2b}$—(CH$_2$)n2- wherein n1 and n2, which may be the same or different, are each an integer of 0 to 3, R$^{2a}$ represents a hydrogen atom, and R$^{2b}$ represents a hydrogen atom, or optionally substituted C$_{1-4}$ alkyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(13) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R¹ represents a hydrogen atom, Q6 represents a five- to seven-membered saturated carbocyclic group or a five- to seven-membered saturated heterocyclic group containing one nitrogen atom and the carbocyclic and heterocyclic groups are optionally substituted by an oxygen atom, and Q7 represents —(CH$_2$)n1-CR$^{2a}$R$^{2b}$—(CH$_2$)n2-, wherein n1 and n2 are 0, R$^{2a}$ represents a hydrogen atom, and R$^{2b}$ represents optionally substituted C$_{1-6}$ alkyl, carboxyl, C$_{1-4}$ alkoxycarbonyl, cyano, —(C=O)—N(—R$^{2c}$)(—R$^{2d}$) wherein R$^{2c}$ and R$^{2d}$ are as defined in formula (I), or optionally substituted phenyl, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted;

(14) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R¹ represents a hydrogen atom, Q6 represents a five- to seven-membered saturated carbocyclic group or a five- to seven-membered saturated heterocyclic group containing one nitrogen atom and the carbocyclic and heterocyclic groups are optionally substituted by an oxygen atom, and Q7 represents —(CH$_2$)n1-CR$^{2a}$R$^{2b}$—(CH$_2$)n2- wherein n1 represents an integer of 0 to 3, n2 is 0, and R$^{2a}$ and R$^{2b}$ represent a halogen atom, and Z represents a halogen atom;

(15) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R¹ represents a hydrogen atom, Q6 represents a five- to seven-membered saturated carbocyclic group or a five- to seven-membered saturated heterocyclic group containing one nitrogen atom and the carbocyclic and heterocyclic groups are optionally substituted by an oxygen atom, and Q7 represents —NH—(CH$_2$)q1-CR$^{4a}$R$^{4b}$—(CH$_2$)q2- wherein q1 and q2 are each an integer of 0 to 2, R$^{4a}$ represents a hydrogen atom, and R$^{4b}$ represents a hydrogen atom, C$_{1-4}$ alkyl, or optionally substituted phenyl, Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted; and

(16) compounds wherein Het represents a monocyclic heterocyclic group represented by formula (IIa), (IIb), or (IIc), or alternatively Het represents a bicyclic heterocyclic group represented by formula (IIIa), (IIIb), (IIIc), (IIId), (IIIe), (IIIf), (IIIg), (IIIh), (IIIi), or (IIIj), preferably 4-pyridyl, 1,3-dioxy-2,3-dihydro-1H-5-isoindolyl, 1H-5-indazolyl, 6-chloro-1,3-dioxy-2,3-dihydro-1H-5-isoindolyl, 1-acetyl-1H-5-indazolyl, 1H-pyrazolo[3,4-d]pyrimidin-4-yl, 1H-5-benzotriazolyl, or 5-isoquinolyl, X represents group (iv) wherein R¹ represents a hydrogen atom, Q6 represents a bond, and Q7 represents a bond, and Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted.

Examples of preferred compounds according to the present invention include compounds prepared in Examples 1 to 322.

Examples of particularly preferred compounds according to the present invention include the following compounds. The number within parentheses represents working example numbers:

(20) N-[1-(4-bromophenyl)ethyl]-N'-(1,3-dioxo-2,3-dihydro-1H-5-isoindolyl)urea;

(21) N-(1-benzyl-3-piperidyl-1-N(1H-5-indazolyl)-amine;

(22) N-[1-(4-bromobenzyl)-4-piperidyl]-N-(1H-5-imidazolyl)amine;

(80) N-(2,6-dichlorobenzyl)-N'-(4-pyridyl)urea;

(83) N-(2-chloro-6-fluorobenzyl)-N'-(1,3-dioxo-2,3-dihydro-1H-6-isoindolyl)urea;

(90) N-(2,6-difluorobenzyl)-N'-(1,3-dioxo-2,3-dihydro-1H-5-isoindolyl)urea;

(95) N-(2,6-difluorobenzyl)-N'-(1H-5-indazolyl)urea;

(102) N-(2-chloro-6-fluorobenzyl)-N'-(1H-5-indazolyl)urea;

(126) N-(1-benzyl-4-piperidyl)-N-(1H-5-indazolyl)-amine;

(127) N-(1-benzyl-4-piperidyl)-N-(1H-5-indazolyl)-amine hydrochloride;

(128) N-(1H-5-indazolyl)-N-(4-piperidyl)amine;

(146) N-(1-benzyl tetrahydro-1H-pyrrolyl)-N-(1H-5-indazolyl)amine;

(164) N-[1-(4-fluorobenzyl)-3-piperidyl]-N-(1H-5-indazolyl)amine;

(221) methyl 2-[3-(1H-5-indazolylamino)piperidino]-2-phenylacetate;

(227) N1-(2-fluoroethyl)-2-[3-(1H-5-indazolylamino)piperidino]-2-phenylacetamide;

(240) N-(1H-5-indazolyl)-N-[1-(2-methyl-1-phenyl-propyl)-3-piperidyl]amine;

(243) N1-(1H-5-indazolyl)-N4-propyl-1,4-cyclohexanediamine;

(246) N1-(2-fluoroethyl)-N4-(1H-5-indazolyl)-1,4-cyclohexanediamine;

(247) N1-cyclopropyl-N4-(1H-5-indazolyl)-1,4-cyclohexanediamine;

(248) N1-(1H-5-indazolyl)-1,4-cyclohexanediamine;

(259) N1-(1H-5-indazolyl)-N4-phenylethyl-1,4-cyclohexanediamine;

(260) N1-(5-isoquinolyl)-N4-propyl-1,4-cyclohexanediamine;

(261) N1-(2-fluoroethyl)-N4-(5-isoquinolyl)-1,4-cyclohexanediamine;

(262) N1-cyclopropyl-N4-(5-isoquinolyl)-1,4-cyclohexanediamine;

(273) N-(5-isoquinolyl)-N-[1-(4,4,4-trifluorobutyl)-3-piperidyl]amine;

(281) N-(1H-5-indazolyl)-N-[1-(2-methylpentyl)-3-piperidyl]amine;

(282) N-(1H-5-indazolyl)-N-[1-(2,4,6-trifluorobenzyl)-3-piperidyl]amine;

(286) N-(1H-5-indazolyl)-N-(1-propyl-4-piperidyl)-amine;
(287) N-[1-(cyclopropylmethyl)-4-piperidyl]-N-(1H-5-indazolyl)amine;
(289) N-[1-(3-fluoropropyl)-4-piperidyl]-N-(1H-5-indazolyl)amine;
(290) N-(1H-5-indazolyl)-N-[1-(3,3,3-trifluoropropyl)-4-piperidyl]amine;
(293) N-[1-(2-chloro-4-fluorobenzyl)-3-piperidyl]-N-(1H-5-indazolyl)amine;
(294) methyl 2-(3,4-difluoropentyl)-2-[3-(1H-5-indazolylamino)piperidino]acetate;
(298) N-(1H-5-indazolyl)-N-{1-[4-(trifluoromethyl)-benzyl]-3-piperidyl}amine;
(300) N-[1-(3,4-difluorobenzyl)-3-piperidyl]-N-(1H-5-indazolyl)amine;
(318) N-(5-isoquinolyl)-N-(1-propyl-4-piperidyl)-amine;
(320) N-[1-(2-ethylbutyl)-4-piperidyl]-N-(5-isoquinolyl)amine; and
(322) N-[1-(3-fluoropropyl)-4-piperidyl]-N-(5-isoquinolyl)amine.

Pharmaceutically acceptable salts of the compounds represented by formula (I) and the compounds represented by formula (Ia) include acid addition salts. Acid addition salts include: salts with inorganic acids such as hydrochloric acid, sulfuric acid, phosphoric acid, hydrobromic acid, and nitric acid; salts with organic acids such as maleic acid, fumaric acid, malic acid, oxalic acid, tartaric acid, succinic acid, citric acid, acetic acid, lactic acid, methanesulfonic acid, p-toluenesulfonic acid and salicylic acid; and salts with amino acids such as lysine. These acid addition salts may be converted to corresponding free bases by a conventional method, for example, by a reaction with an alkali such as sodium hydroxide or potassium hydroxide. Further, the compounds may be brought to quaternary ammonium salts or salts with metals such as sodium, potassium, calcium, magnesium, or aluminum.

Pharmaceutically acceptable solvates of the compounds represented by formula (I) and the compounds represented by formula (Ia) include hydrates.

In the compounds represented by formula (I) and the compounds represented by formula (Ia), optical isomers, racemic forms thereof, and cis/trans isomers may exist, and the compounds according to the present invention include all of these isomers. These isomers may be isolated according to a conventional method, or may be produced using various materials for respective isomers.

Production of Compounds

The compounds represented by formula (I) and the compounds represented by formula (Ia) according to the present invention may be produced according to schemes 1 to 11 below.

Compounds, wherein X represents group (i), may be produced according to schemes 1 and 2.

Compounds, wherein X represents group (ii) or (iii), may be produced according to scheme 3.

Compounds, wherein X represents group (iv), may be produced according to schemes 4, 5, 6, and 7.

Compounds, wherein X represents group (v), may be produced according to scheme 8.

Compounds, wherein X represents group (vi), may be produced according to scheme 9.

Compounds, wherein X represents group (vii), may be produced according to scheme 10.

Compounds, wherein X represents group (viii), may be produced according to scheme 11.

Compounds, wherein X represents group (ix), may be produced according to scheme 11.

Scheme 1

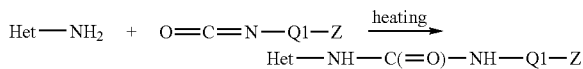

Compounds, wherein X represents group (i), can be produced by adding an isocyanate derivative O=C=N—Q1-Z, wherein Z is as defined above, to an amine derivative Het—NH$_2$, wherein Het is as defined above, in a suitable solvent, such as toluene or N,N-dimethylformamide, and heating the mixture. When there is no suitable aniline derivative, an aniline compound can be produced by catalytically reducing a corresponding nitro compound.

Scheme 2

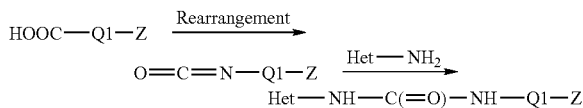

An isocyanate compound is produced by reacting a carboxylic acid derivative Z—Q1-COOH, wherein Z is as defined above, with diphenylphosphoryl azide in a suitable solvent, for example, toluene or N,N-dimethylformamide, in the presence of a base, for example, triethylamine. The compound, wherein X represents group (i), can be produced by reacting the isocyanate compound thus obtained with an amino derivative Het—NH$_2$ wherein Het is as defined above. When there is no suitable aniline derivative, an aniline compound can be produced by catalytically reducing a corresponding nitro compound.

Scheme 3

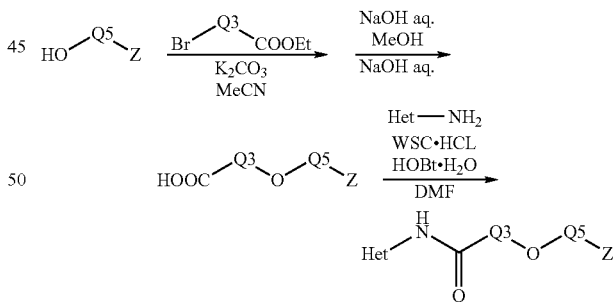

A carbocylic acid compound can be produced by reaction of a phenol derivative Z—OH, wherein Z is as defined above, with Br—Q3-COOEt, wherein Q3 is as defined above, for example, ethyl bromocarbonate, in the presence of a base, for example, potassium carbonate, followed by hydrolysis. Next, the compound, wherein X represents formula (iii) wherein Q4 represents —O—, can be produced by adding a condensing agent to the carboxylic acid compound thus obtained in a suitable solvent, for example, N,N-dimethylformamide, and reacting the mixture with an amino derivative Het—NH$_2$ wherein Het is as defined above.

The compounds, wherein $Q^4$ represents —NH— or —S(=O)m-, can be produced by reacting an amino derivative Het—NH$_2$, wherein Het is as defined above, with a carboxylic acid derivative Z—Q5-Q4-Q3-COOH, wherein Z and Q2 are as defined above, in a suitable solvent, for example, N,N-dimethylformamide, in the presence of a condensing agent.

The compounds, wherein X represents group (ii), can be produced by reacting an amino derivative Het—NH$_2$, wherein Het is as defined above, with a carboxylic acid derivative Z—Q2-COOH, wherein Z and Q2 are as defined above, in a suitable solvent, for example, N,N-dimethylformamide, in the presence of a condensing agent.

Scheme 4

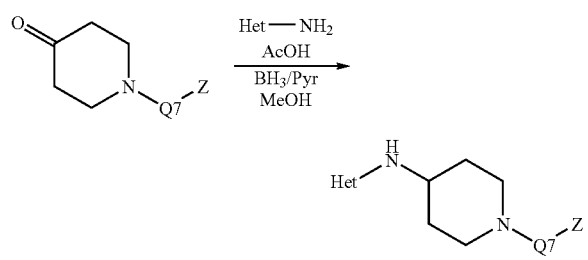

The compounds, wherein X represents group (iv) wherein Q6 represents piperidine, can be produced by condensing a 4-piperidone derivative and an amino derivative Het—NH$_2$, wherein Het is as defined above, for example, 5-aminoindazole, in a suitable solvent, for example, methanol, with an acid to form an imine compound and then reducing the imine compound with a borane-pyridine complex.

Scheme 5

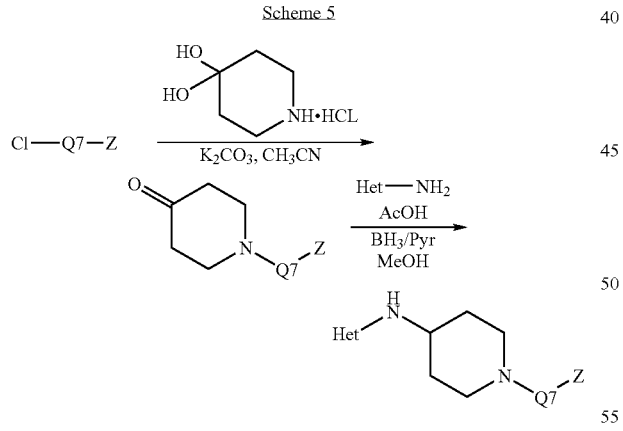

The compounds, wherein X represents group (iv) wherein Q6 represents piperidine, can be produced by reacting 4-piperidone monohydrate with Cl—Q7-Z, wherein Q7 and Z are as defined above, for example, benzyl chloride, in the presence of a base, for example, potassium carbonate, to give an N-benzyl compound, adding an amino derivative Het—NH$_2$, wherein Het is as defined above, for example, 5-aminoindazole, and condensing the mixture with an acid to form an imine compound, and reducing the imine compound with a borane-pyridine complex.

Scheme 6

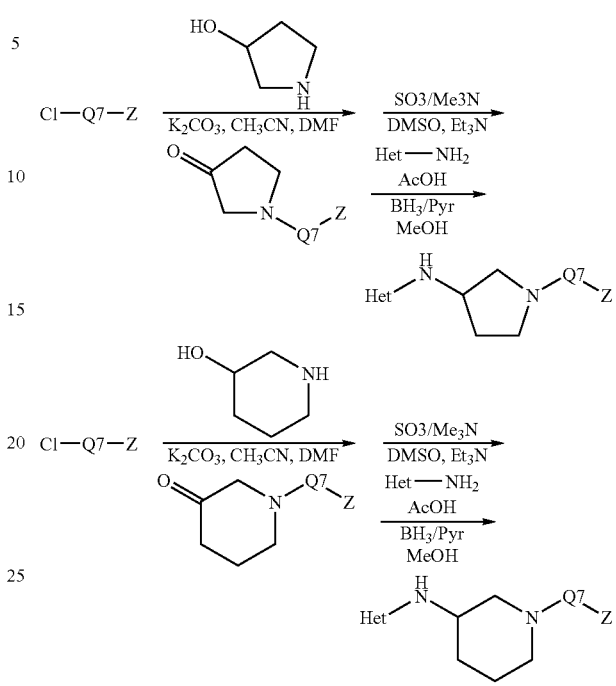

The compounds, wherein X represents group (iv), wherein Q6 represents pyrrolyl, can be produced by first reacting (R)-(−)-3-pyrrolidinol hydrochloride with Cl—Q7-Z, wherein Q7 and Z are as defined above, for example, benzyl chloride, in the presence of a base, for example, potassium carbonate, to give an N-benzyl compound, dissolving triethylamine in anhydrous dimethyl sulfoxide, adding a sulfur trioxide-trimethylamine complex at room temperature in an argon atmosphere, and oxidizing the N-benzyl compound in this system to give an intermediate, then reacting this intermediate with an amino derivative Het—NH$_2$, wherein Het is as defined above, for example, 5-aminoindazole, performing condensation with an acid to form an imine compound, and then reducing the imine compound with a borane-pyridine complex.

The compounds, wherein X represents group (iv) wherein Q6 represents piperidyl, can be produced in the same manner as described above.

Scheme 7

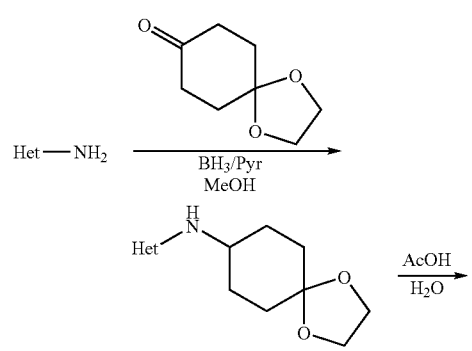

-continued

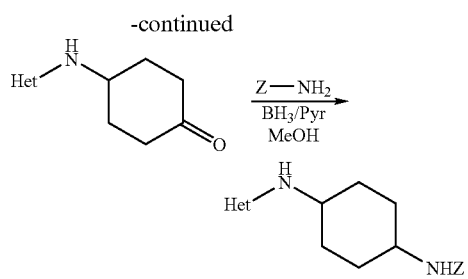

The compounds, wherein X represents group (iv) wherein Q6 represents cyclohexyl, can be produced by dissolving 1,4-cyclohexanedione monoethylene ketal and an amino derivative Het—NH$_2$, wherein Het is as defined above, for example, 5-aminoindazole, in a suitable solvent, for example, methanol, condensing the solution with acetic acid to give an imine compound, reducing the imine compound with a borane-pyridine complex at room temperature to give an amino compound as an intermediate, then dissolving the amino compound as the intermediate in acetic acid-water, stirring the solution at 70 to 100° C., preferably about 80° C., to give a ketone compound, reacting the ketone compound with a suitable amino compound Z—NH$_2$, wherein Z is as defined above, performing condensation with an acid to give an imine compound, and then reducing the imine compound with a suitable reducing agent, for example, a borane-pyridine complex.

Scheme 8

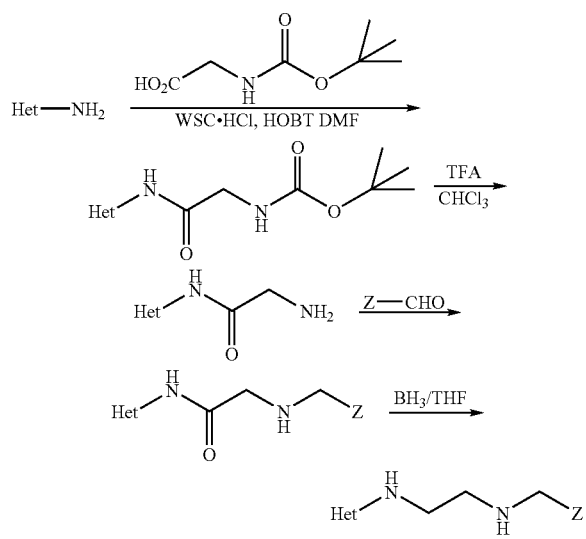

2-[(Tert-butoxycarbonyl)amino]acetic acid and Het—NH$_2$, wherein Het is as defined above, for example, 5-aminoindazole, are dissolved in dimethylaminopyridine and dimethylformamide, and N-[3-(diethylamino)propyl]N'-ethylcarbodiimide hydrochloride and 1-hydroxybenzotriazole were added to the solution obtained at 0 to 25° C., preferably about 0° C. The reaction mixture is stirred at room temperature to give an amide compound.

The compounds, wherein X represents group (v), wherein Q8 and Q10 represent methylene and Q9 represents —NH—, can be produced by removing the protective group in the amide compound with trifluoroacetic acid, then reacting the deprotected compound with benzaldehyde, condensing the reaction product with acetic acid to form an imine compound, reducing the imine compound with sodium triacetoxyborohydride to give an amine compound, and then reducing the amine compound with a borane-pyridine complex. Compounds, wherein Q8 and Q10 represent a group other than methylene, can be produced in the same manner as described above.

Scheme 9

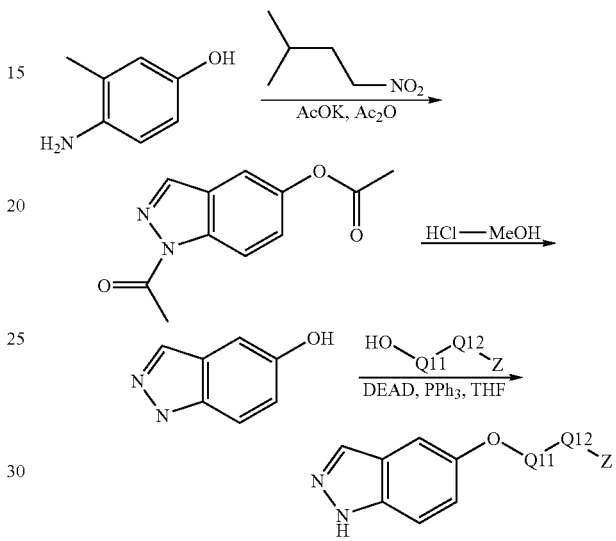

4-Amino-m-cresol is suspended in acetic anhydride and chlorobenzene in the presence of potassium acetate, isoamyl nitrate is added to the suspension at 70° C. to 100° C., preferably about 80° C., and the mixture is stirred to form an indazole skeleton. The intermediate thus obtained is dissolved in hydrochloric acid-methanol, and the mixture is preferably stirred at room temperature to deacetylate the compound.

The compounds, wherein X represents group (vi), can be produced by dissolving this deacetylated compound, HO—Q11-Q12-Z, for example, 1-benzyl-4-hydroxypiperidine, and triphenylphosphine in tetrahydrofuran to prepare a solution and reacting the solution with diethyl azodicarboxylate at room temperature. Compounds other than the compounds indicated in the scheme can be produced by reacting Het—OH with HO—Q11-Q12-Z in the same manner as described above.

Scheme 10

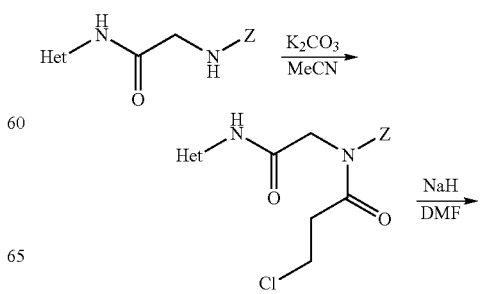

-continued

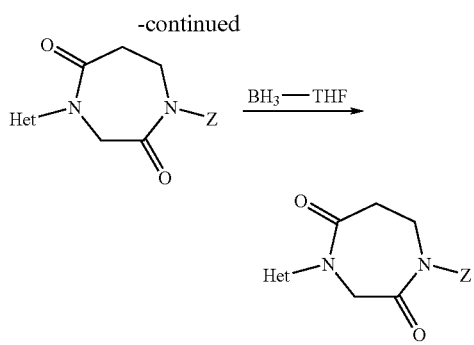

A tertiary amine compound is produced by reacting the final product produced according to scheme 8 with 3-chloropropionyl chloride in a suitable solvent, for example, acetonitrile or N,N-dimethylformamide, in the presence of a base, for example, potassium carbonate. A ring-closed compound is produced by stirring the tertiary amine thus obtained in a suitable solvent, for example, N,N-dimethylformamide, in the presence of a base, for example, sodium hydride, at 70° C. to 100° C., preferably 80° C. The compounds, wherein X represents formula (vii), can be produced by dissolving the ring-closed product thus obtained in tetrahydrofuran, adding a borane-tetrahydrofuran complex to the solution under ice cooling, for example, at 0° C. to 25° C., preferably 0° C., and raising the temperature of the mixture, for example, to 25° C. to 80° C., preferably 60° C., to perform reduction.

The compounds produced according to schemes 1 to 11 can be if necessary separated from the reaction mixture and purified, for example, by recrystallization or chromatography.

Scheme 11

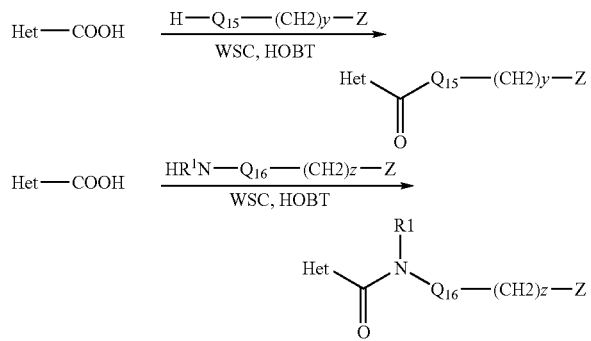

The compounds represented by formula (I), wherein X represents group (viii) or (ix), can be produced by reacting a carboxylic acid derivative: Het—COOH with an amine derivative: H—Q15-(CH$_2$)y-Z or HR$^1$N—Q16-(CH$_2$)z-Z in the presence of a condensing agent.

Use of Compounds

The compounds represented by formulae (I) and (Ia) have Rho kinase inhibitory activity (see Pharmacological Test Example 1). Therefore, the compounds represented by formulae (I) and (Ia) can be used in the treatment of diseases mediated by Rho kinase. Diseases mediated by Rho kinase include hypertension, asthma including bronchial asthma, angina pectoris, cerebrovascular spasm, peripheral circulatory disorder, threatened premature birth, glaucoma, constriction of visual field, pollakiuria, cancer, invasion/metastasis of cancer, arteriosclerosis, retinopathy, immune response, inflammation, autoimmune diseases, cerebral dysfunction, osteoporosis, microbism, chronic renal failure, chronic nephritis, diabetic nephropathy, IgA nephropathia, thrombosis-related diseases, rheumatism, impotence, and fibrosis.

According to the present invention, there is provided a method for treating diseases mediated by Rho kinase, comprising the step of administering the compound represented by formula (Ia) together with a pharmaceutically acceptable carrier, to a mammal.

According to the present invention, there is also provided use of the compound represented by formula (Ia), for the manufacture of a medicament for the treatment of diseases mediated by Rho kinase.

Hypertension, Asthma, etc.

It has been clarified that Rho is activated upon the receipt of signals from various cell membrane acceptors and the activated Rho plays a role in the contraction of smooth muscle through ROCK/Rho kinase and, further, actomyosin system (K. Kimura et al., Science, Vol. 273, No. 5272, pp 245–248 (1996); and Kureishi et al., J. Biol. Chem., Vol. 272, No. 19, pp 12257–60 (1997)). The contraction of smooth muscle is deeply involved in the pathology of hypertension, angina pectoris, cerebrovascular spasm, asthma, peripheral circulatory disorder, threatened premature birth, glaucoma, constriction of visual field, impotence, pollakiuria, and the like (for example, hypertension: AP. Samlyo et al., Rev. Physiol. Biochem. Pharmacol., Vol. 134, pp 209–34 (1999), angina pectoris: Shimokawa et al., Cardiovasc. Res., Vol. 43, No. 4, pp 1029–39 (1999); and Satoh, H., & Kawahara, K: Jpn. J. Pharmacol., 79 (suppl): 211P, 1999, cerebrovascular contraction: Motohiko Sato and Kohzo Kaibuchi: Abstract of the 57th Annual Meeting of the Japan Neurosurgical Society: 153, 1998; N. Ono et al., Pharmacol. Ther., Vol. 82, No. 2–3, pp 123–31(1991); and Shimokawa et al., Cardiovasc. Res., Vol. 43, No. 4, pp 1029–39 (1999), impotence: Andersson, K. E. & Stief, C. G. & World J. Vrol. 15, 14–20 (1997)).

For hypertension, ROCK/Rho kinase inhibitors have antihypertensive activity in spontaneously hypertensive rats (SHR), renal hypertensive rats, and deoxycorticosterone acetate-salt rats (DOCA-salt rats) (Uehata, M., Ishizaki, T. et al.: Nature, 389: 990–994, 1997).

For asthma, ROCK/Rho kinase inhibitors have bronchodilation activity and antiasthmatic activity in extirpated bronchia or bronchial asthma model animals (WO 93/05021 and WO 95/28387). Further, Rho kinase inhibitors suppress an increase in bronchial resistance caused by acetylcholine inhalation in bronchial asthma models in a dose-dependent manner and suppress, in vitro, chemotaxis caused by PAF in eosinophilic leukocytes of human peripheral blood in a concentration-dependent manner (Kunihiko Iitsuka: Arerugi (Allergy), 47: 943, 1998, Kunihiko Iitsuka and Akihiro Yoshii: Journal of The Japanese Respiratory Society, 37: 196, 1999). Further, Rho kinase is also involved in migration of leukocytes.

For impotence, ROCK/Rho kinase inhibitors have corpus carvernosum penis relaxation activity in vitro and have corpus carvernosum penis pressure rising activity in vivo (Kanchan Chitaley et al., Nature Medicine, Vol. 7, No. 1, 119–122 (2001)).

Compounds represented by formula (I) and compounds represented by formula (Ia) according to the present invention actually have leukocyte migration inhibitory activity and blood pressure depression activity (see Pharmacological Test Examples 2 and 5).

Therefore, the compounds represented by formula (I) and the compounds represented by formula (Ia) according to the present invention can be used in the treatment of hypertension, asthma including bronchial asthma, angina pectoris, cerebrovascular contraction, peripheral circulatory disorder, threatened premature birth, glaucoma, constriction of visual field, impotence, pollakiuria and other diseases.

Cancer, Metastasis of Cancer, etc.

Rho is activated upon the receipt of signals from various cell membrane receptors, and the activated Rho functions, through ROCK/Rho kinase and, further, actomyosin system, as a molecular switch of cellular phenomena such as cell movement, cell adhesion, alteration of cytoplasm (formation of actin stressed fibers), control of cell division (sthenia of cytokinesis or activation of gene transcription), cell proliferation, sthenia of carcinogenesis and invasion of cancer and the like (P. Keely et al., Trends Cell Biol. Vol. 8, No. 3, pp 101–6 (1998); and K. Itoh et al., Nat. Med., Vol. 5, No. 2, pp 221–5 (1999)).

Cell movement plays an important role in invasion/metastasis of cancer, arteriosclerosis, retinopathy, immune response and the like. Cell adhesion is deeply involved in metastasis of cancer, inflammation, and autoimmune diseases. The change in character of cells is deeply involved in cerebral dysfunction, osteoporosis, microbism and the like. Cell proliferation is deeply involved in cancer, arteriosclerosis and the like (Jikken Igaku (Experimental Medicine), Vol. 17, No. 7 (1999)).

In particular, for transformation of cells to malignant state and metastasis/invasion of cancer, Rho is involved in the control of morphology of cells and, in addition, in cell proliferation, particularly in the progression of cell cycle from gap1 period (G1 phase) to synthesis period (S phase) (Yamamoto, M., Marui, N., Oncogene, 8: 1449–1455, 1993). Further, it has been found that oncogenes such as Dbl are GDP-GTP exchange factors for Rho family (Hart, M. J., Eva, A., Nature, 354: 311–314, 1991). Further, it has been found that Rac and Rho are activated downstream of information transmission of Ras (Ridley, A. J. & Hall, A.: Cell, 70: 401–410, 1992). Further, it has been demonstrated that Rac and Rho are possibly involved in the transformation of cells to malignant state by Ras downstream of Ras (Qui, R. G., Chen, J., et al.: Nature, 374: 457–459, 1995., Qui, R. G., Chen, J., et al.: Proc. Natl. Acad. Sci. USA, 92: 11781–11785, 1995, and Khosravi-Far, R., Solski, P. A.: Mol. Cell. Biol., 15: 6443–6453, 1995). Furthermore, it has been proven by ROCK/Rho kinase inhibitor (Y-27632) that the path from Rho to ROCK is involved in transformation to malignant state (Sahai, E., Ishizaki, T.: Curr. Biol., 9: 136–145, 1999).

Further, it has been reported in various cell systems that, as with leukocytes, cell movement in cancer invasion is regulated by an actomyosin system as a moving device and an intracellular signal transfer system for controlling the actomyosin system and Rho family protein regulates cytoskeleton protein and controls various cell functions such as alteration of morphology, adhesion, movement, division, transfer regulation and the like of cells (K. Itoh et al., Nat. Med., Vol. 5, No. 2, pp 221–5 (1999); P. Keely et al., Trends Cell Biol. Vol. 8, No. 3, pp 101–6 (1998)).

It has also been reported that ROCK downstream of Rho controls invasive movement through the activation of an actomyosin system (Yoshioka, K., Matsumura, F.: J. Biol. Chem., 273: 5146–5154, 1998). It has been demonstrated that controlling the path from Rho to ROCK by ROCK/Rho kinase inhibitor (Y-27632) suppresses the invasive movement (Itoh, K., Yoshioka, K.: Nature Med., 5: 221–225, 1999).

Therefore, the compounds represented by formula (I) and the compounds represented by formula (Ia) according to the present invention can be used in the treatment of cancer, invasion/metastasis of cancer, arteriosclerosis, retinopathy, immune response, inflammation, autoimmune diseases, cerebral dysfunction, osteoporosis, and microbism.

Renal Diseases

Renal disorder was found in Rho GDI knockout mouse (Oncogene, 1999; 18 (39): 5373–80).

Further, as described above, Rho is activated upon the receipt of signals from various cell membrane receptors, and the activated Rho is involved in cell adhesion or migration of leukocytes through ROCK/Rho kinase and actomyosin system. Cell adhesion and migration of leukocytes are involved in inflammation, particularly nephritis (Osamu Fujimoto and Kohzo Kaibuchi, Journal of The Japanese Society of Internal Medicine, 1999; 88 (1); 148–54).

Furthermore, Rho is involved in nephritis through HGF, oxidized LDL, platelets, or Na—H exchange (Mol. Cell. Biol. 1995; 15 (2): 1110–22; J. Biol. Chem. 1999; 274 (43): 30361–4; J. Biol. Chem., 1999; 274 (40): 28293–300; and EMBO J., 1998; 17 (16): 4712–22).

The compounds represented by formula (I) and the compounds represented by formula (Ia) according to the present invention actually have albuminuria amelioration activity (see Pharmacological Test Examples 3 and 4).

Therefore, the compounds represented by formula (I) and the compounds represented by formula (Ia) according to the present invention can be used in the treatment of chronic renal failure, chronic nephritis, diabetic nephropathy, and IgA nephropathia.

Inflammation, Thrombosis-related Diseases, etc.

It has been known that Rho is activated upon the receipt of signals from various cell membrane receptors, and the activated Rho functions, through Rho kinase and, further, actomyosin system, as a molecular switch of cellular phenomena such as platelet aggregation, leukocyte aggregation, and leukocyte migration (K. Naka et al., Blood, Vol. 90, No. 10, pp 3736–42 (1997)). Platelet aggregation, leukocyte aggregation, and leukocyte migration are deeply involved in thrombus, inflammation, fibrosis and the like.

The compounds represented by formula (I) and the compounds represented by formula (Ia) actually have leukocyte migration inhibitory activity (see Pharmacological Test Example 2).

Therefore, the compounds represented by formula (I) and the compounds represented by formula (Ia) according to the present invention can be used in the treatment of inflammation, asthma, thrombosis-related diseases, for example, cardiac infarction, cerebral infarction, arteriosclerosis obliterans, thrombus obstruction, and generalized angiocoagulation syndrome, rheumatism, and fibrosis.

Pharmaceutical compositions comprising the compounds of the present invention as active ingredient can be administered to a human and a non-human animal orally or parenterally by administration routes, for example, intravenous administration, intramuscular administration, subcutaneous administration, rectal administration, or percutaneous administration. Therefore, the pharmaceutical composition comprising the compound according to the present invention as active ingredient may be formulated into suitable dosage forms according to the administration routes.

Specifically, oral preparations include tablets, capsules, powders, granules, syrups, pills, and troches, and parental preparations include injections, such as solutions and suspensions, inhalants, suppositories, transdermal preparations, for example, tapes, ointments, eye drops, and eye ointments.

These various preparations may be prepared by conventional methods, for example, with commonly used component, such as excipients, disintegrants, binders, lubricants, colorants, diluents, corrigents, flavors, emulsifiers, and solubilizers.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In the formulation of solid preparations, additives are used such as sucrose, lactose, cellulose sugar, D-mannitol, maltitol, dextran, starches, agar, alginates, chitins, chitosans, pectins, tragacanths, gum arabics, gelatins, collagens, caseins, albumin, calcium phosphate, sorbitol, glycine, carboxymethylcellulose, polyvinyl pyrrolidone, hydroxypropylcellulose, hydroxypropyl-methylcellulose, glycerin, polyethylene glycol, sodium hydrogencarbonate, magnesium stearate, and talc. Further, tablets may be those on which, if necessary, conventional coating has been provided, for example, sugar coated tablets, enteric coated tablets, film coated tablets, or two-layer tablets, and multilayer tablets.

In the formulation of semi-solid preparations, vegetable fats and oils, such as olive oils, corn oils, and castor oils, mineral fats and oils, such as petrolatum, white petrolatum, and hard paraffin, waxes, such as jojoba oils, carnauba wax, and beeswax, and partially synthesized or wholly synthesized glycerin fatty acid esters, such as laurylic acid, myristic acid, and palmitic acid, may be used. Examples of commercially available products thereof include Witepsol manufactured by Dynamid Nobel and Pharmasol manufactured by Nippon Oils & Fats Co., Ltd.

In the formulation of solutions, additives may be used such as sodium chloride, glucose, sorbitol, glycerin, olive oil, propylene glycol, and ethyl alcohol. In the formulation of injections, aseptic aqueous solutions, for example, physiological saline, isotonic solutions, oily solutions, for example, sesame oils and soybean oils, may be used. If necessary, suitable suspending agents, for example, sodium carboxymethylcellulose, nonionic surfactants, solubilizers, for example, benzyl benzoate, benzyl alcohol and the like may be used in combination with the above solutions.

In the formulation of eye drops, aqueous liquid preparations or aqueous solutions are used, and, in particular, aseptic aqueous solutions for injections may be used. Various additives, such as buffers, preferably, for example, borate buffers, acetate buffers, and carbonate buffers for abatement of stimulation, isotonicity, solubilizers, preservatives, thickening agents, chelating agents, pH adjustors for adjusting pH preferably to about 2 to 8.5, and aromatics, may be properly added to the liquid preparation for eye drops.

The content of the compound according to the present invention in the pharmaceutical composition may vary according to the dosage form. The content is, however, generally about 0.1 to 100% by weight, preferably about 1 to 50% by weight, based on the whole composition.

The dose may be appropriately determined in consideration of various conditions, for example, the age, weight, sex, type of disease, and severity of condition of patients, and the preparation may be administered, for example, in an amount of about 1 to 500 mg. This dose may be administered at a time daily or divided doses of several times daily.

EXAMPLES

The present invention is further illustrated by the following examples that are not intended as a limitation of the invention.

Example 1

N-(4-Pyridyl)-N'-(2,4,6-trichlorophenyl)urea

4-Aminopyridine (500 mg, 3.56 mmol) and 2,4,6-trichlorophenyl isocyanate (503.6 mg, 3.56 mmol 1.0 moleg), were dissolved in toluene, and the mixture was then stirred at 110° C. for 3 hr.

After the completion of the reaction, the solvent was removed by distillation under the reduced pressure, and the residue was then washed with ether to give the title compound as a colorless crystal (819 mg, 86.6%).

MS m/z: 315 $^1$H-NMR δ: 7.43 (2H, dd, J=1.7, 4.9 Hz), 7.62 (2H, s), 8.35 (2H, dd, J=1.7, 4.9 Hz), 8.48 (1H, s), 9.45 (1H, s)

Example 2

N1-(4-Pyridyl)-2-(2,6-dibromo-4-fluorophenoxy) acetamide

Potassium carbonate (614.4 mg, 4.44 mmol) and methyl bromoacetate (0.4 ml, 4.08 mmol) were added to a solution of 2,6-dibromo-4-fluorophenol (1 g, 3.70 mmol) in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate, and the solvent was then removed by distillation under the reduced pressure. The residue was purified by column chromatography [silica gel, chloroform] to give an ester compound as a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carbonyl compound as a colorless crystal (1.12 g, 87.6%).

MS m/z: 266 $^1$H-NMR δ: 4.59 (2H, s), 7.29 (1H, s), 7.30 (1H, s)

4-Aminopyridine (50 mg, 0.53 mmol) and WSC.HCl (126.2 mg, 0.64 mmol) and HOBt.H$_2$O (86.1 mg, 0.64 mmol) were added to a solution of carboxyl compound (191.6 mg, 0.58 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (122.4 mg, 86.6%).

MS m/z: 404 $^1$H-NMR δ: 4.66 (2H, s), 7.34 (2H, s), 7.16 (1H, s), 7.58 (2H, dd, J=1.7, 4.6 Hz), 8.57 (2H, dd, J=1.5, 4.9 Hz)

Example 3

N1-(4-Pyridyl)-2-(2,6-dichlorophenoxy)acetamide

Potassium carbonate (1.02 g, 7.36 mmol) and methyl bromoacetate (1.12 g, 6.75 mmol) were added to a solution of 2,6-dichlorophenol (1 g, 6.13 mmol) in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give an ester compound as a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal (1.08 g, 79.4%).

4-Aminopyridine (50 mg, 0.53 mmol), WSC.HCl (118.8 mg, 0.60 mmol), and HOBt.H$_2$O (86.1 mg, 0.60 mmol) were added to a solution of carboxyl compound (129.1 mg, 0.58 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (15.5 mg, 10.0%).

MS m/z: 297 $^1$H-NMR δ: 3.74 (2H, d, J=2.7 Hz, C$\underline{H}$2), 7.24–7.30 (3H, m, Ar—H)

Example 4

N1-(1,3-Dioxo-2,3-dihydro-1H-5-isoindolyl)-2'-(2,6-dichloro-4-fluorophenyl)acetamide Potassium carbonate and methyl bromoacetate were added to a solution of 2,6-dichloro-4-fluorophenol in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal.

4-Aminophthalimide (100 mg, 0.62 mmol), WSC.HCl (146.5 mg, 0.74 mmol), and HOBt.H$_2$O (100 mg, 0.74 mmol) were added to a solution of carboxyl compound (162.1 mg, 0.68 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (40.1 mg, 17.0%).

MS m/z: 383 $^1$H-NMR δ: 4.68 (2H, s), 7.61 (2H, dd, J=1.2, 8.3 Hz), 7.78 (1H, d, J=8.1 Hz), 8.01 (1H, dd, J=1.7, 8.1 Hz), 8.01 (1H, dd, J=1.7, 8.1 Hz), 8.23 (1H, d, J=2.0 Hz), 10.70 (1H, s), 11.25 (1H, s)

Example 5

N1-(1,3-Dioxo-2,3-dihydro-1H-5-isoindolyl)-2'-(2,6-dichlorophenoxy)acetamide

Potassium carbonate and methyl bromoacetate were added to a solution of 2,6-dichlorophenol in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give an ester compound as a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal.

4-Aminophthalimide (100 mg, 0.62 mmol), WSC.HCl (146.5 mg, 0.74 mmol), and HOBt.H$_2$O (100 mg, 0.74 mmol) were added to a solution of carboxyl compound (149.9 mg, 0.68 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (63.7 mg, 28.3%).

MS m/z: 365 $^1$H-NMR δ: 4.71 (2H, s), 7.24 (1H, t, J=8.5 Hz), 7.54 (1H, d, J=8.1 Hz), 7.54 (1H, d, J=8.1 Hz), 7.80 (1H, d, J=8.3 Hz), 8.02 (1H, dd, J=2.0, 8.1 Hz), 8.24 (1H, d, J=2.0 Hz), 10.70 (1H, s), 11.245 (1H, s)

Example 6

N-(1,3-Dioxo-2,3-dihydro-1H-5-isoindolyl)-N'-(2,4,6-trichlorophenyl)urea

5-Aminophthalimide (100 mg, 0.62 mmol) and 2,4,6-trichlorophenyl isocyanate (150.9 mg, 0.68 mmol) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (143.0 mg, 60.4%).

MS m/z: 384 $^1$H-NMR δ: 7.74 (2H, d, J=20.0 Hz), 7.77 (2H, s), 8.03 (1H, s), 8.52 (1H, s), 9.69 (1H, s), 11.13 (1H, s)

Example 7

N1-(4-Pyridyl)-(E)-3-(2,6-dichlorophenyl)-2-propeneamide

4-Aminopyridine (50 mg, 0.53 mmol), WSC.HCl (126.3 mg, 0.58 mmol), and HOBt.H$_2$O (500 mg, 0.58 mmol) were added to a solution of 2,6-dichlorocinnamic acid (126.8 mg, 0.58 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (81.9 mg, 52.6%).

MS m/z: 293 $^1$H-NMR δ: 6.94 (1H, d, J=16.1 Hz), 7.32 (1H, t, J=8.1 Hz), 7.48 (2H, d, J=8.1 Hz), 7.75 (2H, dd, J=1.5, 4.9 Hz), 7.86 (1H, d, J=16.1 Hz), 8.42 (2H, dd, J=1.7, 4.9 Hz)

Example 8

N-(2,6-Difluorophenyl)-N'-(4-pyridyl)urea

4-Aminopyridine (100 mg, 1.06 mmol) and 2,6-difluorophenyl isocyanate (181.3 mg, 1.17 mmol) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (249.3 mg, 94.3%).

MS m/z: 249 $^1$H-NMR δ: 6.95 (1H, d, J=8.3 Hz), 6.97 (1H, d, J=8.1 Hz), 7.19 (1H, t, J=8.3 Hz), 7.48 (2H, dd, J=1.5, 5.1 Hz), 8.31 (2H, dd, J=1.5, 4.9 Hz)

Example 9

N-(2,6-Dichlorophenyl)-N'-(4-pyridyl)urea

4-Aminopyridine (100 mg, 1.06 mmol) and 2,6-dichlorophenyl isocyanate (219.7 mg, 1.17 mmol) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (262.2 mg, 87.5%).

MS m/z: 282 $^1$H-NMR δ: 7.20 (1H, t, J=7.8 Hz), 7.39 (2H, d, J=8.3 Hz), 7.49 (2H, dd, J=1.7, 4.9 Hz), 8.31 (2H, dd, J=1.5, 5.1 Hz)

Example 10

N-(2,6-Diisopropylphenyl)-N'-(4-pyridyl)urea

4-Aminopyridine (100 mg, 1.06 mmol) and 2,6-diisopropylphenyl isocyanate (216.0 mg, 1.06 mmol) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (94.3 mg, 29.9%).

MS m/z: 297 $^1$H-NMR (500 MHz) δ: 1.21 (12H, s), 3.16–3.22 (2H, m), 7.19 (2H, d, J=8.0 Hz), 7.30 (1H, t, J=7.9 Hz), 7.49 (2H, d, J=6.1 Hz), 8.30 (2H, d, J=6.1 Hz)

Example 11

N-(4-Methoxyphenyl)-N'-(4-pyridyl)urea

4-Aminopyridine (100 mg, 1.06 mmol) and 4-methoxyphenyl isocyanate (158.5 mg, 1.06 mmol) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (223.7 mg, 86.4%).

MS m/z: 243 $^1$H-NMR δ: 3.77 (3H, s), 6.87 (2H, dd, J=2.1, 6.8 Hz), 7.32 (2H, dd, J=2.1, 6.8 Hz), 7.50 (2H, dd, J=1.5, 5.1 Hz), 8.30 (2H, dd, J=1.5, 5.1 Hz)

Example 12

N-(2,4-Dichlorophenyl)-N'-(4-pyridyl)urea

4-Aminopyridine (100 mg, 1.06 mmol) and 2,4-dichlorophenyl isocyanate (219.7 mg, 1.17 mmol, 1.1 eq) were dissolved in toluene, and the mixture was then stirred at 110° C. for 4 hr.

After the completion of the reaction, the solvent was removed by distillation under the reduced pressure, and the residue was washed with n-hexane to give the title compound as a colorless crystal (279.6 mg, 93.3%).

MS m/z: 282 $^1$H-NMR δ: 7.31 (1H, dd, J=2.4, 9.0 Hz), 7.48 (1H, d, J=2.4 Hz), 7.53 (2H, dd, J=1.7, 4.9 Hz), 8.17 (1H, d, J=9.0 Hz), 8.33 (2H, dd, J=1.7, 4.9 Hz)

Example 13

N-(2,6-Dichlorophenyl)-N'-(1H-5-indazolyl)urea

5-Aminoindazole (100 mg, 0.75 mmol) and 2,6-dichlorophenyl isocyanate (155.3 mg, 0.83 mmol, 1.1 eq) were dissolved in toluene, and the mixture was then stirred at 110° C. for 4 hr.

After the completion of the reaction, the solvent was removed by distillation under the reduced pressure, and the residue was washed with n-hexane to give the title compound as a purple crystal (232.6 mg, 96.5%).

MS m/z: 321 $^1$H-NMR δ: 7.29 (1H, d, J=8.8 Hz), 7.33 (1H, dd, J=1.7, 8.8 Hz), 7.45 (1H, d, J=8.8 Hz), 7.52 (1H, d, J=8.8 Hz), 7.89 (1H, dd, J=1.7, 8.8 Hz), 7.96 (1H, s), 8.14 (1H, s), 8.86 (1H, s)

Example 14

N1-(1H-5-Indazolyl)-2-(2,6-dichlorophenoxy)acetamide

Potassium carbonate and methyl bromoacetate were added to a solution of 2,6-dichlorophenol in acetonitrile, and the mixture was then stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal.

5-Aminoindazole (100 mg, 0.75 mmol), WSC.HCl (178.4 mg, 0.90 mmol), and HOBt.H$_2$O (121.8 mg, 0.90 mmol) were added to a solution of carboxyl compound (182.6 mg, 0.83 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (198.5 mg, 78.7%).

MS m/z: 336 $^1$H-NMR δ: 4.64 (2H, s), 7.23 (1H, t, J=7.8 Hz), 7.49 (1H, d, J=8.8 Hz), 7.53 (2H, d, J=7.8 Hz), 7.53 (2H, dd, J=1.7, 9.0 Hz), 8.04 (1H, s), 8.17 (1H, s), 10.06 (1H, s), 13.00 (1H, s)

Example 15

N1-(1H-5-Indazolyl)-2-(2,6-dichloro-4-fluorophenoxy)acetamide

Potassium carbonate and methyl bromoacetate were added to a solution of 2,6-dichloro-4-fluorophenol in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal.

5-Aminoindazole (100 mg, 0.75 mmol), WSC.HCl (178.4 mg, 0.90 mmol), and HOBt.H$_2$O (121.8 mg, 0.90 mmol) were added to a solution of carboxyl compound (197.4 mg, 0.83 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (210.2 mg, 79.1%).

MS m/z: 354 $^1$H-NMR δ: 4.62 (2H, s), 7.49 (1H, t, J=8.8 Hz), 7.53 (1H, dd, J=1.7, 8.8 Hz), 7.59 (1H, s), 7.61 (1H, s), 8.03 (1H, s), 8.16 (1H, s), 10.06 (1H, s), 12.99 (1H, s)

Example 16

N1-(1H-5-Indazolyl)-2-(2,4,6-trichlorophenoxy)acetamide

Potassium carbonate and methyl bromoacetate were added to a solution of 2,4,6-trichlorophenol in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give an ester compound as a colorless crystal.

A 10% aqueous sodium hydroxide solution was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal.

5-Aminoindazole (50 mg, 0.38 mmol), WSC.HCl (89.2 mg, 0.45 mmol), and HOBt.H$_2$O (60.9 mg, 0.45 mmol) were added to a solution of carboxyl compound (105.4 mg, 0.41 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (75.1 mg, 54.1%).

MS m/z: 370 $^1$H-NMR δ: 4.65 (2H, s), 7.49 (1H, d, J=8.8 Hz), 7.52 (1H, dd, J=1.7, 8.8 Hz), 7.75 (2H, s), 8.03 (1H, s), 8.15 (1H, s), 10.08 (1H, s), 12.99 (1H, s)

Example 17

N1-(4-Pyridyl)-2-[(2,6-dichlorophenyl)-sulfanyl]acetamide

Potassium carbonate (277.8 mg, 2.01 mmol) and methyl bromoacetate (0.2 ml, 1.84 mmol) were added to a solution of 2,6-dichlorothiophenol (300 mg, 1.68 mmol) in acetonitrile, and the mixture was stirred at 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give an ester compound as a colorless crystal.

A 10% aqueous sodium hydroxide solution (500 mg, 3.56 mmol) was added to an ethanol solution of the ester compound, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform] to give a carboxyl compound as a colorless crystal (360.2 mg, 86.6%).

4-Aminopyridine (138.5 mg, 0.58 mmol), WSC.HCl (118.8 mg, 0.60 mmol), and HOBt.H$_2$O (86.1 mg, 0.60 mmol) were added to a solution of the carboxyl compound (50 mg, 0.53 mmol) in dimethylformamide, and the mixture was stirred at room temperature for 4 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a light yellow crystal (26.4 mg, 15.9%).

MS m/z: 313 $^1$H-NMR δ: 3.74 (2H, d, J=2.7, CH2), 7.24–7.30 (3H, m, Ar—H)

Example 18

N-(2-Chloro-6-fluorophenyl)-N'-(4-pyridyl)urea

Diphenylphosphoryl azide (0.15 ml, 0.69 mmol, 1.2 eq) and triethylamine (0.1 ml, 0.69 mmol, 1.2 eq) were added to a solution of 2-chloro-6-fluorobenzoic acid (100 mg, 0.57 mmol) in toluene, and the mixture was stirred at 110° C. for 60 min.

Thereafter, 4-aminopyridine (64.7 mg, 0.69 mmol, 1.2 eq) and a minor amount of DMF were added thereto, and the mixture was stirred at 110° C. for 2 hr.

After the completion of the reaction, water and ethyl acetate were added, and the precipitated crystal was collected by filtration and was washed with ethyl acetate to give the title compound as a crystal (101.5 mg, 66.6%).

MS m/z: 265 $^1$H-NMR δ: 6.08 (2H, d, J=5.37 Hz), 6.73 (1H, t, J=5.37), 7.34 (2H, dd, J=1.58, 4.88), 7.38 (1H, dd, J=1.22, 7.32), 7.51 (2H, d, J=7.81), 8.28 (2H, dd, J=1.71, 4.88), 8.84 (1H, s)

Example 19

N-Cyclohexyl-N'-(4-pyridyl)urea

4-Aminopyridine (100 mg, 1.06 mmol) and cyclohexyl isocyanate (146.3 mg, 1.17 mmol) were dissolved in toluene, and the mixture was then stirred at 110° C. for 4 hr.

After the completion of the reaction, the solvent was removed by distillation under the reduced pressure, and the residue was then washed with n-hexane to give the title compound as a colorless crystal (216 mg, 92.8%).

MS m/z: 219 $^1$H-NMR δ: 1.13–1.36 (5H, m), 1.52–1.55 (1H, m), 1.63–1.68 (2H, m), 1.78–1.82 (2H, m), 3.42–3.51 (1H, m), 7.96 (1H, s), 8.14 (1H, s), 8.86 (1H, s)

Example 20

N-[1-(4-Bromophenyl)ethyl]-N'-(1,3-dioxo-2,3-dihydro-1H-5-isoindolyl)urea

4-Aminophthalimide (100 mg, 0.62 mmol) and 4-bromophenylethyl isocyanate (153.4 mg, 0.68 mmol, 1.0 eq) were dissolved in toluene, and the mixture was then stirred at 110° C. for 4 hr.

After the completion of the reaction, the solvent was removed by distillation under the reduced pressure, and the residue was then washed with n-hexane to give the title compound as a colorless crystal (62.5 mg, 26.1%).

MS m/z: 388 $^1$H-NMR (500 MHz) δ: 1.21 (12H, s), 3.16–3.22 (2H, m), 7.19 (2H, d, J=8.0 Hz), 7.30 (1H, t, J=7.9 Hz), 7.49 (2H, d, J=6.1 Hz), 8.30 (2H, d, J=6.1 Hz)

Example 21

N-(1-Benzyl-3-piperidyl)-N(1H-5-indazolyl)amine

A mixture of 5-Aminoindazole (100 mg, 0.75 mmol), N-benzyl-3-piperidone (186.5 mg, 0.83 mmol), and acetic acid (one drop) in Methanol (1 ml) was stirred at room temperature for 5 min. A borane-pyridine complex (0.08 ml, 0.83 mmol) was added thereto under ice cooling using methanol as a solvent, and the mixture was stirred at room temperature for 4 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound as a colorless crystal (178.7 mg, 77.7%).

MS m/z: 306 $^1$H-NMR δ: 1.40–1.60 (3H, m), 1.70–1.80 (2H, m), 2.10–2.50 (4H, m), 3.45 (2H, s), 3.16–3.22 (2H, m), 6.75 (2H, dd, J=2.4, 11.2 Hz), 7.15–7.28 (10H, m), 7.78 (1H, d, J=0.7 Hz)

Formation of Salt of Compound Prepared in Example 21

The compound prepared in Example 21 was dissolved in hydrochloric acid-methanol, and the mixture was then allowed to stand at room temperature for 18 hr. The resultant white precipitate was then collected by filtration, was washed with methanol which had been cooled in an ice bath, and was dried under the reduced pressure to give the title compound.

Example 22

N-[1-(4-Bromobenzyl)-4-piperidyl]-N-(1H-5-imidazolyl)amine

Potassium carbonate (180 mg, 1.30, 2.0 eq) was added to a solution of 4-piperidone monohydrate hydrochloride (100 mg, 0.65 mmol) and 4-bromobenzyl bromide (162.7 mg, 0.65 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (69.33 mg, 0.52 mmol, 0.8 eq) was added to a solution of the resultant oil in methanol. Acetic acid (one drop) was added thereto, and the mixture was stirred at room temperature for 5 min. A borane-pyridine complex (0.8 ml, 0.78 mmol, 1.2 eq) was added to the reaction solution under ice cooling, and the mixture was stirred at room temperature for 4 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (131.2 mg, 52.4%).

MS m/z: 385 $^1$H-NMR δ: 1.43–1.46 (2H, m), 2.02 (2H, d, J=12.0 H), 2.12 (2H, t, J=9.0H), 2.79 (1H, d, J=9.0 Hz), 2.82 (1H, s), 3.23–3.28 (1H, m), 3.43 (2H, s), 6.73 (2H, dd, J=2.2, 7.8 Hz), 7.15 (1H, d, J=8.3 Hz), 7.19 (1H, d, J=1.0 Hz), 7.22 (1H, dd, J=1.0, 9.5 Hz), 7.38 (2H, dd, J=1.8, 6.6 Hz), 7.80 (1H, d, J=1.0 Hz)

Example 23

N-[1-(3-Bromobenzyl)-4-piperidyl]-4-(1H-5-imidazolyl)amine

Potassium carbonate (180 mg, 1.30, 2.0 eq) was added to a solution of 4-piperidone monohydrate hydrochloride (100 mg, 0.65 mmol) and 3-bromobenzyl bromide (162.7 mg, 0.65 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (69.33 mg, 0.52 mmol, 0.8 eq) was added to a solution of the resultant oil in methanol. Acetic acid (one drop) was added thereto, and the mixture was stirred at room temperature for 5 min. A borane-pyridine complex (0.8 ml, 0.78 mmol, 1.2 eq) was added to the reaction solution under ice cooling, and the mixture was stirred at room temperature for 4 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (47.6 mg, 20.0%).

MS m/z: 385 $^1$H-NMR δ: 2.18–2.25 (4H, m), 3.14 (2H, t, J=12.0 Hz), 3.59 (2H, d, J=12.0 Hz), 3.88–4.00 (1H, m), 4.32 (2H, s), 7.45–7.53 (3H, m), 7.64 (2H, d, J=8.3 Hz), 7.74 (1H, d, J=8.8 Hz), 7.92 (1H, s), 8.18 (1H, d, J=0.7 Hz)

Example 24

N1-(4-Pyridyl)-2-(2,6-dichloro-4-fluorophenoxy)acetamide

Potassium carbonate (1.83 g, 13.26 mmol, 1.2 eq) and methyl bromoacetate (1.69 g, 11.05 mmol, 1.0 eq) were added to a solution of 2,6-dichloro-4-fluorophenol (2.0 g, 11.05 mmol) in acetonitrile, and the mixture was stirred at 80° C. for one hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure to give an ester compound as a white crystal (2.66 g, 95.2%).

A 5% aqueous sodium hydroxide solution (20 ml) was added to a solution of the ester compound (2.66 g, 10.51 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound as a colorless crystal (2.31 g, 92.0%).

4-Aminopyridine (393 mg, 4.18 mmol, 1.0 eq), WSC.HCl (964 mg, 5.02 mmol, 1.2 eq), and HOBt.H$_2$O (678 mg, 5.02 mmol, 1.2 eq) were added to a solution of the carboxyl compound (1.0 g, 4.18 mmol) in dimethylformamide, and the mixture was stirred at room temperature for 3.5 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (155 mg, 11.8%).

MS m/z: 314 ¹H-NMR δ: 4.63 (2H, s), 7.15 (2H, d, J=7.81 Hz), 7.59 (2H, dd, J=1.59, 4.76 Hz), 8.57 (2H, dd, J=1.46, 4.88 Hz), 8.77 (1H, s)

Example 25

N1-(4-Pyridyl)-2-(2,4-dichlorophenyl)acetamide

4-Aminopyridine (230 mg, 2.44 mmol, 1.0 eq), WSC.HCl (470 mg, 2.44 mmol, 1.0 eq), and HOBt.H₂O (330 mg, 2.44 mmol, 1.0 eq) were added to a solution of 2,4-dichlorophenylacetic acid (500 mg, 2.44 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (54 mg, 7.9%).

MS m/z: 280 ¹H-NMR δ: 7.30 (1H, d, J=1.95 Hz), 7.31 (1H, s), 7.39 (1H, d, 1.95), 7.47 (2H, d, J=6.21), 7.78 (1H, s), 8.46 (2H, d, J=6.10)

Example 26

Ethyl 3,5-dichloro-4-[2-oxo-2-(4-pyridylamino)ethoxy]benzoate

Potassium carbonate (1.06 g, 7.66 mmol, 1.2 eq) and methyl bromoacetate (0.98 g, 6.38 mmol, 1.0 eq) were added to a solution of ethyl 3,5-dichloro-4-hydroxybenzoate (1.5 g, 6.38 mmol) in acetonitrile, and the mixture was stirred at 80° C. for one hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure to give an ester compound as a white crystal (1.88 g, 96.0%).

A 5% aqueous sodium hydroxide solution (10 ml) was added to a solution of the ester compound (1.88 g, 6.12 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound of the title compound as a colorless crystal (750 mg, 43.9%).

4-Aminopyridine (266 mg, 2.82 mmol, 1.05 eq), WSC.HCl (542 mg, 2.82 mmol, 1.05 eq), and HOBt.H₂O (381 mg, 2.82 mmol, 1.05 eq) were added to a solution of the carboxyl compound (750 mg, 2.69 mmol) in dimethylformamide, and the mixture was stirred at room temperature for 15.5 hr.

After the completion of the reaction, water and ethyl acetate were added thereto, and the precipitated crystal was collected by filtration and was washed with ethyl acetate to give an intermediate as a crystal (180 mg, 19.6%).

Potassium carbonate (24 mg, 0.18 mmol, 1.2 eq) and ethyl iodide (27 mg, 0.18 mmol, 1.2 eq) were added to a solution of the intermediate (50 mg, 0.15 mmol) in dimethylformamide, and the mixture was stirred at an external temperature of 80° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by a preparative TLC [chloroform/methanol] to give the title compound as a crystal (5 mg, 9.2%).

MS m/z: 369 ¹H-NMR δ: 1.41 (3H, t, J=7.07 Hz), 4.40 (2H, q, J=7.08 Hz), 4.72 (2H, s), 7.60 (2H, d, J=6.10 Hz), 8.05 (2H, s), 8.58 (2H, d, J=5.85 Hz), 8.84 (1H, s)

Example 27

N1-(4-Pyridyl)-2-(2,6-difluorophenyl)acetamide

Potassium carbonate (1.40 g, 9.22 mmol, 1.2 eq) and methyl bromoacetate (1.18 g, 7.69 mmol, 1.0 eq) were added to a solution of 2,6-difluorophenol (1.0 g, 7.69 mmol) in acetonitrile, and the mixture was stirred at 80° C. for one hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure to give an ester compound as a white crystal (1.31 g, 98.5%).

A 5% aqueous sodium hydroxide solution (10 ml) was added to a solution of the ester compound (1.31 g, 7.53 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound as a colorless crystal (1.39 g, 98.2%).

4-Aminopyridine (700 mg, 7.39 mmol, 1.0 eq), WSC.HCl (1.70 g, 8.87 mmol, 1.2 eq), and HOBt.H₂O (1.20 g, 8.87 mmol, 1.2 eq) were added to a solution of the carboxyl compound (1.39 g, 7.39 mmol) in dimethylformamide, and the mixture was stirred at room temperature for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (107 mg, 5.4%).

MS m/z: 264 ¹H-NMR δ: 4.84 (2H, s), 7.11–7.17 (3H, m), 7.60 (2H, dd, J=1.59, 4.76 Hz), 8.44 (2H, dd, J=1.46, 4.88 Hz), 10.48 (1H, s)

Example 28

N1-(4-Pyridyl)-2-(2,4,6-trifluorophenoxy)acetamide

Potassium carbonate (2.12 g, 16.21 mmol, 1.2 eq) and methyl bromoacetate (2.07 g, 13.50 mmol, 1.0 eq) were added to a solution of 2,4,6-trifluorophenol (2.0 g, 13.50 mmol) in acetonitrile, and the mixture was stirred at 80° C. for 1.5 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure to give an ester compound as a white crystal (2.76 g, 92.9%).

A 5% aqueous sodium hydroxide solution (10 ml) was added to a solution of the ester compound (2.76 g, 12.55 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound as a colorless crystal (2.15 g, 83.3%).

4-Aminopyridine (457 mg, 4.85 mmol, 1.0 eq), WSC.HCl (1.12 g, 5.83 mmol, 1.2 eq), and HOBt.H$_2$O (0.79 g, 5.83 mmol, 1.2 eq) were added to a solution of the carboxyl compound (1.0 g, 4.85 mmol) in dimethylformamide, and the mixture was stirred at room temperature for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (73 mg, 5.4%).

MS m/z: 282 $^1$H-NMR δ: 4.80 (2H, s), 7.27 (2H, t, J=9.03 Hz), 7.60 (2H, dd, J=1.59, 4.76 Hz), 8.44 (2H, dd, J=1.57, 4.77 Hz), 10.47 (1H, s)

Example 29

N1-(4-Pyridyl)-2-(2,6-difluoro-4-propionyl-phenoxy)acetamiden

Sodium hydride (77 mg, 3.22 mmol, 1.5 eq) and methyl bromoacetate (329 mg, 2.15 mmol, 1.0 eq) were added to a solution of 3,5-difluoro-4-hydroxypropiophenol (400 mg, 2.15 mmol) in DMF, and the mixture was stirred at 80° C. for one hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give an ester compound as a colorless crystal (390 mg, 70.4%).

A 5% aqueous sodium hydroxide solution (5 ml) was added to a solution of the ester compound (390 mg, 1.51 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound as a colorless crystal (280 mg, 75.9%).

4-Aminopyridine (40 mg, 0.41 mmol, 1.0 eq), WSC.HCl (94 mg, 0.49 mmol, 1.2 eq), and HOBt.H$_2$O (66 mg, 0.49 mmol, 1.2 eq) were added to a solution of the carboxyl compound (100 mg, 0.41 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (17 mg, 13.0%).

MS m/z: 321 $^1$H-NMR δ: 1.23 (3H, t, J=7.20 Hz), 2.94 (2H, q, J=7.16 Hz), 4.82 (2H, s), 7.58 (2H, dd, J=1.59, 4.76 Hz), 7.62 (2H, d, J=4.64), 8.58 (2H, d, J=6.03 Hz), 8.66 (1H, s)

Example 30

N1-(4-Pyridyl)-2-(2,6-dichloro-4-methylphenoxy)acetamide

Potassium carbonate (1.40 g, 10.17 mmol, 1.2 eq) and methyl bromoacetate (1.30 g, 8.47 mmol, 1.0 eq) were added to a solution of 2,6-difluoro-4-cresol (1.50 g, 8.47 mmol) in acetonitrile, and the mixture was stirred at 80° C. for one hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure to give an ester compound as a colorless crystal (1.85 g, 98.4%).

A 5% aqueous sodium hydroxide solution (5 ml) was added to a solution of the ester compound (1.85 g, 8.34 mmol) in ethanol, and the mixture was stirred at an external temperature of 80° C. for one hr.

After the completion of the reaction, the reaction solution was concentrated, and the residue was acidified with a 5% aqueous hydrochloric acid solution and was extracted with ethyl acetate. The ethyl acetate layer was washed with water and saturated brine and was dried over sodium sulfate. The solvent was then removed by distillation under the reduced pressure to give a carboxyl compound as a colorless crystal (1.21 g, 71.6%).

4-Aminopyridine (230 mg, 2.46 mmol, 1.0 eq), WSC.HCl (570 mg, 2.96 mmol, 1.2 eq), and HOBt.H$_2$O (400 mg, 2.96 mmol, 1.2 eq) were added to a solution of the carboxyl compound (500 mg, 2.46 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a colorless crystal (60 mg, 7.8%).

MS m/z: 310 $^1$H-NMR δ: 2.36 (3H, s), 4.64 (2H, s), 7.17 (2H, d, J=0.49 Hz), 7.59 (2H, dd, J=1.58, 4.76 Hz), 8.57 (2H, dd, J=1.57, 4.75 Hz), 8.89 (1H, s)

Example 31

N1-(4-Pyridyl)-2-cyclohexylacetamide

4-Aminopyridine (66 mg, 0.70 mmol, 1.0 eq), WSC.HCl (162 mg, 0.85 mmol, 1.2 eq), and HOBt.H$_2$O (114 mg, 0.85 mmol, 1.2 eq) were added to a solution of cyclohexylacetic acid (100 mg, 0.70 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (23 mg, 15.0%).

MS m/z: 218 $^1$H-NMR δ: 0.91–1.20 (2H, m), 1.10–1.26 (3H, m), 1.56–1.80 (6H, m), 2.22 (2H, d, J=7.08 Hz), 7.55 (2H, dd, J=1.46, 4.64 Hz), 8.39 (2H, d, J=6.10 Hz), 10.21 (1H, s)

Example 32

N1-(1H-Pyrazolo[3,4-d]pyrimidin-4-yl)-2-(2,6-dichloro-4-fluorophenoxy)acetamide 4-Aminopyrazolo (3,4-d)pyrimidine (61 mg, 0.45 mmol, 1.0 eq), WSC.HCl (104 mg, 0.54 mmol, 1.2 eq), and HOBt.H$_2$O (73 mg, 0.54 mmol, 1.2 eq) were added to a solution of the carboxyl compound (100 mg, 0.45 mmol), prepared in Example 4, in dimethylformamide, and the mixture was stirred at room temperature for 5 days.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (63 mg, 39.1%).

MS m/z: 355 $^1$H-NMR δ: 4.91 (2H, s), 7.62 (2H, d, J=8.29 Hz), 8.49 (1H, s), 8.64 (1H, s), 11.25 (1H, s), 13.97 (1H, s)

Example 33

N1-(1H-5-Indazolyl)-1-cyclohexanecarboxyamide

5-Aminoindazole (100 mg, 0.75 mmol, 1.0 eq), WSC.HCl (173 mg, 0.90 mmol, 1.2 eq), and HOBt.H$_2$O (122 mg, 0.75 mmol, 1.2 eq) were added to a solution of cyclohexylcarboxylic acid (96 mg, 0.75 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (80 mg, 44.0%).

MS m/z: 243 $^1$H-NMR δ: 1.14–1.34 (3H, m), 1.44 (2H, q, J=11.38 Hz), 1.62–1.69 (1H, m), 1.73–1.84 (4H, m), 2.33 (1H, tt, J=3.42, 11.59 Hz), 7.42 (1H, dd, J=1.46, 9.03 Hz), 7.45 (1H, d, J=9.03 Hz), 7.98 (1H, s), 8.12 (1H, s), 9.76 (1H, s), 12.92 (1H, s)

Example 34

N1-(1H-5-Indazoyl)-1-cyclohexylacetamide

5-Aminoindazole (100 mg, 0.75 mmol, 1.0 eq), WSC.HCl (173 mg, 0.90 mmol, 1.2 eq), and HOBt.H$_2$O (122 mg, 0.75 mmol, 1.2 eq) were added to a solution of cyclohexylacetic acid (107 mg, 0.75 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (71 mg, 36.8%).

MS m/z: 257 $^1$H-NMR δ: 0.92–1.04 (2H, m), 1.10–1.30 (3H, m), 1.58–1.82 (6H, m), 2.19 (2H, d, J=7.08 Hz), 7.39 (1H, dd, J=1.71, 9.03 Hz), 7.45 (1H, d, J=8.78 Hz), 7.98 (1H, s), 8.11 (1H, s), 9.81 (1H, s), 12.92 (1H, s)

Example 35

N1-(1H-5-Indazolyl)-(E)-3-(2-hydroxyphenyl)-2-propeneamide

5-Aminoindazole (406 mg, 3.05 mmol, 1.0 eq), WSC.HCl (702 mg, 3.65 mmol, 1.2 eq), and HOBt.H$_2$O (493 mg, 6.65 mmol, 1.2 eq) were added to a solution of trans-2-coumaric acid (500 mg, 3.05 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (340 mg, 40.0%).

MS m/z: 279 $^1$H-NMR δ: 6.87 (1H, t, J=7.68 Hz), 6.86 (1H, d, J=15.86), 6.93 (1H, d, J=8.05), 7.22 (1H, dt, J=1.71, 8.78 Hz), 7.48–7.55 (3H, m), 7.79 (1H, d, J=15.86 Hz), 8.04 (1H, S), 8.28 (1H, s), 10.17 (1H, s), 12.98 (1H, s)

Example 36

N1-(1H-5-Indazolyl)-(E)-3-(3-hydroxyphenyl)-2-propeneamide

5-Aminoindazole (406 mg, 3.05 mmol, 1.0 eq), WSC.HCl (702 mg, 3.65 mmol, 1.2 eq), and HOBt.H$_2$O (493 mg, 6.65 mmol, 1.2 eq) were added to a solution of trans-3-coumaric acid (500 mg, 3.05 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was washed with chloroform to give the title compound as a crystal (161 mg, 18.9%).

MS m/z: 279 $^1$H-NMR δ: 6.78 (1H, d, J=15.61 Hz), 6.82 (1H, dd, J=2.20, 8.05 Hz), 7.00 (1H, s), 7.05 (1H, d, J=7.81 Hz), 7.25 (1H, t, J=7.81 Hz), 7.48 (1H, d, J=15.61 Hz), 7.51 (2H, s), 8.04 (1H, s), 8.26 (1H, s), 9.65 (1H, s), 10.21 (1H, s), 13.00 (1H, s)

Example 37

N1-(1H-5-Indazolyl)-(E)-3-(4-hydroxyphenyl)-2-propeneamide

5-Aminoindazole (406 mg, 3.05 mmol, 1.0 eq), WSC.HCl (702 mg, 3.65 mmol, 1.2 eq), and HOBt.H$_2$O (493 mg, 6.65 mmol, 1.2 eq) were added to a solution of trans-4-coumaric acid (500 mg, 3.05 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was washed with chloroform to give the title compound as a crystal (318 mg, 37.4%).

MS m/z: 279 $^1$H-NMR δ: 6.63 (1H, d, J=15.61 Hz), 6.83 (2H, d, J=8.54 Hz), 7.45–7.51 (5H, m), 8.03 (1H, s), 8.25 (1H, s), 9.92 (1H, s), 10.09 (1H, s), 12.97 (1H, s)

Example 38

N1-(1H-5-Indazolyl)-(E)-3-(3,4-dihydroxyphenyl)-2-propeneamide

5-Aminoindazole (406 mg, 3.05 mmol, 1.0 eq), WSC.HCl (702 mg, 3.65 mmol, 1.2 eq), and HOBt.H$_2$O (493 mg, 6.65 mmol, 1.2 eq) were added to a solution of caffeic acid (550 mg, 3.05 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (130 mg, 14.4%).

MS m/z: 295 $^1$H-NMR δ: 6.56 (1H, d, J=15.61 Hz), 6.78 (1H, d, J=8.05 Hz), 6.92 (1H, dd, J=1.95, 8.05 Hz), 7.02 (1H, d, J=1.95 Hz), 7.40 (1H, d, J=15.61 Hz), 7.50 (2H, s), 8.03 (1H, s), 8.25 (1H, s), 10.08 (1H, s), 12.97 (1H, s)

Example 39

N1-(1H-5-Indazolyl)-2-(2,4-dinitrophenyl)acetamide

5-Aminoindazole (176 mg, 1.33 mmol, 1.0 eq), WSC.HCl (306 mg, 1.59 mmol, 1.2 eq), and HOBt.H$_2$O (215 mg, 1.59 mmol, 1.2 eq) were added to a solution of 2,4-dinitrophenylacetic acid (300 mg, 1.33 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the title compound as a crystal (32 mg, 7.1%).

MS m/z: 341 $^1$H-NMR δ: 4.30 (2H, s), 7.40 (1H, dd, J=1.95, 8.78 Hz), 7.49 (1H, d, J=8.78 Hz), 7.91 (1H, d, J=8.54 Hz), 7.98–8.04 (2H, m), 8.67 (1H, d, J=1.95 Hz), 8.78 (1H, d, J=2.44 Hz), 10.30 (1H, s), 12.97 (1H, s)

Example 40

N1-(1H-5-Indazolyl)-(E)-3-(4-hydroxy-3-methoxyphenyl)-2-propeneamide

5-Aminoindazole (149 mg, 1.12 mmol, 1.0 eq), WSC.HCl (259 mg, 1.34 mmol, 1.2 eq), and HOBt.H$_2$O (182 mg, 1.34 mmol, 1.2 eq) were added to a solution of 4-hydroxy-3-methoxycinnamic acid (200 mg, 1.12 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the title compound as a crystal (158 mg, 45.5%).

MS m/z: 309 $^1$H-NMR δ: 3.84 (3H, s), 6.66 (1H, d, J=15.61 Hz), 6.83 (1H, d, J=8.05 Hz), 7.07 (1H, dd, J=1.95, 8.05 Hz), 7.19 (1H, d, J=1.95 Hz), 7.49 (1H, d, J=15.37 Hz), 7.50 (2H, s), 8.03 (1H, s), 8.26 (1H, s), 9.48 (1H, s), 10.07 (1H, s), 12.96 (1H, s)

Example 41

N1-(1H-5-Indazolyl)-(E)-3-(3-hydroxy-4-methoxyphenyl)-2-propeneamide

5-Aminoindazole (149 mg, 1.12 mmol, 1.0 eq), WSC.HCl (259 mg, 1.34 mmol, 1.2 eq), and HOBt.H$_2$O (182 mg, 1.34 mmol, 1.2 eq) were added to a solution of 3-hydroxy-4-methoxycinnamic acid (200 mg, 1.12 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the title compound as a crystal (100 mg, 28.8%).

MS m/z: 309 $^1$H-NMR δ: 3.81 (3H, s), 6.62 (1H, d, J=15.37 Hz), 6.97 (1H, d, J=8.05 Hz), 7.04 (1H, dd, J=1.95, 8.05 Hz), 7.05 (1H, s), 7.44 (1H, d, J=15.61 Hz), 7.50 (2H, s), 8.03 (1H, s), 8.25 (1H, s), 9.22 (1H, s), 10.09 (1H, s), 12.97 (1H, s)

Example 42

N1-(1H-5-Indazolyl)-(E)-3-(3,4-dimethoxyphenyl)-2-propeneamide

5-Aminoindazole (149 mg, 1.12 mmol, 1.0 eq), WSC.HCl (259 mg, 1.34 mmol, 1.2 eq), and HOBt.H$_2$O (182 mg, 1.34 mmol, 1.2 eq) were added to a solution of 3,4-dimethoxycinnamic acid (234 mg, 1.12 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the title compound as a crystal (164 mg, 45.2%).

MS m/z: 323 $^1$H-NMR δ: 3.80 (3H, s), 3.83 (3H, s), 6.73 (1H, d, J=15.61 Hz), 7.02 (1H, d, J=8.54), 7.19 (1H, dd, J=1.95, 8.54 Hz), 7.22 (1H, d, J=1.95 Hz), 7.51 (2H, s), 7.53 (1H, d, J=15.86 Hz), 8.03 (1H, s), 8.27 (1H, s), 10.13 (1H, s), 12.92 (1H, s)

Example 43

N1-(1H-5-Indazolyl)-3-(5-nitro-2-furyl)propeneamide

5-Aminoindazole (175 mg, 1.32 mmol, 1.0 eq), WSC.HCl (303 mg, 1.58 mmol, 1.2 eq), and HOBt.H$_2$O (213 mg, 1.58 mmol, 1.2 eq) were added to a solution of 3-(5-nitro-2-furyl) acrylic acid (240 mg, 1.32 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the tittle compound as a crystal (180 mg, 46.1%).

Palladium hydroxide (one small spatula) was added to a solution of the crystal (30 mg, 0.1 mmol) in DMF, and the mixture was stirred under a hydrogen atmosphere at room temperature for 2 hr.

After the completion of the reaction, the reaction solution was filtered through Celite, and washing with ethyl acetate was carried out. Water was poured into the filtrate, and the mixture was extracted with ethyl acetate. The ethyl acetate layer was washed with water and saturated brine and was then dried over sodium sulfate. The solvent was then removed by distillation under the reduced pressure to give the title compound as a crystal (7 mg, 26.7%).

MS m/z: 300 $^1$H-NMR δ: 2.77 (2H, t, J=7.44 Hz), 3.10 (2H, t, J=7.32 Hz), 6.64 (1H, d, J=3.66 Hz), 7.39 (1H, d, J=9.03 Hz), 7.47 (1H, d, J=8.78 Hz), 7.64 (1H, d, J=3.66 Hz), 8.00 (1H, s), 8.10 (1H, s), 10.03 (1H, s), 12.95 (1H, s)

Example 44

N1-(1H-5-Indazolyl)-2-(3,4-dihydroxyphenyl)acetamide

5-Aminoindazole (158 mg, 1.19 mmol, 1.0 eq), WSC.HCl (274 mg, 1.43 mmol, 1.2 eq), and HOBt.H$_2$O (193 mg, 1.43 mmol, 1.2 eq) were added to a solution of 3,4-dihydroxyacetic acid (200 mg, 1.19 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was then dried over sodium sulfate. The solvent was then removed by distillation under the reduced pressure. The residue was washed with chloroform to give the title compound as a crystal (33 mg, 9.8%).

MS m/z: 283 $^1$H-NMR δ: 3.43 (2H, s), 6.58 (1H, dd, J=2.20, 8.05 Hz), 6.66 (1H, d, J=8.05 Hz), 6.76 (1H, d, J=2.20 Hz), 7.41 (1H, dd, J=1.46, 9.03 Hz), 7.44 (1H, d, J=8.78 Hz), 7.99 (1H, s), 8.11 (1H, s), 8.76 (2H, s), 10.01 (1H, s), 12.94 (1H, s)

Example 45

N1-(1H-5-Indazolyl)-2-(1,3-benzodioxol-5-yl)acetamide

5-Aminoindazole (158 mg, 1.19 mmol, 1.0 eq), WSC.HCl (274 mg, 1.43 mmol, 1.2 eq), and HOBt.H$_2$O (193 mg, 1.43 mmol, 1.2 eq) were added to a solution of 3,4-methylenedioxyphenylacetic acid (214 mg, 1.19 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was then dried over sodium sulfate. The solvent was then removed by distillation under the reduced pressure. The residue was washed with chloroform to give the title compound as a crystal (166 mg, 47.4%).

MS m/z: 295 $^1$H-NMR δ: 3.55 (2H, s), 5.98 (2H, s), 6.80 (1H, dd, J=1.34, 7.93 Hz), 6.86 (1H, d, J=8.05 Hz), 6.92 (1H, d, J=1.46), 7.41 (1H, dd, J=1.71, 8.78 Hz), 7.47 (1H, d, J=9.03 Hz), 7.99 (1H, s), 8.09 (1H, s), 10.07 (1H, s), 12.95 (1H, s)

Example 46

N1-(1H-5-Indazolyl)-3-(3,4-dihydroxyphenyl)-propeneamide

5-Aminoindazole (146 mg, 1.10 mmol, 1.0 eq), WSC.HCl (253 mg, 1.32 mmol, 1.2 eq), and HOBt.H$_2$O (178 mg, 1.32 mmol, 1.2 eq) were added to a solution of 3,4-dihydroxycinnamic acid (200 mg, 1.10 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was washed with chloroform to give the title compound as a crystal (79 mg, 24.2%).

MS m/z: 297 $^1$H-NMR δ: 2.53 (2H, t, J=8.29 Hz), 2.75 (2H, t, J=7.56 Hz), 6.48 (1H, dd, J=2.20, 8.05 Hz), 6.62 (1H, d, J=8.05 Hz), 6.63 (1H, s), 7.38 (1H, dd, J=1.71, 9.03 Hz), 7.45 (1H, d, J=8.78 Hz), 7.99 (1H, s), 8.11 (1H, s), 8.61 (1H, s), 8.70 (1H, s), 9.84 (1H, s), 12.93 (1H, s)

Example 47

N1-(1H-5-Indazolyl)-3-(4-hydroxyphenyl)-propaneamide

5-Aminoindazole (119 mg, 0.89 mmol, 1.0 eq), WSC.HCl (205 mg, 1.07 mmol, 1.2 eq), and HOBt.H$_2$O (145 mg, 1.07 mmol, 1.2 eq) were added to a solution of 3-(4-hydroxyphenyl)propionic acid (148 mg, 0.89 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was then dried over sodium sulfate. The solvent was then removed by distillation under the reduced pressure. The residue was washed with chloroform to give the title compound as a crystal (95 mg, 38.0%).

MS m/z: 281 $^1$H-NMR δ: 2.55 (2H, t, J=7.68 Hz), 2.81 (2H, t, J=7.56 Hz), 6.66 (2H, d, J=8.29 Hz), 7.04 (2H, d, J=8.54 Hz), 7.38 (1H, dd, J=1.71, 8.78 Hz), 7.45 (1H, d, J=9.03 Hz), 7.99 (1H, S), 8.10 (1H, s), 9.84 (1H, s), 12.93 (1H, s)

Example 48

N1-(1H-5-Indazolyl)-2-(3-nitrophenyl)acetamide

5-Aminoindazole (147 mg, 1.10 mmol, 1.0 eq), WSC.HCl (254 mg, 1.32 mmol, 1.2 eq), and HOBt.H$_2$O (179 mg, 1.32 mmol, 1.2 eq) were added to a solution of 3-nitrophenylacetic acid (200 mg, 1.10 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was then dried over sodium sulfate. The solvent was then removed by distillation under the reduced pressure. The residue was washed with chloroform to give the title compound as a crystal (172 mg, 52.6%).

MS m/z: 296 $^1$H-NMR δ: 3.86 (2H, s), 7.43 (1H, dd, J=1.71, 8.78 Hz), 7.49 (1H, d, J=9.03 Hz), 7.65 (1H, t,

J=7.93 Hz), 7.82 (1H, d, J=7.56 Hz), 8.00 (1H, s), 8.12 (1H, s), 8.14 (1H, dd, J=2.44, 8.29 Hz), 8.26 (1H, s), 10.28 (1H, s), 12.98 (1H, s)

Example 49

N1-(1H-5-Indazolyl)-2-(4-nitrophenyl)acetamide

5-Aminoindazole (147 mg, 1.10 mmol, 1.0 eq), WSC.HCl (254 mg, 1.32 mmol, 1.2 eq), and HOBt.H$_2$O (179 mg, 1.32 mmol, 1.2 eq) were added to a solution of 4-nitrophenylacetic acid (200 mg, 1.10 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was washed with chloroform to give the title compound as a crystal (110 mg, 33.7%).

MS m/z: 296 $^1$H-NMR δ: 3.85 (2H, s), 7.42 (1H, dd, J=1.71, 8.78 Hz), 7.48 (1H, d, J=9.03 Hz), 7.64 (2H, d, J=8.78 Hz), 8.00 (1H, s), 8.10 (1H, s), 8.21 (2H, d, J=8.78 Hz), 10.28 (1H, s), 12.98 (1H, s)

Example 50

N1-(1H-5-Indazolyl)-2-(4-hydroxyanilino)acetamide

5-Aminoindazole (159 mg, 1.20 mmol, 1.0 eq), WSC.HCl (276 mg, 1.44 mmol, 1.2 eq), and HOBt.H$_2$O (194 mg, 1.44 mmol, 1.2 eq) were added to a solution of N-(4-hydroxyphenyl)glycine (200 mg, 1.20 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (46 mg, 13.6%).

MS m/z: 283 $^1$H-NMR δ: 3.76 (2H, d, J=5.85 Hz), 5.41 (1H, t, J=5.85 Hz), 6.48 (2H, d, J=8.78 Hz), 6.57 (2H, d, J=8.78 Hz), 7.43 (1H, dd, J=1.46, 9.03 Hz), 7.47 (1H, d, J=9.03 Hz), 8.00 (1H, s), 8.10 (1H, s), 8.48 (1H, s), 9.84 (1H, s), 12.95 (1H, s)

Example 51

N1-(1H-5-Indazolyl)-2-(4-hydroxyphenoxy)acetamide

5-Aminoindazole (158 mg, 1.19 mmol, 1.0 eq), WSC.HCl (274 mg, 1.43 mmol, 1.2 eq), and HOBt.H$_2$0 (193 mg, 1.43 mmol, 1.2 eq) were added to a solution of 4-hydroxyphenoxyacetic acid (200 mg, 1.19 mmol) in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was washed with chloroform to give the title compound as a crystal (229 mg, 68.0%).

MS m/z: 283 $^1$H-NMR δ: 4.57 (2H, s), 6.70 (2H, d, J=9.03 Hz), 6.86 (2H, d, J=9.03 Hz), 7.49 (2H, s), 8.03 (1H, s), 8.13 (1H, s), 9.00 (1H, s), 9.98 (1H, s), 12.99 (1H, s)

Example 52

N1-(1H-5-Indazolyl)-3-(1,3-benzodioxol-5-yl)propaneamide

5-Aminoindazole (137 mg, 1.03 mmol, 1.0 eq), WSC.HCl (237 mg, 1.24 mmol, 1.2 eq), and HOBt.H$_2$O (167 mg, 1.24 mmol, 1.2 eq) were added to a solution of 3-(3,4-methylenedioxyphenyl)propionic acid (200 mg, 1.03 mmol) in dimethylformamide, and the mixture was stirred at room temperature for 16 hr.

After the completion of the reaction, water and ethyl acetate were added thereto, and the precipitated crystal was collected by filtration and was washed with ethyl acetate to give the title compound as a crystal (98 mg, 30.8%).

MS m/z: 309 $^1$H-NMR δ: 2.58 (2H, t, J=7.68 Hz), 2.85 (2H, t, J=7.68 Hz), 5.95 (2H, s), 6071 (1H, dd, J=1.59, 7.93 Hz), 6.81 (1H, d, J=8.05 Hz), 6.84 (1H, d, J=1.46 Hz), 7.38 (1H, dd, J=1.71, 9.03), 7.46 (1H, d, J=9.03 Hz), 8.00 (1H, s), 8.11 (1H, s), 9.86 (1H, s), 12.94 (1H, s)

Example 53

N-(2,4-Dichlorobenzyl)-N'-(4-pyridyl)urea

Diphenylphosphoryl azide (161 mg, 0.59 mmol, 1.2 eq) and triethylamine (59 mg, 0.59 mmol, 1.2 eq) were added to a solution of 2,4-dichlorophenylacetic acid (100 mg, 0.49 mmol) in toluene, and the mixture was stirred at 110° C. for 60 min.

Thereafter, 4-aminopyridine (46 mg, 0.49 mmol, 1.0 eq) and a minor amount of DMF were added thereto, and the mixture was stirred at 110° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (43 mg, 29.9%).

MS m/z: 295 $^1$H-NMR δ: 4.35 (2H, d, J=5.85 Hz), 6.94 (1H, t, J=5.98 Hz), 7.37 (2H, dd, J=1.59, 4.76 Hz), 7.39 (1H, d, J=8.42 Hz), 7.44 (1H, dd, J=2.07, 8.42 Hz), 7.61 (1H, d, J=2.20 Hz), 8.29 (2H, dd, J=1.46, 4.88 Hz), 9.17 (1H, s)

Example 54

N-(2-Chloro-4-nitrobenzyl)-N'-(4-pyridyl)urea

Toluene (1 ml) and a minor amount of DMF were added to 4-aminopyridine (50 mg, 0.53 mmol), and the mixture was heated. Thereafter, 2-chloro-4-nitrophenyl isocyanate (105 mg, 0.53 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (72 mg, 46.4%).

MS m/z: 292 $^1$H-NMR δ: 7.57 (1H, s), 8.23 (2H, dd, J=2.68, 9.27 Hz), 8.36 (2H, d, J=2.44 Hz), 8.53 (2H, d, J=9.27 Hz), 8.96 (1H, s), 10.09 (1H, s)

Example 55

N'-(4-Pyridyl)-N-(2,3,6-trichlorobenzyl)urea

Diphenylphosphoryl azide (182 mg, 0.66 mmol, 1.2 eq) and triethylamine (67 mg, 0.66 mmol, 1.2 eq) were added to a solution of 2,3,6-trichlorophenylacetic acid (132 mg, 0.55 mmol) in toluene, and the mixture was stirred at 110° C. for 60 min.

Thereafter, 4-aminopyridine (52 mg, 0.55 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration and was washed with ethyl acetate to give the title compound as a crystal (153 mg, 84.0%).

MS m/z: 330, 332 $^1$H-NMR δ: 4.74 (2H, s), 7.22 (2H, dd, J=2.68, 8.54 Hz), 7.38 (2H, dd, J=1.46, 5.37 Hz), 8.14 (2H, d, J=5.61 Hz)

Example 56

N-(2-Chloro-6-fluorobenzyl)-N'-(4-pyridyl)urea

Diphenylphosphoryl azide (182 mg, 0.66 mmol, 1.2 eq) and triethylamine (67 mg, 0.66 mmol, 1.2 eq) were added to a solution of 2-chloro-6-fluorophenylacetic acid (104 mg, 0.55 mmol) in toluene, and the mixture was stirred at 110° C. for 60 min.

Thereafter, 4-aminopyridine (52 mg, 0.55 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (96 mg, 62.3%).

MS m/z: 280 $^1$H-NMR δ: 4.60 (2H, d, J=1.46 Hz), 6.99 (1H, dt, J=7.07, 9.51 Hz), 7.15–7.22 (2H, m), 7.31 (2H, dd, J=1.46, 4.88 Hz), 8.24 (2H, dd, J=1.46, 4.88 Hz)

Example 57

N-(2-Bromo-4,6-difluorobenzyl)-N'-(4-pyridyl)urea

Toluene (1 ml) and a minor amount of DMF were added to 4-aminopyridine (50 mg, 0.53 mmol), and the mixture was heated. Thereafter, 2-bromo-4,6-difluorophenyl isocyanate (124 mg, 0.53 mmol, 1.0 eq) was added to the solution, and the mixture was stirred at 110° C. for 120 min.

After the completion of the reaction, water and ethyl acetate were added thereto, and the precipitated crystal was collected by filtration and was washed with ethyl acetate to give the title compound as a crystal (107 mg, 61.5%).

MS m/z: 327, 329 $^1$H-NMR δ: 7.43 (2H, dd, J=1.46, 4.88 Hz), 7.48 (1H, dd, J=2.80, 9.88), 7.59 (1H, dd, J=1.71, 8.29 Hz), 8.27 (1H, s), 8.35 (2H, dd, J=1.46, 4.88 Hz), 9.46 (1H, s)

Example 58

N-[4-Fluoro-6-(trifluoromethyl)phenyl]-N'-(4-pyridyl)urea

Toluene (1 ml) and a minor amount of DMF were added to 4-aminopyridine (50 mg, 0.53 mmol), and the mixture was heated. Thereafter, 2-fluoro-6-(trifluoromethyl)phenyl isocyanate (109 mg, 0.53 mmol, 1.0 eq) was added to the solution, and the mixture was stirred at 110° C. for 120 min.

After the completion of the reaction, water and ethyl acetate were added thereto, and the precipitated crystal was collected by filtration and was washed with ethyl acetate to give the title compound as a crystal (69 mg, 43.7%).

MS m/z: 299 $^1$H-NMR δ: 7.45 (2H, dd, J=1.59, 4.76 Hz), 7.48–7.64 (3H, m), 8.34 (1H, s), 8.39 (2H, dd, J=1.59, 4.76 Hz), 9.28 (1H, s)

Example 59

N-[4-Fluoro-2-(trifluoromethyl)phenyl]-N'-(4-pyridyl)urea

Toluene (1 ml) and a minor amount of DMF were added to 4-aminopyridine (50 mg, 0.53 mmol), and the mixture was heated. Thereafter, 4-fluoro-2-(trifluoromethyl)phenyl isocyanate (109 mg, 0.53 mmol, 1.0 eq) was added to the solution, and the mixture was stirred at 110° C. for 120 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (72 mg, 45.3%).

MS m/z: 299 $^1$H-NMR δ: 7.43 (2H, dd, J=1.59, 4.76 Hz), 7.56 (1H, dt, J=3.03, 8.54 Hz), 7.62 (1H, dd, J=2.93, 9.03 Hz), 7.86 (1H, dd, J=5.12, 8.78 Hz), 8.28 (1H, s), 8.37 (2H, dd, J=1.46, 4.88 Hz), 9.63 (1H, s)

Example 60

N-(4-Bromo-2-fluorophenyl)-N'-(4-pyridyl)urea

Toluene (1 ml) and a minor amount of DMF were added to 4-aminopyridine (50 mg, 0.53 mmol), and the mixture was heated. Thereafter, 4-bromo-2-fluorophenyl isocyanate (115 mg, 0.53 mmol, 1.0 eq) was added to the solution, and the mixture was stirred at 110° C. for 120 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (13 mg, 7.9%).

MS m/z: 309, 311 $^1$H-NMR δ: 7.37 (1H, dt, J=1.34, 8.66 Hz), 7.42 (2H, dt, J=1.59, 4.76 Hz), 7.58 (1H, dd, J=2.32, 10.86 Hz), 8.09 (1H, dt, J=3.17, 8.78 Hz), 8.37 (2H, d, J=6.34 Hz), 8.80 (1H, s), 9.45 (1H, s)

Example 61

N-(2,6-Difluorobenzyl)-N'-(4-pyridyl)urea

Diphenylphosphoryl azide (191 mg, 0.69 mmol, 1.2 eq) and triethylamine (70 mg, 0.69 mmol, 1.2 eq) were added to a solution of 2,6-difluorophenylacetic acid (100 mg, 0.58 mmol) in toluene, and the mixture was stirred at 110° C. for 60 min.

Thereafter, 4-aminopyridine (55 mg, 0.58 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (87 mg, 57.0%).

MS m/z: 263 $^1$H-NMR δ: 4.39 (2H, d, J=5.37 Hz), 6.84 (1H, t, J=5.73 Hz), 7.10 (2H, t, J=8.17 Hz), 7.33 (2H, dd, J=1.59, 4.76 Hz), 7.40 (1H, dt, J=1.59, 8.29 Hz), 8.27 (2H, dd, J=1.59, 4.76 Hz), 8.87 (1H, s)

Example 62

N-Mesitylmethyl-N'-(4-pyridyl)urea

Diphenylphosphoryl azide (191 mg, 0.69 mmol, 1.2 eq) and triethylamine (70 mg, 0.69 mmol, 1.2 eq) were added to a solution of 2,4,6-trimethylphenylacetic acid (103 mg, 0.58 mmol) in toluene, and the mixture was stirred at 110° C. for 60 min.

Thereafter, 4-aminopyridine (55 mg, 0.58 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (88 mg, 56.8%)

MS m/z: 270 $^1$H-NMR δ: 2.25 (3H, s), 2.33 (6H, s), 4.39 (2H, s), 6.85 (2H, s), 7.31 (2H, dd, J=1.71, 4.88 Hz), 8.19 (2H, dd, J=1.71, 4.88 Hz)

Example 63

N-[2,6-Dichloro-4-(trifluoromethyl)phenyl]-N'-(4-pyridyl)urea

Diphenylphosphoryl azide (174 mg, 0.63 mmol, 1.2 eq) and triethylamine (64 mg, 0.63 mmol, 1.2 eq) were added to a solution of 2,6-dichloro-4-trifluoromethylbenzoic acid (137 mg, 0.53 mmol) in toluene, and the mixture was stirred at 110° C. for 60 min.

Thereafter, 4-aminopyridine (50 mg, 0.53 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (102 mg, 54.9%).

MS m/z: 349 $^1$H-NMR δ: 4.63 (2H, d, J=5.37 Hz), 6.87 (1H, t, J=5.49 Hz), 7.34 (2H, dd, J=1.46, 4.88 Hz), 7.94 (2H, s), 8.28 (2H, dd, J=1.34, 5.00 Hz), 8.90 (1H, s)

Example 64

N-[2-Fluoro-6-(trifluoromethyl)benzyl]-N'-(4-pyridyl)urea

Diphenylphosphoryl azide (174 mg, 0.63 mmol, 1.2 eq) and triethylamine (64 mg, 0.63 mmol, 1.2 eq) were added to a solution of 2-fluoro-6-trifluoromethylacetic acid (112 mg, 0.53 mmol) in toluene, and the mixture was stirred at 110° C. for 60 min.

Thereafter, 4-aminopyridine (50 mg, 0.53 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (102 mg, 54.9%).

MS m/z: 313 $^1$H-NMR δ: 4.51 (2H, d, J=4.88 Hz), 6.69 (1H, t, J=5.00 Hz), 7.34 (2H, dd, J=1.46, 4.88 Hz), 7.59–7.64 (3H, m), 8.28 (2H, s), 8.28 (2H, d, J=6.34 Hz), 8.82 (1H, s)

Example 65

4-{[(2,6-Dichloroanilino)carbonyl]amino}-benzamide

Toluene (1 ml) and a minor amount of DMF were added to 4-aminobenzamide (113 mg, 0.73 mmol), and the mixture was heated. Thereafter, 2,6-dichlorophenyl isocyanate (138 mg, 0.73 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (205 mg, 86.2%).

MS m/z: 323 $^1$H-NMR δ: 7.16 (1H, s), 7.33 (1H, t, J=8.17 Hz), 7.51 (2H, d, J=8.24 Hz), 7.54 (2H, d, J=8.29 Hz), 7.80 (2H, d, J=8.54 Hz), 8.30 (1H, s), 9.21 (1H, s)

Example 66

N-(1H-3-Indolyl)-N'-(4-pyridyl)urea

Diphenylphosphoryl azide (205 mg, 0.75 mmol, 1.2 eq) and triethylamine (75 mg, 0.75 mmol, 1.2 eq) were added to a solution of 3-indolecarboxylic acid (100 mg, 0.62 mmol) in toluene, and the mixture was stirred at 110° C. for 60 min.

Thereafter, 4-aminopyridine (58 mg, 0.62 mmol, 1.0 eq) and a minor amount of DMF were added thereto, and the mixture was stirred at 110° C. for 2 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (54 mg, 34.5%).

MS m/z: 326 $^1$H-NMR δ: 7.02 (1H, t, J=7.44 Hz), 7.11 (1H, t, J=7.56 Hz), 7.35 (1H, d, J=8.05 Hz), 7.46 (2H, dd, J=1.59, 4.76 Hz), 7.51 (1H, d, J=5.12 Hz), 7.52 (1H, s), 8.43 (2H, d, J=6.34 Hz), 8.66 (1H, s), 9.02 (1H, s), 10.79 (1H, s)

Example 67

N-(2,6-Dichlorophenyl)-N'-(1,3-dioxo-2,3-dihydro-1H-isoindolyl)urea

Toluene (1 ml) and a minor amount of DMF were added to 4-aminophthalimide (86 mg, 0.53 mmol), and the mixture was heated. Thereafter, 2,6-dichlorophenyl isocyanate (100 mg, 0.53 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (150 mg, 80.6%).

MS m/z: 349 $^1$H-NMR δ: 7.35 (1H, dd, J=7.81, 8.03 Hz), 7.60 (2H, d, J=8.05 Hz), 7.72 (2H, d, J=1.22 Hz), 8.04 (1H, d, J=1.22 Hz), 8.50 (1H, s), 9.69 (1H, s), 11.13 (1H, s)

Example 68

N1-(2,6-Dichlorobenzyl)-N'-(1,3-dioxo-2,3-dihydro-1H-5-isoindolyl)urea

Diphenylphosphoryl azide (161 mg, 0.59 mmol, 1.2 eq) and triethylamine (59 mg, 0.59 mmol, 1.2 eq) were added to a solution of 2,6-dichlorophenylacetic acid (100 mg, 0.49 mmol) in toluene, and the mixture was stirred at 110° C. for 60 min.

Thereafter, 4-aminophthalimide (79 mg, 0.49 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (120 mg, 67.6%).

MS m/z: 364 $^1$H-NMR δ: 4.60 (2H, d, J=5.37 Hz), 6.78 (1H, t, J=5.37 Hz), 7.39 (1H, d, J=7.30 Hz), 7.51 (2H, d, J=7.81 Hz), 7.55 (1H, dd, J=1.95, 8.29 Hz), 7.67 (1H, d, J=8.29 Hz), 8.01 (1H, d, J=1.95 Hz), 9.14 (1H, s), 11.09 (1H, s)

Example 69

N-(1,3-Dioxo-2,3-dihydro-1H-5-isoindolyl)-N'-(1H-3-indolyl)urea

Diphenylphosphoryl azide (161 mg, 0.59 mmol, 1.2 eq) and triethylamine (59 mg, 0.59 mmol, 1.2 eq) were added to a solution of 3-indoleacetic acid (79 mg, 0.49 mmol) in toluene, and the mixture was stirred at 110° C. for 60 min.

Thereafter, 4-aminophthalimide (79 mg, 0.49 mmol, 1.0 eq) and a minor amount of DMF were added thereto, and the mixture was stirred at 110° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by a preparative TLC [chloroform-acetone] to give the title compound as a crystal (30 mg, 19.1%).

MS m/z: 320 $^1$H-NMR δ: 7.02 (1H, t, J=7.56 Hz), 7.11 (1H, t, J=7.56 Hz), 7.16 (1H, d, J=7.81 Hz), 7.35 (1H, d, J=8.05 Hz), 7.54 (2H, d, J=7.81 Hz), 7.67 (1H, dd, J=1.83, 8.17 Hz), 7.72 (1H, d, J=8.05 Hz), 8.12 (1H, d, J=1.22), 9.35 (1H, s), 10.81 (1H, s), 11.11 (1H, s)

Example 70

N-(1,3-Dioxo-2,3-dihydro-1H-5-isoindolyl)-N'-(1H-5-indolyl)urea

Diphenylphosphoryl azide (161 mg, 0.59 mmol, 1.2 eq) and triethylamine (59 mg, 0.59 mmol, 1.2 eq) were added to a solution of 5-indoleacetic acid (79 mg, 0.49 mmol) in toluene, and the mixture was stirred at 110° C. for 60 min.

Thereafter, 4-aminophthalimide (79 mg, 0.49 mmol, 1.0 eq) and a minor amount of DMF were added thereto, and the mixture was stirred at 110° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by a preparative TLC [chloroform-acetone] to give the title compound as a crystal (50 mg, 31.9%).

MS m/z: 320 $^1$H-NMR δ: 6.36–6.39 (1H, m), 7.29–7.34 (3H, m), 7.64–7.75 (3H, m), 8.07 (1H, d, J=1.46. Hz), 8.64 (1H, s), 9.29 (1H, s), 10.98 (1H, s), 11.11 (1H, s)

Example 71

N-(2-Nitrobenzyl)-N'-(4-pyridyl)urea

Toluene (1 ml) and a minor amount of DMF were added to 4-aminopyridine (80 mg, 0.85 mmol), and the mixture was heated. Thereafter, 2-nitrophenyl isocyanate (139 mg, 0.85 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (170 mg, 77.8%).

MS m/z: 258 $^1$H-NMR δ: 7.26 (1H, dt, J=1.22, 7.08 Hz), 7.46 (2H, dd, J=1.59, 4.76 Hz), 7.73 (1H, dt, J=1.59, 7.20 Hz), 8.10 (1H, dd, J=1.59, 8.42 Hz), 8.24 (1H, dd, J=1.34, 8.42 Hz), 8.40 (2H, dd, J=1.59, 4.76 Hz), 9.69 (1H, s), 10.16 (1H, s)

Example 72

N1-(1,3-Dioxo-2,3-dihydro-1H-5-isoindolyl)-N'-phenylurea

Toluene (1 ml) and a minor amount of DMF were added to 4-aminophthalimide (80 mg, 0.50 mmol), and the mixture was heated. Thereafter, phenyl isocyanate (59 mg, 0.50 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (95 mg, 68.3%).

MS m/z: 281 $^1$H-NMR δ: 7.01 (1H, t, J=7.32 Hz), 7.31 (2H, t, J=7.93 Hz), 7.48 (2H, dd, J=0.98, 8.54 Hz), 7.67 (1H, dd, J=1.83, 8.17 Hz), 7.73 (1H, d, J=8.29 Hz), 8.05 (1H, d, J=1.46 Hz), 8.89 (1H, s), 9.36 (1H, s), 11.14 (1H, s)

Example 73

N-Benzyl-N'-(1,3-dioxo-2,3-dihydro-1H-5-isoindolyl)urea

Toluene (1 ml) and a minor amount of DMF were added to 4-aminophthalimide (80 mg, 0.50 mmol), and the mixture was heated. Thereafter, benzyl isocyanate (66 mg, 0.50 mmol, 1.0 eq) was added to the solution, and the mixture was stirred at 110° C. for 150 min.

After the completion of the reaction, water and ethyl acetate were added thereto, and the precipitated crystal was collected by filtration and was washed with ethyl acetate to give the title compound as a crystal (96 mg, 65.7%).

MS m/z: 295 $^1$H-NMR δ: 4.33 (2H, d, J=4.39 Hz), 6.90 (1H, t, J=5.98 Hz), 7.22–7.35 (5H, m), 7.61 (1H, dd, J=1.83, 8.17 Hz), 7.67 (1H, d, J=8.29 Hz), 8.02 (1H, dd, J=0.49, 1.95 Hz), 9.30 (1H, s), 11.08 (1H, s)

Example 74

N-(1,3-Dioxo-2,3-dihydro-1H-5-isoindolyl)-N'-propylurea

Toluene (1 ml) and a minor amount of DMF were added to 4-aminophthalimide (80 mg, 0.50 mmol), and the mixture was heated. Thereafter, n-propyl isocyanate (42 mg, 0.50 mmol, 1.0 eq) was added thereto, and the mixture was stirred at 110° C. for 150 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by a preparative TLC [chloroform-acetone] to give the title compound as a crystal (35 mg, 28.9%).

MS m/z: 247 $^1$H-NMR δ: 0.88 (3H, t, J=7.44 Hz), 1.41–1.51 (2H, m), 3.07 (2H, q, J=5.60 Hz), 6.40 (1H, t, J=5.60 Hz), 7.58 (1H, dd, J=2.07, 8.17 Hz), 7.66 (1H, d, J=8.29 Hz), 8.00 (1H, d, J=1.71 Hz), 9.14 (1H, s), 11.06 (1H, s)

Example 75

N-Cyclohexylmethyl-N'-(4-pyridyl)urea

Diphenylphosphoryl azide (232 mg, 0.85 mmol, 1.2 eq) and triethylamine (85 mg, 0.85 mmol, 1.2 eq) were added to a solution of cyclohexylacetic acid (100 mg, 0.70 mmol) in toluene, and the mixture was stirred at 110° C. for 60 min.

Thereafter, 4-aminopyridine (66 mg, 0.70 mmol, 1.0 eq) and a minor amount of DMF were added thereto, and the mixture was stirred at 110° C. for 150 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (13 mg, 7.9%).

MS m/z: 234 $^1$H-NMR δ: 0.84–0.96 (2H, m), 1.09–1.25 (3H, m), 1.33–1.45 (1H, m), 1.58–1.72 (5H, m), 2.94 (2H, t, J=6.22 Hz), 6.37 (1H, t, J=5.73 Hz), 7.34 (2H, dd, J=1.46, 4.88 Hz), 8.26 (2H, dd, J=1.59, 4.76 Hz), 8.80 (1H, s)

Example 76

N-Cyclohexylmethyl-N'-(1,3-dioxo-2,3-dihydro-1H-5-isoindolyl)urea

Diphenylphosphoryl azide (232 mg, 0.85 mmol, 1.2 eq) and triethylamine (85 mg, 0.85 mmol, 1.2 eq) were added to a solution of cyclohexylacetic acid (100 mg, 0.70 mmol) in toluene, and the mixture was stirred at 110° C. for 60 min.

Thereafter, 4-aminophthalimide (114 mg, 0.70 mmol, 1.0 eq) and a minor amount of DMF were added thereto, and the mixture was stirred at 110° C. for 150 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by a preparative TLC [chloroform-acetone] to give the title compound as a crystal (46 mg, 21.7%).

MS m/z: 301 $^1$H-NMR δ: 0.85–0.96 (2H, m), 1.07–1.26 (3H, m), 1.35–1.47 (1H, m), 1.58–1.73 (5H, m), 2.97 (2H, t, J=6.22 Hz), 6.42 (1H, t, J=5.73 Hz), 7.56 (1H, dd, J=1.95, 8.29 Hz), 7.66 (1H, d, J=8.30 Hz), 8.01 (1H, d, J=1.71 Hz), 9.11 (1H, s), 11.06 (1H, s)

Example 77

N-(4-Pyridyl)-N'-(2,4,6-trifluorobenzyl)urea

Diphenylphosphoryl azide (174 mg, 0.63 mmol, 1.2 eq) and triethylamine (64 mg, 0.63 mmol, 1.2 eq) were added to a solution of 2,4,6-trifluorophenylacetic acid (100 mg, 0.53 mmol) in toluene, and the mixture was stirred at 110° C. for 60 min.

Thereafter, 4-aminopyridine (50 mg, 0.53 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration and was washed with ethyl acetate to give the title compound as a crystal (80 mg, 56.5%).

MS m/z: 269 $^1$H-NMR δ: 4.34 (2H, d, J=5.61 Hz), 6.86 (1H, t, J=5.61 Hz), 7.19 (2H, t, J=8.78 Hz), 7.33 (2H, dd, J=1.59, 4.88 Hz), 8.28 (2H, dd, J=1.58, 4.88 Hz), 8.88 (1H, s)

Example 78

N-(1,3-Dioxo-2,3-dihydro-1H-5-isoindolyl)-N'-(3-nitrophenyl)urea

Toluene (1 ml) and a minor amount of DMF were added to 4-aminopyridine (80 mg, 0.85 mmol), and the mixture was heated. Thereafter, 3-nitrophenyl isocyanate (81 mg, 0.85 mmol, 1.0 eq) was added to the solution, and the mixture was stirred at 110° C. for 180 min.

After the completion of the reaction, water and ethyl acetate were added thereto, and the precipitated crystal was collected by filtration and was washed with ethyl acetate to give the title compound as a crystal (150 mg, 93%).

MS m/z: 326 $^1$H-NMR δ: 7.60 (1H, t, J=8.17 Hz), 7.71–7.80 (3H, m), 7.85–7.89 (1H, m), 8.04–8.06 (1H, m), 8.56 (1H, t, J=0.85 Hz), 9.46 (1H, s), 9.55 (1H, s), 11.17 (1H, s)

Example 79

N-(1,3-Dioxo-2,3-dihydro-1H-5-isoindolyl)-N'-(4-aminophenyl)urea

A minor amount of palladium hydroxide was added to a solution of the compound (84 mg, 0.26 mmol), prepared in Example 78, in DMF, and the mixture was stirred under a hydrogen atmosphere at room temperature for one hr.

After the completion of the reaction, the reaction solution was filtered through Celite, and washing with ethyl acetate was carried out. The filtrate was washed with water and saturated brine and was then dried over sodium sulfate. The solvent was then removed by distillation under the reduced pressure to give the title compound as a crystal (44 mg, 57.9%).

MS m/z: 296 $^1$H-NMR δ: 5.05 (2H, s), 6.23 (1H, dd, J=1.71, 7.81 Hz), 6.58 (1H, dd, J=1.46, 7.81 Hz), 6.78 (1H, t, J=2.07 Hz), 6.92 (1H, t, J=7.93 Hz), 7.63 (1H, dd, J=1.83, 8.17 Hz), 7.71 (1H, d, J=8.05 Hz), 8.05 (1H, d, J=1.95 Hz), 8.58 (1H, s), 9.24 (1H, s), 11.12 (1H, s)

Example 80

N-(2,6-Dichlorobenzyl)-N'-(4-pyridyl)urea

Diphenylphosphoryl azide (242 mg, 0.88 mmol, 1.2 eq) and triethylamine (89 mg, 0.88 mmol, 1.2 eq) were added to a solution of 2,6-dichlorophenylacetic acid (150 mg, 0.73 mmol) in toluene, and the mixture was stirred at 110° C. for 60 min.

Thereafter, 4-aminopyridine (69 mg, 0.73 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration and was washed with ethyl acetate to give the title compound as a crystal (76 mg, 32.4%).

MS m/z: 296 $^1$H-NMR δ: 6.08 (2H, d, J=5.37 Hz), 6.73 (1H, t, J=5.37 Hz), 7.34 (2H, dd, J=1.58, 4.88 Hz), 7.38 (1H, dd, J=1.22, 7.32 Hz), 7.51 (2H, d, J=7.81 Hz), 8.28 (2H, dd, J=1.71, 4.88 Hz), 8.84 (1H, s)

Example 81

N-(6-Chloro-1,3-dioxo-2,3-dihydro-1H-5-isoindolyl)-N'-(2,6-dichlorobenzyl)urea

Diphenylphosphoryl azide (242 mg, 0.88 mmol, 1.2 eq) and triethylamine (89 mg, 0.88 mmol, 1.2 eq) were added to a solution of 2,6-dichlorophenylacetic acid (150 mg, 0.73 mmol) in toluene, and the mixture was stirred at 110° C. for 60 min.

Thereafter, 4-amino-5-chlorophthalimide (130 mg, 0.66 mmol, 0.9 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate. The resultant crystal was purified by a preparative TLC [chloroform/methanol] to give the title compound as a crystal (11 mg, 3.8%).

MS m/z: 397, 399 $^1$H-NMR δ: 4.60–4.64 (2H, m), 7.36–7.46 (3H, m), 7.54 (2H, d, J=7.81 Hz), 7.87 (1H, s), 8.71 (1H, s), 11.28 (1H, s)

Example 82

N-(2-Chlorobenzyl)-N'-(1,3-dioxo-2,3-dihydro-1H-5-isoindolyl)urea

Diphenylphosphoryl azide (165 mg, 0.60 mmol, 1.2 eq) and triethylamine (61 mg, 0.60 mmol, 1.2 eq) were added to a solution of 2-chlorophenylacetic acid (85 mg, 0.50 mmol) in toluene, and the mixture was stirred at 110° C. for 60 min.

Thereafter, 4-aminophthalimide (81 mg, 0.50 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration and was washed with ethyl acetate to give the title compound as a crystal (37 mg, 22.6%).

MS m/z: 329 $^1$H-NMR δ: 4.40 (2H, d, J=5.61 Hz), 6.94 (1H, t, J=5.98 Hz), 7.28–7.38 (2H, m), 7.41 (1H, dd, J=1.71, 7.56 Hz), 7.46 (1H, dd, J=1.71, 7.56 Hz), 7.61 (1H, dd, J=1.83, 8.17 Hz), 7.68 (1H, d, J=8.54 Hz), 8.01 (1H, d, J=1.46 Hz), 9.42 (1H, s), 11.08 (1H, s)

Example 83

N-(2-Chloro-6-fluorobenzyl)-N'-(1,3-dioxo-2,3-dihydro-1H-6-isoindolyl)urea

Diphenylphosphoryl azide (165 mg, 0.60 mmol, 1.2 eq) and triethylamine (61 mg, 0.60 mmol, 1.2 eq) were added to a solution of 2-chloro-6-fluorophenylacetic acid (94 mg, 0.50 mmol) in toluene, and the mixture was stirred at 110° C. for 60 min.

Thereafter, 4-aminophthalimide (81 mg, 0.50 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration and was washed with ethyl acetate to give the title compound as a crystal (58 mg, 33.5%).

MS m/z: 346, 348 $^1$H-NMR δ: 4.49 (2H, d, J=4.15 Hz), 6.84 (1H, t, J=5.49 Hz), 7.25 (1H, dt, J=1.59, 7.81 Hz), 7.32–7.43 (2H, m), 7.55 (1H, dd, J=1.83, 8.17 Hz), 7.66 (1H, d, J=8.29 Hz), 7.99 (1H, d, J=1.95 Hz), 9.15 (1H, s), 11.08 (1H, s)

Example 84

N-Benzyl-N'-(1H-5-indazolyl)urea

Toluene (1 ml) and a minor amount of DMF were added to 5-aminoindazole (67 mg, 0.50 mmol), and the mixture was heated. Thereafter, benzyl isocyanate (66 mg, 0.50 mmol, 1.0 eq) was added to the solution, and the mixture was stirred at 110° C. for 180 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

Methanol was added to the residue, followed by filtration to give the title compound as a crystal (21 mg, 15.9%).

MS m/z: 266 $^1$H-NMR δ: 4.31 (2H, d, J=5.85 Hz), 6.53 (1H, t, J=5.85 Hz), 7.21–7.28 (2H, m), 7.29–7.36 (3H, m), 7.41 (1H, d, J=8.78 Hz), 7.85 (1H, s), 7.93 (1H, s), 8.46 (1H, s), 12.84 (1H, s)

Example 85

N-(1,3-Dioxo-2,3-dihydro-1H-5-isoindolyl)-N'-(1-naphthylmethyl)urea

Diphenylphosphoryl azide (204 mg, 0.74 mmol, 1.2 eq) and triethylamine (75 mg, 0.74 mmol, 1.2 eq) were added to a solution of 1-naphthylacetic acid (115 mg, 0.62 mmol) in toluene, and the mixture was stirred at 110° C. for 60 min.

Thereafter, 4-aminophthalimide (100 mg, 0.62 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (91 mg, 42.7%).

MS m/z: 345 $^1$H-NMR δ: 4.80 (2H, d, J=4.39 Hz), 6.95 (1H, t, J=5.73 Hz), 7.47–7.62 (5H, m), 7.67 (1H, d, J=8.29 Hz), 7.87 (1H, dd, J=1.95, 7.32 Hz), 7.96 (1H, dd, J=1.46, 8.05 Hz), 8.04 (1H, d, J=1.22 Hz), 8.14 (1H, d, J=8.54 Hz), 9.27 (1H, s), 11.08 (1H, s)

Example 86

N-(1,3-Dioxo-2,3-dihydro-1H-5-isoindolyl)-N'-(2-nitrobenzyl)urea

Diphenylphosphoryl azide (165 mg, 0.60 mmol, 1.2 eq) and triethylamine (61 mg, 0.60 mmol, 1.2 eq) were added to a solution of 2-nitrophenylacetic acid (90 mg, 0.50 mmol) in toluene, and the mixture was stirred at 110° C. for 60 min.

Thereafter, 4-aminophthalimide (81 mg, 0.50 mmol, 1.0 eq) and a minor amount of DMF were added thereto, and the mixture was stirred at 110° C. for 2 hr.

After the completion of the reaction, water and ethyl acetate were added thereto, and the precipitated crystal was collected by filtration, was washed with ethyl acetate, and was further washed with a chloroform/methanol solution to give the title compound as a crystal (11 mg, 6.5%).

MS m/z: 340 $^1$H-NMR δ: 4.61 (2H, d, J=5.37 Hz), 7.00 (1H, t, J=5.73 Hz), 7.53–7.70 (4H, m), 7.76 (1H, t, J=7.44 Hz), 8.00 (1H, s), 8.06 (1H, d, J=7.44 Hz), 9.48 (1H, s), 11.09 (1H, s)

Example 87

N'-(2-Aminobenzyl)-N'-(1,3-dioxo-2,3-dihydro-1H-5-isoindolyl)urea

Palladium hydroxide (one small spatula) was added to a solution of the crystal (100 mg, 0.29 mmol) of the compound prepared in Example 86 (mixed with 4-aminophthalimide) in DMF, and the mixture was stirred under a hydrogen atmosphere at room temperature for 60 min.

After the completion of the reaction, the reaction solution was filtered through Celite, and washing with ethyl acetate was carried out. Water was then added to the filtrate, and the mixture was extracted with ethyl acetate. The ethyl acetate layer was washed with water and saturated brine and was dried over sodium sulfate. The solvent was then removed by distillation under the reduced pressure.

Methanol was added to the residue, followed by filtration to give the title compound as a crystal (27 mg, 29.7%).

MS m/z: 310 $^1$H-NMR δ: 4.19 (2H, d, J=5.37 Hz), 5.09 (2H, s), 6.52 (1H, t, J=7.32 Hz), 6.63 (1H, d, J=7.32 Hz), 6.72 (1H, t, J=5.73 Hz), 6.97 (1H, dt, J=1.46, 7.56 Hz), 7.04 (1H, d, J=7.56 Hz), 7.59 (1H, dd, J=1.95, 8.29 Hz), 7.67 (1H, d, J=8.29 Hz), 8.01 (1H, d, J=1.95 Hz), 9.28 (1H, s), 11.08 (1H, s)

Example 88

N-(2,4-Dichlorobenzyl)-N'-(1,3-dioxo-2,3-dihydro-1H-5-isoindolyl)urea

Diphenylphosphoryl azide (162 mg, 0.59 mmol, 1.2 eq) and triethylamine (60 mg, 0.59 mmol, 1.2 eq) were added to a solution of 2,4-dichlorophenylacetic acid (101 mg, 0.49 mmol) in toluene, and the mixture was stirred at 110° C. for 60 min.

Thereafter, 4-aminophthalimide (80 mg, 0.49 mmol, 1.0 eq) and a minor amount of DMF were added thereto, and the mixture was stirred at. 110° C. for 2.5 hr.

After the completion of the reaction, water and ethyl acetate were added thereto, and the precipitated crystal was collected by filtration and was washed with ethyl acetate. The resultant crystal was washed with a chloroform/methanol solution to give the title compound as a crystal (9 mg, 5.0%).

MS m/z: 363, 365 $^1$H-NMR δ: 4.37 (2H, d, J=4.88 Hz), 6.99 (1H, t, J=5.22 Hz), 7.38–7.44 (2H, m), 7.57–7.63 (2H, m), 7.68 (1H, d, J=8.29 Hz), 8.01 (1H, s), 9.46 (1H, s), 11.08 (1H, s)

Example 89

N-(1,3-Dioxo-2,3-dihydro-1H-5-isoindolyl)-N'-(2,3,6-trichlorobenzyl)urea

Diphenylphosphoryl azide (162 mg, 0.59 mmol, 1.2 eq) and triethylamine (60 mg, 0.59 mmol, 1.2 eq) were added to a solution of 2,3,6-trichlorophenylacetic acid (118 mg, 0.49 mmol) in toluene, and the mixture was stirred at 110° C. for 60 min.

Thereafter, 4-aminophthalimide (80 mg, 0.49 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (57 mg, 29.1%).

MS m/z: 397, 399 $^1$H-NMR δ: 4.63–4.66 (2H, m), 6.87 (1H, t, J=5.24 Hz), 7.55 (1H, d, J=8.54 Hz), 7.57 (1H, dd, J=1.95, 8.05 Hz), 7.67 (2H, d, J=8.54 Hz), 8.00 (1H, d, J=1.71 Hz), 9.14 (1H, s), 11.09 (1H, s)

Example 90

N-(2,6-Difluorobenzyl)-N'-(1,3-dioxo-2,3-dihydro-1H-5-isoindolyl)urea

Diphenylphosphoryl azide (162 mg, 0.59 mmol, 1.2 eq) and triethylamine (60 mg, 0.59 mmol, 1.2 eq) were added to a solution of 2,6-difluorophenylacetic acid (101 mg, 0.49 mmol) in toluene, and the mixture was stirred at 110° C. for 60 min.

Thereafter, 4-aminophthalimide (80 mg, 0.49 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate. The resultant crystal was washed with a chloroform/methanol solution to give the title compound as a crystal (10 mg, 6.1%).

MS m/z: 331 $^1$H-NMR δ: 4.64 (2H, d, J=4.64 Hz), 6.88 (1H, t, J=5.73 Hz), 7.11 (2H, t, J=8.05 Hz), 7.56 (1H, dd, J=1.83, 8.29 Hz), 7.66 (1H, d, J=8.29 Hz), 7.98 (1H, d, J=1.71 Hz), 9.15 (1H, s), 11.08 (1H, s)

Example 91

N-(1,3-Dioxo-2,3-dihydro-1H-5-isoindolyl)-N'-[2-fluoro-6-(trifluoromethyl)benzyl]urea Diphenylphosphoryl azide (163 mg, 0.59 mmol, 1.2 eq) and triethylamine (60 mg, 0.59 mmol, 1.2 eq) were added to a solution of 2-fluoro-6-trifluoromethylphenylacetic acid (104 mg, 0.49 mmol) in toluene, and the mixture was stirred at 110° C. for 60 min.

Thereafter, 4-aminophthalimide (80 mg, 0.49 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate. The resultant crystal was washed with a chloroform/methanol solution to give the title compound as a crystal (18 mg, 9.6%).

MS m/z: 381 $^1$H-NMR δ: 4.53 (2H, s), 6.74 (1H, t, J=5.49 Hz), 7.55 (1H, dd, J=1.71, 8.29 Hz), 7.60–7.64 (3H, m), 7.67 (1H, d, J=8.29 Hz), 8.00 (1H, d, J=1.71 Hz), 9.11 (1H, s), 11.09 (1H, s)

Example 92

N-Benzyl-N'-(4-pyridyl)urea

Toluene (1 ml) and a minor amount of DMF were added to 4-aminopyridine (50 mg, 0.53 mmol), and the mixture was heated. Thereafter, benzyl isocyanate (71 mg, 0.53 mmol, 1.0 eq) was added to the solution, and the mixture was stirred at 110° C. for 120 min.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (18 mg, 15.0%).

MS m/z: 227 $^1$H-NMR δ: 4.31 (2H, d, J=5.85 Hz), 6.85 (1H, t, J=5.85 Hz), 7.24 (1H, tt, J=1.71, 6.83 Hz), 7.28–7.36 (4H, m), 7.37 (2H, dd, J=1.56, 4.76 Hz), 8.28 (2H, d, J=6.10 Hz), 9.01 (1H, s)

Example 93

N-(2-Nitrobenzyl)-N'-(4-pyridyl)urea

Diphenylphosphoryl azide (175 mg, 0.64. mmol, 1.2 eq) and triethylamine (65 mg, 0.64 mmol, 1.2 eq) were added to a solution of 2-nitrophenylacetic acid (96 mg, 0.53 mmol) in toluene, and the mixture was stirred at 110° C. for 60 min.

Thereafter, 4-aminopyridine (50 mg, 0.53 mmol, 1.0 eq) and a minor amount of DMF were added thereto, and the mixture was stirred at 110° C. for 2.5 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (25 mg, 17.4%).

MS m/z: 272, 273 $^1$H-NMR δ: 4.58 (2H, d, J=6.10 Hz), 6.96 (1H, t, J=6.10 Hz), 7.35 (2H, dd, J=1.59, 4.76 Hz), 7.55 (1H, dt, J=1.46, 7.80 Hz), 7.61 (1H, dd, J=1.10, 7.68 Hz), 7.75 (1H, dt, J=1.46, 7.56 Hz), 8.05 (1H, dd, J=1.46, 8.17 Hz), 8.29 (2H, d, J=6.34 Hz), 9.20 (1H, s)

Example 94

N-(2-Chlorobenzyl)-N'-(4-pyridyl)urea

Diphenylphosphoryl azide (175 mg, 0.64 mmol, 1.2 eq) and triethylamine (65 mg, 0.64 mmol, 1.2 eq) were added to a solution of 2-chlorophenylacetic acid (91 mg, 0.53 mmol) in toluene, and the mixture was stirred at 110° C. for 60 min.

Thereafter, 4-aminopyridine (5.0 mg, 0.53 mmol, 1.0 eq) and a minor amount of DMF were added thereto, and the mixture was stirred at 110° C. for 2.5 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (53 mg, 38.1%).

MS m/z: 262 $^1$H-NMR δ: 4.38 (2H, d, J=6.10 Hz), 6.90 (1H, t, J=5.85 Hz), 7.28–7.41 (4H, m), 7.37 (2H, dd, J=1.46, 4.88 Hz), 7.45 (1H, dd, J=1.46, 7.68 Hz), 8.29 (2H, dd, J=1.46, 4.88 Hz), 9.13 (1H, s)

Example 95

N-(2,6-Difluorobenzyl)-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of 2,6-difluorophenylacetic acid (129 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (14 mg, 6.2%).

MS m/z: 302 $^1$H-NMR δ: 4.39 (2H, d, J=5.85 Hz), 6.51 (1H, t, J=5.73 Hz), 7.10 (2H, t, J=8.17 Hz), 7.21 (1H, dd, J=1.95, 8.78 Hz), 7.35–7.44 (2H, m), 7.83 (1H, d, J=1.22 Hz), 7.92 (1H, d, J=0.98 Hz), 8.36 (1H, s), 12.83 (1H, s)

Example 96

N-[2-fluoro-6-(trifluoromethyl)benzyl]-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of 2-fluoro-6-trifluorophenylacetic acid (158 mg, 0.75 mmol) in toluene, and the mixture was stirred at 110° C. for 60 min.

Thereafter, 5-aminoindazole (100 mg, 0.75 mmol,. 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (12 mg, 4.5%).

MS m/z: 352 $^1$H-NMR δ: 4.52 (2H, d, J=5.12 Hz), 6.36 (1H, t, J=5.37 Hz), 7.21 (1H, dd, J=1.83, 8.78 Hz), 7.40 (1H, d, J=8.78 Hz), 7.59–7.64 (3H, m), 7.84 (1H, d, J=1.22 Hz), 8.35 (1H, s), 12.84 (1H, s)

Example 97

N-(2,3,4,5,6-Pentafluorobenzyl)-N'-(4-pyridyl)urea

Diphenylphosphoryl azide (146 mg, 0.53 mmol, 1.2 eq) and triethylamine (54 mg, 0.53 mmol, 1.2 eq) were added to a solution of 2,3,4,5,6-pentafluorophenylacetic acid (100 mg, 0.44 mmol) in toluene, and the mixture was stirred at 110° C. for 60 min.

Thereafter, 4-aminopyridine (42 mg, 0.44 mmol, 1.0 eq) and a minor amount of DMF were added thereto, and the mixture was stirred at 110° C. for 2.5 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (52 mg, 36.9%).

MS m/z: 317 $^1$H-NMR δ: 4.43 (2H, d, J=4.88 Hz), 7.01 (1H, t, J=5.73 Hz), 7.34 (2H, dd, J=1.46, 4.88 Hz), 8.28 (2H, d, J=6.34 Hz), 9.00 (1H, s)

Example 98

N-(1,3-Dioxo-2,3-dihydro-1H-5-isoindolyl)-N'-(2,3,4,5,6-pentafluorobenzyl)urea

Diphenylphosphoryl azide (248 mg, 0.90 mmol, 1.2 eq) and triethylamine (91 mg, 0.90 mmol, 1.2 eq) were added to a solution of 2,3,4,5,6-pentafluorophenylacetic acid (158 mg, 0.75 mmol) in toluene, and the mixture was stirred at 110° C. for 60 min.

Thereafter, 4-aminophthalimide (59 mg, 0.75 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (12 mg, 7.0%).

MS m/z: 385 $^1$H-NMR δ: 4.45 (2H, d, J=5.12 Hz), 7.07 (1H, t, J=5.98 Hz), 7.58 (1H, dd, J=1.71, 8.05 Hz), 7.66 (1H, d, J=8.05 Hz), 7.97 (1H, d, J=1.95 Hz), 9.30 (1H, s), 11.09 (1H, s)

Example 99

N-(1,3-Dioxo-2,3-dihydro-1H-5-isoindolyl)-N'-(2,4,6-trifluorobenzyl)urea

Diphenylphosphoryl azide (198 mg, 0.72 mmol, 1.2 eq) and triethylamine (73 mg, 0.72 mmol, 1.2 eq) were added to a solution of 2,4,6-trifluorophenylacetic acid (114 mg, 0.60 mmol) in toluene, and the mixture was stirred at 110° C. for 60 min.

Thereafter, 4-aminophthalimide (97 mg, 0.60 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (97 mg, 46.4%).

MS m/z: 349 $^1$H-NMR δ: 4.36 (2H, d, J=4.64 Hz), 6.91 (1H, t, J=5.73 Hz), 7.19 (2H, t, J=8.66 Hz), 7.57 (1H, dd, J=1.71, 8.05 Hz), 7.66 (1H, d, J=8.29 Hz), 7.98 (1H, d, J=1.71 Hz), 9.17 (1H, s), 11.08 (1H, s)

Example 100

N-(2,4-Dichlorobenzyl)-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of 2,4-dichlorophenylacetic acid (154 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (12 mg, 4.8%).

MS m/z: 334, 336 $^1$H-NMR δ: 4.35 (2H, d, J=5.86 Hz), 6.64 (1H, t, J=5.86 Hz), 7.26 (1H, dd, J=1.71, 8.90 Hz), 7.39–7.47 (3H, m), 7.61 (1H, d, J=1.71 Hz), 7.85 (1H, s), 7.93 (1H, s), 8.63 (1H, s), 12.85 (1H, s)

Example 101

N-(1H-5-Indazolyl)-N'-(2,3,6-trichloro-benzyl)urea

Diphenylphosphoryl azide (248 mg, 0.90 mmol, 1.2 eq) and triethylamine (91 mg, 0.90 mmol, 1.2 eq) were added to a solution of 2,3,6-trichlorophenylacetic acid (180 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (10 mg, 3.6%).

MS m/z: 368, 370 $^1$H-NMR δ: 4.62 (2H, d, J=5.37 Hz), 6.51 (1H, t, J=5.49 Hz), 7.21 (1H, d, J=8.78 Hz), 7.40 (1H, d, J=9.03 Hz), 7.55 (1H, d, J=8.78 Hz), 7.66 (1H, d, J=8.78 Hz), 7.85 (1H, s), 7.93 (1H, s), 8.38 (1H, s), 12.84 (1H, s)

Example 102

N-(2-Chloro-6-fluorobenzyl)-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of 2-chloro-6-fluorophenylacetic acid (142 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (12 mg, 5.0%).

MS m/z: 317, 319 $^1$H-NMR δ: 4.47 (2H, d, J=5.61 Hz), 6.48 (1H, t, J=5.61 Hz), 7.18–7.28 (2H, m), 7.34–7.43 (3H, m), 7.84 (1H, s), 7.92 (1H, s), 8.39 (1H, s), 12.84 (1H, s)

Example 103

N-(1H-5-Indazolyl)-N'-(2,4,6-trifluorobenzyl)urea

Diphenylphosphoryl azide (248 mg, 0.90 mmol, 1.2 eq) and triethylamine (91 mg, 0.90 mmol, 1.2 eq) were added to a solution of 2,4,6-trifluorophenylacetic acid (143 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (23 mg, 9.6%).

MS m/z: 320 $^1$H-NMR δ: 4.34 (2H, d, J=5.61 Hz), 6.53 (1H, t, J=5.86 Hz), 7.18 (2H, t, J=8.78 Hz), 7.21 (1H, dd, J=1.95, 8.78 Hz), 7.39 (1H, d, J=9.03 Hz), 7.82 (1H, d, J=0.98 Hz), 7.92 (1H, s), 8.36 (1H, s), 8.36 (1H, s), 12.83 (1H, s)

Example 104

N-(2-Chlorobenzyl)-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of 2-chlorophenylacetic acid (128 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (19 mg, 8.4%).

MS m/z: 300 $^1$H-NMR δ: 4.38 (2H, d, J=5.61 Hz), 6.60 (1H, t, J=5.98 Hz), 7.25–7.37 (3H, m), 7.39–7.44 (2H, m), 7.45 (1H, dd, J=1.46, 7.81 Hz), 7.85 (1H, s), 7.93 (1H, s), 8.59 (1H, s), 12.84 (1H, s)

Example 105

N-Cyclohexylmethyl-N'-(1H-5-indazolyl)urea

Diphenylphosphoryl azide (248 mg, 0.90 mmol, 1.2 eq) and triethylamine (91 mg, 0.90 mmol, 1.2 eq) were added to a solution of cyclohexylacetic acid (107 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (15 mg, 7.4%).

MS m/z: 272 $^1$H-NMR δ: 0.91 (2H, q, J=11.22 Hz), 1.10–1.26 (2H, m), 1.32–1.44 (1H, m), 1.59–1.74 (6H, m), 2.95 (2H, t, J=5.86 Hz), 6.07 (1H, t, J=5.73 Hz), 7.23 (1H, d, J=9.03 Hz), 7.39 (1H, d, J=8.78 Hz), 7.83 (1H, s), 7.92 (1H, s), 8.28 (1H, s), 12.82 (1H, s)

Example 106

N-(2,6-Dichlorobenzyl)-N'-(1H-5-indazolyl)urea

Diphenylphosphoryl azide (198 mg, 0.72 mmol, 1.2 eq) and triethylamine (73 mg, 0.72 mmol, 1.2 eq) were added to a solution of 2,6-dichlorophenylacetic acid (123 mg, 0.60 mmol) in toluene, and the mixture was stirred at 110° C. for 60 min.

Thereafter, 5-aminoindazole (80 mg, 0.60 mmol, 1.0 eq) and a minor amount of DMF were added thereto, and the mixture was stirred at 110° C. for 2.5 hr.

After the completion of the reaction, water and ethyl acetate were added thereto, and the precipitated crystal was collected by filtration and was washed with ethyl acetate to give the title compound as a crystal (7 mg, 3.5%).

MS m/z: 334, 336 $^1$H-NMR δ: 4.58 (2H, d, J=4.88 Hz), 6.40 (1H, t, J=5.24 Hz), 7.21 (1H, dd, J=1.83, 8.90 Hz), 7.34–7.42 (2H, m), 7.51 (2H, d, J=8.05 Hz), 7.85 (1H, s), 7.93 (1H, s), 8.38 (1H, s), 12.84 (1H, s)

Example 107

N-(1H-5-Indazolyl)-N'-(1-naphthylmethyl)urea

Diphenylphosphoryl azide (248 mg, 0.90 mmol, 1.2 eq) and triethylamine (91 mg, 0.90 mmol, 1.2 eq) were added to a solution of 1-naphthylacetic acid (140 mg, 0.75 mmol) in toluene, and the mixture was stirred at 110° C. for 60 min.

Thereafter, 5-aminoindazole (100 mg, 0.75 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (20 mg, 8.4%).

MS m/z: 316 $^1$H-NMR δ: 4.78 (2H, d, J=5.61 Hz), 5.78 (1H, t, J=5.61 Hz), 7.26 (1H, dd, J=1.95, 8.78 Hz), 7.41 (1H, d, J=8.78 Hz), 7.47–7.62 (4H, m), 7.84–7.88 (2H, m), 7.93–7.98 (2H, m), 8.16 (1H, d, J=8.29 Hz), 8.45 (1H, s), 12.85 (1H, s)

Example 108

N-(Pyridyl)-N'-(2,3,6-trifluorobenzyl)urea

Diphenylphosphoryl azide (173 mg, 0.63 mmol, 1.2 eq) and triethylamine (64 mg, 0.63 mmol, 1.2 eq) were added to a solution of 2,3,6-trifluorophenylacetic acid (100 mg, 0.53 mmol) in toluene, and the mixture was stirred at 110° C. for 60 min.

Thereafter, 4-aminopyridine (50 mg, 0.53 mmol, 1.0 eq) and a minor amount of DMF were added thereto, and the mixture was stirred at 110° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (62 mg, 42.2%).

MS m/z: 281 $^1$H-NMR δ: 4.41 (2H, d, J=5.61 Hz), 6.94 (1H, t, J=5.86 Hz), 7.10–7.17 (1H, m), 7.34 (2H, dd, J=1.59, 4.76 Hz), 7.42–7.47 (1H, m), 8.28 (2H, dd, J=1.46, 4.88 Hz), 8.94 (1H, s)

Example 109

N-(1,3-Dioxo-2,3-dihydro-1H-5-isoindolyl)-N'-(2,3,6-trifluorobenzyl)urea

Diphenylphosphoryl azide (173 mg, 0.63 mmol, 1.2 eq) and triethylamine (64 mg, 0.63 mmol, 1.2 eq) were added to a solution of 2,3,6-trifluorophenylacetic acid (100 mg, 0.53 mmol) in toluene, and the mixture was stirred at 110° C. for 60 min.

Thereafter, 4-aminophthalimide (85 mg, 0.53 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give the title compound as a crystal (100 mg, 54.6%).

MS m/z: 349 $^1$H-NMR δ: 4.43 (2H, d, J=5.37 Hz), 6.98 (1H, t, J=5.86 Hz), 7.11–7.18 (1H, m), 7.40–7.50 (1H, m), 7.58 (1H, dd, J=1.83, 8.05 Hz), 7.66 (1H, d, J=8.05 Hz), 7.98 (1H, d, J=1.46 Hz), 9.21 (1H, s), 11.08 (1H, s)

Example 110

N-(1H-5-Indazolyl)-N'-(2,3,6-trifluorobenzyl)urea

Diphenylphosphoryl azide (173 mg, 0.63 mmol, 1.2 eq) and triethylamine (64 mg, 0.63 mmol, 1.2 eq) were added to a solution of 2,3,6-trifluorophenylacetic acid (100 mg, 0.53 mmol) in toluene, and the mixture was stirred at 110° C. for 60 min.

Thereafter, 5-aminoindazole (70 mg, 0.53 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate as a crystal (15 mg, 8.9%).

MS m/z: 320 $^1$H-NMR δ: 4.41 (2H, d, J=5.61 Hz), 6.62 (1H, t, J=5.86 Hz), 7.10–7.17 (1H, m), 7.21 (1H, dd, J=1.83, 8.78 Hz), 7.40 (1H, d, J=8.78 Hz), 7.40–7.48 (1H, m), 7.82 (1H, d, J=1.71 Hz), 7.92 (1H, s), 8.41 (1H, s), 12.85 (1H, s)

Example 111

N-(3-Nitrobenzyl)-N'-(4-pyridyl)urea

Diphenylphosphoryl azide (182 mg, 0.66 mmol, 1.2 eq) and triethylamine (67 mg, 0.66 mmol, 1.2 eq) were added to a solution of 3-nitrophenylacetic acid (100 mg, 0.55 mmol) in toluene, and the mixture was stirred at 110° C. for 60 min.

Thereafter, 4-aminopyridine (52 mg, 0.55 mmol, 1.0 eq) and a minor amount of DMF were added thereto, and the mixture was stirred at 110° C. for 3 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound as a crystal (25 mg, 16.7%).

MS m/z: 273 $^1$H-NMR δ: 4.41 (2H, d, J=6.10 Hz), 7.07 (1H, t, J=5.98 Hz), 7.38 (2H, dd, J=1.59, 4.76 Hz), 7.64 (1H, t, J=7.81 Hz), 7.78 (1H, d, J=7.81 Hz), 8.12 (1H, dd, J=1.46, 8.05 Hz), 8.17 (1H, s), 8.29 (2H, dd, J=1.46, 4.88 Hz), 9.19 (1H, s)

Example 112

N-(3-Aminobenzyl)-N'-(1,3-dioxo-2,3-dihydro-1H-5-isoindolyl)urea

Diphenylphosphoryl azide (182 mg, 0.66 mmol, 1.2 eq) and triethylamine (67 mg, 0.66 mmol, 1.2 eq) were added to a solution of 3-nitrophenylacetic acid (100 mg, 0.55 mmol) in toluene, and the mixture was stirred at 110° C. for 60 min.

Thereafter, 4-aminophthalimide (89 mg, 0.55 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate. The resultant crystal was washed with chloroform/methanol to give a nitro compound (45 mg, 24.1%) containing a minor amount of 4-aminophthalimide as the starting compound.

DMF was added to the nitro compound (containing the starting compound, 40 mg, 0.12 mmol). Palladium hydroxide (one small spatula) was added thereto, and the mixture was stirred under a hydrogen atmosphere at room temperature for 60 min.

After the completion of the reaction, the reaction solution was filtered through Celite, and washing with ethyl acetate was carried out. Water was then added to the filtrate, and the mixture was extracted with ethyl acetate. The ethyl acetate layer was washed with water and saturated brine and was dried over sodium sulfate. The solvent was then removed by distillation under the reduced pressure to give the title compound as a crystal (16 mg, 44.4%).

MS m/z: 310 $^1$H-NMR δ: 4.17 (2H, d, J=5.37 Hz), 5.03 (2H, s), 6.38 (1H, s), 6.44 (2H, d, J=7.81 Hz), 6.51 (1H, s), 6.79 (1H, dd, J=1.95, 8.05 Hz), 6.96 (1H, t, J=7.68 Hz), 7.60 (1H, dd, J=1.71, 8.29 Hz), 7.67 (1H, d, J=8.29 Hz), 7.74 (1H, s), 8.03 (1H, d, J=1.95 Hz), 11.08 (1H, s)

Example 113

N-(4-Hydroxy-3-methoxybenzyl)-N'-(1H-5-indazolyl)urea

Diphenylphosphoryl azide (242 mg, 0.88 mmol, 1.2 eq) and triethylamine (89 mg, 0.88 mmol, 1.2 eq) were added to a solution of 4-benzyloxy-3-methoxyphenylacetic acid (200 mg, 0.73 mmol) in toluene, and the mixture was stirred at 110° C. for 60 min.

Thereafter, 5-aminoindazole (98 mg, 0.73 mmol, 1.0 eq) and a minor amount of DMF were added thereto, and the mixture was stirred at 110° C. for 3 hr.

After the completion of the reaction, water and ethyl acetate were added thereto, and the precipitated crystal was collected by filtration and was washed with ethyl acetate to give a crystal (26 mg, 8.8%).

Palladium hydroxide (one small spatula) was added to a solution of the resultant crystal (20 mg, 0.05 mmol) in DMF, and the mixture was stirred under a hydrogen atmosphere at room temperature for 60 min.

After the completion of the reaction, the reaction solution was filtered through Celite, and washing with ethyl acetate was carried out. Water was then added to the filtrate, and the mixture was extracted with ethyl acetate. The ethyl acetate layer was washed with water and saturated brine and was dried over sodium sulfate. The solvent was then removed by distillation under the reduced pressure to give the title compound as a crystal (8 mg, 53.3%).

MS m/z: 312 $^1$H-NMR δ: 3.75 (3H, s), 5.69 (2H, d, J=5.61 Hz), 6.39 (1H, t, J=5.61 Hz), 6.72 (2H, s), 6.89 (1H, s), 7.25 (1H, dd, J=1.83, 8.78 Hz), 7.40 (1H, d, J=8.78 Hz), 7.85 (1H, s), 7.93 (1H, s), 8.40 (1H, s), 8.82 (1H, s), 12.84 (1H, s)

Example 114

N-[1-(3,4-Dichlorobenzyl)-4-piperidyl]-N-(1H-5-indazolyl)amine

Potassium carbonate (138 mg, 1.0 mmol, 2.0 eq) was added to a solution of 4-piperidone monohydrate hydrochloride (77 mg, 0.50 mmol) and 3,4-dichlorobenzyl chloride (98 mg, 0.50 mmol, 1.0 eq) in acetonitrile, and the mixture was stirred at room temperature for 15 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (53 mg, 0.40 mmol, 0.8 eq) was added to a solution of the resultant oil in methanol. Acetic acid (one drop) was added thereto, and the mixture was stirred at room temperature for 5 min. A borane-pyridine complex (56 mg, 0.60 mmol, 1.2 eq) was added thereto under ice cooling, and the mixture was stirred at room temperature for 18 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (100 mg, 53.2%).

MS m/z: 375 $^1$H-NMR δ: 1.34–1.45 (2H, m), 1.94 (2H, d, J=11.47 Hz), 2.12 (2H, t, J=10.86 Hz), 2.77 (2H, d, J=11.47 Hz), 3.12–3.30 (1H, m), 3.49 (2H, s), 5.10 (1H, d, J=7.56 Hz), 6.67 (1H, s), 6.81 (1H, dd, J=2.07, 8.90 Hz), 7.25 (1H, d, J=8.78 Hz), 7.31 (1H, dd, J=1.83, 8.17 Hz), 7.55 (1H, d, J=1.95 Hz), 7.58 (1H, d, J=8.05 Hz), 7.73 (1H, s), 12.55 (1H, s)

Example 115

N-[1-(3,4-Dimethylbenzyl)-4-piperidyl]-N-(1H-5-indazolyl)amine

Potassium carbonate (138 mg, 1.0 mmol, 2.0 eq) was added to a solution of 4-piperidone monohydrate hydrochloride (77 mg, 0.50 mmol) and 3,4-dimethylbenzyl chloride (97 mg, 0.50 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (53 mg, 0.40 mmol, 0.8 eq) was added to a solution of the resultant oil in methanol. Acetic acid (one drop) was added thereto, and the mixture was stirred at room temperature for 5 min. A borane-pyridine complex (56 mg, 0.60 mmol, 1.2 eq) was added thereto under ice cooling, and the mixture was stirred at room temperature for 4 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (45 mg, 26.9%).

MS m/z: 335 $^1$H-NMR δ: 1.32–1.45 (2H, m), 1.94 (2H, d, J=11.71 Hz), 2.19 (3H, s), 2.13–2.18 (2H, m), 2.21 (3H, s), 2.76–2.87 (2H, m), 3.15–3.25 (1H, m), 3.43 (2H, s), 5.07–5.19 (1H, m), 6.66 (1H, s), 6.81 (1H, dd, J=1.95, 8.78 Hz), 7.01 (1H, d, J=7.07 Hz), 7.07 (1H, s), 7.08 (1H, d, J=7.07), 7.25 (1H, d, J=8.78 Hz), 7.73 (1H, s), 12.55 (1H, s)

Example 116

N-(1H-5-Indazolyl)-N-[1-(2-naphthylmethyl)-4-piperidyl]amine

Potassium carbonate (138 mg, 1.0 mmol, 2.0 eq) was added to a solution of 4-piperidone monohydrate hydrochloride (77 mg, 0.50 mmol) and 2-(bromomethyl)naphthalene (110 mg, 0.50 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (53 mg, 0.40 mmol, 0.8 eq) was added to a solution of the resultant oil in methanol. Acetic acid (one drop) was added thereto, and the mixture was stirred at room temperature for 5 min. A borane-pyridine complex (56 mg, 0.60 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (98 mg, 54.9%).

MS m/z: 357 $^1$H-NMR δ: 1.37–1.50 (2H, m), 1.92–2.01 (2H, m), 2.13–2.22 (2H, m), 2.83–2.95 (2H, m), 3.18–3.29 (1H, m), 3.63–3.76 (2H, m), 5.10–5.15 (1H, m), 6.67 (1H, s), 6.82 (1H, dd, J=1.95, 8.78 Hz), 7.25 (1H, d, J=8.78 Hz), 7.46–7.54 (3H, m), 7.73 (1H, s), 7.81 (1H, s), 7.86–7.92 (3H, m), 12.55 (1H, s)

Example 117

N-[1-(3-Fluorobenzyl)-4-piperidyl]-N-(1H-5-indazolyl)amine

Potassium carbonate (276 mg, 2.0 mmol, 2.0 eq) was added to a solution of 4-piperidone monohydrate hydrochloride (154 mg, 1.0 mmol) and 3-fluorobenzyl chloride (145 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (195 mg, 60.0%).

MS m/z: 324 $^1$H-NMR δ: 1.34–1.45 (2H, m), 1.94 (2H, d, J=11.22 Hz), 2.11 (2H, t, J=10.73 Hz), 2.79 (2H, d, J=11.71 Hz), 3.15–3.27 (1H, m), 3.50 (2H, s), 5.10 (1H, d, J=8.05 Hz), 6.66 (1H, s), 6.81 (1H, dd, J=1.95, 9.03 Hz), 7.63 (1H, dt, J=2.68, 8.78 Hz), 7.12 (1H, d, J=8.78 Hz), 7.15 (1H, d, J=7.56 Hz), 7.25 (1H, d, J=8.78 Hz), 7.36 (1H, q, J=7.34 Hz), 7.72 (1H, s), 12.55 (1H, s)

Example 118

N-(1H-5-Indazolyl)-N-{1-[4-(trifluoromethyl)benzyl]-4-piperidyl}amine

Potassium carbonate (276 mg, 2.0 mmol, 2.0 eq) was added to a solution of 4-piperidone monohydrate hydrochloride (154 mg, 1.0 mmol) and 4-trifluoromethylbenzyl chloride (239 mg, 1.0 mmol, 1.0 eq) in acetonitrile, and the mixture was stirred. at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (210 mg, 62.4%).

MS m/z: 374 $^1$H-NMR δ: 1.35–1.46 (2H, m), 1.95 (2H, d, J=10.98 Hz), 2.14 (2H, t, J=11.22 Hz), 2.79 (2H, d, J=11.22 Hz), 3.12–3.24 (1H, m), 3.58 (2H, s), 5.11 (1H, d, J=8.05 Hz), 6.67 (1H, s), 6.82 (1H, dd, J=2.07, 8.78 Hz), 7.25 (1H, d, J=8.78 Hz), 7.54 (2H, d, J=8.05 Hz), 7.69 (2H, d, J=8.05 Hz), 7.73 (1H, s), 12.55 (1H, s)

Example 119

N-(1H-5-Indazolyl)-N-[1-(3-methoxybenzyl)-4-piperidyl]amine

Potassium carbonate (276 mg, 2.0 mmol, 2.0 eq) was added to a solution of 4-piperidone monohydrate hydrochloride (154 mg, 1.0 mmol) and 3-methoxybenzyl chloride (157 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (167 mg, 49.6%).

MS m/z: 336 $^1$H-NMR δ: 1.38–1.48 (2H, m), 1.92–2.00 (2H, m), 2.20–2.31 (2H, m), 2.68–2.90 (2H, m), 3.20–3.28 (1H, m), 3.48–3.70 (2H, m), 3.75 (3H, S), 5.10–5.17 (1H, m), 6.67 (1H, s), 6.81 (1H, dd, J=1.95, 9.03 Hz), 6.83–6.93 (3H, m), 7.22–7.28 (2H, m), 7.73 (1H, s), 12.56 (1H, s)

Example 120

N-[1-(4-Ethylbenzyl)-4-piperidyl]-N-(1H-5-indazolyl)amine

Potassium carbonate (276 mg, 2.0 mmol, 2.0 eq) was added to a solution of 4-piperidone monohydrate hydrochloride (154 mg, 1.0 mmol) and 4-ethylbenzyl chloride [containing 30% of 2-position isomer] (155 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (105 mg, 31.4%).

MS m/z: 334 $^1$H-NMR δ: 1.34 (3H, t, J=7.56 Hz), 1.47–1.59 (2H, m), 2.09 (2H, d, J=11.71 Hz), 2.19 (2H, t, J=10.49 Hz), 2.90 (2H, d, J=11.95 Hz), 3.28–3.37 (1H, m), 3.54 (2H, s), 6.79 (1H, dd, J=2.20, 8.29 Hz), 6.81 (1H, s), 7.16 (2H, d, J=8.05 Hz), 7.25 (2H, d, J=8.05 Hz), 7.29 (1H, d, J=8.78 Hz), 7.87 (1H, d, J=0.98 Hz)

Example 121

N-[1-(2-Ethylbenzyl)-4-piperidyl]-N-(1H-5-indazolyl)amine

In the purification of the compound of Example 120 by column chromatography [silica gel, chloroform/methanol], the 2-position isomer stemmed from the starting compound was obtained (52 mg, 15.5%).

MS m/z: 334 $^1$H-NMR δ: 1.23 (3H, t, J=7.44 Hz), 1.43–1.55 (2H, m), 2.07 (2H, d, J=11.95 Hz), 2.21 (2H, t, J=10.86 Hz), 2.74 (2H, q, J=7.48 Hz), 2.89 (2H, d, J=11.71 Hz), 3.29–3.39 (1H, m), 3.54 (2H, s), 6.78 (1H, dd, J=2.07, 8.66 Hz), 6.81 (1H, d, J=1.71 Hz), 7.11–7.25 (3H, m), 7.26 (1H, d, J=7.81 Hz), 7.32 (1H, d, J=7.32 Hz), 7.88 (1H, d, J=0.98 Hz)

Example 122

N-(1H-5-Indazolyl)-N-[1-(4-isopropylbenzyl)-4-piperidyl]amine

Potassium carbonate (276 mg, 2.0 mmol, 2.0 eq) was added to a solution of 4-piperidone monohydrate hydrochloride (154 mg, 1.0 mmol) and 4-isopropylbenzyl chloride [containing 10% of 2-position isomer] (169 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (88 mg, 25.2%).

MS m/z: 348 $^1$H-NMR δ: 1.24 (3H, s), 1.26 (3H, s), 1.45–1.56 (2H, m), 2.08 (2H, d, J=12.20 Hz), 2.18 (2H, t, J=11.34 Hz), 2.86–2.29 (3H, m), 3.27–3.36 (1H, m), 3.52 (2H, s), 6.80 (1H, dd, J=2.20, 9.03 Hz), 6.81 (1H, s), 7.18 (2H, d, J=8.05 Hz), 7.25 (2H, d, J=8.78 Hz), 7.28 (1H, d, J=8.54 Hz), 7.87 (1H, d, J=0.98 Hz)

Example 123

N-(1H-5-Indazolyl)-N-[1-(3-phenoxybenzyl)-4-piperidyl]amine

Potassium carbonate (276 mg, 2.0 mmol, 2.0 eq) was added to a solution of 4-piperidone monohydrate hydrochloride (154 mg, 1.0 mmol) and 3-phenoxybenzyl chloride (219 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was purified by column chromatography [silica gel, chloroform/methanol] to give the title compound (164 mg, 41.1%).

MS m/z: 398 $^1$H-NMR δ: 1.44–1.56 (2H, m), 2.08 (2H, d, J=12.20 Hz), 2.13–2.23 (2H, m), 2.87 (2H, d, J=11.47 Hz), 3.27–3.35 (1H, m), 3.53 (2H, s), 6.80 (1H, dd, J=2.20, 8.05 Hz), 6.81 (1H, s), 6.89 (1H, dd, J=1.71, 8.05 Hz), 6.99–7.12 (5H, m), 7.27–7.36 (4H, m), 7.87 (1H, d, J=0.98 Hz)

Example 124

N-(1H-5-Indazolyl)-N-[1-(4-methyl-3-nitrobenzyl)-5-piperidyl]amine

Potassium carbonate (276 mg, 2.0 mmol, 2.0 eq) was added to a solution of 4-piperidone monohydrate hydrochloride (154 mg, 1.0 mmol) and 4-methyl-3-nitrobenzyl chloride (186 mg, 1.0 mmol, 1.0 eq) in acetonitrile, and the mixture was stirred at room temperature for 17 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure.

5-Aminoindazole (106 mg, 0.80 mmol, 0.8 eq) was added to a solution of the resultant oil in methanol. Acetic acid (one drop) was added thereto, and the mixture was stirred at room temperature for 5 min. A borane-pyridine complex (112 mg, 1.20 mmol, 1.2 eq) was added thereto under ice cooling, and the mixture was stirred at room temperature for 15 hr.

After the completion of the reaction, the reaction solution was poured into an aqueous sodium hydrogencarbonate solution, and the mixture was extracted with chloroform. The chloroform layer was washed with water and saturated brine and was dried over sodium sulfate, and the solvent was then removed by distillation under the reduced pressure. The residue was washed with chloroform to give the title compound as a crystal (103 mg, 35.5%).

MS m/z: 366 $^1$H-NMR δ: 1.34–1.46 (2H, m), 1.94 (2H, d, J=10.98 Hz), 2.13 (2H, t, J=10.37 Hz), 2.50 (3H, s), 2.79 (2H, d, J=11.71 Hz), 3.14–3.26 (1H, m), 3.56 (2H, s), 5.11 (1H, d, J=7.81 Hz), 6.67 (1H, s), 6.52 (1H, dd, J=2.07, 8.78 Hz), 7.25 (1H, d, J=8.78 Hz), 7.46 (1H, d, J=7.81 Hz), 7.56 (1H, dd, J=1.59, 7.81 Hz), 7.73 (1H, s), 7.91 (1H, d, J=1.46 Hz), 12.55 (1H, s)

Example 125

N-(1-Ethyl-4-piperidyl)-N-(1H-5-indazolyl)-amine

1-Ethyl-4-piperidone (76 mg), 5-aminoindazole (67 mg), and acetic acid (0.02 ml) were dissolved in methanol (1 ml), and a borane-pyridine complex (0.06 ml) was added dropwise to the solution at room temperature. The reaction-mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (50 mg, yield 41%).

$^1$H-NMR (CDCl$_3$, 400 MHz): 1.06 (t, J=7.3 Hz, 3H), 1.42–1.53 (m, 2H), 2.02–2.17 (m, 4H), 2.42 (q, J=7.1 Hz, 2H), 2.86–2.95 (m, 2H), 3.21–3.33 (m, 1H), 6.70–6.76 (m, 2H), 7.23 (d, J=8.5 Hz, 1H), 7.81 (s, 1H) Mass spectrum (ESI-MS, m/z): 245 (M$^+$+1)

Example 126

N-(1-Benzyl-4-piperidyl)-N-(1H-5-indazolyl)amine

1-Benzyl-4-piperidone (635 mg), 5-aminoindazole (532 mg), and acetic acid (0.20 ml) were dissolved in methanol (10 ml), and a borane-pyridine complex (0.51 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (1.00 g, yield 82%).

$^1$H-NMR (CDCl$_3$, 400 MHz): 1.46–1.59 (m, 2H), 2.05–2.13 (m, 4H), 2.15–2.25 (m, 2H), 2.85–2.93 (m, 2H), 3.27–3.37 (m, 1H), 3.56 (s, 2H), 6.77–6.82 (m, 2H), 7.24–7.35 (m, 6H), 7.88 (s, 1H) Mass spectrum (ESI-MS, m/z): 307 (M$^+$+1)

Formation of Salt of Compound Prepared in Example 126

The compound prepared in Example 126 was dissolved in hydrochloric acid-methanol, and the mixture was then allowed to stand at room temperature for 18 hr. The resultant white precipitate was then collected by filtration, was washed with methanol which had been cooled in an ice bath, and was dried under the reduced pressure to give the title compound.

Example 127

N-(1-Benzyl-4-piperidyl)-N-(1H-5-indazolyl)amine hydrochloride

1-Benzyl-4-piperidone (11.44 ml), 5-aminoindazole (10.42 g), and acetic acid (1 ml) were dissolved in methanol (100 ml), and a borane-pyridine complex (10.10 ml) was added dropwise thereto at room temperature. The reaction mixture was stirred at room temperature for 18 hr. A saturated aqueous sodium hydrogencarbonate solution (100 ml) was then added thereto, and the mixture was extracted with chloroform-propanol (3/1). The organic layer was dried over anhydrous sodium sulfate, and the solvent was removed by distillation under the reduced pressure. Hydrochloric acid-methanol (100 ml) was added to the residue. The mixture was allowed to stand at room temperature for 18 hr, and the resultant white precipitate was then collected by filtration, was washed with methanol which had been cooled in an ice bath, and was dried under the reduced pressure to give 18.86 g of the title compound.

$^1$H-NMR (DMSO-d$_6$, 400 MHz): 2.14–2.30 (m, 4H), 2.88–3.10 (m, 2H), 3.40–3.50 (m, 2H), 3.70–3.80 (m, 1H), 4.25 (s, 2H), 7.26–7.76 (m, 6H), 7.99 (s, 1H), 8.23 (s, 1H), 10.96 (s, 1H), 11.45 (s, 1H) Mass spectrum (ESI-MS, m/z): 307 (M$^+$+1)

Example 128

N-(1H-5-Indazolyl)-N-(4-piperidyl)amine tert-Butyl-4-oxo-1-piperidine carboxylate (796 mg), 5-aminoindazole (532 mg), and acetic acid (0.2 ml) were dissolved in methanol (10 ml), and a borane-pyridine complex (0.51 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give an intermediate (750 mg, yield 60%).

This intermediate (107 mg) was dissolved in chloroform (3 ml), and trifluoroacetic acid (2 ml) was added to the solution. The reaction mixture was stirred at room temperature for 3 hr and was then concentrated, and trifluoroacetic acid was removed. A saturated aqueous sodium hydrogencarbonate solution (2 ml) was then added to the residue, and the mixture was extracted with chloroform-propanol (3/1). The organic layer was dried over anhydrous sodium sulfate, and the solvent was removed by distillation under the reduced pressure to give the title compound (24 mg, yield 56%).

$^1$H-NMR (CDCl$_3$, 400 MHz): 1.28–1.42 (m, 2H), 2.08–2.17 (m, 2H), 2.70–2.80 (m, 2H), 3.12–3.20 (m, 2H), 3.34–3.45 (m, 1H), 6.79–6.86 (m, 2H), 7.30 (d, J=8.8 Hz, 1H), 7.88 (s, 1H) Mass spectrum (ESI-MS, m/z): 217 (M$^+$+1)

Example 129

N-Cyclohexyl-N-(1H-5-indazolyl)amine

Cyclohexanone (59 mg), 5-aminoindazole (67 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (94 mg, yield 87%).

$^1$H-NMR (CDCl$_3$, 400 MHz): 1.12–1.30 (m, 3H), 1.33–1.46 (m, 2H), 1.62–1.72 (m, 1H), 1.72–1.83 (m, 2H), 3.22–3.31 (m, 1H), 6.78–6.84 (m, 2H), 7.29 (d, J=8.5 Hz, 1H), 7.88 (s, 1H) Mass spectrum (FD, m/z): 215 (M$^+$)

Example 130

N-(1H-5-Indazolyl)-N-(1-phenethyl-4-piperidyl) amine 1-(2-Phenethyl)-4-piperidone (142 mg), 5-aminoindazole (67 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr.

A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (104 mg, yield 65%).
$^1$H-NMR (CDCl$_3$, 400 MHz): 1.49–1.61 (m, 2H), 2.10–2.20 (m, 2H), 2.20–2.30 (m, 2H), 2.60–2.68 (m, 2H), 2.80–2.87 (m, 2H), 2.97–3.05 (m, 2H), 3.30–3.40 (m, 1H), 6.79–6.84 (m, 2H), 7.18–7.23 (m, 3H), 7.26–7.33 (m, 3H), 7.88 (s, 1H) Mass spectrum (ESI-MS, m/z): 321 (M$^+$+1)

Example 131

N-(1H-5-Indazolyl)-N-[1-(2-pyridylmethyl)-4-piperidyl]amine 2-(Chloromethyl)pyridine hydrochloride (82 mg), 4-piperidone monohydrate hydrochloride (77 mg), and potassium carbonate (138 mg) were dissolved in acetonitrile (1 ml), and the solution was stirred at room temperature for 18 hr. The reaction mixture was filtered through Celite, and the filtrate was then concentrated to give an intermediate.
This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (85 mg, yield 55%)
$^1$H-NMR (CDCl$_3$, 400 MHz): 1.50–1.65 (m, 2H), 2.06–2.17 (m, 2H), 2.25–2.40 (m, 2H), 2.90–2.99 (m, 2H), 3.30–3.40 (m, 1H), 3.73 (s, 2H), 6.79–6.84 (m, 2H), 7.15–7.21 (m, 1H), 7.30 (d, J=8.3 Hz, 1H), 7.44 (d, J=7.8 Hz, 1H), 7.67 (t, J=7.6 Hz, 1H), 7.88 (s, 1H), 8.58 (d, J=4.2 Hz, 1H) Mass spectrum (ESI-MS, m/z): 308 (M$^+$+1)

Example 132

N-(1H-5-Indazolyl)-N-[1-(3-pyridylmethyl)-4-piperidyl]amine 3-(Chloromethyl)pyridine hydrochloride (82 mg), 4-piperidone monohydrate hydrochloride (77 mg), and potassium carbonate (138 mg) were dissolved in acetonitrile (1 ml), and the solution was stirred at room temperature for 18 hr. The reaction mixture was filtered through Celite, and the filtrate was then concentrated to give an intermediate.
This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (57 mg, yield 47%).
$^1$H-NMR (CDCl$_3$, 400 MHz): 1.43–1.52 m, 2H), 2.05–2.14 (m, 2H), 2.16–2.26 (m, 2H), 2.82–2.91 (m, 2H), 3.28–3.38 (m, 1H), 3.55 (s, 2H), 6.78–6.84 (m, 2H), 7.24–7.27 (m, 1H), 7.29 (d, J=9.5 Hz, 1H), 7.68 (t, J=7.6 Hz, 1H), 7.88 (s, 1H), 8.52 (d, J=4.6 Hz, 1H), 8.56 (s, 1H) Mass spectrum (ESI-MS, m/z): 308 (M$^+$+1)

Example 133

N-(1H-5-Indazolyl)-N-[1-(4-pyridylmethyl)-4-piperidyl]amine 4-(Chloromethyl)pyridine hydrochloride (82 mg), 4-piperidone monohydrate hydrochloride (77 mg), and potassium carbonate (138 mg) were dissolved in acetonitrile (1 ml), and the solution was stirred at room temperature for 18 hr. The reaction mixture was filtered through Celite, and the filtrate was then concentrated to give an intermediate.
This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (49 mg, yield 40%).
$^1$H-NMR (CDCl$_3$, 400 MHz): 1.46–1.59 (m, 2H), 2.06–2.15 (m, 2H), 2.17–2.29 (m, 2H), 2.80–2.90 (m, 2H), 3.29–3.39 (m, 1H), 3.54 (s, 2H), 6.79–6.84 (m, 2H), 7.26–7.32 (m, 3H), 7.88 (s, 1H), 8.55 (d, J=6.1 Hz, 2H) Mass spectrum (ESI-MS, m/z): 308 (M$^+$+1)

Example 134

N-[1-(2-Chlorobenzyl)-4-piperidyl]-N-(1H-5-indazolyl)amine

2-Chlorobenzyl chloride (81 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.
This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (109 mg, yield 80%).
$^1$H-NMR (CDCl$_3$, 400 MHz): 1.47–1.60 (m, 2H), 2.06–2.16 (m, 2H), 2.25–2.36 (m, 2H), 2.87–2.97 (m, 2H), 3.30–3.40 (m, 1H), 3.67 (s, 2H), 6.78–6.84 (m, 2H), 7.16–7.34 (m, 4H), 7.35 (d, J=7.8 Hz, 1H), 7.49 (d, J=6.8 Hz, 1H), 7.88 (s, 1H) Mass spectrum (ESI-MS, m/z): 341 (M$^+$+1)

Example 135

N-[1-(3-Chlorobenzyl)-4-piperidyl]-N-(1H-5-indazolyl)amine

3-Chlorobenzyl chloride (81 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (104 mg, yield 79%).

$^1$H-NMR (CDCl$_3$, 400 MHz): 1.45–1.58 (m, 2H), 2.05–2.14 (m, 2H), 2.15–2.25 (m, 2H), 2.82–2.90 (m, 2H), 3.28–3.37 (m, 1H), 3.52 (s, 2H), 6.78–6.83 (m, 2H), 7.18–7.26 (m, 3H), 7.29 (d, J=8.5 Hz, 1H), 7.35 (s, 1H), 7.88 (s, 1H) Mass spectrum (ESI-MS, m/z): 341 (M$^+$+1)

Example 136

N-[1-(4-Chlorobenzyl)-4-piperidyl]-N-(1H-5-indazolyl)amine

4-Chlorobenzyl chloride (81 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (106 mg, yield 79%).

$^1$H-NMR (CDCl$_3$, 400 MHz): 1.45–1.59 (m, 2H), 2.05–2.13 (m, 2H), 2.13–2.25 (m, 2H), 2.81–2.91 (m, 2H), 3.25–3.37 (m, 1H), 3.51 (s, 2H), 6.78–6.82 (m, 2H), 7.27–7.32 (m, 6H), 7.87 (s, 1H) Mass spectrum (ESI-MS, m/z): 341 (M$^+$+1)

Example 137

N-[1-(4-Fluorobenzyl)-4-piperidyl]-N-(1H-5-indazolyl)amine

4-Fluorobenzyl chloride (72 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (102 mg, yield 79%).

$^1$H-NMR (CDCl$_3$, 400 MHz): 1.44–1.58 (m, 2H), 2.05–2.13 (m, 2H), 2.12–2.23 (m, 2H), 2.82–2.92 (m, 2H), 3.27–3.37 (m, 1H), 3.51 (s, 2H), 6.78–6.82 (m, 2H), 6.97–7.05 (m, 2H), 7.26–7.32 (m, 4H), 7.87 (s, 1H) Mass spectrum (ESI-MS, m/z): 325 (M$^+$+1)

Example 138

N-(1H-5-Indazolyl)-N-[1-(4-methoxybenzyl)-4-piperidyl]amine

4-Methoxybenzyl chloride (79 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (100 mg, yield 74%).

$^1$H-NMR (CDCl$_3$, 400 MHz): 1.43–1.56 (m, 2H), 2.03–2.13 (m, 2H), 2.12–2.22 (m, 2H), 2.83–2.92 (m, 2H), 3.26–3.36 (m, 1H), 3.50 (s, 2H), 3.81 (s, 3H), 6.77–6.82 (m, 2H), 6.86 (d, J=8.8 Hz, 2H), 7.24 (d, J=8.5 Hz, 2H), 7.29 (d, J=9.0 Hz, 1H), 7.87 (s, 1H) Mass spectrum (ESI-MS, m/z): 337 (M$^+$+1)

Example 139

N-(1H-5-Indazolyl)-N-[1-(4-methylbenzyl)-4-piperidyl]amine

4-Methylbenzyl chloride (71 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (100 mg, yield 76%).

$^1$H-NMR (CDCl$_3$, 400 MHz): 1.44–1.57 (m, 2H), 2.03–2.13 (m, 2H), 2.12–2.23 (m, 2H), 2.34 (s, 3H), 2.84–2.92 (m, 2H), 3.25–3.36 (m, 1H), 3.52 (s, 2H), 6.77–6.82 (m, 2H), 7.13 (d, J=7.8 Hz, 2H), 7.21 (d, J=8.1 Hz, 2H), 7.28 (d, J=8.5 Hz, 1H), 7.87 (s, 1H) Mass spectrum (ESI-MS, m/z): 321 (M$^+$+1)

Example 140

N-(1H-5-Indazolyl)-N-[1-(3-nitrobenzyl)-4-piperidyl]amine

3-Nitrobenzyl chloride (86 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (91 mg, yield 65%).

$^1$H-NMR (CDCl$_3$, 400 MHz): 1.45–1.60 (m, 2H), 2.07–2.15 (m, 2H), 2.18–2.32 (m, 2H), 2.82–2.92 (m, 2H), 3.30–3.40 (m, 1H), 3.63 (s, 2H), 6.79–6.84 (m, 2H), 7.31 (d, J=9.8 Hz, 1H), 7.49 (d, J=7.8 Hz, 1H), 7.68 (d, J=7.1 Hz, 1H), 7.88 (s, 1H), 8.12 (d, J=6.9 Hz, 1H), 8.23 (s, 1H)

Example 141

N-(1H-5-Indazolyl)-N-[1-(4-nitrobenzyl)-4-piperidyl]amine

4-Nitrobenzyl chloride (86 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (92 mg, yield 65%).

$^1$H-NMR (CDCl$_3$, 400 MHz): 1.46–1.58 (m, 2H), 2.06–2.15 (m, 2H), 2.15–2.30 (m, 2H), 2.80–2.90 (m, 2H), 3.29–3.40 (m, 1H), 3.63 (s, 2H), 6.79–6.83 (m, 2H), 7.31 (d, J=8.8 Hz, 1H), 7.52 (d, J=8.3 Hz, 2H), 7.88 (s, 1H), 8.19 (d, J=8.8 Hz, 2H)

Example 142

N-{1-[4-(Benzyloxy)benzyl]-4-piperidyl}-N-(1H-5-indazolyl)amine

4-Benzyloxybenzyl chloride (116 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (124 mg, yield 75%).

$^1$H-NMR (CDCl$_3$, 400 MHz): 1.44–1.57 (m, 2H), 2.04–2.12 (m, 2H), 2.12–2.22 (m, 2H), 2.83–2.92 (m, 2H), 3.26–3.36 (m, 1H), 3.49 (s, 2H), 5.06 (s, 2H), 6.77–6.82 (m, 2H), 6.93 (d, J=8.8 Hz, 2H), 7.24 (d, J=8.5 Hz, 2H), 7.25–7.46 (m, 6H), 7.87 (s, 1H) Mass spectrum (ESI-MS, m/z): 413 (M$^+$+1)

Example 143

N-[1-(3,5-Dimethoxybenzyl)-4-piperidyl]-N-(1H-5-indazolyl)amine 3,5-Dimethoxybenzyl chloride (94 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (102 mg, yield 69%).

$^1$H-NMR (CDCl$_3$, 400 MHz): 1.45–1.59 (m, 2H), 2.04–2.13 (m, 2H), 2.14–2.25 (m, 2H), 2.84–2.94 (m, 2H), 3.27–3.37 (m, 1H), 3.49 (s, 2H), 3.79 (s, 6H), 6.35–6.39 (m, 1H), 6.50–6.54 (m, 2H), 6.78–6.83 (m, 2H), 7.26–7.31 (m, 1H), 7.87 (s, 1H) Mass spectrum (ESI-MS, m/z): 367 (M$^+$+1)

Example 144

N-{1-[(6-Chloro-1,3-benzodioxol-5-yl)methyl]-4-piperidyl}-N-(1H-5-indazolyl)amine 6-Chloropiperonyl chloride (103 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (120 mg, yield 78%).

$^1$H-NMR (CDCl$_3$, 400 MHz): 1.46–1.58 (m, 2H), 2.05–2.14 (m, 2H), 2.22–2.33 (m, 2H), 2.85–2.93 (m, 2H), 3.29–3.39 (m, 1H), 3.56 (s, 2H), 5.96 (s, 2H), 6.79–6.84 (m, 3H), 7.00 (s, 1H), 7.30 (d, J=8.3 Hz, 1H), 7.88 (s, 1H) Mass spectrum (ESI-MS, m/z): 385 (M$^+$+1)

Example 145

4-{[4-(1H-5-Indazolylamino)piperidino]methyl}phenol

N-{1-[4-(Benzyloxy)benzyl]-4-piperidyl}-N-(1H-5-indazolyl)amine (Example 142, 33 mg) and palladium-charcoal (10 mg) were suspended in ethanol (3 ml), and the suspension was stirred under a hydrogen atmosphere of 1 atm at room temperature for 18 hr. The reaction mixture was filtered through Celite, and the filtrate was then concentrated to give the title compound (21 mg, yield 82%).

$^1$H-NMR (CDCl$_3$, 400 MHz): 1.45–1.55 (m, 2H), 2.04–2.20 (m, 4H), 2.83–2.91 (m, 2H), 3.25–3.35 (m, 1H), 3.47 (s, 2H), 6.70–6.83 (m, 3H), 6.76 (d, J=8.3 Hz, 2H), 7.17 (d, J=8.5 Hz, 2H), 7.29 (d, J=8.8 Hz, 1H), 7.87 (s, 1H) Mass spectrum (ESI-MS, m/z): 323 (M$^+$+1)

Example 146

N-(1-Benzyltetrahydro-1H-pyrrolyl)-N-(1H-5-indazolyl)amine

1-Benzyl-3-pyrrolidinone (105 mg), 5-aminoindazole (67 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (49 mg, yield 34%).

$^1$H-NMR (CDCl$_3$, 400 MHz): 1.66–1.78 (m, 1H), 2.30–2.41 (m, 1H), 2.44–2.53 (m, 1H), 2.61–2.68 (m, 1H), 2.77–2.87 (m, 2H), 3.66 (s, 2H), 4.00–4.08 (m, 1H), 6.73–6.76 (m, 1H), 6.77–6.83 (m, 1H), 7.24–7.36 (m, 6H), 7.88 (s, 1H) Mass spectrum (ESI-MS, m/z): 293 (M$^+$+1)

Formation of Salt of Compound Prepared in Example 146

The compound prepared in Example 146 was dissolved in hydrochloric acid-methanol, and the mixture was then allowed to stand at room temperature for 18 hr. The resultant white precipitate was then collected by filtration, was washed with methanol which had been cooled in an ice bath, and was dried under the reduced pressure to give the title compound.

Example 147

Methyl 3-{[4-(1H-5-indazolylamino)piperidino]methyl}benzoate

Methyl 3-(chloromethyl)benzoate (92 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (62 mg, yield 44%).

$^1$H-NMR (CDCl$_3$, 400 MHz): 1.46–1.58 (m, 2H), 2.05–2.14 (m, 2H), 2.16–2.28 (m, 2H), 2.83–2.91 (m, 2H), 3.26–3.37 (m, 1H), 3.60 (s, 2H), 3.92 (s, 3H), 6.78–6.83 (m, 2H), 7.29 (d, J=9.0 Hz, 1H), 7.40 (t, J=7.7 Hz, 1H), 7.56 (d, J=7.6 Hz, 1H), 7.87 (s, 1H), 7.94 (d, J=7.6 Hz, 1H), 7.99 (s, 1H) Mass spectrum (ESI-MS, m/z): 365 (M$^+$+1)

Example 148

Methyl 4-{[4-(1H-5-indazolylamino)piperidino]methyl}benzoate

Methyl 4-(chloromethyl)benzoate (92 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (51 mg, yield 35%).

$^1$H-NMR (CDCl$_3$, 400 MHz): 1.46–1.58 (m, 2H), 2.05–2.14 (m, 2H), 2.16–2.27 (m, 2H), 2.82–2.92 (m, 2H), 3.29–3.38 (m, 1H), 3.60 (s, 2H), 3.91 (s, 3H), 6.78–6.83 (m, 2H), 7.30 (d, J=9.8 Hz, 1H), 7.42 (t, J=8.1 Hz, 2H), 7.87 (s, 1H), 7.99 (d, J=8.3 Hz, 2H) Mass spectrum (ESI-MS, m/z): 365 (M$^+$+1)

Example 149

4-{[4-(1H-5-Indazolylamino)piperidino]methyl}phenyl acetate 4-(Chloromethyl)phenyl acetate (92 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (33 mg, yield 23%).

$^1$H-NMR (CDCl$_3$, 400 MHz): 1.45–1.70 (m, 2H), 2.01–2.20 (m, 2H), 2.20–2.28 (m, 2H), 2.30 (s, 3H), 2.85–2.94 (m, 2H), 3.28–3.38 (m, 1H), 3.55 (s, 2H), 6.78–6.83 (m, 2H), 7.04 (d, J=8.5, 2H), 7.29 (d, J=9.8 Hz, 1H), 7.35 (d, J=8.3 Hz, 2H), 7.87 (s, 1H) Mass spectrum (ESI-MS, m/z): 365 (M$^+$+1)

Example 150

N-[1-(2-Chloro-6-fluorobenzyl)-4-piperidyl]-N-(1H-5-indazolyl)amine

2-Chloro-6-fluorobenzyl chloride (89 mg), 4-piperidone monohydrate hydrochloride (77 mg), and potassium carbonate (138 mg) were dissolved in acetonitrile (1 ml), and the mixture was then stirred at room temperature for 18 hr. The reaction mixture was filtered through Celite, and the filtrate was then concentrated to give an intermediate.

This intermediate, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (89 mg, yield 62%).

$^1$H-NMR (CDCl$_3$, 400 MHz): 1.42–1.55 (m, 2H), 2.03–2.12 (m, 2H), 2.30–2.40 (m, 2H), 2.91–3.00 (m, 2H), 3.25–3.34 (m, 1H), 3.75 (s, 2H), 6.76–6.81 (m, 2H), 6.93–7.03 (m, 1H), 7.17–7.23 (m, 2H), 7.25–7.33 (m, 1H), 7.87 (s, 1H) Mass spectrum (ESI-MS, m/z): 359 (M$^+$+1)

Example 151

N-[1-(2-Chlorobenzyl)tetrahydro-1H-3-pyrrolyl]-N-(1H-5-indazolyl)amine (R)-(−)-3-Pyrrolidinol hydrochloride (77 mg) and potassium carbonate (268 mg) were dissolved in dimethylformamide (1 ml), and a solution (1 ml) of 2-chlorobenzyl chloride (112 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was then concentrated to give intermediate B.

This intermediate B and 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (54 mg, yield 41%).

$^1$H-NMR (CDCl$_3$, 400 MHz): 1.61–1.75 (m, 1H), 2.23–2.34 (m, 1H), 2.44–2.53 (m, 1H), 2.63–2.70 (m, 1H), 2.77–2.88 (m, 2H), 3.73 (s, 2H), 3.95–4.03 (m, 1H), 6.68–6.71 (m, 1H), 6.72–6.77 (m, 1H), 7.11–7.18 (m, 2H), 7.20–7.24 (m, 1H), 7.26–7.30 (m, 1H), 7.40 (d, J=6.8 Hz, 1H), 7.82 (s, 1H) Mass spectrum (ESI-MS, m/z): 327 (M$^+$+1)

Example 152

N-[1-(3-Chlorobenzyl)tetrahydro-1H-3-pyrrolyl]-N-(1H-5-indazolyl)amine (R)-(−)-3-Pyrrolidinol hydrochloride (77 mg) and potassium carbonate (268 mg) were dissolved in dimethylformamide (1 ml), and a solution of 3-chlorobenzyl chloride (112 mg) in acetonitrile (1 ml) was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B and 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (94 mg, yield 72%).

$^1$H-NMR (CDCl$_3$, 400 MHz): 1.68–1.79 (m, 1H), 2.30–2.41 (m, 1H), 2.42–2.51 (m, 1H), 2.61–2.67 (m, 1H), 2.76–2.86 (m, 2H), 3.62 (s, 2H), 4.01–4.08 (m, 1H), 6.74–6.77 (m, 1H), 6.79–6.83 (m, 1H), 7.18–7.26 (m, 3H), 7.29 (d, J=8.8 Hz, 1H), 7.35 (s, 1H), 7.89 (s, 1H) Mass spectrum (ESI-MS, m/z): 327 (M$^+$+1)

Example 153

N-[1-(4-Chlorobenzyl)tetrahydro-1H-3-pyrrolyl]-N-(1H-5-indazolyl)amine (R)-(−)-3-Pyrrolidinol hydrochloride (77 mg) and potassium carbonate (268 mg) were dissolved in dimethylformamide (1 ml), and a solution (1 ml) of 4-chlorobenzyl chloride (112 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B and 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (88 mg, yield 67%).

$^1$H-NMR (CDCl$_3$, 400 MHz): 1.67–1.77 (m, 1H), 2.30–2.41(m, 1H), 2.41–2.50(m, 1H), 2.59–2.65 (m, 1H), 2.75–2.85 (m, 2H), 3.61 (s, 2H), 4.00–4.07 (m, 1H), 6.73–6.76 (m, 1H), 6.77–6.82 (m, 1H), 7.24–7.30 (m, 5H), 7.88 (s, 1H) Mass spectrum (ESI-MS, m/z): 327 (M$^+$+1)

Example 154

N-[1-(4-Fluorobenzyl)tetrahydro-1H-3-pyrrolyl]-N-(1H-5-indazolyl)amine (R)-(−)-3-Pyrrolidinol hydrochloride (77 mg) and potassium carbonate (268 mg) were dissolved in dimethylformamide (1 ml), and a solution (1 ml) of 4-fluorobenzyl chloride (100 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (55 mg, yield 44%).

$^1$H-NMR (CDCl$_3$, 400 MHz): 1.67–1.78 (m, 1H), 2.30–2.40(m, 1H), 2.41–2.50 (m, 1H), 2.60–2.68 (m, 1H), 2.76–2.84 (m, 2H), 3.62 (s, 2H), 4.00–4.08 (m, 1H), 6.73–6.76 (m, 1H), 6.76–6.81 (m, 1H), 6.96–7.03 (m, 3H), 7.26–7.32 (m, 2H), 7.88(s, 1H) Mass spectrum (ESI-MS, m/z): 311 (M$^+$+1)

Example 155

N-[1-(4-Bromobenzyl)tetrahydro-1H-3-pyrrolyl]-N-(1H-5-indazolyl)amine (R)-(−)-3-Pyrrolidinol hydrochloride (96 mg) and potassium carbonate (268 mg) were dissolved in dimethylformamide (1 ml), and a solution (1 ml) of 4-bromobenzyl bromide (175 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (88 mg, yield 59%).

$^1$H-NMR (CDCl$_3$, 400 MHz): 1.60–1.70 (m, 1H), 2.23–2.33 (m, 1H), 2.33–2.42 (m, 1H), 2.52–2.58 (m, 1H), 2.67–2.78 (m, 2H), 3.53 (s, 3H), 3.92–4.00 (m, 1H), 6.66–6.69 (m, 1H), 6.70–6.75 (m, 1H), 7.14 (d, J=8.3 Hz, 2H), 7.21 (d, J=9.0 Hz, 1H), 7.36 (d, J=8.3 Hz, 2H), 7.81 (s, 1H) Mass spectrum (ESI-MS, m/z): 371, 373 (M$^+$, M$^+$+2)

Example 156

N-(1H-5-Indazolyl)-N-[1-(4-methoxybenzyl)tetrahydro-1H-3-pyrrolyl]amine (R)-(−)-3-Pyrrolidinol hydrochloride (96 mg) and potassium carbonate (268 mg) were dissolved in dimethylformamide (1 ml), and a solution (1 ml) of 4-methoxybenzyl chloride (109 mg) in acetonitrile was added dropwise to the solution at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (56 mg, yield 44%).

$^1$H-NMR (CDCl$_3$, 400 MHz): 1.64–1.75 (m, 1H), 2.27–2.38 (m, 1H), 2.40–2.49 (m, 1H), 2.58–2.63 (m, 1H), 2.74–2.88 (m, 2H), 3.58 (s, 2H), 3.77 (s, 3H), 3.97–4.05 (m, 1H), 6.70–6.73 (m, 1H), 6.75–6.78 (m, 1H), 6.84 (d, J=8.8 Hz, 2H), 7.20–7.26 (m, 3H), 7.85 (s, 1H) Mass spectrum (ESI-MS, m/z): 323 (M$^+$+1)

Example 157

N-(1H-5-Indazolyl)-N-[1-(4-methylbenzyl)tetrahydro-1H-3-pyrrolyl]amine (R)-(−)-3-Pyrrolidinol hydrochloride (96 mg) and potassium carbonate (268 mg) were dissolved in dimethylformamide (1 ml), and a solution (1 ml) of 4-methylbenzyl chloride (98 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (56 mg, yield 40%).

$^1$H-NMR (CDCl$_3$, 400 MHz): 1.64–1.76 (m, 1H), 2.30–2.38 (m, 1H), 2.31 (s, 3H), 2.41–2.50 (m, 1H), 2.58–2.65 (m, 1H), 2.75–2.85 (m, 2H), 3.56–3.65 (m, 2H), 3.95–4.05 (m, 1H), 6.71–6.73 (m, 1H), 6.74–6.79 (m, 1H), 7.10 (d, J=7.6 Hz, 2H), 7.20 (d, J=7.8 Hz, 2H), 7.23–7.28 (m, 1H), 7.86 (s, 1H) Mass spectrum (ESI-MS, m/z): 307 (M$^+$+1)

Example 158

N-(1H-5-Indazolyl)-N-[1-(3-nitrobenzyl)tetrahydro-1H-3-pyrrolyl]amine (R)-(−)-3-Pyrrolidinol hydrochloride (96 mg) and potassium carbonate (268 mg) were dissolved in dimethylformamide (1 ml), and a solution (1 ml) of 3-nitrobenzyl chloride (120 mg) in acetonitrile was added dropwise to the solution at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (81 mg, yield 60%).

$^1$H-NMR (CDCl$_3$, 400 MHz): 1.63–1.74 (m, 1H), 2.26–2.36 (m, 1H), 2.37–2.46 (m, 1H), 2.55–2.63 (m, 1H), 2.69–2.84 (m, 2H), 3.67 (s, 2H), 3.96–4.03 (m, 1H), 6.68–6.71 (m, 1H), 6.73–6.78 (m, 1H), 7.23 (d, J=8.8 Hz, 1H), 7.41 (t, J=7.8 Hz, 1H), 7.61 (d, J=7.6 Hz, 1H), 7.82 (s, 1H), 8.04 (d, J=8.3 Hz, 1H), 8.16 (s, 1H) Mass spectrum (ESI-MS, m/z): 338 (M$^+$+1)

Example 159

N-(1H-5-Indazolyl)-N-[1-(4-nitrobenzyl)tetrahydro-1H-3-pyrrolyl]amine (R)-(−)-3-Pyrrolidinol hydrochloride (96 mg) and potassium carbonate (268 mg) were dissolved in dimethylformamide (1 ml), and a solution (1 ml) of 4-nitrobenzyl chloride (120 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (80 mg, yield 60%).

¹H-NMR (CDCl₃, 400 MHz): 1.55–1.75 (m, 1H), 2.26–2.36 (m, 1H), 2.36–2.48 (m, 1H), 2.50–2.63 (m, 1H), 2.70–2.85 (m, 2H), 3.65–3.71 (m, 2H), 3.95–4.04 (m, 1H), 6.67–6.70 (m, 1H), 6.75 (d, J=8.8 Hz, 1H), 7.24 (d, J=8.8 Hz, 1H), 7.41–7.28 (m, 2H), 7.81 (s, 1H), 8.11 (d, J=8.5 Hz, 2H) Mass spectrum (ESI-MS, m/z): 338 (M⁺+1)

Example 160

N-[1-(3,5-Dimethoxybenzyl)tetrahydro-1H-3-pyrrolyl]-N-(1H-5-indazolyl)amine (R)-(−)-3-Pyrrolidinol hydrochloride (96 mg) and potassium carbonate (268 mg) were dissolved in dimethylformamide (1 ml), and a solution (1 ml) of 3,5-dimethoxybenzyl chloride (130 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (72 mg, yield 51%).

¹H-NMR (CDCl₃, 400 MHz): 1.67–1.77 (m, 1H), 2.28–2.39 (m, 1H), 2.42–2.51 (m, 1H), 2.61–2.69 (m, 1H), 2.74–2.88 (m, 2H), 3.53–3.63 (m, 2H), 3.75 (s, 6H), 4.00–4.10 (m, 1H), 6.32–6.35 (m, 1H), 6.48–6.51 (m, 2H), 6.72–6.74 (m, 1H), 6.75–6.80 (m, 1H), 7.23–7.29 (m, 1H), 7.86 (s, 1H) Mass spectrum (ESI-MS, m/z): 353 (M⁺+1)

Example 161

N-[1-(2-Chlorobenzyl)-3-piperidyl]-N-(1H-5-indazolyl)amine

3-Hydroxypiperidine (71 mg) and potassium carbonate (138 mg) were dissolved in dimethylformamide (1 ml), and a solution (1 ml) of 2-chlorobenzyl chloride (112 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (85 mg, yield 63%).

¹H-NMR (CDCl13, 400 MHz): 1.42–1.74 (m, 4H), 2.31–2.53 (m, 3H), 2.65–2.75 (m, 1H), 3.51–3.60 (m, 3H), 6.71–6.79 (m, 2H), 7.07–7.18 (m, 2H), 7.21 (d, J=8.8 Hz, 1H), 7.28 (dd, J=1.7 Hz, 7.6 Hz, 1H), 7.34–7.42 (m, 1H), 7.78 (s, 1H) Mass spectrum (ESI-MS, m/z): 341 (M⁺+1)

Example 162

N-[1-(3-Chlorobenzyl)-3-piperidyl]-N-(1H-5-indazolyl)amine

3-Hydroxypiperidine (71 mg) and potassium carbonate (138 mg) were dissolved in dimethylformamide (1 ml), and a solution (1 ml) of 3-chlorobenzyl chloride (112 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (63 mg, yield 46%).

¹H-NMR (CDCl₃, 400 MHz): 1.49–1.65 (m, 2H), 1.68–1.78 (m, 2H), 2.33–2.54 (m, 3H), 2.60–2.73 (m, 1H), 3.42–3.54 (m, 2H), 3.54–3.64 (m, 1H), 6.78–6.86 (m, 2H), 7.16–7.22 (m, 3H), 7.27 (d, J=8.8 Hz, 1H), 7.34 (s, 1H), 7.85 (s, 1H) Mass spectrum (ESI-MS, m/z): 341 (M⁺+1)

Example 163

N-[1-(4-Chlorobenzyl)-3-piperidyl]-N-(1H-5-indazolyl)amine

3-Hydroxypiperidine (71 mg) and potassium carbonate (138 mg) were dissolved in dimethylformamide (1 ml), and a solution (1 ml) of 4-chlorobenzyl chloride (113 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (39 mg, yield 29%).

$^1$H-NMR (CDCl$_3$, 400 MHz): 1.43–1.57 (m, 2H), 1.62–1.74 (m, 2H), 2.20–2.40 (m, 3H), 2.63–2.70 (m, 1H), 3.33–3.48 (m, 2H), 3.48–3.58 (m, 1H), 6.72–6.78 (m, 2H), 7.18–7.24 (m, 5H), 7.79 (s, 1H) Mass spectrum (ESI-MS, m/z): 341 (M$^+$+1)

Example 164

N-[1-(4-Fluorobenzyl)-3-piperidyl]-N-(1H-5-indazolyl)amine

3-Hydroxypiperidine (71 mg) and potassium carbonate (113 mg) were dissolved in dimethylformamide (1 ml), and a solution (1 ml) of 4-fluorobenzyl chloride (100 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was. extracted with chloroform-propanol (3/1). The organic layer was dried over anhydrous sodium sulfate, and the solvent was removed by distillation under the reduced pressure. The residue was purified by HPLC [chloroform/methanol] to give the title compound (20 mg, yield 15%).

$^1$H-NMR (CDCl$_3$, 400 MHz): 1.43–1.58 (m, 2H), 1.60–1.75 (m, 2H), 2.20–2.40 (m, 3H), 2.61–2.75 (m, 1H), 3.34–3.47 (m, 2H), 3.47–3.58 (m, 1H), 6.72–6.78 (m, 2H), 6.89–6.96 (m, 2H), 7.19–7.25 (m, 3H), 7.79 (s, 1H) Mass spectrum (ESI-MS, m/z): 325 (M$^+$+1)

Example 165

N-[1-(4-Bromobenzyl)-3-piperidyl]-N-(1H-5-indazolyl)amine

3-Hydroxypiperidine (71 mg) and potassium carbonate (113 mg) were dissolved in dimethylformamide (1 ml), and a solution (1 ml) of 4-bromobenzyl bromide (174 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution in an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (62 mg, yield 40%).

$^1$H-NMR (CDCl$_3$, 400 MHz): 1.42–1.57 (m, 2H), 1.60–1.73 (m, 2H), 2.20–2.38 (m, 3H), 2.60–2.75 (m, 1H), 3.33–3.47 (m, 2H), 3.48–3.57 (m, 1H), 6.71–6.78 (m, 2H), 7.14 (d, J=8.1 Hz, 2H), 7.22 (d, J=8.5 Hz, 1H), 7.36 (d, J=8.3 Hz, 2H), 7.80 (s, 1H) Mass spectrum (ESI-MS, m/z): 385, 387 (M$^+$, M$^+$+2)

Example 166

N-(1H-5-Indazolyl)-N-[1-(4-methoxybenzyl)-3-piperidyl]amine

3-Hydroxypiperidine (71 mg) and potassium carbonate (113 mg) were dissolved in dimethylformamide (1 ml), and a solution (1 ml) of 4-methoxybenzyl chloride (109 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg, yield 19%).

$^1$H-NMR (CDCl$_3$, 400 MHz): 1.43–1.56 (m, 2H), 1.60–1.73 (m, 2H), 2.23–2.40 (m, 3H), 2.61–2.80 (m, 1H), 3.33–3.47 (m, 2H), 3.48–3.58 (m, 1H), 3.72 (s, 3H), 6.74 (s, 1H), 6.78 (d, J=8.8 Hz, 2H), 7.16 (d, J=8.5 Hz, 2H), 7.21 (d, J=8.5 Hz, 1H), 7.79 (s, 1H) Mass spectrum (ESI-MS, m/z): 337 (M$^+$+1)

Example 167

N-(1H-5-Indazolyl)-N-[1-(4-methylbenzyl)-3-piperidyl]amine

3-Hydroxypiperidine (71 mg) and potassium carbonate (113 mg) were dissolved in dimethylformamide (1 ml), and a solution (1 ml) of 4-methylbenzyl chloride (98 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (28 mg, yield 22%).

$^1$H-NMR (CDCl$_3$, 400 MHz): 1.42–1.57 (m, 2H), 1.60–1.72 (m, 2H), 2.26 (s, 3H), 2.24–2.39 (m, 3H), 2.62–2.75 (m, 1H), 3.35–3.48 (m, 2H), 3.48–3.58 (m, 1H), 6.71–6.78 (m, 2H), 7.05 (d, J=7.8 Hz, 2H), 7.14 (d, J=8.1 Hz, 2H), 7.21 (d, J=8.8 Hz, 1H), 7.79 (s, 1H) Mass spectrum (ESI-MS, m/z): 321 (M$^+$+1)

Example 168

N-(1H-5-Indazolyl)-N-[1-(3-nitrobenzyl)-3-piperidyl]amine

3-Hydroxypiperidine (71 mg) and potassium carbonate (113 mg) were dissolved in dimethylformamide (1 ml), and a solution (1 ml) of 3-nitrobenzyl chloride (120 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (60 mg, yield 43%).

$^1$H-NMR (CDCl$_3$, 400 MHz): 1.52–1.66 (m, 2H), 1.71–1.84 (m, 2H), 2.26–2.50 (m, 3H), 2.70–2.80 (m, 1H), 3.52–3.65 (m, 3H), 6.77–6.85 (m, 2H), 7.27 (d, J=8.8 Hz, 1H), 7.44 (dd, J=7.8 Hz, 8.1 Hz, 1H), 7.63 (d, J=6.8 Hz, 1H), 7.83 (s, 1H), 8.07 (d, J=8.3 Hz, 1H), 8.23 (s, 1H) Mass spectrum (ESI-MS, m/z): 352 (M$^+$+1)

Example 169

N-(1H-5-Indazolyl)-N-[1-(4-nitrobenzyl)-3-piperidyl]amine

3-Hydroxypiperidine (71 mg) and potassium carbonate (113 mg) were dissolved in dimethylformamide (1 ml), and a solution (1 ml) of 4-nitrobenzyl chloride (120 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (35 mg, yield 25%).
$^1$H-NMR (CDCl$_3$, 400 MHz): 1.51–1.68 (m, 2H), 1.69–1.86 (m, 2H), 2.26–2.47 (m, 3H), 2.71–2.83 (m, 1H), 3.52–3.65 (m, 3H), 6.79–6.83 (m, 2H), 7.28 (d, J=9.5 Hz, 1H), 7.49 (d, J=8.5 Hz, 2H), 7.84 (s, 1H), 8.15 (d, J=8.8 Hz, 2H) Mass spectrum (ESI-MS, m/z): 352 (M$^+$+1)

Example 170

N-[1-(3,5-Dimethoxybenzyl)-3-piperidyl]-N-(1H-5-indazolyl)amine

3-Hydroxypiperidine (71 mg) and potassium carbonate (113 mg) were dissolved in dimethylformamide (1 ml), and a solution (1 ml) of 3,5-dimethoxybenzyl chloride (130 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (1 ml), and a sulfur trioxide-trimethylamine complex (209 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

This intermediate B, 5-aminoindazole (53 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (55 mg, yield 38%).
$^1$H-NMR (CDCl$_3$, 400 MHz): 1.40–1.57 (m, 2H), 1.62–1.75 (m, 2H), 2.20–2.43 (m, 3H), 2.70–2.80 (m, 1H), 3.35–3.47 (m, 2H), 3.50–3.60 (m, 1H), 3.73 (s, 6H), 6.29 (s, 1H), 6.45 (s, 2H), 6.72–6.79 (m, 2H), 7.22 (d, J=8.5 Hz, 1H), 7.79 (s, 1H) Mass spectrum (ESI-MS, m/z): 367 (M$^+$+1)

Example 171

N1-Benzyl-N4-(1H-5-indazolyl)-1,4-cyclohexanediamine 1,4-Cyclohexanedione monoethylene ketal (3.90 g), 5-aminoindazole (2.66 g), and acetic acid (0.5 ml) were dissolved in methanol (50 ml), and a borane-pyridine complex (2.50 ml) was added dropwise to the solution at room temperature. The reaction mixture was stirred at room temperature for 18 hr. A saturated aqueous sodium hydrogencarbonate solution (50 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give intermediate A (4.09 g, yield 75%).

Intermediate A was dissolved in acetic acid-water (1:1, 50 ml), and the mixture was then stirred at 80° C. for 3 hr. The reaction mixture was concentrated to remove a major part of acetic acid. A saturated aqueous sodium hydrogencarbonate solution was then added to the residue, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give intermediate B (3.21 g, yield 93%).

This intermediate B (115 mg), benzylamine (64 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by preparative TLC [chloroform/methanol] to give the title compound as a mixture of two diastereoisomers (1:1) (43 mg, yield 13%).
$^1$H-NMR (CDCl$_3$, 400 MHz) (mixture of two diastereoisomers): 1.08–1.22 (m, 2H), 1.32–1.46 (m, 2H), 1.64–1.92 (m, 8H), 2.05–2.14 (m, 2H), 2.17–2.25 (m, 2H), 2.56–2.67 (m, 1H), 2.74–2.83 (m, 1H), 3.22–3.31 (m, 1H), 3.53 (m, 1H), 3.86 (s, 2H), 3.87 (s, 2H), 6.75–6.86 (m, 4H), 7.23–7.45 (m, 12H), 7.86 (s, 1H), 7.88 (s, 1H) Mass spectrum (ESI-MS, m/z): 321 (M$^+$+1)

Example 172

N1-(1H-5-Indazolyl)-N4-phenyl-1,4-cyclohexanediamine 1,4-Cyclohexanedione monoethylene ketal (3.90 g), 5-aminoindazole (2.66 g), and acetic acid (0.5 ml) were dissolved in methanol (50 ml), and a borane-pyridine complex (2.50 ml) was added dropwise to the solution at room temperature. The reaction mixture was stirred at room temperature for 18 hr. A saturated aqueous sodium hydrogencarbonate solution (50 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give intermediate A (4.09 g, yield 75%).

Intermediate A was dissolved in acetic acid-water (1:1, 50 ml), and the mixture was stirred at 80° C. for 3 hr. The reaction mixture was concentrated to remove a major part of acetic acid. A saturated aqueous sodium hydrogencarbonate solution was then added to the residue, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give intermediate B (3.21 g, yield 93%).

This intermediate B (115 mg), aniline (56 mg), and acetic acid (0.02 ml) were dissolved in methanol (1 ml), and a borane-pyridine complex (0.06 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound as one diastereoisomer (12 mg, yield 8%).

$^1$H-NMR (CDCl$_3$, 400 MHz): 1.25–1.35 (m, 2H), 1.65–1.95 (m, 4H), 2.18–2.32 (m, 2H), 3.27–3.36 (m, 1H), 3.47–3.57 (m, 1H), 6.56–6.64 (m, 2H), 6.65–6.72 (m, 2H), 6.78–6.84 (m, 2H), 7.13–7.20 (m, 2H), 7.30 (d, J=9.0 Hz, 1H), 7.89 (s, 1H)

Example 173

N$_1$-($_1$H-5-Indazolyl)-2-(benzylamino)acetamide

2-[(Tert-butoxycarbonyl)amino]acetic acid (963 mg), 5-aminoindazole (665 mg), and dimethylaminopyridine (10 mg) were dissolved in dimethylformamide (20 ml). N-[3-(Diethylamino)propyl]-N'-ethylcarbodiimide hydrochloride (1.54 g) and 1-hydroxybenzotriazole (1.22 g) were added to the solution at 0° C. The reaction mixture was stirred at room temperature for 18 hr. A saturated aqueous sodium hydrogencarbonate solution (20 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give intermediate A (849 mg, yield 59%).

Intermediate A was dissolved in chloroform (5 ml), and trifluoroacetic acid (5 ml) was added to the solution at room temperature. The reaction mixture was stirred at room temperature for 3 hr and was then concentrated to prepare intermediate B.

Intermediate B (546 mg), benzaldehyde (106 mg), and acetic acid (0.05 ml) were dissolved in methanol (2 ml), and sodium triacetoxyborohydride (212 mg) was added to the solution at 0° C. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (121 mg, yield 43%).

$^1$H-NMR (CDCl$_3$, 400 MHz): 3.46 (s, 2H), 3.86 (s, 2H), 7.25–7.46 (m, 7H), 8.02 (s, 1H), 8.10 (bs, 1H), 9.31 (bs, 1H) Mass spectrum (ESI-MS, m/z): 281 (M$^+$+1)

Example 174

N1-Benzyl-N2-(1H-5-indazolyl)-1,2-ethanediamine

N1-(1H-5-Indazolyl)-2-(benzylamino)acetamide (Example 173) (56 mg) was dissolved in tetrahydrofuran (1 ml), and a borane-tetrahydrofuran complex (1.0 ml) was added to the solution at room temperature. The reaction mixture was stirred at 50° C. for 6 hr, and 1 N hydrochloric acid (0.5 ml) was then added, followed by stirring at the same temperature for one hr. A saturated aqueous sodium hydrogencarbonate solution (2 ml) was added thereto, and the mixture was extracted with chloroform-propanol (3/1). The organic layer was dried over anhydrous sodium sulfate, and the solvent was removed by distillation under the reduced pressure. The residue was purified by preparative TLC [chloroform/methanol] to give the title compound (23 mg, yield 43%)

$^1$H-NMR (CDCl$_3$, 400 MHz): 2.86–2.91 (m, 2H), 3.16–3.21 (m, 2H), 3.76 (s, 2H), 6.66–6.82 (m, 2H), 7.18–7.24 (m, 6H), 7.81 (s, 1H) Mass spectrum (ESI-MS, m/z): 267 (M$^+$+1)

Example 175

N1-(1-Benzyl-4-piperidyl)-N1-(1H-5-indazolyl)acetamide

Example 176

1-{5-[(1-Benzyl-4-piperidyl)amino]-1H-5-indazolyl}-1-ethanone

N-(1-Benzyl-4-piperidyl)-N-(1H-5-indazolyl)amine (Example 126) (153 mg), triethylamine (0.14 ml), and dimethylaminopyridine (5 mg) were dissolved in chloroform (1 ml), and acetic anhydride (0.048 ml) was added dropwise to the solution at 0° C. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give a compound of Example 175 (11 mg, yield 6%) and a compound of Example 176 (40 mg, yield 23%).

Example 175

$^1$H-NMR (CDCl$_3$, 400 MHz): 1.23–1.40 (m, 1H), 1.50–1.70 (m, 1H), 1.70–1.80 (m, 1H), 1.82–1.92 (m, 1H), 2.02 (s, 3H), 2.11–2.29 (m, 2H), 2.11–2.29 (m, 2H), 2.91–3.08 (m, 2H), 3.48 (d, J=12.7 Hz, 1H), 3.55 (d, J=13.0 Hz, 1H), 4.66–4.76 (m, 1H), 6.92–6.98 (m, 1H), 7.20–7.27 (m, 6H), 7.52 (s, 1H), 8.05 (s, 1H) Mass spectrum (ESI-MS, m/z): 349 (M$^+$+1)

Example 176

$^1$H-NMR (CDCl$_3$, 400 MHz): 1.50–1.62 (m, 2H), 2.05–2.13 (m, 2H), 2.18–2.28 (m, 2H), 2.73 (s, 3H), 2.85–2.95 (m, 2H), 3.30–3.40 (m, 1H), 3.58 (s, 2H), 6.73–6.76 (m, 1H), 6.84–6.89 (m, 1H), 7.24–7.36 (m, 5H), 7.94 (s, 1H), 8.19 (d, J=9.0 Hz, 1H) Mass spectrum (ESI-MS, m/z): 349 (M$^+$+1)

Example 177

1-Benzyl-4-piperidyl(1H-5-indazolyl)ether

4-Amino-m-cresol (123 mg), potassium acetate (244 mg), and acetic anhydride (0.47 ml) were suspended in chlorobenzene (2 ml), and isoamyl nitrate (0.20 ml) was added to the suspension at 80° C. The reaction mixture was stirred at the same temperature for 18 hr, water (1 ml) was then added thereto, and the mixture was extracted with chloroform. The organic layer was dried over anhydrous sodium sulfate, and the solvent was removed by distillation under the reduced pressure. The residue was purified by HPLC [chloroform/methanol] to give intermediate A.

Intermediate A was dissolved in hydrochloric acid-methanol (2 ml), and the mixture was then stirred at 80° C. for 5 hr. A saturated aqueous sodium hydrogencarbonate solution (2 ml) was added to the reaction mixture, and the mixture was extracted with chloroform-propanol (3/1). The organic layer was dried over anhydrous sodium sulfate, and the solvent was removed by distillation under the reduced pressure to give intermediate B.

This intermediate B, 1-benzyl-4-hydroxypiperidine (105 mg), and triphenylphosphine (131 mg) were dissolved in tetrahydrofuran (1 ml), and diethyl azodicarboxylate (0.20 ml) was added to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (35 mg, yield 11%).

$^1$H-NMR (CDCl$_3$, 400 MHz): 1.71–1.84 (m, 2H), 1.92–2.00 (m, 2H), 2.20–2.30 (m, 2H), 2.65–2.75 (m, 2H), 3.48 (s, 2H), 4.16–4.28 (m, 2H), 6.96–7.03 (m, 1H), 7.07–7.09 (m, 1H), 7.20–7.28 (m, 5H), 7.30 (d, J=9.0 Hz, 1H), 7.89 (s, 1H) Mass spectrum (ESI-MS, m/z): 308 (M$^+$+1)

Example 178

N1-(4-Pyridyl)-2-(2,4,6-trichlorophenoxy)acetamide

4-Aminopyridine (266 mg, 1.96 mmol, 1.0 eq), WSC.HCl (451 mg, 2.35 mmol, 1.2 eq), and HOBt.H$_2$O (320 mg, 2.35 mmol, 1.2 eq) were added to a solution of the carboxyl compound (500 mg, 1.96 mmol) prepared in Example 16 in dimethylformamide, and the mixture was stirred at room temperature for 16 hr.

After the completion of the reaction, the reaction solution was poured into water, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (276 mg, 42.6%).

MS m/z: 330, 332 $^1$H-NMR δ: 4.69 (2H, s), 7.67 (2H, dd, J=1.59, 4.76 Hz), 7.70 (2H, s), 8.46 (2H, dd, J=1.59, 4.76), 10.51 (1H, s)

Intermediate 1

1H-5-Indazolol

4-Amino-m-cresol (12.3 g), potassium acetate (24.4 g), and acetic anhydride (47.1 ml) were suspended in chlorobenzene (200 ml), and isoamyl nitrate (0.20 ml) was added to the suspension at 80° C. The reaction mixture was stirred at the same temperature for 18 hr. Water (100 ml) was then added thereto, and the mixture was extracted with chloroform. The organic layer was dried over anhydrous sodium sulfate, and the solvent was removed by distillation under the reduced pressure. The residue was purified by column chromatography on silica gel [chloroform/methanol] to give intermediate A.

Intermediate A was dissolved in hydrochloric acid-methanol (200 ml), and the mixture was then stirred at 80° C. for 5 hr. A saturated aqueous sodium hydrogencarbonate solution (200 ml) was added to the reaction mixture, and the mixture was extracted with chloroform-propanol (3/1). The organic layer was dried over anhydrous sodium sulfate, and the solvent was removed by distillation under the reduced pressure to give the title compound (7.99 g).

$^1$H-NMR (CDCl$_3$, 400 MHz): 6.95 (d, J=8.8 Hz, 1H), 7.03 (s, 1H), 7.31 (d, J=8.8 Hz, 1H), 7.88 (s, 1H)

Intermediate 2

1H-5-Indazolecarboxylic acid

Methyl 4-amino-3-methylbenzoate (0.85 g), potassium acetate (1.47 mg), and acetic anhydride (1.42 ml) were suspended in chlorobenzene (20 ml), and isoamyl nitrate (1.17 g) was added to the suspension at 80° C. The reaction mixture was stirred at the same temperature for 18 hr. Water (20 ml) was then added thereto, and the mixture was extracted with chloroform. The organic layer was dried over anhydrous sodium sulfate, and the solvent was removed by distillation under the reduced pressure. The residue was dissolved in hydrochloric acid-methanol (20 ml), and the mixture was then stirred at 80° C. for 5 hr. A saturated aqueous sodium hydrogencarbonate solution (20 ml) was added to the reaction mixture, and the mixture was extracted with chloroform-propanol (3/1). The organic layer was dried over anhydrous sodium sulfate, and the solvent was removed by distillation under the reduced pressure. The residue was purified by chromatography on silica gel [chloroform/methanol] to give intermediate A.

Intermediate A was dissolved in methanol (20 ml), and a 3 N aqueous sodium hydroxide solution (3 ml) was added thereto. The reaction mixture was stirred at room temperature for 18 hr. The solvent was then removed by distillation under the reduced pressure, and the residue was purified by ODS chromatography [water/acetonitrile] to give the title compound (0.32 g).

Mass spectrum (ESI-MS, m/z): 161 (M$^+$−1)

Example 179

Tert-butyl (1H-5-indazolylamino)-1-pyrrolidinecarboxylate (R)-(−)-3-Pyrrolidinol hydrochloride (1.23 g) was dissolved in a 3 N aqueous sodium hydroxide solution (10 ml), and a solution (10 ml) of di-tert-butyl dicarbonate (2.40 g) in THF was added dropwise thereto at room temperature. The reaction mixture was stirred at room temperature for one hr and was then extracted with ethyl acetate. The organic layer was dried over anhydrous sodium sulfate and was concentrated to give intermediate A.

This intermediate A and triethylamine (2 ml) were dissolved in anhydrous dimethyl sulfoxide (10 ml), and a sulfur trioxide-trimethylamine complex (4.44 g) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

This intermediate B, 5-aminoindazole (0.98 g), and acetic acid (0.2 ml) were dissolved in methanol (10 ml), and a borane-pyridine complex (1.0 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by chromatography on silica gel [chloroform/methanol] to give the title compound (1.59 g).

$^1$H-NMR (CDCl$_3$, 400 MHz): 1.44 (s, 9H), 1.68–1.78 (m, 1H), 1.96–2.06 (m, 1H), 2.85–3.00 (m, 1H), 3.03–3.20 (m, 1H), 3.35–3.43 (m, 1H), 3.65–3.75 (m, 1H), 3.98–4.20 (m, 1H), 6.80 (d, J=8.8 Hz, 1H), 6.87 (s, 1H), 7.30 (d, J=9.0 Hz, 1H), 7.86 (s, 1H)

Example 180

Tert-butyl 3-(1H-indazolylamino)-1-piperidinecarboxylate

3-Hydroxypiperidine (1.01 g) was dissolved in a 3 N aqueous sodium hydroxide solution (10 ml), and a solution (10 ml) of di-tert-butyl dicarbonate (2.40 g) in THF was added dropwise thereto at room temperature. The reaction mixture was stirred at room temperature for one hr and was then extracted with ethyl acetate. The organic layer was dried over anhydrous sodium sulfate and was concentrated to give intermediate A.

This intermediate A and triethylamine (2 ml) were dissolved in anhydrous dimethyl sulfoxide (10 ml), and a sulfur trioxide-trimethylamine complex (4.44 g) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

This intermediate B, 5-aminoindazole (0.98 g), and acetic acid (0.2 ml) were dissolved in methanol (10 ml), and a borane-pyridine complex (1 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by chromatography on silica gel [chloroform/methanol] to give the title compound (2.30 g).

$^1$H-NMR (CDCl$_3$, 400 MHz): 1.44 (s, 9H), 1.83–2.02 (m, 3H), 2.15–2.25 (m, 1H), 3.30–3.56 (m, 4H), 3.98–4.10 (m, 1H), 4.40–4.46 (m, 1H), 6.77–6.81 (m, 2H), 7.30 (d, J=8.3 Hz, 1H), 7.88 (s, 1H)

Intermediate 3

4-(1H-5-Indazolylamino)-1-cyclohexanone 1,4-Cyclohexanedione monoethylene ketal (3.90 g), 5-aminoindazole (2.66 g), and acetic acid (0.5 ml) were dissolved in methanol (50 ml), and a borane-pyridine complex (2.50 ml) was added dropwise to the solution at room temperature. The reaction mixture was stirred at room temperature for 18 hr, was then cooled to room temperature, and was concentrated. The residue was dissolved in acetic acid-water (1:1, 50 ml), and the mixture was then stirred at 80° C. for 3 hr. The reaction mixture was concentrated to remove a major part of acetic acid. A saturated aqueous sodium hydrogencarbonate solution was then added to the residue, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (3.21 g).

$^1$H-NMR (CDCl$_3$, 400 MHz): 1.70–1.84 (m, 2H), 2.31–2.54 (m, 6H), 3.72–3.84 (m, 1H), 6.83 (d, J=8.83 Hz, 1H), 6.87 (s, 1H), 7.32 (d, J=8.8 Hz, 1H), 7.89 (s, 1H)

Intermediate 4

4-(5-Isoquinolylamino)-1-cyclohexanone 1,4-Cyclohexanedione monoethylene ketal (6.2 g), 5-amino-isoquinoline (4.3 g), and acetic acid (0.5 ml) were dissolved in methanol (50 ml), and a borane-pyridine complex (4.0 ml) was added dropwise to the solution at room temperature. The reaction mixture was stirred at room temperature for 18 hr, was then cooled to room temperature, and was concentrated. The residue was dissolved in acetic acid-water (1:1, 50 ml), and the mixture was then stirred at 80° C. for 3 hr. The reaction mixture was concentrated to remove a major part of acetic acid. A saturated aqueous sodium hydrogencarbonate solution was then added to the residue, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (5.8 g).

$^1$H-NMR (CDCl$_3$, 400 MHz): 1.83–1.96 (m, 2H), 2.40–2.60 (m, 6H), 3.90–4.00 (m, 1H), 4.22–4.31 (m, 1H), 6.85 (d, J=7.6 Hz, 1H), 7.35 (d, J=8.1 Hz, 1H), 7.47 (t, J=7.8 Hz, 1H), 7.53 (d, J=6.1 Hz, 1H), 8.47 (d, J=6.1 Hz, 1H), 9.16 (s, 1H)

Example 181

N-(1H-5-Indazolyl)-N-(4-piperidyl)amine

Example 179 (450 mg) was dissolved in chloroform (3 ml), and 95% trifluoroacetic acid (3 ml) was added dropwise to the solution at room temperature. The reaction mixture was stirred at room temperature for 2 hr and was then concentrated to give the title compound (420 mg).

Mass spectrum (ESI-MS, m/z): 203 (M$^+$+1)

Example 182

N-(1H-5-Indazolyl)-N-tetrahydro-1H-3-pyrrolylamine

Example 180 (474 mg) was dissolved in chloroform (3 ml), and 95% trifluoroacetic acid (3 ml) was added dropwise to the solution at room temperature. The reaction mixture was stirred at room temperature for 2 hr and was then concentrated to give the title compound (510 mg).

Mass spectrum (ESI-MS, m/z): 217 (M$^+$+1)

Example 183

N-[1-(Cyclohexylmethyl)-4-piperidyl]-N-(1H-5-indazolyl)amine

4-Piperidone hydrochloride monohydrate (77 mg) and cyclohexanecarboxyaldehyde (62 mg) were dissolved in methanol (1 ml), and sodium triacetoxyborohydride (106 mg) was added to the solution. The reaction mixture was stirred at room temperature for 18 hr. Further, 5-aminoindazole (54 mg) was added thereto, and the mixture was stirred for 30 min. A borane-pyridine complex (0.05 ml) was added thereto. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (15 mg).

$^1$H-NMR (CDCl$_3$, 400 MHz): 0.80–0.90 (m, 2H), 1.10–1.30 (m, 2H), 1.30–1.59 (m, 3H), 1.60–1.80 (m, 6H), 2.03–2.20 (m, 6H), 2.80–2.90 (m, 2H), 3.25–3.35 (m, 1H), 6.75–6.82 (m, 2H), 7.28 (d, J=8.8 Hz, 1H), 7.86 (s, 1H)

Mass spectrum (ESI-MS, m/z): 313 (M$^+$+1)

Example 184

N-(1H-5-Indazolyl)-N-(1-pentyl-4-piperidyl)amine

4-Piperidone hydrochloride monohydrate (77 mg) and valeraldehyde (43 mg) were dissolved in methanol (1 ml), and sodium triacetoxyborohydride (106 mg) was added to the solution. The reaction mixture was stirred at room temperature for 18 hr. Further, 5-aminoindazole (54 mg) was added thereto. The mixture was stirred for 30 min, and a borane-pyridine complex (0.05 ml) was added thereto. The reaction mixture was stirred at room temperature for 18 hr. A saturated aqueous sodium hydrogencarbonate solution (1 ml) was then added, and the mixture was extracted with chloroform-propanol (3/1). The organic layer was dried over anhydrous sodium sulfate, and the solvent was removed by distillation under the reduced pressure. The residue was purified by HPLC [g chloroform/methanol] to give the title compound (2 mg).

Mass spectrum (ESI-MS, m/z): 287 (M$^+$+1)

Example 185

N-(1-Hexyl-4-piperidyl)-N-(1H-5-indazolyl)amine

4-Piperidone hydrochloride monohydrate (77 mg) and capronaldehyde (50 mg) were dissolved in methanol (1 ml), and sodium triacetoxyborohydride (106 mg) was added to the solution. The reaction mixture was stirred at room temperature for 18 hr. Further, 5-aminoindazole (54 mg) was added thereto, and the mixture was stirred for 30 min, followed by the addition of a borane-pyridine complex (0.05 ml). The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (2 mg).

Mass spectrum (ESI-MS, m/z): 301 (M$^+$+1)

Example 186

N-(1H-5-Indazolyl)-N-(1-isobutyl-4-piperidyl)amine

4-Piperidone hydrochloride monohydrate (77 mg) and isobutylaldehyde (36 mg) were dissolved in methanol (1 ml), and sodium triacetoxyborohydride (106 mg) was added thereto. The reaction mixture was stirred at room temperature for 18 hr. 5-Aminoindazole (54 mg) was further added thereto, and the mixture was stirred for 30 min, and a borane-pyridine complex (0.05 ml) was then added thereto. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (1 mg).

Mass spectrum (ESI-MS, m/z): 272 (M$^+$+1)

Example 187

N-(1H-5-Indazolyl)-N-[1-(2-phenylpropyl)-4-piperidyl]amine

4-Piperidone hydrochloride monohydrate (77 mg) and 2-phenylpropionaldehyde (68 mg) were dissolved in methanol (1 ml), and sodium triacetoxyborohydride (106 mg) was added to the solution. The reaction mixture was stirred at room temperature for 18 hr. 5-Aminoindazole (54 mg) was further added thereto, and the mixture was stirred for 30 min, followed by the addition of borane-pyridine complex (0.05 ml). The reaction mixture was stirred at room temperature for 18 hr. A saturated aqueous sodium hydrogencarbonate solution (1 ml) was then added, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (21 mg).

Mass spectrum (ESI-MS, m/z): 335 (M$^+$+1)

Example 188

N-[1-(2-Cyclohexenylmethyl)-4-piperidyl]-N-(1H-5-indazolyl)amine

4-Piperidone hydrochloride monohydrate (77 mg) and 1,2,3,6-tetrahydrobenzaldehyde (55 mg) were dissolved in methanol (1 ml), and sodium triacetoxyborohydride (106 mg) was added to the solution. The reaction mixture was stirred at room temperature for 18 hr. Further, 5-aminoindazole (54 mg) was added thereto, and the mixture was stirred for 30 min, followed by the addition of a borane-pyridine complex (0.05 ml). The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (6 mg).

Mass spectrum (ESI-MS, m/z): 301 (M$^+$+1)

Example 189

(4-Benzylpiperazino)(1H-5-indazolyl)methanone

1-Benzylpiperazine (256 mg) and 1H-5-indazolecarboxylic acid (intermediate 2) (243 mg) were dissolved in dimethylformamide (3 ml), and 1-ethyl-3-(3-dimethylaminopropyl)-carbodiimide hydrochloride (263 mg), 1-hydroxybenzotriazole (225 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (30 mg).

$^1$H-NMR (CDCl$_3$, 400 MHz): 2.20–2.80 (m, 4H), 3.20–4.10 (m, 6H), 7.18–7.33 (m, 5H), 7.38 (d, J=8.6 Hz, 1H), 7.43 (d, J=8.8 Hz, 1H), 7.78 (s, 1H), 8.04 (s, 1H) Mass spectrum (ESI-MS, m/z): 321 (M$^+$+1)

Example 190

N5-(1-Benzyltetrahydro-1H-3-pyrrolyl)-1H-5-indazolecarboxyamide

1-Benzyl-3-aminopyrrolidine (256 mg) and 1H-5-indazolecarboxylic acid (intermediate 2) (243 mg) were dissolved in dimethylformamide (3 ml), and 1-ethyl-3-(3-dimethylaminopropyl)-carbodiimide hydrochloride (383 mg), 1-hydroxybenzotriazole (306 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (21 mg).

$^1$H-NMR (CDCl$_3$, 400 MHz): 1.90–2.03 (m, 1H), 2.37–2.57 (m, 2H), 2.73–2.83 (m, 1H), 3.02–3.12 (m, 1H), 3.20–3.32 (m, 1H), 3.83 (s, 2H), 4.79–4.89 (m, 1H), 7.23–7.40 (m, 6H), 7.81 (d, J=8.8 Hz, 1H), 8.07 (s, 1H), 8.24 (s, 1H) Mass spectrum (ESI-MS, m/z): 321 (M$^+$+1)

Example 191

N5-(1-Benzyltetrahydro-1H-3-pyrrolyl)-1H-5-indazolecarboxyamide

4-Amino-1-benzylpiperidine (280 mg) and 1H-5-indazolecarboxylic acid (intermediate 2) (243 mg) were dissolved in dimethylformamide (3 ml), and 1-ethyl-3-(3-dimethylaminopropyl)-carbodiimide hydrochloride (383 mg), 1-hydroxybenzotriazole (306 mg), and dimethylaminopyridine. (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (42 mg).

$^1$H-NMR (CDCl$_3$, 400 MHz): 1.60–1.80 (m, 2H), 1.95–2.08 (m, 2H), 2.20–2.32 (m, 2H), 2.90–2.98 (m, 2H), 3.07 (s, 2H), 3.80–3.86 (m, 1H), 7.16–7.40 (m, 5H), 7.46 (d, J=8.8 Hz, 1H), 7.75 (d, J=8.8 Hz, 1H), 8.07 (s, 1H), 8.14 (s, 1H) Mass spectrum (ESI-MS, m/z): 335 (M$^+$+1)

Example 192

Ethyl 4-(1H-5-indazolylamino)-1-cyclohexanecarboxylate

Ethyl 4-oxocyclohexanecarboxylate (0.85 g) and 5-aminoindazole (0.60 g) were dissolved in methanol (10 ml) thereto, and a borane-pyridine complex (0.81 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by chromatography on silica gel [chloroform/methanol] to give the title compound (1.37 g) as substantially 1:1 enantiomers.

$^1$H-NMR (CDCl$_3$, 400 MHz): 1.15–1.23 (m, 6H), 1.40–1.56 (m, 3H), 1.60–1.70 (m, 3H), 1.74–1.82 (m, 1H), 1.87–2.05 (m, 5H), 2.15–2.32 (m, 3H), 2.40–2.48 (m, 1H), 3.14–3.23 (m, 1H), 3.38–3.46 (m, 1H), 4.03–4.14 (m, 4H), 6.75–6.99 (m, 4H), 7.23 (d, J=8.8 Hz, 2H), 7.81 (s, 1H), 7.83 (s, 1H)

Example 193

Ethyl 2-(1H-5-indazolylamino)-1-cyclohexanecarboxylate

Ethyl 2-oxocyclohexanecarboxylate (0.85 g) and 5-aminoindazole (0.60 g) were dissolved in methanol (10 ml), and a borane-pyridine complex (0.81 ml) was added dropwise to the solution at room temperature. The reaction mixture was stirred at room temperature for 18 hr. A saturated aqueous sodium hydrogencarbonate solution (10 ml) was then added thereto, and the mixture was extracted with chloroform-propanol (3/1). The organic layer was dried over anhydrous sodium sulfate, and the solvent was removed by distillation under the reduced pressure. The residue was purified by chromatography on silica gel [chloroform/methanol] to give the title compound (1.37 g) as substantially 1:1 enantiomers.

$^1$H-NMR (CDCl$_3$, 400 MHz): 1.10 (t, J=7.1 Hz, 3H), 1.13 (d, J=7.3 Hz, 3H), 1.33–1.46 (m, 4H), 1.55–1.75 (m, 5H), 1.80–1.88 (m, 1H), 1.90–1.99 (m, 2H), 2.10–2.20 (m, 1H), 2.25–2.37 (m, 1H), 2.78–2.88 (m, 2H), 3.49 (dt, J=3.9 Hz, 10.5 Hz, 1H), 3.67–3.74 (m, 2H), 3.94–4.10 (m, 5H), 6.75–6.95 (m, 4H), 7.23 (d, J=8.5 Hz, 2H), 7.81 (s, 2H)

Example 194

(3R)-1-Benzyltetrahydro-1H-3-pyrrolyl(1H-5-indazolyl)ether 1H-5-Indazolol (intermediate 1) (67 mg), (S)-1-benzyl-3-pyrrolidinol (89 mg), and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (42 mg).

1H-NMR (CDCl$_3$, 400 MHz): 1.94–2.02 (m, 1H), 2.21–2.33 (m, 1H), 2.48–2.63 (m, 1H), 2.65–2.77 (m, 2H), 2.90–3.00 (m, 1H), 3.60 (d, J=12.7 Hz, 1H), 3.65 (d, J=12.7 Hz, 1H), 4.73–4.84 (m, 1H), 6.92 (s, 1H), 6.97 (d, J=9.0 Hz, 1H), 7.20–7.31 (m, 6H), 7.88 (s, 1H).

Example 195

(3S)-1-Benzyltetrahydro-1H-3-pyrrolyl(1H-5-indazolyl)ether (R)-(–)-Pyrrolidinol hydrochloride (73 mg) and potassium carbonate (165 mg) were dissolved in dimethylformamide (1 ml), and a solution (1 ml) of benzyl chloride (70 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (45 mg).

$^1$H-NMR (CDCl$_3$, 400 MHz): 1.94–2.02 (m, 1H), 2.21–2.33 (m, 1H), 2.48–2.63 (m, 1H), 2.65–2.77 (m, 2H), 2.90–3.00 (m, 1H), 3.60 (d, J=12.7 Hz, 1H), 3.65 (d, J=12.7 Hz, 1H), 4.73–4.84 (m, 1H), 6.92 (s, 1H), 6.97 (d, J=9.0 Hz, 1H), 7.20–7.31 (m, 6H), 7.88 (s, 1H) Mass spectrum (ESI-MS, m/z): 294 (M$^+$+1)

Example 196

1-Benzyl-3-piperidyl(1H-5-indazolyl)ether

3-Hydroxypiperidine (61 mg) and potassium carbonate (165 mg) were dissolved in dimethylformamide (1 ml), and a solution (1 ml) of benzyl chloride (70 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (46 mg).

Mass spectrum (ESI-MS, m/z): 308 (M$^+$+1)

Example 197

1H-5-Indazolyl(1-methyl-3-piperidyl)ether 1H-5-Indazolol (intermediate 1) (67 mg), 1-methyl-3-hydroxypiperidine (58 mg), and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (36 mg).

$^1$H-NMR (CDCl$_3$, 400 MHz): 1.45–1.50 (m, 1H), 1.50–1.65 (m, 1H), 1.75–1.90 (m, 1H), 1.90–2.05 (m, 1H), 2.05–2.25 (m, 2H), 2.25 (s, 3H), 2.50–2.60 (m, 1H), 2.85–2.95 (m, 1H), 4.26–4.36 (m, 1H), 7.02 (d, J=9.0 Hz, 1H), 7.13 (s, 1H), 7.30 (d, J=9.0 Hz, 1H), 7.88 (s, 1H) Mass spectrum (ESI-MS, m/z): 232 (M$^+$+1)

Example 198

1H-5-Indazolyl(1-methyl-3-piperidyl)ether 1H-5-Indazolol (intermediate 1) (67 mg), 1-methyl-3-hydroxypiperidine (58 mg), and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (36 mg).

$^1$H-NMR (CDCl$_3$, 400 MHz): 1.14 (t, J=7.2 Hz, 3H), 1.70–1.90 (m, 3H), 1.96–2.05 (m, 1H), 2.21–2.36 (m, 1H), 2.38–2.50 (m, 1H), 2.80–2.91 (m, 1H), 2.93–3.05 (m, 1H), 3.15–3.25 (m, 1H), 3.85 (dd, J=6.8 Hz, 9.0 Hz, 1H), 3.98–4.06 (m, 1H), 7.04–7.10 (m, 2H), 7.35 (d, J=9.8 Hz, 1H), 7.94 (s, 1H) Mass spectrum (ESI-MS, m/z): 246 (M$^+$+1)

Example 199

1-(3-Cyclohexenylmethyl)-3-piperidyl(1H-5-indazolyl)ether

3-Hydroxypiperidine (71 mg) and 1,2,3,6-tetrahydrobenzaldehyde (77 mg) were dissolved in methanol/THF (1:1, 2 ml), and sodium triacetoxyborohydride (211 mg) was added by portions to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (20 mg).

Mass spectrum (ESI-MS, m/z): 312 (M$^+$+1)

Example 200

1-(2-Chlorobenzyl)-4-piperidyl(1H-5-indazolyl)ether

4-Hydroxypiperidine (61 mg) and potassium carbonate (165 mg) were dissolved in dimethylformamide (1 ml), and a solution (1 ml) of 2-chlorobenzyl chloride (100 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (2 mg).

$^1$H-NMR (CDCl$_3$, 400 MHz): 1.80–1.92 (m, 2H), 1.95–2.08 (m, 2H), 2.30–2.45 (m, 2H), 2.76–2.90 (m, 2H), 3.58–3.70 (m, 2H), 4.27–4.36 (m, 1H), 7.08 (d, J=9.0 Hz, 1H), 7.14 (s, 1H), 7.24–7.28 (m, 3H), 7.33 (d, J=8.0 Hz, 1H), 7.37 (d, J=9.0 Hz, 1H), 7.94 (s, 1H) Mass spectrum (ESI-MS, m/z): 342 (M$^+$+1)

Example 201

1-(3-Chlorobenzyl)-4-piperidyl(1H-5-indazolyl)ether

4-Hydroxypiperidine (61 mg) and potassium carbonate (165 mg) were dissolved in dimethylformamide (1 ml), and a solution (1 ml) of 3-chlorobenzyl chloride (100 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (7 mg).

$^1$H-NMR (CDCl$_3$, 400 MHz): 1.79–1.92 (m, 2H), 1.95–2.08 (m, 2H), 2.20–2.40 (m, 2H), 2.68–2.80 (m, 2H), 3.48 (s, 2H), 4.23–4.35 (m, 1H), 7.06 (d, J=9.0 Hz, 1H), 7.14 (s, 1H), 7.18–7.28 (m, 3H), 7.34 (s, 1H), 7.37 (d, J=9.0 Hz, 1H), 7.94 (s, 1H) Mass spectrum (ESI-MS, m/z): 342 (M$^+$+1)

Example 202

1-(4-Chlorobenzyl)-4-piperidyl(1H-5-indazolyl)ether

4-Hydroxypiperidine (61 mg) and potassium carbonate (165 mg) were dissolved in dimethylformamide (1 ml), and a solution (1 ml) of 4-chlorobenzyl chloride (100 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (4 mg).

$^1$H-NMR (CDCl$_3$, 400 MHz): 1.76–1.92 (m, 2H), 1.95–2.08 (m, 2H), 2.20–2.40 (m, 2H), 2.68–2.80 (m, 2H), 3.48 (s, 2H), 4.23–4.36 (m, 1H), 7.05 (d, J=9.0 Hz, 1H), 7.13 (s, 1H), 7.24–7.28 (m, 4H), 7.36 (d, J=9.0 Hz, 1H), 7.94 (s, 1H) Mass spectrum (ESI-MS, m/z): 342 (M$^+$+1)

Example 203

1-(4-Fluorobenzyl)-4-piperidyl(1H-5-indazolyl)ether

4-Hydroxypiperidine (61 mg) and potassium carbonate (165 mg) were dissolved in dimethylformamide (1 ml), and a solution (1 ml) of 4-fluorobenzyl chloride (86 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (7 mg).

$^1$H-NMR (CDCl$_3$, 400 MHz): 1.72–1.85 (m, 2H), 1.88–2.03 (m, 2H), 2.15–2.33 (m, 2H), 2.60–2.75 (m, 2H), 3.44 (s, 2H), 4.20–4.30 (m, 1H), 6.88–6.97 (m, 2H), 7.01 (d, J=9.0 Hz, 1H), 7.08 (s, 1H), 7.20–7.28 (m, 2H), 7.31 (d, J=9.0 Hz, 1H), 7.89 (s, 1H) Mass spectrum (ESI-MS, m/z): 326 (M$^+$+1)

Example 204

1H-5-Indazolyl[1-(3-nitrobenzyl)-4-piperidyl]ether

4-Hydroxypiperidine (61 mg) and potassium carbonate (165 mg) were dissolved in dimethylformamide (1 ml), and a solution (1 ml) of 3-nitrobenzyl chloride (103 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (11 mg).

¹H-NMR (CDCl₃, 400 MHz): 1.80–1.92 (m, 2H), 1.95–2.08 (m, 2H), 2.28–2.40 (m, 2H), 2.68–2.80 (m, 2H), 3.61 (s, 2H), 4.28–4.38 (m, 1H), 7.07 (d, J=9.0 Hz, 1H), 7.36 (d, J=8.8 Hz, 1H), 7.49 (dd, J=5.6 Hz, 7.8 Hz, 1H), 7.67 (d, J=6.8 Hz, 1H), 7.95 (s, 1H), 8.10 (d, J=8.0 Hz, 1H), 8.21 (s, 1H)

Example 205

1H-5-Indazolyl[1-(4-nitrobenzyl)-4-piperidyl]ether

4-Hydroxypiperidine (61 mg) and potassium carbonate (165 mg) were dissolved in dimethylformamide (1 ml), and a solution (1 ml) of 4-nitrobenzyl chloride (103 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (7 mg).

¹H-NMR (CDCl₃, 400 MHz): 1.80–1.92 (m, 2H), 1.95–2.08 (m, 2H), 2.28–2.40 (m, 2H), 2.68–2.80 (m, 2H), 3.61 (s, 2H), 4.28–4.38 (m, 1H), 7.06 (d, J=9.0 Hz, 1H), 7.14 (s, 1H), 7.38 (d, J=8.8 Hz, 1H), 7.51 (d, J=8.5 Hz, 2H), 7.95 (s, 1H), 8.16 (d, J=8.8 Hz, 1H) Mass spectrum (ESI-MS, m/z): 353 (M⁺+1)

Example 206

(3S)-1-(2-Chlorobenzyl)tetrahydro-1H-3-pyrrolyl (1H-5-indazolyl)ether (R)-(–)-Pyrrolidinol hydrochloride (73 mg) and potassium carbonate (165 mg) were dissolved in dimethylformamide (1 ml), and a solution (1 ml) of 2-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg).

¹H-NMR (CDCl₃, 400 MHz): 1.95–2.08 (m, 1H), 2.33 (dt, J=7.3 Hz, 14.2 Hz, 1H), 2.65–2.73 (m, 1H), 2.82–2.92 (m, 2H), 3.08 (dd, J=6.1 Hz, 10.5 Hz, 1H), 3.82 (s, 2H), 4.80–4.88 (m, 1H), 6.99 (s, 1H), 7.02 (d, J=9.0 Hz, 1H), 7.13–7.24 (m, 2H), 7.30–7.37 (m, 2H), 7.49 (d, J=7.6 Hz, 1H), 7.95 (s, 1H) Mass spectrum (ESI-MS, m/z): 328 (M⁺+1)

Example 207

(3S)-1-(3-Chlorobenzyl)tetrahydro-1H-3-pyrrolyl (1H-5-indazolyl)ether (R)-(–)-Pyrrolidinol hydrochloride (73 mg) and potassium carbonate (165 mg) were dissolved in dimethylformamide (1 ml), and a solution (1 ml) of 3-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg).

¹H-NMR (CDCl₃, 400 MHz): 1.92–2.08 (m, 1H), 2.33 (dt, J=7.1 Hz, 13.9 Hz, 1H), 2.55–2.65 (m, 1H), 2.70–2.85 (m, 2H), 2.98 (dd, J=6.1 Hz, 10.3 Hz, 1H), 3.63 (d, J=13.2 Hz, 1H), 3.65 (d, J=12.9 Hz, 1H), 4.80–4.88 (m, 1H), 6.97 (s, 1H), 7.02 (d, J=9.0 Hz, 1H), 7.16–7.24 (m, 3H), 7.34 (d, J=8.8 Hz, 1H), 7.33–7.37 (m, 1H), 7.95 (s, 1H) Mass spectrum (ESI-MS, m/z): 328 (M⁺+1)

Example 208

(3S)-1-(4-Chlorobenzyl)tetrahydro-1H-3-pyrrolyl (1H-5-indazolyl)ether (R)-(–)-Pyrrolidinol hydrochloride (73 mg) and potassium carbonate (165 mg) were dissolved in dimethylformamide (1 ml), and a solution (1 ml) of 4-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (14 mg).

¹H-NMR (CDCl₃, 400 MHz): 1.95–2.08 (m, 1H), 2.29 (dt, J=7.3 Hz, 13.9 Hz, 1H), 2.52–2.62 (m, 1H), 2.70–2.80 (m, 2H), 2.94 (dd, J=6.3 Hz, 10.5 Hz, 1H), 3.60 (d, J=13.2 Hz, 1H), 3.63 (d, J=13.2 Hz, 1H), 4.77–4.84 (m, 1H), 6.94 (s, 1H), 7.02 (d, J=9.0 Hz, 1H), 7.25–7.35 (m, 4H), 7.32 (d, J=9.0 Hz, 1H), 7.91 (s, 1H) Mass spectrum (ESI-MS, m/z): 328 (M⁺+1)

Example 209

(3S)-1-(4-Fluorobenzyl)tetrahydro-1H-3-pyrrolyl (1H-5-indazolyl)ether (R)-(−)-Pyrrolidinol hydrochloride (73 mg) and potassium carbonate (165 mg) were dissolved in dimethylformamide (1 ml), and a solution (1 ml) of 4-fluorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (18 mg).

$^1$H-NMR (CDCl$_3$, 400 MHz): 1.92–2.02 (m, 1H), 2.26 (dt, J=6.8 Hz, 14.2 Hz, 1H), 2.48–2.57 (m, 1H), 2.65–2.77 (m, 2H), 2.90 (dd, J=6.3 Hz, 10.5 Hz, 1H), 3.60 (d, J=2.9 Hz, 1H), 3.59 (d, J=12.9 Hz, 1H), 4.73–4.84 (m, 1H), 6.87–6.97 (m, 4H), 7.20–7.27 (m, 2H), 7.29 (d, J=9.0 Hz, 1H), 7.91 (s, 1H) Mass spectrum (ESI-MS, m/z): 312 (M$^+$+1)

Example 210

(3S)-($^1$H-5-Indazolyl)[1-(3-nitrobenzyl)tetrahydro-1H-3-pyrrolyl]ether (R)-(−)-Pyrrolidinol hydrochloride (73 mg) and potassium carbonate (165 mg) were dissolved in dimethylformamide (1 ml), and a solution (1 ml) of 3-nitrobenzyl chloride (103 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg).

$^1$H-NMR (CDCl$_3$, 400 MHz): 2.00–2.10 (m, 1H), 2.33 (dt, J=7.3 Hz, 13.9 Hz, 1H), 2.55–2.65 (m, 1H), 2.75–2.86 (m, 2H), 2.98 (dd, J=6.1 Hz, 10.5 Hz, 1H), 3.75 (d, J=13.7 Hz, 1H), 3.76 (d, J=13.4 Hz, 1H), 4.82–4.88 (m, 1H), 6.97 (s, 1H), 7.02 (d, J=8.8 Hz, 1H), 7.35 (d, J=9.0 Hz, 1H), 7.45 (t, J=7.8 Hz, 1H), 7.67 (d, J=7.6 Hz, 1H), 7.93 (s, 1H), 8.08 (d, J=6.8 Hz, 1H), 8.21 (s, 1H)

Example 211

(3S)-(1H-5-Indazolyl) [1-(4-nitrobenzyl)tetrahydro-1H-3-pyrrolyl]ether (R)-(−)-Pyrrolidinol hydrochloride (73 mg) and potassium carbonate (165 mg) were dissolved in dimethylformamide (1 ml), and a solution (1 ml) of 4-nitrobenzyl chloride (103 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (40 mg).

$^1$H-NMR (CDCl$_3$, 400 MHz): 2.02–2.10 (m, 1H), 2.33 (dt, J=7.6 Hz, 13.9 Hz, 1H), 2.55–2.63 (m, 1H), 2.75–2.86 (m, 2H), 2.98 (dd, J=5.8 Hz, 10.2 Hz, 1H), 3.75 (d, J=13.9 Hz, 1H), 3.76 (d, J=13.9 Hz, 1H), 4.82–4.88 (m, 1H), 6.97 (s, 1H), 7.02. (d, J=9.0 Hz, 1H), 7.36 (d, J=9.0 Hz, 1H), 7.51 (t, J=8.8 Hz, 2H), 7.93 (s, 1H), 8.15 (d, J=8.8 Hz, 2H) Mass spectrum (ESI-MS, m/z): 339 (M$^+$+1)

Example 212

1-(2-Chlorobenzyl)-3-piperidyl(1H-5-indazolyl)ether

3-Hydroxypiperidine (61 mg) and potassium carbonate (165 mg) were dissolved in dimethylformamide (1 ml), and a solution (1 ml) of 2-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (23 mg).

Mass spectrum (ESI-MS, m/z): 342 (M$^+$+1)

Example 213

1-(3-Chlorobenzyl)-3-piperidyl(1H-5-indazolyl)ether

3-Hydroxypiperidine (61 mg) and potassium carbonate (165 mg) were dissolved in dimethylformamide (1 ml), and a solution (1 ml) of 3-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg).

Mass spectrum (ESI-MS, m/z): 342 ($M^+$+1)

Example 214

1-(4-Chlorobenzyl)-3-piperidyl(1H-5-indazolyl)ether

3-Hydroxypiperidine (61 mg) and potassium carbonate (165 mg) were dissolved in dimethylformamide (1 ml), and a solution (1 ml) of 4-chlorobenzyl chloride (97 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol]to give the title compound (27 mg).

Mass spectrum (ESI-MS, m/z): 342 ($M^+$+1)

Example 215

1-(4-Fluorobenzyl)-3-piperidyl(1H-5-indazolyl)ether

3-Hydroxypiperidine (61 mg) and potassium carbonate (165 mg) were dissolved in dimethylformamide (1 ml), and a solution (1 ml) of 4-fluorobenzyl chloride (86 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (14 mg).

Mass spectrum (ESI-MS, m/z): 326 ($M^+$+1)

Example 216

1H-5-Indazolyl[1-(3-nitrobenzyl)-3-piperidyl]ether

3-Hydroxypiperidine (61 mg) and potassium carbonate (165 mg) were dissolved in dimethylformamide (1 ml), and a solution (1 ml) of 3-nitrobenzyl chloride (103 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (25 mg).

$^1$H-NMR (CDCl$_3$, 400 MHz): 1.46–1.57 (m, 1H), 1.57–1.70 (m, 1H), 1.73–1.88 (m, 1H), 2.05–2.15 (m, 1H), 2.15–2.34 (m, 2H), 2.63–2.68 (m, 1H), 2.3.04 (m, 2H), 3.63 (s, 1H), 4.32–4.38 (m, 1H), 7.05 (d, J=9.0 Hz, 1H), 7.14 (s, 1H), 7.36 (d, J=9.0 Hz, 1H), 7.43 (t, J=7.8 Hz, 1H), 7.62 (d, J=7.8 Hz, 1H), 7.93 (s, 1H), 8.07 (d, J=8.0 Hz, 2H), 8.21 (s, 1H)

Example 217

1H-5-Indazolyl[1-(1-phenylethyl)-3-piperidyl]ether

3-Hydroxypiperidine (61 mg) and potassium carbonate (165 mg) were dissolved in dimethylformamide (1 ml), and a solution (1 ml) of (1-bromoethyl)benzene (111 mg) in acetonitrile was added dropwise thereto at room temperature. The reaction mixture was stirred at room temperature for 18 hr and was then filtered through Celite, and the filtrate was concentrated to give intermediate A.

1H-5-Indazolol (intermediate 1) (67 mg), intermediate A, and triphenylphosphine (131 mg) were dissolved in tetrahydrofuran (1 ml), and a solution (0.50 ml) of 40% diethyl azodicarboxylate in toluene was added thereto at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give the title compound (23 mg).

Mass spectrum (ESI-MS, m/z): 322 ($M^+$+1)

Example 218

N-(1H-5-Indazolyl)-N-[1-(1-phenylethyl)-4-piperidyl]amine

4-Piperidone hydrochloride monohydrate (77 mg) and potassium carbonate (138 mg) were dissolved in dimethylformamide (1 ml), and a solution (1 ml) of (1-bromoethyl)benzene (93 mg) in acetonitrile was added dropwise thereto at room temperature. The reaction mixture was stirred at room temperature for 18 hr and was then filtered through Celite, and the filtrate was concentrated to give intermediate A.

This intermediate A, 5-aminoindazole (52 mg), and acetic acid (0.02 ml) were dissolved in methanol (1 ml), and a borane-pyridine complex (0.07 ml) was added dropwise to the solution at room temperature. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (14 mg) as two diastereomers (ratio=ca. 50:50).

$^1$H-NMR (CDCl$_3$, 400 MHz) as a mixture of 2 diastereomers: 1.40–1.75 (m, 10H), 1.98–2.28 (m, 8H), 2.80–2.95 (m, 2H), 3.00–3.15 (m, 2H), 3.20–3.32 (m, 2H), 3.50–3.63 (m, 2H), 6.73–6.78 (m, 4H), 7.23–7.28 (m, 6H), 7.30–7.34 (m, 6H), 7.84 (s, 2H) Mass spectrum (ESI-MS, m/z): 321 (M$^+$+1)

Example 219

N-(1H-5-Indazolyl)-N-[1-(1-phenylethyl)tetrahydro-1H-3-pyrrolidyl]amine

The compound prepared in Example 179 (700 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (690 mg) and dimethylformamide (3 ml) were added to the concentrate, and the mixture was stirred. A solution (2 ml) of (1-bromoethyl)benzene (408 mg) in acetonitrile was added dropwise to the reaction solution, and the reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 150 mg of the title compound as two diastereomers (ratio=ca. 50:50).

$^1$H-NMR (CDCl$_3$, 400 MHz) as a mixture of 2 diastereomers: 1.30–1.39 (m, 6H), 1.54–1.72 (m, 1H), 2.17–2.28 (m, 2H), 2.28–2.45 (m, 3H), 2.53–2.61 (m, 1H), 2.65–2.70 (m, 2H), 2.70–2.77 (m, 2H), 3.17–3.25 (m, 2H), 3.88–3.98 (m, 2H), 6.63–6.73 (m, 4H), 7.10–7.30 (m, 12H), 7.80 (s, 1H), 7.82 (s, 1H) Mass spectrum (ESI-MS, m/z): 307 (M$^+$+1)

Example 220

N-(1H-5-Indazolyl)-N-[1-(1-phenylethyl)-3-piperidyl]amine

The compound prepared in Example 181 (700 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (690 mg) and dimethylformamide (3 ml) were added to the concentrate, and the mixture was stirred. A solution (2 ml) of (1-bromoethyl)benzene (408 mg) in acetonitrile was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 185 mg of the title compound as two diastereomers (ratio=ca. 50:50).

$^1$H-NMR (CDCl$_3$, 400 MHz) as a mixture of 2 diastereomers: 1.28–1.34 (m, 6H), 1.40–1.55 (m, 4H), 1.55–1.70 (m, 4H), 2.18–2.45 (m, 3H), 2.64–2.74 (m, 2H), 3.41–3.54 (m, 4H), 6.66–6.78 (m, 4H), 7.12–7.26 (m, 12H), 7.80 (s, 2H) Mass spectrum (ESI-MS, m/z): 321 (M$^+$+1)

Example 221

Methyl 2-[3-(1H-5-indazolylamino)piperidino]-2-phenyl acetate

3-Hydroxypiperidine (1.41 g) and potassium carbonate (2.76 g) were dissolved in dimethylformamide (20 ml), and a solution (20 ml) of methyl α-bromophenylacetate (3.23 g) in acetonitrile was added dropwise thereto at room temperature. The reaction mixture was stirred at room temperature for 18 hr and was then filtered through Celite, and the filtrate was concentrated to give intermediate A.

This intermediate A and triethylamine (3 ml) were dissolved in anhydrous dimethyl sulfoxide (5 ml), and a sulfur trioxide-trimethylamine complex (3.69 g) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

This intermediate B, 5-aminoindazole (1.33 g), and acetic acid (0.2 ml) were dissolved in methanol (20 ml), and a borane-pyridine complex (1.5 ml) was added dropwise to the solution at room temperature. The reaction mixture was stirred at room temperature for 18 hr. A saturated aqueous sodium hydrogencarbonate solution (20 ml) was then added thereto, and the mixture was extracted with chloroform-propanol (3/1). The organic layer was dried over anhydrous sodium sulfate, and the solvent was removed by distillation under the reduced pressure. The residue was purified by column chromatography on silica gel [chloroform/methanol] to give the title compound (3.55 g) as two diastereomers (ratio=ca. 50:50).

$^1$H-NMR (CDCl$_3$, 400 MHz) as a mixture of 2 diastereomers: 1.44–1.62 (m, 4H), 1.64–1.78 (m, 4H), 2.18–2.52 (m, 6H), 2.67–2.88 (m, 2H), 3.46–3.56 (m, 2H), 3.60 (s, 1H), 3.62 (s, 1H), 4.06–4.10 (m, 2H), 6.65–6.81 (m, 4H), 7.18–7.38 (m, 12H), 7.79 (s, 2H) Mass spectrum (ESI-MS, m/z): 365 (M$^+$+1)

Example 222

2-[3-(1H-5-Indazolylamino)piperidino]-2-phenylacetic acid

The compound prepared in Example 221 (500 mg) was dissolved in methanol (1 ml) and a 3 N aqueous sodium hydroxide solution (1 ml) which was then stirred at room temperature for 18 hr. The reaction mixture was neutralized and adjusted to pH=about 7 by the addition of 1 N hydrochloric acid and was then concentrated.

The residue was purified by ODS column chromatography [water/acetonitrile] to give 450 mg of the title compound as two diastereomers (ratio=ca. 50:50).

Mass spectrum (ESI-MS, m/z): 349 (M$^+$−1)

Example 223

N1-Methyl-2-[3-(1H-5-indazolylamino)piperidino]-2-phenylacetamide

Methylamine (30 mg) and the compound prepared in Example 222 (88 mg) were dissolved in dimethylformamide (1 ml), and 1-ethyl-3-(3-dimethylaminopropyl)carbodiimide hydrochloride (86 mg), 1-hydroxybenzotriazole (77 mg), and dimethylaminopyridine (5 mg) were added to the solution. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 52 mg of the title compound as two diastereomers (ratio=ca. 50:50).

$^1$H-NMR (CDCl$_3$, 400 MHz) as a mixture of 2 diastereomers: 1.33–1.50 (m, 2H), 1.55–1.69 (m, 2H), 1.70–1.95 (m, 4H), 2.12–2.42 (m, 3H), 2.42–2.55 (m, 1H), 2.58–2.67 (m, 3H), 2.76 (s, 3H), 2.77 (s, 3H), 3.48–3.58 (m, 2H), 3.89 (s, 1H), 3.94 (s, 1H), 6.72–6.83 (m, 4H), 7.20–7.38 (m, 12H), 7.83 (s, 2H) Mass spectrum (ESI-MS, m/z): 364 (M$^+$+1)

Example 224

N1-Propyl-2-[3-(1H-5-indazolylamino)piperidino]-2-phenylacetamide

Propylamine (30 mg) and the compound prepared in Example 222 (88 mg) were dissolved in dimethylformamide (1 ml), and 1-ethyl-3-(3-dimethylaminopropyl)carbodiimide hydrochloride (86 mg), 1-hydroxybenzotriazole (77 mg), and dimethylaminopyridine (5 mg) were added to the solution. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 72 mg of the title compound as two diastereomers (ratio=ca. 50:50).

$^1$H-NMR (CDCl$_3$, 400 MHz) as a mixture of 2 diastereomers: 0.79 (t, J=7.3, 3H), 0.82 (t, J=7.6, 3H), 1.25–1.50 (m, 6H), 1.52–1.65 (m, 2H), 1.65–1.78 (m, 2H), 1.78–1.94 (m, 2H), 2.00–2.20 (m, 2H), 2.22–2.33 (m, 1H), 2.40–2.55 (m, 2H), 2.70–2.87 (m, 3H), 2.90–3.03 (m, 1H), 3.10–3.19 (m, 4H), 3.45–3.54 (m, 2H), 3.83 (s, 1H), 3.86 (S, 1H), 6.65–6.76 (m, 4H), 7.15–7.27 (m, 12H), 7.78 (s, 2H) Mass spectrum (ESI-MS, m/z): 391 (M$^+$+1)

Example 225

N1-Cyclopropyl-2-[3-(1H-5-indazolylamino)piperidino]-2-phenylacetamide

Cyclopropylamine (30 mg) and the compound prepared in Example 222 (88 mg) were dissolved in dimethylformamide (1 ml), and 1-ethyl-3-(3-dimethylaminopropyl)carbodiimide hydro-chloride (86 mg), 1-hydroxybenzotriazole (77 mg), and dimethylaminopyridine (5 mg) were added to the solution. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol]t to give 64 mg of the title compound as a single diastereomers.

$^1$H-NMR (CDCl$_3$, 400 MHz) as a mixture of 2 diastereomers: −0.50–0.06 (m, 4H), 0.16–0.34 (m, 4H), 1.10–1.23 (m, 2H), 1.23–1.35 (m, 2H), 1.40–1.50 (m, 2H), 1.55–1.75 (m, 3H), 1.80–1.90 (m, 1H), 1.98–2.10 (m, 2H), 2.12–2.18 (m, 1H), 2.18–2.28 (m, 1H), 2.30–2.39 (m, 1H), 2.40–2.50 (m, 1H), 3.00–3.10 (m, 2H), 3.40 (s, 1H), 3.41 (s, 1H), 6.25–6.35 (m, 4H), 6.75–6.87 (m, 12H), 7.39 (s, 1H), 7.40 (s, 1H) Mass spectrum (ESI-MS, m/z): 390 (M$^+$+1)

Example 226

N1,N1-Diethyl-2-[3-(1H-5-indazolylamino)piperidino]-2-phenylacetamide

Diethylamine (35 mg) and the compound prepared in Example 222 (88 mg) were dissolved in dimethylformamide (1 ml), and 1-ethyl-3-(3-dimethylaminopropyl)carbodiimide hydrochloride (86 mg), 1-hydroxybenzotriazole (77 mg), and dimethylaminopyridine (5 mg) were added to the solution. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 58 mg of the title compound as a single diastereomers.

$^1$H-NMR (CDCl$_3$, 400 MHz) one diastereomer: 0.95 (t, J=7.1, 3H), 1.01 (t, J=7.1, 3H), 1.42–1.58 (m, 2H), 1.60–1.75 (m, 2H), 2.35–2.50 (m, 2H), 2.58–2.68 (m, 1H), 2.74–2.82 (m, 1H), 3.02–3.32 (m, 6H), 3.35–3.53 (m, 2H), 4.31 (s, 1H), 6.68 (s, 1H), 6.72 (t, J=8.8, 1H), 7.15–7.30 (m, 4H), 7.30–7.37 (m, 2H), 7.76 (s, 2H) Mass spectrum (ESI-MS,m/z): 406 (M$^+$+1)

Example 227

N1-(2-Fluoroethyl)-2-[3-(1H-5-indazolylamino)piperidino]-2-phenylacetamide

2-Fluoroethylamine hydrochloride (50 mg) and the compound prepared in Example 222 (88 mg) were dissolved in dimethylformamide (1 ml), and 1-ethyl-3-(3-dimethylaminopropyl)carbodiimide hydro-chloride (86 mg), 1-hydroxybenzotriazole (77 mg), and dimethylaminopyridine (5 mg) were added to the solution. The reaction mixture was stirred at room temperature for 18 hr. A saturated aqueous sodium hydrogencarbonate solution (1 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 39 mg of the title compound as two diastereomers (ratio=ca. 50:50).

$^1$H-NMR (CDCl$_3$, 400 MHz) as a mixture of 2 diastereomers: 1.27–1.40 (m, 2H), 1.55–1.68 (m, 2H), 1.68–1.80 (m, 2H), 1.80–1.92 (m, 2H), 1.95–2.15 (m, 2H), 2.24–2.35 (m, 2H), 2.45–2.60 (m, 2H), 2.75–2.85 (m, 2H), 3.25–3.45 (m, 2H), 3.45–3.62 (m, 2H), 3.90 (s, 2H), 4.27–4.40 (m, 2H), 4.40–4.55 (m, 2H), 6.67–6.73 (m, 4H), 7.15–7.30 (m, 12H), 7.79 (s, 1H), 7.80 (s, 1H) Mass spectrum (ESI-MS, m/z): 396 (M$^+$+1)

Example 228

N1,N1-Dimethyl-2-[3-(1H-5-indazolylamino)piperidino]-2-phenylacetamide

Dimethylamine (100 mg) and the compound prepared in Example 222 (350 mg) were dissolved in dimethylformamide (5 ml), and 1-ethyl-3-(3-dimethylaminopropyl)carbodiimide hydrochloride (257 mg), 1-hydroxybenzotriazole (227 mg), and dimethylaminopyridine (5 mg) were added to the solution. The reaction mixture was stirred at room temperature for 18 hr. A saturated aqueous sodium hydrogencarbonate solution (5 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol]t to give 180 mg of the title compound as two diastereomers (ratio=ca. 50:50)).

$^1$H-NMR (CDCl$_3$, 400 MHz) as a mixture of 2 diastereomers: 1.40–1.60 (m, 4H), 1.60–1.77 (m, 4H), 2.22–2.52 (m, 4H), 2.52–2.65 (m, 2H), 2.70–3.03 (m, 2H), 2.86 (s, 6H), 3.44–3.54 (m, 4H), 4.32–4.45 (m, 2H), 6.65–6.79 (m, 4H), 7.15–7.40 (m, 12H), 7.75–7.80 (m, 2H) Mass spectrum (ESI-MS, m/z): 378 (M$^+$+1)

Example 229

Methyl 2-(4-fluorophenyl)-2-[3-(1H-5-indazolylamino)piperidino]-2-phenylacetate Methyl 4-fluorophenylacetate (252 mg), N-bromosuccinimide (354 mg), and azobisisobutyronitrile (10 mg) were dissolved in carbon tetrachloride (3 ml), and the mixture was then stirred at 80° C. for 18 hr. The reaction mixture was cooled to room temperature, and ether was then added thereto. The mixture was filtered through Celite and concentrated to give intermediate A.

The compound prepared in Example 180 (407 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (mg) and dimethylformamide (3 ml) were added to the concentrate, and the mixture was stirred. A solution of intermediate A in acetonitrile (2 ml) was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 370 mg of the title compound as two diastereomers (ratio=ca. 50:50).

$^1$H-NMR (CDCl$_3$, 400 MHz) as a mixture of 2 diastereomers: 1.52–1.70 (m, 4H), 1.70–1.90 (m, 4H), 2.32–2.64 (m, 6H), 2.75–2.95 (m, 2H), 3.55–3.65 (m, 2H), 3.65 (s, 3H), 3.66 (s, 3H), 4.12–4.28 (m, 2H), 6.90–7.04 (m, 8H), 7.34–7.48 (m, 6H), 7.83 (s, 2H) Mass spectrum (ESI-MS, m/z): 383 (M$^+$+1)

Example 230

Methyl 2-(4-chlorophenyl)-2-[3-(1H-5-indazolylamino)piperidino]-2-phenyl acetate Methyl 4-chlorophenylacetate (276 mg), N-bromosuccinimide (354 mg), and azobisisobutyronitrile (10 mg) were dissolved in carbon tetrachloride (3 ml), and the mixture was then stirred at 80° C. for 18 hr. The reaction mixture was cooled to room temperature, and ether was then added thereto. The mixture was filtered through Celite and concentrated to give intermediate A.

The compound prepared in Example 180 (407 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (mg) and dimethylformamide (3 ml) were added to the concentrate, and the mixture was stirred. A solution of intermediate A in acetonitrile (2 ml) was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 420 mg of the title compound as two diastereomers (ratio=ca. 50:50).

$^1$H-NMR (CDCl$_3$, 400 MHz) as a mixture of 2 diastereomers: 1.52–1.70 (m, 4H), 1.68–1.90 (m, 4H), 2.32–2.60 (m, 6H), 2.75–2.93 (m, 2H), 3.53–3.65 (m, 2H), 3.65 (s, 3H), 3.66 (s, 3H), 4.10–4.22 (m, 2H), 6.80–6.97 (m, 4H), 7.22–7.40 (m, 12H), 7.84 (s, 2H) Mass spectrum (ESI-MS, m/z): 399 (M$^+$+1)

Example 231

N1-(2-Fluoroethyl)-2-(4-fluorophenyl)-2-[3-(1H-5-indazolylamino)piperidino]-2-phenylacetamide The compound prepared in Example 229 (192 mg) was dissolved in methanol (1 ml) and a 3 N aqueous sodium hydroxide solution (1 ml), and the mixture was then stirred at room temperature for 18 hr. The reaction mixture was neutralized and adjusted to pH=about 7 by the addition of 1 N hydrochloric acid and was then concentrated to give intermediate A.

2-Fluoroethylamine hydrochloride (99 mg) and intermediate A were dissolved in dimethylformamide (2 ml), and 1-ethyl-3-(3-dimethylaminopropyl)carbodiimide hydrochloride (191 mg), 1-hydroxybenzotriazole (153 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 111 mg of the title compound as two diastereomers (ratio=ca. 50:50).

$^1$H-NMR (CDCl$_3$, 400 MHz) as a mixture of 2 diastereomers: 1.25–1.42 (m, 2H), 1.45–1.67 (m, 2H), 1.68–1.77 (m, 2H), 1.80–1.92 (m, 2H), 2.00–2.20 (m, 2H), 2.24–2.35 (m, 2H), 2.40–2.55 (m, 2H), 2.70–2.80 (m, 2H), 3.25–3.63 (m, 6H), 3.89 (s, 1H), 3.92 (s, 1H), 4.27–4.38 (m, 2H), 4.40–4.55 (m, 2H), 6.63–6.77 (m, 4H), 6.85–6.97 (m, 4H), 7.10–7.25 (m, 4H), 7.50–7.65 (m, 2H), 7.79 (s, 1H), 7.80 (s, 1H) Mass spectrum (ESI-MS, m/z): 414 (M$^+$+1)

Example 232

N1-(2-Fluoroethyl)-2-(4-chlorophenyl)-2-[3-(1H-5-indazolylamino)piperidino]-2-phenylacetamide The compound prepared in Example 230 (200 mg) was dissolved in methanol (1 ml) and a 3 N aqueous sodium hydroxide solution (1 ml). The solution was stirred at room temperature for 18 hr and was then neutralized and adjusted to pH=about 7 by the addition of 1 N hydrochloric acid, followed by concentration to give intermediate A.

2-Fluoroethylamine hydrochloride (99 mg) and intermediate A were dissolved in dimethylformamide (2 ml), and 1-ethyl-3-(3-dimethylaminopropyl)carbodiimide hydrochloride (191 mg), 1-hydroxybenzotriazole (153 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 109 mg of the title compound as two diastereomers (ratio=ca. 50:50).

$^1$H-NMR (CDCl$_3$, 400 MHz) as a mixture of 2 diastereomers: 1.25–1.40 (m, 2H), 1.50–1.67 (m, 2H), 1.68–1.77 (m, 2H), 1.77–1.92 (m, 2H), 2.00–2.20 (m, 2H), 2.24–2.35 (m, 2H), 2.40–2.57 (m, 2H), 2.70–2.90 (m, 2H), 3.25–3.65 (m, 6H), 3.89 (s, 1H), 3.92 (s, 1H), 4.27–4.40 (m, 2H), 4.40–4.55 (m, 2H), 6.63–6.77 (m, 4H), 7.10–7.25 (m, 10H), 7.50–7.70 (m, 2H), 7.79 (s, 1H), 7.80 (s, 1H) Mass spectrum (ESI-MS, m/z): 430 (M$^+$+1)

Example 233

N1-(O-Methylhydroxyl)-2-[3-(1H-5-indazolylamino)piperidino]-2-phenylacetamide

The compound prepared in Example 222 (175 mg) was dissolved in methanol (1 ml) and a 3 N aqueous sodium hydroxide solution (1 ml), and the mixture was then stirred at room temperature for 18 hr. The reaction mixture was neutralized and adjusted to pH=about 7 by the addition of 1 N hydrochloric acid and was then concentrated to give intermediate A.

O-Methylhydroxylamine hydrochloride (84 mg) and intermediate A were dissolved in dimethylformamide (2 ml), and 1-ethyl-3-(3-dimethylaminopropyl)carbodiimide hydrochloride (263 mg), 1-hydroxybenzotriazole (225 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 202 mg of the title compound as two diastereomers (ratio=ca. 50:50).

$^1$H-NMR (CDCl$_3$, 400 MHz) as a mixture of 2 diastereomers: 1.32–1.50 (m, 2H), 1.55–1.70 (m, 2H), 1.72–1.94 (m, 4H), 2.00–2.45 (m, 4H), 2.50–2.65 (m, 2H), 2.73–2.95 (m, 2H), 3.25–3.45 (m, 2H), 3.45–3.62 (m, 2H), 3.64 (s, 6H), 4.00–4.15 (m, 2H), 6.72–6.83 (m, 4H), 7.25–7.35 (m, 12H), 7.83 (s, 2H)

Example 234

N1-(O-Ethylhydroxyl)-2-[3-(1H-5-indazolylamino)piperidino]-2-phenylacetamide

The compound prepared in Example 222 (175 mg) was dissolved in methanol (1 ml) and a 3 N aqueous sodium hydroxide solution (1 ml), and the mixture was then stirred at room temperature for 18 hr. The reaction mixture was neutralized and adjusted to pH=about 7 by the addition of 1 N hydrochloric acid and was then concentrated to give intermediate A.

O-Ethylhydroxylamine hydrochloride (98 mg) and intermediate A were dissolved in dimethylformamide (2 ml), and 1-ethyl-3-(3-dimethylaminopropyl)carbodiimide hydrochloride (263 mg), 1-hydroxybenzotriazole (225 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 204 mg of the title compound as two diastereomers (ratio=ca. 50:50).

$^1$H-NMR (CDCl$_3$, 400 MHz) as a mixture of 2 diastereomers: 1.11 (t, J=7.1, 6H), 1.30–1.45 (m, 2H), 1.55–1.65 (m, 2H), 1.68–1.88 (m, 4H),. 2.15–2.40 (m, 4H), 2.45–2.60 (m, 2H), 2.73–2.85 (m, 2H), 3.45–3.55 (m, 2H), 3.70–3.88 (m, 4H), 3.96–4.15 (m, 2H), 6.70–6.77 (m, 4H), 7.20–7.27 (m, 12H), 7.78 (s, 2H)

Example 235

N1-(O-Methylhydroxyl)-N1-methyl-2-[3-(1H-5-indazolylamino)piperidino]-2-phenylacetamide The compound prepared in Example 222 (175 mg) was dissolved in methanol (1 ml) and a 3 N aqueous sodium hydroxide solution (1 ml), and the mixture was then stirred at room temperature for 18 hr. The reaction mixture was neutralized and adjusted to pH=about 7 by the addition of 1 N hydrochloric acid and was then concentrated to give intermediate A.

N,O-Dimethylhydroxylamine hydrochloride (98 mg) and intermediate A were dissolved in dimethylformamide (2 ml), and 1-ethyl-3-(3-dimethylaminopropyl)carbodiimide hydrochloride (263 mg), 1-hydroxybenzotriazole (225 mg), and dimethylaminopyridine (5 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 124 mg of the title compound as two diastereomers (ratio=ca. 50:50).

$^1$H-NMR (CDCl$_3$, 400 MHz) as a mixture of 2 diastereomers: 1.45–2.05 (m, 8H), 2.33–3.05 (m, 8H), 3.15 (s, 6H), 3.42 (s, 6H), 3.55–3.73 (m, 2H), 4.76 (s, 1H), 4.87 (s, 1H), 6.76–6.85 (m, 4H), 7.23–7.38 (m, 8H), 7.38–7.48 (m, 4H), 7.79 (s, 2H)

Example 236

N-(1H-5-Indazolyl)-N-[1-(1-phenylpropyl)-3-piperidyl]amine

Ethylbenzene (110 mg), N-bromosuccinimide (267 mg), and azobisisobutyronitrile (10 mg) were dissolved in carbon tetrachloride (3 ml), and the mixture was then stirred at 80° C. for 18 hr. The reaction mixture was cooled to room temperature, and ether was then added thereto. The mixture was filtered through Celite and was concentrated to give intermediate A.

The compound prepared in Example 180 (252 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (276 mg) and dimethylformamide (3 ml) were added to the concentrate, and the mixture was stirred. A solution of intermediate A in acetonitrile (2 ml) was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 130 mg of the title compound as two diastereomers (ratio=ca. 50:50).

$^1$H-NMR (CDCl$_3$, 400 MHz) as a mixture of 2 diastereomers: 0.73 (q, J=7.3 Hz, 6H), 1.35–1.90 (m, 8H), 2.20–2.75 (m, 2H), 2.20–2.45 (m, 4H), 3.20–3.30 (m, 2H), 3.38–3.58 (m, 2H), 6.66–6.76 (m, 4H), 7.07–7.27 (m, 12H), 7.80 (s, 2H) Mass spectrum (ESI-MS, m/z): 335 (M$^+$+1)

Example 237

N-(1H-5-Indazolyl)-N-[1-(1-phenylbutyl)-3-piperidyl]amine

Propylbenzene (120 mg), N-bromosuccinimide (267 mg), and azobisisobutyronitrile (10 mg) were dissolved in carbon tetrachloride (3 ml), and the mixture was then stirred at 80° C. for 18 hr. The reaction mixture was cooled to room temperature, and ether was then added thereto. The mixture was filtered through Celite and was concentrated to give intermediate A.

The compound prepared in Example 180 (252 mg) was dissolved in chloroform (3 ml), and 95% trifluoroacetic acid (3 ml) was added dropwise to the solution at room temperature. The reaction mixture was stirred at room temperature for 2 hr and was then concentrated. Potassium carbonate (276 mg) and dimethylformamide (3 ml) were added to the concentrate, and the mixture was stirred. A solution of intermediate A in acetonitrile (2 ml) was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 125 mg of the title compound as two diastereomers (ratio=ca. 50:50).

$^1$H-NMR (CDCl$_3$, 400 MHz) as a mixture of 2 diastereomers: 0.37 (q, J=7.3 Hz, 6H), 0.60–0.85 (m, 4H), 0.85–1.46 (m, 8H), 1.70–2.00 (m, 6H), 2.05–2.40 (m, 2H), 2.85–2.97 (m, 2H), 2.97–3.15 (m, 2H), 6.25–6.33 (m, 4H), 6.65–6.85 (m, 12H), 7.38 (s, 2H) Mass spectrum (ESI-MS, m/z): 349 (M$^+$+1)

Example 238

2-[3-(1H-5-Indazolylamino)piperidino]-2-phenyl-1-ethanol

Lithium aluminum hydride (50 mg) was suspended in THF (2 ml), and a solution of Ki16245 (364 mg) in THF (2 ml) was added dropwise to the suspension at 0° C. The reaction mixture was stirred at room temperature for 18 hr and was then cooled to 0° C., and water (0.5 ml) was added dropwise to the cooled mixture. Sodium sulfate (300 mg) was added thereto, and the reaction mixture was stirred at room temperature for 3 hr and was then filtered through Celite. The solvent was removed from the filtrate by distillation under the reduced pressure, and the residue was purified by HPLC [chloroform/methanol] to give 293 mg of the title compound as two diastereomers (ratio=ca. 50:50).

$^1$H-NMR (CDCl$_3$, 400 MHz) as a mixture of 2 diastereomers: 1.40–1.80 (m, 8H), 2.40–2.55 (m, 2H), 2.55–2.75 (m, 2H), 2.75–3.05 (m, 2H), 3.40–3.80 (m, 6H), 3.90–4.10 (m, 2H), 6.71–6.79 (m, 4H), 7.15–7.35 (m, 12H), 7.80 (s, 2H) Mass spectrum (ESI-MS, m/z): 337 (M$^+$+1)

Example 239

N1-(3,4-Dimethoxybenzyl)-2-[3-(1H-5-indazolylamino)piperidino]-2-phenylacetamide Veratolylamine (257 mg) and the compound prepared in Example 222 (350 mg) were dissolved in dimethylformamide (2 ml), and 1-ethyl-3-(3-dimethylaminopropyl)carbodiimide hydro-chloride (256 mg), 1-hydroxybenzotriazole (227 mg), and dimethylaminopyridine (10 mg) were added to the solution. The reaction mixture was stirred at room temperature for 18 hr. A saturated aqueous sodium hydrogencarbonate solution (2 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol]t to give the title compound (310 mg).

Mass spectrum (ESI-MS, m/z): 500 (M$^+$+1)

Example 240

N-(1H-5-Indazolyl)-N-[1-(2-methyl-1-phenylpropyl)-3-piperidyl]amine

Isobutylbenzene (201 mg), N-bromosuccinimide (354 mg), and azobisisobutyronitrile (10 mg) were dissolved in carbon tetrachloride (3 ml), and the mixture was then stirred at 80° C. for 18 hr. The reaction mixture was cooled to room temperature, and ether was then added thereto. The mixture was filtered through Celite and was concentrated to give intermediate A.

Example 180 (407 mg) was dissolved in chloroform (3 ml),. and 95% trifluoroacetic acid. (3 ml) was added dropwise to the solution at room temperature. The reaction mixture was stirred at room temperature for 2 hr and was then concentrated. Potassium carbonate (414 mg) and dimethylformamide (3 ml) were added to the concentrate, and the mixture was stirred. A solution of intermediate A in acetonitrile (2 ml) was added dropwise to the reaction mixture. The reaction mixture was stirred at room temperature for 18 hr. A saturated aqueous sodium hydrogencarbonate solution (3 ml) was then added thereto, and the mixture was extracted with chloroform-propanol (3/1). The organic layer was dried over anhydrous sodium sulfate, and the solvent was removed by distillation under the reduced pressure. The residue was purified by HPLC [chloroform/methanol] to give 62 mg of the title compound as two diastereomers (ratio=ca. 50:50).

$^1$H-NMR (CDCl$_3$, 400 MHz) as a mixture of 2 diastereomers: 0.62 (d, J=6.6 Hz, 3H), 0.63 (d, J=6.6 Hz, 3H), 1.02 (d, J=6.0 Hz, 3H), 1.07 (d, J=6.4 Hz, 3H), 1.30–1.72 (m, 10H), 2.00–2.32 (m, 6H), 2.32–2.60 (m, 2H), 2.93 (d, J=10.0

Hz, 1H), 2.96 (d, J=11.2 Hz, 1H), 3.42–3.57 (m, 2H), 6.70–6.77 (m, 4H), 7.00–7.06 (m, 4H), 7.15–7.28 (m, 8H), 7.81 (s, 2H) Mass spectrum (ESI-MS, m/z): 349 (M$^+$+1)

Example 241

N1-Benzyl-N4-(1H-5-indazolyl)-1,4-cyclohexanediamine 4-(1H-5-Indazolylamino)-1-cyclohexanone (intermediate 3) (57 mg) and benzylamine (53 mg) were dissolved in methanol (1 ml), and sodium triacetoxyborohydride (105 mg) was added by portions at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, follwed by extraction with chloroform-propanol (3/1). The organic layers were dried over anhydrous sodium sulfate, and the solvent was removed by distillation under the reduced pressure to give an anti-form compound (14 mg) and a syn-form compound (24 mg).

(Anti Form)
$^1$H-NMR (CDCl$_3$, 400 MHz): 1.05–1.32 (m, 4H), 1.95–2.03 (m, 2H), 2.05–2.20 (m, 2H), 2.52 (tt, J=3.9 Hz, 11.0 Hz, 1H), 3.20 (tt, J=3.7 Hz, 11.0 Hz, 1H), 3.70 (s, 2H), 6.68–6.77 (m, 2H), 7.22 (d, J=8.8 Hz, 1H), 7.25–7.30 (m, 5H), 7.81 (s, 1H) Mass spectrum (ESI-MS, m/z): 321 (M$^+$+1)

(Syn Form)
$^1$H-NMR (CDCl$_3$, 400 MHz): 1.50–1.82 (m, 8H), 2.68 (tt, J=3.9 Hz, 7.6 Hz, 1H), 3.44–3.52 (m, 1H), 3.90 (s, 2H), 6.70–6.77 (m, 2H), 7.20–7.32 (m, 6H), 7.80 (s, 1H) Mass spectrum (ESI-MS, m/z): 321 (M$^+$+1)

Example 242

N1-(1H-5-Indazolyl)-N4-methyl-1,4-cyclohexanediamine 4-(1H-5-Indazolylamino)-1-cyclohexanone (intermediate 3) (57 mg) and methylamine (20 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (1 mg) and a syn-form compound (1 mg).

(Anti Form)
Mass spectrum (ESI-MS, m/z): 245 (M$^+$+1)

(Syn Form)
Mass spectrum (ESI-MS, m/z): 245 (M$^+$+1)

Example 243

N1-(1H-5-Indazolyl)-N4-propyl-1,4-cyclohexanediamine 4-(1H-5-Indazolylamino)-1-cyclohexanone (intermediate 3) (57 mg) and propylamine (30 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (5 mg) and a syn-form compound (5 mg).

(Anti Form)
$^1$H-NMR (CDCl$_3$, 400 MHz): 0.87 (t, J=7.3 Hz, 3H), 1.04–1.32 (m, 4H), 1.42–1.53 (m, 2H), 1.91–2.03 (m, 2H), 2.10–2.20 (m, 2H), 2.42–2.53 (m, 1H), 2.58 (t, J=7.4 Hz, 2H), 3.19 (tt, J=3.4 Hz, 10.5 Hz, 1H), 6.68–6.77 (m, 2H), 7.22 (d, J=8.5 Hz, 1H), 7.81 (s, 1H) Mass spectrum (ESI-MS, m/z): 273 (M$^+$+1)

(Syn Form)
$^1$H-NMR (CDCl$_3$, 400 MHz): 0.87 (t, J=7.4 Hz, 3H), 1.50–1.95 (m, 10H), 2.76–2.90 (m, 2H), 2.95–3.08 (m, 1H), 3.53–3.60 (m, 1H), 6.69 (s, 1H), 6.72 (d, J=9.0 Hz, 1H), 7.16 (d, J=8.8 Hz,. 1H), 7.75 (s, 1H) Mass spectrum (ESI-MS, m/z): 273 (M$^+$+1)

Example 244

N1-(1H-5-Indazolyl)-N4-(1-phenylethyl)-1,4-cyclohexanediamine 4-(1H-5-Indazolylamino)-1-cyclohexanone (intermediate 3) (57 mg) and 1-phenylethylamine (61 mg) were dissolved in methanol (1 ml), and sodium triacetoxyborohydride (105 mg) was added by portions at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (20 mg) and a syn-form compound (15 mg).

(Anti Form)
$^1$H-NMR (CDCl$_3$, 400 MHz): 0.90–1.30 (m, 4H), 1.30 (d, J=2.6 Hz, 3H), 1.70–1.80 (m, 2H), 2.00–2.15 (m, 2H), 2.91 (tt, J=3.7 Hz, 11.0 Hz, 2H), 3.14 (tt, J=3.6 Hz, 10.7 Hz, 1H), 3.90 (s, 1H), 6.66–6.76 (m, 2H), 7.15–7.30 (m, 6H), 7.80 (s, 1H) Mass spectrum (ESI-MS, m/z): 335 (M$^+$+1)

(Syn Form)
$^1$H-NMR (CDCl$_3$, 400 MHz): 1.31 (d, J=6.6 Hz, 3H), 1.48–1.78 (m, 8H), 2.40–2.50 (m, 1H), 3.40–3.48 (m, 1H), 3.85–3.92 (m, 1H), 6.70–6.77 (m, 2H), 7.15–7.30 (m, 6H), 7.79 (s, 1H) Mass spectrum (ESI-MS, m/z): 335 (M$^+$+1)

Example 245

N1-(4-Fluorobenzyl)-N4-(1H-5-indazolyl)-1,4-cyclohexanediamine 4-(1H-5-Indazolylamino)-1-cyclohexanone (intermediate 3) (57 mg) and 4-fluorobenzylamine (70 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (20 mg) and a syn-form compound (12 mg).

(Anti Form)
$^1$H-NMR (CDCl$_3$, 400 MHz): 1.01–1.30 (m, 4H), 1.92–2.04 (m, 2H), 2.08–2.18 (m, 2H), 2.49 (tt, J=3.6 Hz, 10.7 Hz, 1H), 3.19 (tt, J=3.7 Hz, 10.8 Hz, 1H), 3.74 (s, 2H), 6.68–6.76 (m, 2H), 6.94 (t, J=8.8 Hz, 2H), 7.16–7.28 (m, 3H), 7.81 (s, 1H) Mass spectrum (ESI-MS, m/z): 339 (M$^+$+1)

(Syn Form)
$^1$H-NMR (CDCl$_3$, 400 MHz): 1.45–1.60 (m, 2H), 1.60–1.71 (m, 4H), 1.71–1.82 (m, 2H), 2.62–2.70 (m, 1H), 3.43–3.50 (m, 1H), 3.72 (s, 2H), 6.70–6.77 (m, 2H), 6.93 (t, J=8.8 Hz, 2H), 7.16–7.28 (m, 3H), 7.81 (s, 1H) Mass spectrum (ESI-MS, m/z): 339 (M$^+$+1)

Example 246

N1-(2-Fluoroethyl)-N4-(1H-5-indazolyl)-1,4-cyclohexanediamine 4-(1H-5-Indazolylamino)-1-cyclohexanone (intermediate 3) (57 mg) and 2-fluoroethylamine hydrochloride (50 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added to the reaction mixture, and the mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (12 mg) and a syn-form compound (12 mg).

(Anti Form)
$^1$H-NMR (CDCl$_3$, 400 MHz): 1.00–1.40 (m, 4H), 1.91–2.00 (m, 2H), 2.10–2.20 (m, 2H), 2.49 (tt, J=7.4 Hz, 10.7 Hz, 1H), 2.85 (t, J=4.9 Hz, 1H), 2.92 (t, J=4.9 Hz, 1H), 3.19 (tt, J=3.7 Hz, 10.6 Hz, 1H), 4.43 (t, J=4.8 Hz, 1H), 4.55 (t, J=4.8 Hz, 1H), 6.68–6.77 (m, 2H), 7.22 (d, J=8.8 Hz, 1H), 7.82 (s, 1H) Mass spectrum (ESI-MS, m/z): 277 (M$^+$+1)

(Syn Form)
$^1$H-NMR (CDCl$_3$, 400 MHz): 1.45–1.56 (m, 2H), 1.58–1.70 (m, 4H), 1.70–1.82 (m, 2H), 2.60 (m, 1H), 2.84 (t, J=4.9 Hz, 1H), 2.91 (t, J=4.9 Hz, 1H), 3.45–3.53 (m, 1H), 4.44 (t, J=4.9 Hz, 1H), 4.56 (t, J=4.9 Hz, 1H), 6.68–6.75 (m, 2H), 7.22 (d, J=9.5 Hz, 1H), 7.80 (s, 1H) Mass spectrum (ESI-MS, m/z): 277 (M$^+$+1)

Example 247

N1-Cyclopropyl-N4-(1H-5-indazolyl)-1,4-cyclohexanediamine 4-(1H-5-Indazolylamino)-1-cyclohexanone (intermediate 3) (57 mg) and cyclopropylamine (30 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (5 mg) and a syn-form compound (12 mg).

(Anti Form)
$^1$H-NMR (CDCl$_3$, 400 MHz): −0.13–−0.07 (m, 2H), −0.03–0.02 (m, 2H), 0.65–0.85 (m, 4H), 1.60–1.75 (m, 5H), 2.12–2.21 (m, 1H), 2.72–2.81 (m, 1H), 6.28–6.33 (m, 2H), 6.80 (d, J=8.6 Hz, 1H), 7.40 (s, 1H) Mass spectrum (ESI-MS, m/z): 271 (M$^+$+1)

(Syn Form)
$^1$H-NMR (CDCl$_3$, 400 MHz): −0.13–−0.07 (m, 2H), −0.04–0.02 (m, 2H), 1.02–1.16 (m, 2H), 1.18–1.38 (m, 6H), 1.64 (tt, J=3.7 Hz, 6.6 Hz, 1H), 2.28–2.38 (m, 1H), 3.04–3.10 (m, 1H), 6.28–6.35 (m, 2H), 6.80 (d, J=9.5 Hz, 1H), 7.39 (s, 1H) Mass spectrum (ESI-MS, m/z): 271 (M$^+$+1)

Example 248

N1-(1H-5-Indazolyl)-1,4-cyclohexanediamine 4-(1H-5-Indazolylamino)-1-cyclohexanone (intermediate 3) (57 mg) and ammonium acetate (100 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile ] to give an anti-form compound (10 mg) and a syn-form compound (12 mg).

(Anti Form)
Mass spectrum (ESI-MS, m/z): 231 (M$^+$+1)

(Syn Form)
Mass spectrum (ESI-MS, m/z): 231 (M$^+$+1)

Example 249

N1-Cyclohexylmethyl-N4-(1H-5-indazolyl)-1,4-cyclohexanediamine

4-(1H-5-Indazolylamino)-1-cyclohexanone (intermediate 3) (57 mg) and cyclohexanemethylamine (57 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (29 mg) and a syn-form compound (35 mg).

(Anti Form)
$^1$H-NMR (CDCl$_3$, 400 MHz): 0.78–0.92 (m, 2H), 1.06–1.28 (m, 7H), 1.30–1.45 (m, 1H), 1.55–1.80 (m, 5H), 1.90–2.00 (m, 2H), 2.10–2.20 (m, 2H), 2.38–2.51 (m, 3H), 3.15–3.25 (m, 1H), 6.71–6.77 (m, 2H), 7.22 (d, J=8.3 Hz, 1H), 7.81 (s, 1H) Mass spectrum (ESI-MS, m/z): 327 (M$^+$+1)

(Syn Form)
$^1$H-NMR (CDCl$_3$, 400 MHz): 0.76–0.90 (m, 2H), 1.05–1.25 (m, 4H), 1.35–1.45 (m, 1H), 1.45–1.82 (m, 12H), 2.41 (d, J=6.6 Hz, 1H), 2.56 (tt, J=3.9 Hz, 8.3 Hz, 1H), 3.90–4.10 (m, 2H), 6.67–6.75 (m, 2H), 7.21 (d, J=9.5 Hz, 1H), 7.80 (s, 1H) Mass spectrum (ESI-MS, m/z): 327 (M$^+$+1)

Example 250

N1-Cyclopropylmethyl-N4-(1H-5-indazolyl)-1,4-cyclohexanediamine

4-(1H-5-Indazolylamino)-1-cyclohexanone (intermediate 3) (57 mg) and cyclopropylmethylamine (54 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (13 mg) and a syn-form compound (7 mg).

(Anti Form) Mass spectrum (ESI-MS, m/z): 285 (M$^+$+1)

(Syn Form)
$^1$H-NMR (CDCl$_3$, 400 MHz): −0.09–0.04 (m, 2H), 0.30–0.40 (m, 2H), 0.82–0.88 (m, 2H), 1.42–1.80 (m, 8H), 2.39 (d, J=6.8 Hz, 2H), 2.55–2.63 (m, 1H), 3.40–3.50 (m, 1H), 6.62–6.68 (m, 2H), 7.12 (d, J=9.8 Hz, 1H), 7.70 (s, 1H) Mass spectrum (ESI-MS, m/z): 285 (M$^+$+1)

Example 251

N1-Cyclohexyl-N4-(1H-5-indazolyl)-1,4-cyclohexanediamine

4-(1H-5-Indazolylamino)-1-cyclohexanone (intermediate 3) (57 mg) and cyclohexylamine (50 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an antiform compound (22 mg) and a syn-form compound (23 mg).

(Anti Form)
$^1$H-NMR (CDCl$_3$, 400 MHz): 1.01–1.38 (m, 10H), 1.61–1.74 (m, 2H), 1.82–1.92 (m, 2H), 1.92–2.04 (m, 2H), 2.08–2.18 (m, 2H), 2.55–2.75 (m, 2H), 3.12–3.25 (m, 1H), 6.66–6.77 (m, 2H), 7.22 (d, J=8.6 Hz, 1H), 7.81 (s, 1H) Mass spectrum (ESI-MS, m/z): 313 (M$^+$+1)

(Syn Form)
$^1$H-NMR (CDCl$_3$, 400 MHz): 1.02–1.25 (m, 4H), 1.35–1.58 (m, 4H), 1.58–1.75 (m, 2H), 1.77–2.10 (m, 8H), 2.85–2.98 (m, 1H), 3.01–3.14 (m, 1H), 3.50–3.61 (m, 1H), 6.70 (m, 1H), 6.75 (d, J=8.8 Hz, 1H), 7.14 (d, J=8.8 Hz, 1H), 7.73 (s, 1H) Mass spectrum (ESI-MS, m/z): 313 (M$^+$+1)

Example 252

N1-Cycloheptyl-N4-(1H-5-indazolyl)-1,4-cyclohexanediamine

4-(1H-5-Indazolylamino)-1-cyclohexanone (intermediate 3) (57 mg) and cycloheptylamine (57 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (20 mg) and a syn-form compound (31 mg).

(Anti Form)
$^1$H-NMR (CDCl$_3$, 400 MHz): 1.03–1.28 (m, 4H), 1.30–1.39 (m, 4H), 1.39–1.54 (m, 4H), 1.55–1.67 (m, 2H), 1.72–1.86 (m, 2H), 1.90–2.00 (m, 2H), 2.10–2.20 (m, 2H), 2.56 (tt, J=3.6 Hz, 10.5 Hz, 1H), 2.70–2.82 (m, 1H), 3.17 (tt, J=3.6 Hz, 10.7 Hz, 1H), 6.67–6.75 (m, 2H), 7.22 (d, J=8.8 Hz, 1H), 7.81 (s, 1H) Mass spectrum (ESI-MS, m/z): 327 (M$^+$+1)

(Syn Form)
$^1$H-NMR (CDCl$_3$, 400 MHz): 1.23–1.69 (m, 14H), 1.72–1.88 (m, 4H), 1.88–2.05 (m, 2H), 2.84–3.04 (m, 2H), 3.50–3.60 (m, 1H), 6.71 (s, 1H), 6.75 (d, J=8.8 Hz, 1H), 7.17 (d, J=9.0 Hz, 1H), 7.75 (s, 1H) Mass spectrum (ESI-MS, m/z): 327 (M$^+$+1)

Example 253

N1-(2,3-Dihydro-1H-indenyl)-N4-(1H-5-indazolyl)-1,4-cyclohexanediamine 4-(1H-5-Indazolylamino)-1-cyclohexanone (intermediate 3) (57 mg) and 1-aminoindan (67 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (17 mg) and a syn-form compound (18 mg).

(Anti Form)
$^1$H-NMR (CDCl$_3$, 400 MHz): 1.06–1.23 (m, 2H), 1.24–1.40 (m, 2H), 1.70–1.82 (m, 1H), 1.94–2.09 (m, 2H), 2.11–2.20 (m, 2H), 2.32–2.42 (m, 1H), 2.67–2.80 (m, 2H), 2.90–3.00 (m, 1H), 3.22 (tt, J=3.9 Hz, 11.0 Hz, 1H), 4.31 (t, J=6.6 Hz, 1H), 6.70–6.77 (m, 2H), 7.10–7.19 (m, 3H), 7.22 (d, J=8.8 Hz, 1H), 7.29 (d, J=4.4 Hz, 1H), 7.81 (s, 1H) Mass spectrum (ESI-MS, m/z): 347 (M$^+$+1)

(Syn Form)
$^1$H-NMR (CDCl$_3$, 400 MHz): 1.50–1.89 (m, 9H), 2.32–2.43 (m, 1H), 2.68–2.79 (m, 1H), 2.82–3.00 (m, 2H), 3.45–3.54 (m, 1H), 4.28 (t, J=6.6 Hz, 1H), 6.71–6.77 (m, 2H), 7.08–7.15 (m, 3H), 7.19 (d, J=9.5 Hz, 1H), 7.31 (d, J=3.7 Hz, 1H), 7.80 (s, 1H) Mass spectrum (ESI-MS, m/z): 347 (M$^+$+1)

Example 254

N1-(1H-5-Indazolyl)-N4-[(1S)-1,2,3,4-tetrahydro-1-naphthalenyl]-1,4-cyclohexanediamine 4-(1H-5-Indazolylamino)-1-cyclohexanone (intermediate 3) (57 mg) and (S)-1,2,3,4-tetrahydro-1-naphthylamine (74 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (9 mg) and a syn-form compound (14 mg).

(Anti Form)
$^1$H-NMR (CDCl$_3$, 400 MHz): 1.08–1.38 (m, 4H), 1.57–1.95 (m, 5H), 2.04–2.21 (m, 3H), 2.58–2.70 (m, 3H), 3.22 (tt, J=3.7 Hz, 10.7 Hz, 1H), 3.82 (t, J=4.4 Hz, 1H), 6.71–6.77 (m, 2H), 6.97–7.04 (m, 1H), 7.04–7.25 (m, 2H), 7.22 (d, J=8.6 Hz, 1H), 7.26–7.32 (m, 1H), 7.81 (s, 1H) Mass spectrum (ESI-MS, m/z): 361 (M$^+$+1)

(Syn Form)
$^1$H-NMR (CDCl$_3$, 400 MHz): 1.52–2.04 (m, 12H), 2.64 (dt, J=8.3 Hz, 16.8 Hz, 1H), 2.77 (dt, J=5.4 Hz, 17.1 Hz, 1H), 2.86–2.95 (m, 1H), 3.45–3.54 (m, 1H), 3.78–3.93 (m, 1H), 6.75 (s, 1H), 6.78 (d, J=8.8 Hz, 1H), 7.33–7.41 (m, 1H), 7.78 (s, 1H) Mass spectrum (ESI-MS, m/z): 361 (M$^+$+1)

Example 255

N1-(1H-5-Indazolyl)-N4-(1,2,2-trimethylpropyl)-1,4-cyclohexanediamine 4-(1H-5-Indazolylamino)-1-cyclohexanone (intermediate 3) (57 mg) and (2-amino-3,3-dimethylbutane (51 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (8 mg) and a syn-form compound (5 mg).

(Anti Form)
$^1$H-NMR (CDCl$_3$, 400 MHz): 0.89 (s, 9H), 1.01–1.20 (m, 5H), 1.93–2.21 (m, 3H), 2.26–2.75 (m, 1H), 3.15–3.25 (m, 1H), 6.66–6.75 (m, 2H), 7.22 (d, J=8.8 Hz, 1H), 7.79 (s, 1H) Mass spectrum (ESI-MS, m/z): 315 (M$^+$+1)

(Syn Form)
$^1$H-NMR (CDCl$_3$, 400 MHz): 0.85 (s, 9H), 0.91–1.05 (m, 3H), 1.40–1.83 (m, 8H), 2.20–2.37 (m, 1H), 2.57–2.75 (m, 1H), 3.38–3.50 (m, .1H), 6.73 (s, 1H), 6.76 (d, J=8.8 Hz, 1H), 7.22 (d, J=8.8 Hz, 1H), 7.79 (s, 1H) Mass spectrum (ESI-MS, m/z): 315 (M$^+$+1)

Example 256

N1-(1H-5-Indazolyl)-N4-[1-(1H-3-indolyl)ethyl]-1,4-cyclohexanediamine 4-(1H-5-Indazolylamino)-1-cyclohexanone (intermediate 3) (57 mg) and tryptamine (80 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was added to fractions containing respective compounds, followed by extraction with chloroform-propanol (3/1). The organic layers were dried over anhydrous sodium sulfate, and the solvent was removed by distillation under the reduced pressure to give an anti-form compound (26 mg) and a syn-form compound (24 mg).

(Anti Form)

$^1$H-NMR (CDCl$_3$, 400 MHz): 1.02–1.25 (m, 4H), 1.85–1.95 (m, 2H), 2.05–2.17 (m, 2H), 2.44 (tt, J=3.9 Hz, 10.8 Hz, 1H), 2.86–2.97 (m, 4H), 3.16 (tt, J=3.6 Hz, 10.8 Hz, 1H), 6.67–6.73 (m, 2H), 6.98 (s, 1H), 7.05 (t, J=7.8 Hz, 1H), 7.13 (t, J=8.0 Hz, 1H), 7.20 (d, J=9.8 Hz, 1H), 7.29 (t, J=8.1 Hz, 1H), 7.56 (t, J=8.0 Hz, 1H), 7.81 (s, 1H), 8.02 (s, 1H) Mass spectrum (ESI-MS, m/z): 374 (M$^+$+1)

(Syn Form)

$^1$H-NMR (CDCl$_3$, 400 MHz): 1.38–1.52 (m, 2H), 1.53–1.76 (m, 9H), 2.59 (tt, J=3.9 Hz, 8.3 Hz, 1H), 2.93 (s, 1H); 3.43–3.51 (m, 1H), 6.65–6.73 (m, 2H), 6.97 (s, 1H), 7.05 (t, J=8.1 Hz, 1H), 7.13 (t, J=8.3 Hz, 1H), 7.18 (d, J=8.6 Hz, 1H), 7.28 (t, J=8.0 Hz, 1H), 7.56 (t, J=7.8 Hz, 1H), 7.79 (s, 1H), 8.05 (s, 1H) Mass spectrum (ESI-MS, m/z): 374 (M$^+$+1)

Example 257

N1-[2-(1H-5-Imidazolyl)ethyl]-N4-(1H-5-indazolyl)-1,4-cyclohexanediamine 4-(1H-5-Indazolylamino)-1-cyclohexanone (intermediate 3) (57 mg) and histamine hydrochloride (92 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (1 mg) and a syn-form compound (2 mg).

(Anti Form)

Mass spectrum (ESI-MS, m/z): 374 (M$^+$+1)

(Syn Form)

Mass spectrum (ESI-MS, m/z): 374 (M$^+$+1)

Example 258

N1-(1H-5-Indazolyl)-N4-[2-(3-thienyl)ethyl]-1,4-cyclohexanediamine 4-(1H-5-Indazolylamino)-1-cyclohexanone (intermediate 3) (57 mg) and 2-thiophenethylamine (64 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (30 mg) and a syn-form compound (23 mg).

(Anti Form)

$^1$H-NMR (CDCl$_3$, 400 MHz): 1.05–1.28 (m, 4H), 1.90–2.00 (m, 2H), 2.08–2.20 (m, 2H), 2.46 (tt, J=3.6 Hz, 10.5 Hz, 1H), 2.90 (t, J=5.6 Hz, 2H), 2.96 (t, J=8.0 Hz, 1H), 3.16 (tt, J=3.7 Hz, 10.7 Hz, 1H), 6.67–6.75 (m, 2H), 6.77 (d, J=3.4 Hz, 1H), 6.86 (dd, J=3.4 Hz, 5.1 Hz, 1H), 7.07 (d, J=5.1 Hz, 1H), 7.21 (d, J=8.6 Hz, 1H), 7.81 (s, 1H) Mass spectrum (ESI-MS, m/z): 341 (M$^+$+1)

(Syn Form)

$^1$H-NMR (CDCl$_3$, 400 MHz): 1.42–1.54 (m, 2H), 1.58–1.78 (m, 6H), 2.64 (tt, J=3.9 Hz, 8.0 Hz, 1H), 2.89 (t, J=6.8 Hz, 1H), 2.99 (t, J=6.4 Hz, 2H), (s, 1H), 3.43–3.51 (m, 1H), 6.67–6.74 (m, 2H), 6.75–6.78 (m, 1H), 6.83–6.88 (m, 1H), 7.07 (d, J=5.1 Hz, 1H), 7.20 (d, J=9.3 Hz, 1H), 7.79 (s, 1H) Mass spectrum (ESI-MS, m/z): 341 (M$^+$+1)

Example 259

N1-(1H-5-Indazolyl)-N4-phenylethyl-1,4-cyclohexanediamine 4-(1H-5-Indazolylamino)-1-cyclohexanone (intermediate 3) (57 mg) and 2-phenethylamine (61 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was added thereto, and the mixture was stirred and was then concentrated. The residue was purified by HPLC [0.5% aqueous trifluoroacetic acid. solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (30 mg) and a syn-form compound (24 mg).

(Anti Form)

$^1$H-NMR (CDCl$_3$, 400 MHz): 1.02–1.25 (m, 4H), 1.88–1.96 (m, 2H), 2.07–2.16 (m, 2H), 2.45 (tt, J=3.7 Hz, 10.5 Hz, 1H), 2.75 (t, J=7.1 Hz, 2H), 2.87 (t, J=6.8 Hz, 2H), 3.17 (tt, J=3.7 Hz, 10.5 Hz, 1H), 6.67–6.75 (m, 2H), 7.10–7.17 (m, 3H), 7.17–7.25 (m, 3H), 7.81 (s, 1H) Mass spectrum (ESI-MS, m/z): 335 (M$^+$+1)

(Syn Form)

$^1$H-NMR (CDCl$_3$, 400 MHz): 1.50–1.65 (m, 2H), 1.65–1.88 (m, 6H), 2.76–2.88 (m, 1H), 2.97 (s, 4H), 3.45–3.55 (m, 1H), 6.65–6.70 (m, 2H), 7.07–7.19 (m, 6H), 7.74 (s, 1H) Mass spectrum (ESI-MS, m/z): 335 (M$^+$+1)

Example 260

N1-(5-Isoquinolyl)-N4-propyl-1,4-cyclohexanediamine 4-(5-Isoquinolylamino)-1-cyclohexanone (intermediate 4) (60 mg) and propylamine (30 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (18 mg) and a syn-form compound (22 mg).

(Anti Form)
$^1$H-NMR (CDCl$_3$, 400 MHz): 0.87 (t, J=7.4 Hz, 3H), 1.18–1.33 (m, 4H), 1.41–1.52 (m, 2H), 1.94–2.06 (m, 2H), 2.14–2.26 (m, 2H), 2.44–2.58 (m, 1H), 2.57 (t, J=7.5 Hz, 2H), 3.31–3.44 (m, 1H), 4.06–4.20 (m, 1H), 6.70 (d, J=7.6 Hz, 1H), 7.21 (d, J=8.0 Hz, 1H), 7.38 (t, J=7.8 Hz, 1H), 7.44 (d, J=6.1 Hz, 1H), 8.38 (d, J=5.9 Hz, 1H), 9.07 (s, 1H) Mass spectrum (ESI-MS, m/z): 284 (M$^+$+1)

(Syn Form)
$^1$H-NMR (CDCl$_3$, 400 MHz): 0.86 (t, J=7.3 Hz, 3H), 1.40–1.50 (m, 2H), 1.50–1.60 (m, 2H), 1.68–1.76 (m, 4H), 1.80–1.90 (m, 2H), 2.57 (t, J=7.3 Hz, 2H), 2.58–2.68 (m, 1H), 3.60–3.70 (m, 1H), 4.33–4.45 (m, 1H), 6.68 (d, J=7.8 Hz, 1H), 7.20 (d, J=7.6 Hz, 1H), 7.36 (t, J=7.7 Hz, 1H), 7.47 (d, J=5.8 Hz, 1H), 8.37 (d, J=6.1 Hz, 1H), 9.07 (s, 1H) Mass spectrum (ESI-MS, m/z): 284 (M$^+$+1)

Example 261

N1-(2-Fluoroethyl)-N4-(5-isoquinolyl)-1,4-cyclohexanediamine 4-(5-Isoquinolylamino)-1-cyclohexanone (intermediate 4) (60 mg) and 2-fluoroethylamine hydrochloride (50 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC g [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (18 mg) and a syn-form compound (12 mg).

(Anti Form)
$^1$H-NMR (CDCl$_3$, 400 MHz): 1.18–1.34 (m, 4H), 1.95–2.05 (m, 2H), 2.16–2.30 (m, 2H), 2.45–2.60 (m, 1H), 2.86 (t, J=4.9 Hz, 1H), 2.93 (t, J=4.9 Hz, 1H), 3.33–3.45 (m, 1H), 4.07–4.21 (m, 1H), 4.44 (t, J=4.8 Hz, 1H), 4.56 (t, J=4.7 Hz, 1H), 6.71 (d, J=7.8 Hz, 1H), 7.22 (d, J=8.1 Hz, 1H), 7.38 (t, J=8.0 Hz, 1H), 7.45 (d, J=6.1 Hz, 1H), 8.38 (d, J=6.1 Hz, 1H), 9.07 (s, 1H) Mass spectrum (ESI-MS, m/z): 288 (M$^+$+1)

(Syn Form)
$^1$H-NMR (CDCl$_3$, 400 MHz): 1.50–1.62 (m, 2H), 1.63–1.78 (m, 4H), 1.80–1.90 (m, 2H), 2.69 (tt, J=3.9 Hz, 7.8 Hz, 1H), 2.84 (t, J=4.9 Hz, 1H), 2.91 (t, J=4.7 Hz, 1H), 3.60–3.70 (m, 1H), 4.31–4.41 (m, 1H), 4.44 (t, J=5.0 Hz, 1H), 4.56 (t, J=5.0 Hz, 1H), 6.69 (d, J=7.6 Hz, 1H), 7.21 (d, J=8.0 Hz, 1H), 7.36 (t, J=7.9 Hz, 1H), 7.46 (d, J=6.1 Hz, 1H), 8.38 (d, J=6.1 Hz, 1H), 9.07 (s, 1H) Mass spectrum (ESI-MS, m/z): 284 (M$^+$+1)

Example 262

N1-Cyclopropyl-N4-(5-isoquinolyl)-1,4-cyclohexanediamine 4-(5-Isoquinolylamino)-1-cyclohexanone (intermediate 4) (60 mg) and cyclopropylamine (30 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was. stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (11 mg) and a syn-form compound (12 mg).

(Anti Form)
$^1$H-NMR (CDCl$_3$, 400 MHz): −0.16–−0.09 (m, 2H), −0.04–0.20 (m, 2H), 0.75–0.93 (m, 4H), 1.58–1.72 (m, 3H), 1.75–1.85 (m, 2H), 2.16–2.27 (m, 1H), 2.87–3.03 (m, 1H), 3.60–3.85 (m, 1H), 6.29 (d, J=7.6 Hz, 1H), 6.79 (d, J=8.1 Hz, 1H), 7.00 (t, J=8.0 Hz, 1H), 7.02 (d, J=6.0 Hz, 1H), 7.96 (d, J=6.1 Hz, 1H), 8.65 (s, 1H) Mass spectrum (ESI-MS, m/z): 282 (M$^+$+1)

(Syn Form)
$^1$H-NMR (CDCl$_3$, 400 MHz): −0.04–0.02 (m, 2H), 0.07–0.13 (m, 2H), 0.90–1.58 (m, 8H), 1.68–1.78 (m, 1H), 2.48 (tt, J=3.9 Hz, 7.8 Hz, 1H), 3.28–3.40 (m, 1H), 3.95–4.13 (m, 1H), 6.39 (d, J=7.6 Hz, 1H), 6.89 (d, J=8.8 Hz, 1H), 7.06 (t, J=8.0 Hz, 1H), 7.16 (t, J=6.1 Hz, 1H), 8.08 (d, J=5.8 Hz, 1H), 8.76 (s, 1H) Mass spectrum (ESI-MS, m/z): 282 (M$^+$+1)

Example 263

N1-(5-Isoquinolyl)-N4-phenylethyl-1,4-cyclohexanediamine 4-(5-Isoquinolylamino)-1-cyclohexanone (intermediate 4) (60 mg) and 2-phenylethylamine (61 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile]. A saturated aqueous sodium hydrogencarbonate solution (2 ml) was then added to fractions containing respective compounds, followed by extraction with chloroform-propanol (3/1). The organic layers were dried over anhydrous sodium sulfate, and the solvent was removed by distillation under the reduced pressure to give an anti-form compound (24 mg) and a syn-form compound (11 mg).

(Anti Form)
$^1$H-NMR (CDCl$_3$, 400 MHz): 1.15–1.30 (m, 4H), 1.92–2.03 (m, 2H), 2.12–2.25 (m, 2H), 2.45–2.55 (m, 1H), 2.76 (t, J=7.1 Hz, 2H), 2.88 (t, J=7.1 Hz, 2H), 3.29–3.42 (m, 1H), 4.05–4.18 (m, 1H), 6.69 (d, J=7.6 Hz, 1H), 7.12–7.26 (m, 6H), 7.37 (d, J=7.9 Hz, 1H), 7.43 (t, J=6.1 Hz, 1H), 8.37 (d, J=6.1 Hz, 1H), 9.06 (s, 1H) Mass spectrum (ESI-MS, m/z): 346 (M$^+$+1)

(Syn Form)
$^1$H-NMR (CDCl$_3$, 400 MHz): 1.46–1.58 (m, 2H), 1.64–1.74 (m, 4H), 1.76–1.86 (m, 2H), 2.65 (tt, J=3.7 Hz, 8.1 Hz, 1H), 2.76 (tt, J=6.8 Hz, 7.3 Hz, 2H), 2.86 (tt, J=6.8 Hz, 7.1 Hz, 2H), 3.60–3.70 (m, 1H), 4.28–4.42 (m, 1H), 6.69 (d, J=7.6 Hz, 1H), 7.10–7.26 (m, 6H), 7.37 (t, J=7.9 Hz, 1H), 7.46 (d, J=6.1 Hz, 1H), 8.38 (d, J=6.1 Hz, 1H), 9.07 (s, 1H) Mass spectrum (ESI-MS, m/z): 346 (M$^+$+1)

Example 264

N1-(1H-5-Indazolyl)-N4-isopropyl-1,4-cyclohexanediamine 4-(1H-5-Indazolylamino)-1-cyclohexanone (intermediate 3) (57 mg) and 2-thiophenethylamine (64 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile] to give an anti-form compound (21 mg) and a syn-form compound (14 mg).

(Anti Form)
  Mass spectrum (ESI-MS, m/z): 273 ($M^+$+1)

(Syn Form)
  Mass spectrum (ESI-MS, m/z): 273 ($M^+$+1)

Example 265

N1-(1H-5-Indazolyl)-N4-isobutyl-1,4-cyclohexanediamine 4-(1H-5-Indazolylamino)-1-cyclohexanone (intermediate 3) (57 mg) and isobutylamine (37 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile] to give an anti-form compound (8 mg) and a syn-form compound (6 mg).

(Anti Form)
  Mass spectrum (ESI-MS, m/z): 287 ($M^+$+1)

(Syn Form)
  Mass spectrum (ESI-MS, m/z): 287 ($M^+$+1)

Example 266

N1-Ethyl-N4-(1H-5-indazolyl)-1,4-cyclohexanediamine 4-(1H-5-Indazolylamino)-1-cyclohexanone (intermediate 3) (57 mg) and ethylamine (23 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile] to give an anti-form compound (10 mg) and a syn-form compound (10 mg).

(Anti Form)
  Mass spectrum (ESI-MS, m/z): 259 ($M^+$+1)

(Syn Form)
  Mass spectrum (ESI-MS, m/z): 259 ($M^+$+1)

Example 267

N1-(1H-5-Indazolyl)-N4-pentyl-1,4-cyclohexanediamine 4-(1H-5-Indazolylamino)-1-cyclohexanone (intermediate 3) (57 mg) and amylamine (44 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile] to give an anti-form compound (10 mg) and a syn-form compound (10 mg).

(Anti Form)
  Mass spectrum (ESI-MS, m/z): 301 ($M^+$+1)

(Syn Form)
  Mass spectrum (ESI-MS, m/z): 301 ($M^+$+1)

Example 268

N1-(1H-5-Indazolyl)-N4-pentyl-1,4-cyclohexanediamine 4-(1H-5-Indazolylamino)-1-cyclohexanone (intermediate 3) (57 mg) and N-phenylethylenediamine (68 mg) were dissolved in methanol (1 ml), and sodium triacetoxyborohydride (105 mg) was added by portions to the solution at room temperature. The reaction mixture was stirred at room temperature for 18 hr. Hydrochloric acid-methanol was then added thereto, and the reaction mixture was stirred and was then concentrated. The residue was purified by HPLC [0.5% aqueous trifluoroacetic acid solution/acetonitrile] to give an anti-form compound (51 mg) and a syn-form compound (45 mg).

(Anti Form)
  Mass spectrum (ESI-MS, m/z): 350 ($M^+$+1)

(Syn Form)
  Mass spectrum (ESI-MS, m/z): 350 ($M^+$+1)

Example 269

N-(5-Isoquinolyl)-N-[1-(4-methylpentyl)-3-piperidyl]amine

3-Hydroxypiperidine (1 g) and potassium carbonate (2.76 g) were dissolved in anhydrous N,N-dimethylformamide (10 ml), and 1-bromo-4-methylpentane (1.65 g) was added dropwise to the solution at room temperature. The reaction solution was stirred at room temperature for 18 hr. Ethyl acetate was then added thereto, and the mixture was washed with water and saturated brine and was dried over anhydrous sodium sulfate. The organic layer was concentrated under the reduced pressure to give an intermediate.

This intermediate and triethylamine (2.01 g) were dissolved in anhydrous dimethyl sulfoxide (10.2 ml), and a sulfur trioxide-trimethylamine complex (2.78 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated under the reduced pressure to give 1.52 g of an intermediate as a crude compound.

This intermediate (760 mg) and 5-aminoisoquinoline (473 mg) were dissolved in titanium tetraisopropoxide (3.8 ml), and the mixture was then stirred at room temperature for 18 hr. Methanol (3.8 ml) and sodium borohydride (77.6 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give: the title compound (17.4 mg, yield 1.36%).

$^1$H-NMR (CDCl$_3$, 400 MHz): 0.91 (dd, J=2.0, 6.6 Hz, 6H), 1.22–1.28 (m, 2H), 1.48–1.61 (m, 4H), 1.73–1.78 (m, 2H), 2.29–2.41 (m, 4H), 2.47–2.59 (m, 1H), 2.66–2.75 (m, 1H), 3.74–3.84 (m, 1H), 6.77 (d, J=7.6 Hz, 1H), 7.5 (d, J=6.6 Hz, 1H), 7.27 (s, 1H), 7.44 (t, J=7.8 Hz, 1H), 7.57 (d, J=5.9 Hz, 1H), 8.45 (d, J=6.1 Hz, 1H) Mass spectrum (ESI-MS, m/z): 312 (M$^+$+1)

Example 270

N-(1H-5-Indazolyl)-N-[1-(4-methylpentyl)-3-piperidyl]amine

The above intermediate (760 mg) and 5-aminoindazole (437 mg) were dissolved in titanium tetraisopropoxide (3.8 ml), and the mixture was then stirred at room temperature for 18 hr. Methanol (3.8 ml) and sodium borohydride (77.6 mg) were added to the reaction solution, and the mixture was stirred for 18 hr. The reaction solution was diluted with 40 ml of ethyl acetate, and a minor amount of water was added thereto, and the mixture was then filtered under the reduced pressure. The filtrate was concentrated under the reduced pressure, and the residue was purified by column chromatography on silica gel [chloroform/methanol] to give the title compound (8.0 mg, yield 0.53%).

$^1$H-NMR (CDCl$_3$, 400 MHz): 0.88 (d, J=6.6 Hz, 6H), 1.14–1.20 (m, 2H), 1.45–1.59 (m, 1H), 1.72–1.83 (m, 2H), 2.27–2.35 (m, 4H), 2.45–2.55 (m, 1H), 2.72–2.82 (m, 1H), 3.54–3.66 (m, 1H), 6.82–6.85 (m, 2H), 7.28–7.30 (m, 1H), 7.87 (s, 1H) Mass spectrum (ESI-MS, m/z): 301 (M$^+$+1)

Example 271

N-(1H-5-Indazolyl)-N-[1-(4-methylpentyl)-4-piperidyl]amine

4-Piperidone hydrochloride monohydrate (768 mg) and potassium carbonate (1.38 g) were dissolved in anhydrous N,N-dimethylformamide (10 ml), and 1-bromo-4-methylpentane (603 mg) was added dropwise to the solution at room temperature. The reaction-solution was stirred at room temperature for 18 hr. Ethyl acetate was then added thereto, and the mixture was washed with water and saturated brine and was dried over anhydrous sodium sulfate. The organic layer was concentrated under the reduced pressure to give an intermediate.

This intermediate (766 mg) was dissolved in titanium tetraisopropoxide (3.8 ml). 5-Aminoindazole (445 mg) was added to the solution, and the mixture was stirred at room temperature for 18 hr. Methanol (3.8 ml) and sodium borohydride (79 mg) were added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (200 mg, yield 13.3%).

$^1$H-NMR (CDCl$_3$, 400 MHz): 0.89 (d, J=6.6 Hz, 6H), 1.15–1.26 (m, 2H), 1.49–1.59 (m, 5H), 2.07–2.23 (m, 1H), 2.35–2.39 (m, 2H), 2.90–3.00 (m, 2H), 3.29–3.38 (m, 1H), 6.80–6.82 (m, 2H), 7.26 (s, 1H), 7.88 (s, 1H) Mass spectrum (ESI-MS, m/z): 301 (M$^+$+1), 299 (M$^+$−1)

Example 272

N-(1H-5-Indazolyl)-N-[1-(4,4,4-trifluorobutyl)-3-piperidyl]amine

3-Hydroxypiperidine (1 g) and potassium carbonate (2.76 g) were dissolved in acetonitrile (10 ml), and 1-bromo-4,4,4-trifluorobutane (1.91 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate (800 mg) and 5-aminoindazole (403 mg) were dissolved in titanium tetraisopropoxide (3.2 g), and the mixture was then stirred at room temperature for 18 hr. A minor amount of methanol and sodium borohydride (71 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (125 mg, yield 3.83%).

$^1$H-NMR (CDCl$_3$, 400 MHz): 1.56–1.58 (m, 1H), 1.70–1.78 (m, 5H), 2.09–2.21 (m, 2H), 2.37–2.42 (m, 5H), 2.70–2.80 (m, 1H), 3.54–3.64 (m, 1H), 6.81–6.85 (m, 2H), 7.29–7.32 (m, 1H), 7.88 (s, 1H) Mass spectrum (ESI-MS, m/z): 327 (M$^+$+1), 325 (M$^+$−1)

Example 273

N-(5-Isoquinolyl)-N-[1-(4,4,4-trifluorobutyl)-3-piperidyl]amine

The above intermediate (800 mg) and 5-aminoisoquinoline (433 mg) were dissolved in titanium tetraisopropoxide (3.2 g), and the mixture was then stirred at room temperature for 18 hr. A minor amount of methanol and sodium borohydride (71 mg) were added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (263 mg, yield 1.56%).

$^1$H-NMR (CDCl$_3$, 400 MHz): 1.60–1.83 (m, 8H), 2.42–2.52 (m, 2H), 3.75–3.84 (m, 1H), 4.85–5.00 (m, 1H), 6.76–6.78 (d, J=7.6 Hz, 1H), 7.28 (d, J=8.0 Hz, 1H), 7.45 (t, J=7.8 Hz, 1H), 7.52 (d, J=6.1 Hz, 1H), 8.46 (d, J=6.1 Hz, 1H) Mass spectrum (ESI-MS, m/z): 338 (M$^+$+1), 336 (M$^+$−1)

Example 274

N-(1H-5-Indazolyl)-N-(1-isopentyl-3-piperidyl)amine

3-Hydroxypiperidine (1 g) and potassium carbonate (2.76 g) were dissolved in acetonitrile (10 ml), and 1-chloro-3-methylbutane (1.07 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate (775 mg) and 5-aminoindazole (482 mg) were dissolved in titanium tetraisopropoxide (3.8 g), and the mixture was then stirred at room temperature for 18 hr. A minor amount of methanol and sodium borohydride (85 mg) were then added to the reaction solution, and the mixture was stirred for 18 hr. The reaction solution was diluted with ethyl acetate (40 ml), and a minor amount of water was added thereto, and the mixture was then. filtered under the reduced pressure. The filtrate was concentrated under the reduced pressure, and the residue was purified by column chromatography on silica gel [chloroform/methanol] to give the title compound (105 mg, yield 3.67%).

$^1$H-NMR (CDCl$_3$, 400 MHz): 0.89–0.91 (m, 6H), 1.35–1.41 (m, 3H), 1.54–1.76 (m, 6H), 2.32–2.37 (m, 3H), 2.45–2.50 (m, 1H), 3.55–3.63 (m, 1H), 6.82–6.97 (m, 2H), 7.28–7.32 (m, 1H), 7.87–7.88 (m, 1H) Mass spectrum (ESI-MS, m/z): 278 (M$^+$+1)

Example 275

N-(1-Isopentyl-3-piperidyl)-N-(5-isoquinolyl)amine

The above intermediate (775 mg) and 5-aminoisoquinoline (523 mg) were dissolved in titanium tetraisopropoxide (3.8 g), and the mixture was then stirred at room temperature for 18 hr. A minor amount of methanol and sodium borohydride (85 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (145 mg, yield 4.87%).

$^1$H-NMR (CDCl$_3$, 400 MHz): 0.94 (dd, J=4.6, 6.6 Hz, 6H), 1.39–1.45 (m, 2H), 1.51–1.73 (m, 6H), 2.36–2.70 (m, 5H), 4.21 (m, 1H), 6.94–6.98 (m, 1H), 7.25–7.27 (m, 1H), 7.38–7.46 (m, 1H), 7.52–7.58 (m, 1H), 8.44–8.50 (m, 1H), 9.13–9.18 (m, 1H) Mass spectrum (ESI-MS, m/z): 297 (M$^+$+1)

Example 276

N-(5-Isoquinolyl)-N-[1-(2,4,6-trifluorobenzyl)-3-piperidyl]amine

3-Hydroxypiperidine (1 g) and potassium carbonate (2.76 g) were dissolved in acetonitrile (10 ml), and 2,4,6-trifluorobenzyl bromide (2.25 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate (766 mg) was dissolved in titanium tetraisopropoxide (2.3 g). 5-Aminoisoquinoline (304 mg) was added to the solution, and the mixture was stirred at room temperature for 18 hr. Methanol (2.8 ml) and sodium borohydride (50 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (172 mg, yield 4.63%).

$^1$H-NMR (CDCl$_3$, 400 MHz): 1.52–1.80 (m, 6H), 2.61–2.71 (m, 2H), 3.68 (s, 2H), 3.76–3.84 (m, 1H), 5.06–5.19 (m, 1H), 6.63–6.72 (m, 3H), 7.24 (s, 1H), 7.42 (t, J=7.8 Hz, 1H), 7.52–7.53 (d, J=6.0 Hz, 1H), 8.47 (d, J=6.0 Hz, 1H) Mass spectrum (ESI-MS, m/z): 372 (M$^+$+1), 370 (M$^+$−1)

Example 277

N-(1H-5-Indazolyl)-N-[1-(2-methylbutyl)-3-piperidyl]amine

3-Hydroxypiperidine (1 g) and potassium carbonate (2.76 g) were dissolved in acetonitrile (10 ml), and 1-chloro-3-methylbutane (1.07 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution in an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate (723 mg) and 5-aminoindazole (450 mg) were dissolved in titanium tetraisopropoxide (3.6 g), and the mixture was stirred at room temperature for 18 hr. A minor amount of methanol and sodium borohydride (80 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (162 mg, yield 5.66%).

$^1$H-NMR (CDCl$_3$, 400 MHz): 0.86–0.92 (m, 6H), 1.04–1.17 (m, 1H), 1.37–1.65 (m, 7H), 2.01–2.71 (m, 1H), 2.12–2.19 (m, 1H), 2.30–2.40 (m, 2H), 2.50–2.66 (m, 1H), 3.55–3.64 (m, 1H), 6.83 (s, 1H), 6.84 (d, J=5.1 Hz, 1H), 7.30 (d, J=9.3 Hz, 1H), 7.87 (s, 1H) Mass spectrum (ESI-MS, m/z): 287 (M$^+$+1), 285 (M$^+$−1)

Example 278

N-(5-Isoquinolyl)-N-[1-(2-methylbutyl)-3-piperidyl]amine

3-Hydroxypiperidine (1 g) and potassium carbonate (2.76 g) were dissolved in acetonitrile (10 ml), and 1-chloro-3-methylbutane (1.07 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate (723 mg) and 5-aminoisoquinoline (487 mg) were dissolved in titanium tetraisopropoxide (3.6 g), and the mixture was stirred at room temperature for 18 hr. A minor amount of methanol and sodium borohydride (80 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (138 mg, yield 4.64%).

$^1$H-NMR (CDCl$_3$, 400 MHz): 0.91–0.98 (m, 6H), 1.14–1.26 (m, 8H), 2.06–2.25 (m, 2H), 2.57–2.65 (m, 2H), 3.77–3.85 (m, 1H), 6.77 (d, J=7.6 Hz, 1H), 7.28 (d, J=8.0 Hz, 1H), 7.45 (t, J=7.8 Hz, 1H), 7.53 (d, J=6.1 Hz, 1H), 8.46 (d, J=6.1 Hz, 1H), 9.14 (s, 1H) Mass spectrum (ESI-MS, m/z): 298 (M$^+$+1), 296 (M$^+$−1)

Example 279

N-(1H-5-Indazolyl)-N-(1-isopentyl-4-piperidyl)amine

4-Piperidone hydrochloride monohydrate (768 mg) and potassium carbonate (1.38 g) were dissolved in anhydrous N,N-dimethylformamide (10 ml), and 1-chloro-4-methylbutane (533 mg) was added dropwise to the solution at room temperature. The reaction solution was stirred at room temperature for 18 hr. Ethyl acetate was then added thereto, and the mixture was washed with water and saturated brine and was dried over anhydrous sodium sulfate. The organic layer was concentrated under the reduced pressure to give an intermediate.

This intermediate (1.25 g) was dissolved in titanium tetraisopropoxide (6.25 g). 5-Aminoindazole (666 mg) was added to the solution, and the mixture was stirred at room temperature for 18 hr. Methanol (3.8 ml) and sodium borohydride (95 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (200 mg, yield 16.4%).

$^1$H-NMR (CDCl$_3$, 400 MHz): 0.91 (d, J=6.6 Hz, 6H), 1.38–1.63 (m, 5H), 2.10–2.17 (m, 4H), 2.35–2.39 (m, 2H), 2.89–2.95 (m, 2H), 3.26–3.36 (m, 1H), 6.79–6.82 (m, 2H), 7.29 (d, J=8.5 Hz, 1H), 7.88 (d, J=1.0 Hz, 1H) Mass spectrum (ESI-MS, m/z): 287 (M$^+$+1), 285 (M$^+$−1)

Example 280

N-(1H-5-Indazolyl)-N-[1-(2-methylbutyl)-4-piperidyl]amine

4-Piperidone hydrochloride monohydrate (768 mg) and potassium carbonate (1.38 g) were dissolved in anhydrous N,N-dimethylformamide (10 ml), and 1-chloro-2-methylbutane (533 mg) was added dropwise to the solution at room temperature. The reaction solution was stirred at room temperature for 18 hr. Ethyl acetate was then added thereto, and the mixture was washed with water and saturated brine and was dried over anhydrous sodium sulfate. The organic layer was concentrated under the reduced pressure to give an intermediate.

This intermediate (1.00 g) was dissolved in titanium tetraisopropoxide (5 g). 5-Aminoindazole (666 mg) was added to the solution, and the mixture was stirred at room temperature for 18 hr. Methanol (3.8 ml) and sodium borohydride (95 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (627 mg, yield 43.8%).

$^1$H-NMR (CDCl$_3$, 400 MHz): 0.84 (m, 6H), 1.04–1.14 (m, 1H), 1.40–1.61 (m, 4H), 2.01–2.11 (m, 6H), 2.81–2.86 (m, 2H), 3.28–3.33 (m, 1H), 6.80–6.82 (m, 2H), 7.29 (d, J=8.5 Hz, 1H), 7.88 (s, 1H) Mass spectrum (ESI-MS, m/z): 287 (M$^+$+1), 285 (M$^+$−1)

Example 281

N-(1H-5-Indazolyl)-N-[1-(2-methylpentyl)-3-piperidyl]amine

3-Hydroxypiperidine (1 g) and potassium carbonate (2.76 g) were dissolved in acetonitrile (10 ml), and 1-chloro-2-methylpentane (1.21 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution in an argon atmosphere at room temperature. The reaction mixture was stirred at room temperature for 18 hr. A saturated aqueous sodium hydrogencarbonate solution (7.55 ml) was then. added thereto, and the mixture was extracted with chloroform. The organic layer was dried over anhydrous sodium sulfate and was concentrated to give an intermediate.

This intermediate (1.0 g) and 5-aminoindazole (575 mg) were dissolved in titanium tetraisopropoxide (5.0 g), and the mixture was stirred at room temperature for 18 hr. A minor amount of methanol and sodium borohydride (128 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (376 mg, yield 12.5%)

$^1$H-NMR (CDCl$_3$, 400 MHz): 0.03–0.93 (m, 6H), 1.04–1.08 (m, 1H), 1.19–1.42 (m, 4H), 2.01–2.17 (m, 2H), 2.37–2.60 (m, 3H), 3.56–3.63 (m, 1H), 6.82–6.84 (m, 2H), 7.29 (d, J=9.5, 1H), 7.87 (s, 1H) Mass spectrum (ESI-MS, m/z): 301 (M$^+$+1)

Example 282

N-(1H-5-Indazolyl)-N-[1-(2,4,6-trifluorobenzyl)-3-piperidyl]amine

3-Hydroxypiperidine (130 mg) and potassium carbonate (659 mg) were dissolved in acetonitrile (5 ml), and 2,4,6-trifluorobenzyl bromide (290 mg) was added dropwise to the solution at room temperature. The reaction mixture was stirred at room temperature for 18 hr and was then filtered through Celite, and the filtrate was concentrated to give an intermediate.

This intermediate and triethylamine (275 mg) were dissolved in anhydrous dimethyl sulfoxide (1.73 ml), and a sulfur trioxide-trimethylamine complex (379 mg) was added to the solution under an argon atmosphere at room temperature. The reaction mixture was stirred at room temperature for 18 hr. A saturated aqueous sodium hydrogencarbonate solution was then added. thereto, and the mixture was extracted with chloroform. The organic layer was dried over anhydrous sodium sulfate and was then concentrated to give an intermediate.

This intermediate (290 mg) was dissolved in titanium tetraisopropoxide (1.45 g). 5-Aminoindazole (121 mg) was added to the solution, and the mixture was stirred at room temperature for 18 hr. Methanol and sodium borohydride (21 mg) were then added to the reaction solution, and the mixture was stirred for 18 hr. The reaction solution was then diluted with ethyl acetate, and a minor amount of water was added thereto, and the mixture was then filtered under the reduced pressure. The filtrate was concentrated under the reduced pressure, and the residue was purified by column chromatography on silica gel [chloroform/methanol] to give the title compound (58 mg, yield 12.5%).

$^1$H-NMR (CDCl$_3$, 400 MHz): 1.57–1.74 (m, 5H), 2.45 (m, 3H), 2.74–2.77 (m, 1H), 3.59–3.65 (m, 3H), 6.61–6.69 (m, 2H), 6.80–6.83 (m, 2H), 7.27–7.30 (m, 1H), 7.86 (s, 1H) Mass spectrum (ESI-MS, m/z): 361 (M$^+$+1)

Example 283

N-(1H-5-Indazolyl)-N-[1-(2,4,6-trifluorobenzyl)-4-piperidyl]amine

4-Piperidone hydrochloride monohydrate (198 mg) and potassium carbonate (659 mg) were dissolved in acetonitrile (5 ml), and 2,4,6-trifluorobenzyl bromide (290 mg) was added dropwise to the solution at room temperature. The reaction mixture was stirred at room temperature for 18 hr and was then filtered through Celite, and the filtrate was concentrated to give an intermediate.

This intermediate and triethylamine (275 mg) were dissolved in anhydrous dimethyl sulfoxide (1.73 ml), and a sulfur trioxide-trimethylamine complex (379 mg) was added to the solution under an argon atmosphere at room temperature. The reaction mixture was stirred at room temperature for 18 hr. A saturated aqueous sodium hydrogencarbonate solution was then added thereto, and the mixture was extracted with chloroform. The organic layer was dried over anhydrous sodium sulfate and was concentrated to give an intermediate.

This intermediate (292 mg) was dissolved in titanium tetraisopropoxide (1.45 g). 5-Aminoindazole (128 mg) was added to the solution, and the mixture was stirred at room temperature for 18 hr. Methanol and sodium borohydride (23 mg) were then added to the reaction solution, and the mixture was stirred for 18 hr. The reaction solution was diluted with ethyl acetate, and a minor amount of water was added thereto, and the mixture was then filtered under the reduced pressure. The filtrate was concentrated under the reduced pressure, and the residue was purified by column chromatography on silica gel [chloroform/methanol] to give the title compound (215 mg, yield 46.2%).

$^1$H-NMR (CDCl$_3$, 400 MHz): 1.43–1.62 (m, 2H), 2.07–2.11 (m, 2H), 2.24–2.30 (m, 2H), 2.91–2.94 (m, 2H), 3.21–3.29 (m, 1H), 6.65–6.72 (m, 2H), 6.77–6.81 (m, 2H), 7.28–7.30 (m, 1H), 7.86 (s, 1H) Mass spectrum (ESI-MS, m/z): 361 (M$^+$+1)

Example 284

N-(1H-5-Indazolyl)-N-(1-methyl-4-piperidyl)amine

1-Methyl-4-piperidone (300 mg) was dissolved in titanium tetraisopropoxide (1.5 g). 5-Aminoindazole (282 mg) was added to the solution, and the mixture was stirred at room temperature for 18 hr. Methanol and sodium borohydride (50 mg) were added to the reaction solution, and the mixture was stirred for 18 hr. The reaction solution was diluted with ethyl acetate, and a minor amount of water was added thereto, and the mixture was then filtered under the reduced pressure. The filtrate was concentrated under the reduced pressure, and the residue was purified by column chromatography on silica gel [chloroform/methanol] to give the title compound (202 mg, yield 41.4%).

$^1$H-NMR (CDCl$_3$, 400 MHz): 1.47–1.57 (m, 2H), 2.10–2.18 (m, 4H), 2.30 (s, 3H), 2.83–2.86 (m, 2H), 3.28–3.33 (m, 1H), 6.80–6.82 (m, 2H), 7.28–7.31 (m, 1H), 7.88 (s, 1H) Mass spectrum (ESI-MS, m/z): 230 (M$^+$+1)

Example 285

N-(1H-5-Indazolyl)-N-(1-propyl-3-piperidyl)amine

3-Hydroxypiperidine (1.00 g) and potassium carbonate (2.76 g) were dissolved in acetonitrile (10 ml), and 3-bromopropane (1.23 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution was then added thereto, and the mixture was extracted with chloroform. The organic layer was dried over anhydrous sodium sulfate and was concentrated to give an intermediate.

This intermediate and 5-aminoindazole (200 mg) were dissolved in titanium tetraisopropoxide (1.0 g), and the mixture was stirred at room temperature for 18 hr. A minor amount of methanol and sodium borohydride (100 mg) were added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (100 mg, yield 3.87%).

$^1$H-NMR (CDCl$_3$, 400 MHz): 0.90 (t, J=7.6 Hz, 3H), 1.51–2.07 (m, 4H), 2.07–2.21 (m, 4H), 2.36–2.40 (m, 2H), 2.96–2.99 (m, 2H), 3.29–3.36 (m, 1H), 6.75–6.81 (m, 2H), 7.25 (d, J=12.0 Hz, 1H), 7.88 (s, 1H) Mass spectrum (ESI-MS, m/z): 259 (M$^+$+1)

Example 286

N-(1H-5-Indazolyl)-N-(1-propyl-4-piperidyl)amine

4-Piperidone hydrochloride monohydrate (1.53 g) and potassium carbonate (2.76 g) were dissolved in anhydrous N,N-dimethylformamide, and 1-bromopropane (1.29 g) was added dropwise to the solution at room temperature. The reaction solution was stirred at room temperature for 18 hr. Ethyl acetate was then added to the solution, and the mixture was washed with water and saturated brine and was dried over anhydrous sodium sulfate. The organic layer was concentrated under the reduced pressure to give an intermediate.

This intermediate (1.03 g) was dissolved in titanium tetraisopropoxide (5.5 g). 5-Aminoindazole (971 mg) was added to the solution, and the mixture was stirred at room temperature for 18 hr. Methanol and sodium borohydride (276 mg) were then added solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (1.3 g, yield 50.3%).

$^1$H-NMR (CDCl$_3$, 400 MHz): 0.91 (t, J=7.3 Hz, 3H), 1.48–1.59 (m, 4H), 2.10–2.18 (m, 4H), 2.33–2.37 (m, 2H), 2.92–2.95 (m, 2H), 3.30–3.36 (m, 1H), 6.78–6.82 (m, 2H), 7.27–7.29 (d, J=8.8 Hz, 1H), 7.88 (d, J=1.0 Hz, 1H) Mass spectrum (ESI-MS, m/z): 259 (M$^+$+1)

Example 287

N-[1-(Cyclopropylmethyl)-4-piperidyl]-N-(1H-5-indazolyl)amine

4-Piperidone hydrochloride monohydrate (1.14 g) and potassium carbonate (1.38 g) were dissolved in anhydrous acetonitrile, and (bromomethyl)cyclopropane (1 g) was added dropwise to the solution at room temperature. The reaction solution was stirred at room temperature for 18 hr. Ethyl acetate was then added to the solution, and the mixture was washed with water and saturated brine and was dried over anhydrous sodium sulfate. The organic layer was concentrated under the reduced pressure to give an intermediate.

This intermediate was dissolved in titanium tetraisopropoxide (4.3 g). 5-Aminoindazole (600 mg) was added to the solution, and the mixture was stirred at room temperature for 18 hr. Methanol and sodium borohydride (170 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (338 mg, yield 16.9%).

$^1$H-NMR (CDCl$_3$, 400 MHz): 0.11–0.13 (m, 2H), 0.49–0.57 (m, 2H), 0.86–0.93 (m, 1H), 1.50–1.59 (m, 2H), 2.11–2.22 (m, 4H), 2.29–2.31 (m, 2H), 3.04–3.07 (m, 2H), 3.29–3.35 (m, 1H), 6.79–6.82 (m, 2H), 7.28–7.31 (m, 1H), 7.88 (s, 1H) Mass spectrum (ESI-MS, m/z): 271 (M$^+$+1)

Example 288

N-[1-(2-Fluoroethyl)-4-piperidyl]-N-(1H-5-indazolyl)amine

4-Piperidone hydrochloride monohydrate (1.53 g) and potassium carbonate (2.76 g) were dissolved in anhydrous acetonitrile. 1-Bromo-2-fluoroethane (1.27 g) was added dropwise to the solution at room temperature. The reaction solution was stirred at room temperature for 18 hr. Ethyl acetate was then added to the solution, and the mixture was washed with water and saturated brine and was dried over anhydrous sodium sulfate. The organic layer was concentrated under the reduced pressure to give an intermediate.

This intermediate (257 mg) was dissolved in titanium tetraisopropoxide (1.2 g). 5-Aminoindazole (188 mg) was added to the solution, and the mixture was stirred at room temperature for 18 hr. Methanol and sodium borohydride (33 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (80 mg, yield 3.05%).

$^1$H-NMR (CDCl$_3$, 400 MHz): 1.50–1.59 (m, 2H), 2.10–2.14 (m, 2H), 2.26–2.32 (m, 2H), 2.71 (t, J=4.9 Hz, 1H), 2.79 (t, J=4.9 Hz, 1H), 2.96–2.99 (m, 2H), 3.30–3.37 (m, 1H), 4.53 (t, J=4.9 Hz, 1H), 4.65 (t, J=4.9 Hz, 1H), 6.79–6.82 (m, 2H), 7.30 (d, J=8.3 Hz, 1H), 7.89 (s, 1H) Mass spectrum (ESI-MS, m/z): 263 (M$^+$+1)

Example 289

N-[1-(3-Fluoropropyl)-4-piperidyl]-N-(1H-5-indazolyl)amine

4-Piperidone hydrochloride monohydrate (768 mg) and potassium carbonate (1.38 g) were dissolved in anhydrous acetonitrile. 1-Bromo-3-fluoroethane (705 mg) was added dropwise to the solution at room temperature. The reaction solution was stirred at room temperature for 18 hr. Ethyl acetate was then added to the solution, and the mixture was washed with water and saturated brine and was dried over anhydrous sodium sulfate. The organic layer was concentrated under the reduced pressure to give an intermediate.

This intermediate (510 mg) was dissolved in titanium tetraisopropoxide (2.6 g). 5-Aminoindazole (464 mg) was added to the solution, and the mixture was stirred at room temperature for 18 hr. Methanol and sodium borohydride (66 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (710 mg, yield 51.4%).

$^1$H-NMR (CDCl$_3$, 400 MHz): 1.46–1.55 (m, 2H), 1.86–1.98 (m, 2H), 2.10–2.20 (m, 4H), 2.51 (t, J=7.1 Hz, 2H), 2.90–2.92 (m, 2H), 3.29–3.36 (m, 1H), 4.46 (t, J=6.1 Hz, 1H), 4.57 (t, J=6.1 Hz, 1H), 6.79–6.82 (m, 2H), 7.29 (d, J=8.5 Hz, 1H), 7.89 (m, 1H) Mass spectrum (ESI-MS, m/z): 277 (M$^+$+1)

Example 290

N-(1H-5-Indazolyl)-N-[1-(3,3,3-trifluoropropyl)-4-piperidyl]amine

4-Piperidone hydrochloride monohydrate (768 mg) and potassium carbonate (1.38 g) were dissolved in anhydrous acetonitrile. 1-Bromo-3,3,3-trifluoropropane (884 mg) was added dropwise to the solution at room temperature. The reaction solution was stirred at room temperature for 18 hr. Ethyl acetate was then added to the solution, and the mixture was washed with water and saturated brine and was dried over anhydrous sodium sulfate. The organic layer was concentrated under the reduced pressure to give an intermediate.

This intermediate (430 mg) was dissolved in titanium tetraisopropoxide (2.6 g). 5-Aminoindazole (234 mg) was added to the solution, and the mixture was stirred at room temperature for -18 hr. Methanol and sodium borohydride (83.6 mg) were then added to the reaction solution, and the mixture was stirred for 18. hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (160 mg, yield 10.2%).

$^1$H-NMR (CDCl$_3$, 400 MHz): 1.44–1.51 (m, 2H), 2.05–2.17 (m, 4H), 2.24–2.36 (m, 2H), 2.59–2.62 (m, 2H), 2.82–2.84 (m, 2H), 3.27 (m, 1H), 6.72 (d, J=8.8 Hz, 1H), 6.79 (s, 1H), 7.17 (d, J=8.8 Hz, 1H), 7.92 (s, 1H) Mass spectrum (ESI-MS, m/z): 313 (M$^+$+1)

Example 291

N-[1-(4,4-Dimethylpentyl)-4-piperidyl]-N-(1H-5-indazolyl)amine

4-Piperidone hydrochloride monohydrate (768 mg) and potassium carbonate (1.38 g) were dissolved in anhydrous acetonitrile, and 1-bromo-4,4,4-trifluorobutane (955 mg) was added dropwise to the solution at room temperature. The reaction solution was stirred at room temperature for 18 hr. Ethyl acetate was then added, and the mixture was washed with water and saturated brine and was dried over anhydrous sodium sulfate. The organic layer was concentrated under the reduced pressure to give an intermediate.

This intermediate (684 mg) was dissolved in titanium tetraisopropoxide (3.4 g). 5-Aminoindazole (348 mg) was added to the solution, and the mixture was stirred at room temperature for 18 hr. Methanol and sodium borohydride (124 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (522 mg, yield 38.3%).

$^1$H-NMR (CDCl$_3$, 400 MHz): 1.45–1.52 (m, 2H), 1.71–1.78 (m, 2H), 2.08–2.16 (m, 6H), 2.38–2.41 (m, 2H), 2.85–2.88 (m, 2H), 3.28–3.33 (m, 1H), 6.76 (d, J=8.8 Hz, 1H), 6.81 (s, 1H), 7.23 (d, J=8.5 Hz, 1H), 7.91 (s, 1H) Mass spectrum (ESI-MS, m/z): 273 (M$^+$+1)

Example 292

N-[1-(3-Fluoropropyl)-3-piperidyl]-N-(1H-5-indazolyl)amine

3-Hydroxypiperidine (718 mg) and potassium carbonate (1.96 g) were dissolved in acetonitrile. 1Bromo-3-fluoropropane (1.0 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution was then added thereto, and the mixture was extracted with chloroform. The organic layer was dried over anhydrous sodium sulfate and was concentrated to give an intermediate.

This intermediate and 5-aminoindazole (150 mg) were dissolved in titanium tetraisopropoxide (750 mg), and the mixture was stirred at room temperature for 18 hr. A minor amount of methanol and sodium borohydride (100 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (62 mg, yield 3.16%).

$^1$H-NMR (CDCl$_3$, 400 MHz): 1.59 (m, 2H), 1.75–1.77 (m, 2H), 1.83–1.96 (m, 2H), 2.37–2.54 (m, 4H), 2.75 (m, 2H), 3.61 (m, 1H), 4.46 (t, J=5.9 Hz, 1H), 4.58 (t, J=6.1 Hz, 1H), 6.82–6.85 (m, 2H), 7.29–7.31 (m, 1H), 7.88 (s, 1H) Mass spectrum (ESI-MS, m/z): 277 (M$^+$+1)

Example 293

N-[1-(2-Chloro-4-fluorobenzyl)-3-piperidyl]-N-(1H-5-indazolyl)amine

3-Hydroxypiperidine (1 g) and potassium carbonate (2.76 g) were dissolved in acetonitrile (10 ml), and 2-chloro-4-fluorobenzyl bromide (2.23 g) was added dropwise to the solution at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution was then added thereto, and the mixture was extracted with chloroform. The organic layer was dried over anhydrous sodium sulfate and was concentrated to give an intermediate.

This intermediate (317 mg) and 5-aminoindazole (139 mg) were dissolved in titanium tetraisopropoxide (1.6 g), and the mixture was stirred at room temperature for 18 hr. A minor amount of methanol and sodium borohydride (100 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (150 mg, yield 4.18%).

$^1$H-NMR (CDCl$_3$, 400 MHz): 1.56–1.74 (m, 5H), 2.42–2.49 (m, 2H), 2.73–2.76 (m, 1H), 3.56 (s, 2H), 3.59–3.62 (m, 1H), 6.79–6.83 (m, 1H), 6.94 (dt, J=2.7, 8.3 Hz, 1H), 7.12 (dd, J=2.7, 8.5 Hz, 2H), 7.27–7.30 (m, 1H), 7.39–7.42 (m, 1H), 7.86 (d, J=1.0 Hz, 1H) Mass spectrum (ESI-MS, m/z): 359 (M$^+$+1)

Example 294

Methyl 2-(3,4-difluoropentyl)-2-[3-(1H-5-indazolylamino)piperidino]acetate 3,4-Difluorophenylacetic acid (3.42 g) and potassium carbonate (2.76 g) were dissolved in acetonitrile (10 ml), and methyl iodide (2.82 g) was added dropwise to the solution at room temperature. The reaction mixture was stirred at room temperature for 18 hr and was then filtered through Celite, and the filtrate was concentrated to give an intermediate.

This intermediate (2.02 g) was dissolved in carbon tetrachloride. N-Bromosuccinimide (2.88 g) was added to the solution, and the mixture was refluxed for 18 hr. The reaction solution was then filtered through Celite, and the filtrate was concentrated to give an intermediate.

This intermediate (1.60 g) and potassium carbonate (1.73 g) were dissolved in acetonitrile (10 ml), and 3-hydroxypiperidine (631 mg) was added to the solution. The reaction mixture was stirred at room temperature for 18 hr and was then filtered through Celite, and the filtrate was concentrated to give an intermediate.

This intermediate (2.02 g) was dissolved in anhydrous dimethyl sulfoxide, and triethylamine (552 mg) and sulfur trioxide-trimethylamine complex (758 mg) were then added to the solution under an argon atmosphere. The reaction mixture was stirred at room temperature for 18 hr. A saturated aqueous sodium hydrogencarbonate solution was then added thereto, and the mixture was extracted with chloroform. The organic layer was dried over anhydrous sodium sulfate and was concentrated to give an intermediate.

This intermediate (763 mg) and 5-aminoindazole (287 mg) were dissolved in titanium tetraisopropoxide (3.87 g), and the mixture was stirred at room temperature for 18 hr. A minor amount of methanol and sodium borohydride (101 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (345 mg, yield 0.43%).

$^1$H-NMR (CDCl$_3$, 400 MHz): 1.59–1.63 (m, 2H), 1.76–1.78 (m, 2H), 2.31–2.49 (m, 4H), 3.69 (d, J=6.4 Hz, 2H), 6.76–6.84 (m, 2H), 7.07–7.13 (m, 2H), 7.28–7.37 (m, 1H), 7.86 (s, 1H) Mass spectrum (ESI-MS, m/z): 399 (M$^+$–1)

Example 295

N-(1H-5-Indazolyl)-N-{1-[(2S)-2-methylbutyl]-3-piperidyl}amine

3-Hydroxypiperidine (1 g) and potassium carbonate (2.76 g) were dissolved in acetonitrile (10 ml), and a solution (15.1 ml) of (S)-(+)-1-bromo-2-methylbutane (1.51 g) in acetonitrile was added dropwise thereto at room temperature. The reaction mixture was stirred at room temperature for 18 hr and was then filtered through Celite, and the filtrate was concentrated to give an intermediate.

This intermediate and triethylamine (1.78 g) were dissolved in anhydrous dimethyl sulfoxide (7.55 ml), and a sulfur trioxide-trimethylamine complex (2.45 g) was added to the solution under an argon atmosphere at room temperature. The reaction mixture was stirred at room temperature for 18 hr. A saturated aqueous sodium hydrogencarbonate solution (7.55 ml) was then added thereto, and the mixture was extracted with chloroform. The organic layer was dried over anhydrous sodium sulfate and was concentrated to give an intermediate.

This intermediate and 5-aminoindazole (939 mg) were dissolved in titanium tetraisopropoxide (4.7 g), and the mixture was stirred at room temperature for 18 hr. Methanol (0.94 ml) and sodium borohydride (134 mg) were then added to the reaction solution, and the mixture was stirred for 18 hr. The reaction solution was diluted with ethyl acetate (40 ml), and a minor amount of water was added thereto, and the mixture was then filtered under the reduced pressure. The filtrate was concentrated under the reduced pressure, and the residue was purified by column chromatography on silica gel [chloroform/methanol] to give the title compound (253 mg, yield 8.8%).

$^1$H-NMR (CDCl$_3$, 400 MHz): 0.89 (dd, J=7.3, 13.9 Hz, 3H), 0.89 (d, J=5.8 Hz, 3H), 1.06–1.15 (m, 1H), 1.37–1.79 (m, 6H), 2.01–2.08 (m, 2H), 2.12–2.19 (m, 2H), 2.52–2.69 (m, 1H), 3.56–3.62 (m, 1H), 6.83 (s, 1H), 6.84 (dd, J=2.2, 6.6 Hz, 1H), 7.29 (d, J=9.5 Hz, 1H), 7.87 (s, 1H) Mass spectrum (ESI-MS, m/z): 278 (M$^+$+1)

Example 296

N-(1-Benzyl-3-methyl-4-piperidyl)-N-(1H-5-indazolyl)amine

1-Benzyl-3-methyl-4-piperidone (152.7 mg), 5-aminoindazole (100 mg), and acetic acid (0.02 ml) were dissolved in methanol (10 ml). Acetic acid (five drops) was added to the solution, and a borane-pyridine complex (0.06 ml) was then added dropwise to the solution at room temperature. The reaction mixture was stirred at room temperature for 18 hr. After the completion of the reaction, a saturated aqueous sodium hydrogencarbonate solution (1 ml) was added thereto, and the mixture was extracted with ethyl acetate. The ethyl acetate layer was washed with water and saturated brine and was dried over sodium sulfate. The solvent was then removed by distillation under the reduced pressure. The residue was purified by column chromatography [silica gel, chloroform/methanol] to give the title compound (95.3 mg, yield 65%).

$^1$H-NMR (CDCl$_3$, 400 MHz): 1.45–1.60 (m, 2H), 2.07–2.15 (m, 2H), 2.18–2.32 (m, 2H), 2.82–2.92 (m, 2H), 3.30–3.40 (m, 1H), 3.63 (s, 2H), 6.79–6.84 (m, 2H), 7.31 (d, J=9.8 Hz, 1H), 7.49 (d, J=7.8 Hz, 1H), 7.68 (d, J=7.1 Hz, 1H), 7.88 (s, 1H), 8.12 (d, J=6.9 Hz, 1H), 8.23 (s, 1H) Mass spectrum (ESI-MS, m/z): 320 (M$^+$+1)

Example 297

N-[1-(4-Fluorobenzyl)-3-piperidyl]-N-(5-isoquinolyl)amine

3-Hydroxypiperidine (200 mg) and potassium carbonate (327.8 mg) were dissolved in dimethylformamide (10 ml), and a solution (10 ml) of 4-fluorobenzyl chloride (312.2 mg) in acetonitrile was added dropwise thereto at room temperature. The reaction mixture was stirred at room temperature for 18 hr and was then filtered through Celite. The filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was then concentrated to give intermediate B.

Titanium isopropoxide was added to this intermediate B and 5-aminoisoquinoline (210.5 mg), and the mixture was stirred at room temperature for 30 min, followed by dissolution in methanol. Sodium borohydride was added to the solution, and. the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (166 mg).

$^1$H-NMR (CDCl$_3$, 400 MHz): 1.70–1.82 (1H, m), 1.85–2.00 (1H, m), 2.00–2.10 (1H, m), 2.97 (2H, q, J=11.7 Hz), 3.39 (1H, d, J=12.2 Hz), 3.65 (1H, d, J=11.7 Hz), 4.15–4.30 (1H, m), 4.25–4.42 (2H, m), 7.02–7.17 (3H, m), 7.36 (1H, d, J=8.1 Hz), 7.59–7.65 (2H, m), 7.75 (1H, t, J=8.1 Hz), 8.37 (1H, d, J=6.8 Hz), 8.66 (1H, d, J=6.8 Hz), 9.49 (1H, s) Mass spectrum (ESI-MS, m/z): 335 (M$^+$+1)

Example 298

N-(1H-5-Indazolyl)-N-{1-[4-(trifluoromethyl)benzyl]-3-piperidyl}amine

3-Hydroxypiperidine (200 mg) and potassium carbonate (327.8 mg) were dissolved in dimethylformamide (10 ml), and a solution (10 ml) of 4-trifluoromethylbenzyl chloride (421.4 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (154 mg).

$^1$H-NMR (CD$_3$OD, 400 MHz): 1.75–2.00 (2H, m), 2.00–2.23 (2H, m), 3.00–3.20 (1H, m), 3.20–3.45 (2H, m), 3.50–3.60 (1H, m), 4.09 (1H, s), 4.47 (1H, s), 7.42 (1H, d, J=8.5 Hz), 7.61 (3H, d, J=8.1 Hz), 7.66 –7.75 (1H, m), 7.74 (2H, d, J=7.1 Hz), 8.19 (1H, s) Mass spectrum (ESI-MS, m/z): 374 (M$^+$+1)

Example 299

N-(5-Isoquinolyl)-N-{1-[4-(trifluoromethyl)benzyl]-3-piperidyl}amine

3-Hydroxypiperidine (200 mg) and potassium carbonate (327.8 mg) were dissolved in dimethylformamide (10 ml), and a solution (10 ml) of 4-trifluoromethylbenzyl chloride (421.4 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoisoquinoline (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (163 mg).

$^1$H-NMR (CDCl$_3$, 400 MHz): 1.43–1.56 (m, 2H), 1.60 –1.73 (m, 2H), 2.23–2.40 (m, 3H), 2.61–2.80 (m, 1H), 3.33–3.47 (m, 2H), 3.48–3.58 (m, 1H), 3.72 (s, 3H), 6.74 (s,

1H), 6.78 (d, J=8.8 Hz, 2H), 7.16 (d, J=8.5 Hz, 2H), 7.21 (d, J=8.5 Hz, 1H), 7.79 (s, 1H) Mass spectrum (ESI-MS, m/z): 385 (M$^+$+1)

Example 300

N-[1-(3,4-Difluorobenzyl)-3-piperidyl)-N-(1H-5-indazolyl)amine

3-Hydroxypiperidine (200 mg) and potassium carbonate (327.8 mg) were dissolved in dimethylformamide (10 ml), and a solution (1 ml) of 3,4-difluorobenzyl bromide (448.4 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (181 mg).

$^1$H-NMR (CDCl$_3$, 400 MHz): 1.30–1.40 (1H, m), 1.59–1.69 (1H, m), 1.74–1.80 (1H, m), 1.91–1.94 (1H, m), 2.00 (1H, m), 2.18 (1H, t, J=7.0 Hz), 2.63 (1H, m), 2.93 (1H, d, J=10.0 Hz), 3.30–3.32 (1H, m), 3.48 (1H, q, J=8.0 Hz), 6.85 (1H, d, J=1.5 Hz), 6.92 (1H, dd, J=2.2, 8.8 Hz), 7.07–7.10 (1H, m), 7.14 (1H, dd, J=8.1, 10.2 Hz), 7.26 (1H, ddd, J=2.0, 8.1, 11.5 Hz), 7.31 (1H, d, J=8.8 Hz), 7.77 (1H, d, J=1.0 Hz) Mass spectrum (ESI-MS, m/z): 342 (M$^+$+1)

Example 301

N-[1-(3,4-Difluorobenzyl)-3-piperidyl]-N-(5-isoquinolyl)amine

3-Hydroxypiperidine (200 mg) and potassium carbonate (327.8 mg) were dissolved in dimethylformamide (10 ml), and a solution (10 ml) of 3,4-difluorobenzyl chloride (448.4 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was then concentrated to give intermediate B.

Titanium isopropoxide was added to this intermediate B and 5-aminoisoquinoline (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (156 mg).

$^1$H-NMR (CDCl$_3$, 400 MHz): 1.43–1.56 (m, 2H), 1.60–1.73 (m, 2H), 2.23–2.40 (m, 3H), 2.61–2.80 (m, 1H), 3.33–3.47 (m, 2H), 3.48–3.58 (m, 1H), 3.72 (s, 3H), 6.74 (s, 1H), 6.78 (d, J=8.8 Hz, 2H), 7.16 (d, J=8.5 Hz, 2H), 7.21 (d, J=8.5 Hz, 1H), 7.79 (s, 1H) Mass spectrum (ESI-MS, m/z): 353 (M$^+$+1)

Example 302

N-{1-[4-Fluoro-3-(trifluoromethyl)benzyl]3-piperidyl}-N-(1H-5-indazolyl)amine

3-Hydroxypiperidine (200 mg) and potassium carbonate (327.8 mg) were dissolved in dimethylformamide (10 ml), and a solution (10 ml) of 4-fluoro-3-trifluoromethylbenzyl chloride (556.7 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (161 mg).

$^1$H-NMR (CD$_3$OD, 400 MHz): 1.80–1.90 (1H, m), 1.90–2.05 (1H, m), 2.05–2.11 (2H, m), 3.00–3.10 (1H, m), 3.10–3.35 (1H, m), 3.35–3.50 (1H, m), 3.60–3.70 (1H, m), 4.10–4.20 (1H, m), 4.51 (2H, q, J=13.2 Hz), 7.43 (1H, t, J=9.3 Hz), 7.49 (1H, d, J=9.0 Hz), 7.70 (2H, d, J=9.0 Hz), 7.93–7.98 (1H, m), 8.02 (1H, d, J=6.3 Hz), 8.33 (1H, d, J=0.7 Hz) Mass spectrum (ESI-MS, m/z): 392 (M$^+$+1)

Example 303

N-[1-(3,4-Dichlorobenzyl)-3-piperidyl]-N-(1H-5-indazolyl)amine

3-Hydroxypiperidine (200 mg) and potassium carbonate (327.8 mg) were dissolved in dimethylformamide (1 ml), and a solution (1 ml) of 3, 4-dichlorobenzyl chloride (423.4 mg) in acetonitrile was added dropwise thereto at room temperature. The reaction mixture was stirred at room temperature for 18 hr and was then filtered through Celite, and the filtrate was concentrated to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (210.5 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (133 mg).

$^1$H-NMR (CDCl$_3$, 400 MHz): 1.70–2.20 (4H, m), 3.00–3.20 (1H, m), 3.40–3.55 (1H, m), 3.40–3.55 (1H, m), 3.65 (1H, bs), 4.15 (1H, bs), 4.43 (2H, q, J=10.5 Hz), 7.51 (1H, d, J=9.27 Hz), 7.57 (1H, s), 7.71 (1H, d, J=9.0 Hz), 7.85 (1H, s), 8.33 (1H, d, J=0.7 Hz) Mass spectrum (ESI-MS, m/z): 375 (M$^+$+1)

Example 304

N-[1-(4-Chlorobenzyl)-3-piperidyl]-N-(1H-5-indazolyl)amine

4-Chlorobenzyl chloride (318.3 mg) was added dropwise to a solution (10 ml) of 3-hydroxypiperidine (200 mg) and potassium carbonate (327.8 mg) in acetonitrile at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (171 mg).

$^1$H-NMR (CDCl$_3$, 400 MHz): 1.30–1.45 (1H, m), 1.59–1.70 (1H, m), 1.75–1.83 (1H, m), 1.94–1.97 (1H, m), 2.00–2.10 (1H, m), 2.24 (1H, t, J=9.3 Hz), 2.71 (1H, d, J=10.7 Hz), 3.00 (1H, d, J=9.3 Hz), 3.48–3.52 (1H, m), 3.56 (2H, q, J=9.3 Hz), 6.84 (1H, d, J=2.0 Hz), 6.91 (1H, dd, J=2.0, 9.0 Hz), 7.31 (1H, d, J=1.7 Hz), 7.77 (1H, d, J=1.0 Hz) Mass spectrum (ESI-MS, m/z): 340 (M$^+$+1)

Example 305

N-(1H-5-Indazolyl)-N-[1-(phenylsulfonyl)-3-piperidyl]amine

Benzenesulfonyl chloride (382.8 mg) was added dropwise to a solution (20 ml) of 3-hydroxypiperidine (200 mg) and triethylamine (0.33 ml) in acetonitrile at room temperature. The reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min, followed by dissolution in methanol. Sodium borohydride was then added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (146.7 mg).

$^1$H-NMR (CDCl$_3$, 400 MHz): 1.49–1.56 (1H, m), 1.69–1.75 (1H, m), 1.83–1.90 (2H, m), 2.70 (1H, dd, J=7.3, 11.2 Hz), 2.89 (1H, dd, J=3.7, 8.3 Hz), 3.23 (1H, dd, J=6.6, 10.7 Hz), 3.54 (1H, dd, J=3.7, 11.5 Hz), 3.62 (1H, m), 6.84 (1H, dd, J=2.2, 8.8 Hz), 6.89 (1H, d, J=2.2 Hz), 7.35 (1H, d, J=8.8 Hz), 7.53 (2H, t, J=7.1 Hz), 7.61 (1H, t, J=7.3 Hz), 7.76 (2H, d, J=7.1 Hz), 7.91 (1H, s) Mass spectrum (ESI-MS, m/z): 358 ($M^+$+1)

Example 306

N-(1H-5-Indazolyl)-N-{1-[(4-methylphenyl)sulfonyl]-3-piperidyl}amine p-toluenesulfonyl chloride (423.3 mg) was added dropwise to a solution (20 ml) of 3-hydroxypiperidine (200 mg) and triethylamine (0.33 ml) in acetonitrile at room temperature. The reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (212 mg).

$^1$H-NMR (CDCl$_3$, 400 MHz): 1.40–1.44 (1H, m), 1.60–1.70 (2H, m), 2.36 (3H, s), 2.61 (1H, dd, J=7.1, 11.5 Hz), 2.80 (1H, t, J=8.5 Hz), -3.12 (1H, dd, J=7.1, 8.5 Hz), 3.43 (1H, d, J=11.5 Hz), 3.54 (1H, m), 6.75 (1H, dd, J=2.0, 8.5 Hz), 6.78 (1H, s), 7.24 (2H, d, J=8.5 Hz), 7.25 (1H, d, J=8.3 Hz), 7.56 (2H, d, J=8.3 Hz), 7.83 (1H, s) Mass spectrum (ESI-MS, m/z): 370 ($M^+$+1)

Example 307

N-{1-[(4-Chlorophenyl)sulfonyl-3-piperidyl]-N-(1H-5-indazolyl)amine

4-Fluorobenzenesulfonyl chloride (423.3 mg) was added dropwise to a solution (20 ml) of 3-hydroxypiperidine (200 mg) and triethylamine (0.33 ml) in acetonitrile at room temperature. The reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (216.2 mg).

$^1$H-NMR (CDCl$_3$, 400 MHz): 1.40–1.51 (1H, m), 1.62–1.75 (1H, m), 1.89–1.90 (2H, m), 1.90–2.05 (1H, m), 2.64 (1H, t, J=11.0 Hz), 2.84 (1H, t, J=8.5 Hz), 3.18–3.25 (1H, m), 3.52 (1H, d, J=11.0 Hz), 6.79 (1H, d, J=8.8 Hz), 6.83 (1H, s), 7.15–7.25 (2H, m), 7.30 (1H, d, J=8.8 Hz), 7.70–7.80 (2H, m), 7.89 (1H, s) Mass spectrum (ESI-MS, m/z): 374 ($M^+$+1)

Example 308

N-(1H-5-Indazolyl)-N-(1-{[4-(trifluoromethyl)phenyl]sulfonyl}-3-piperidyl)amine

4-Trifluorobenzenesulfonyl chloride (532 mg) was added dropwise to a solution (20 ml) of 3-hydroxypiperidine (200 mg) and triethylamine (0.33 ml) in acetonitrile at room temperature. The reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.55 ml) were dissolved in anhydrous dimethyl sulfoxide (10 ml), and a sulfur trioxide-trimethylamine complex (550.3 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (181.2 mg).

$^1$H-NMR (CDCl$_3$, 400 MHz): 1.40–1.44 (1H, m), 1.60–1.70 (2H, m), 2.36 (3H, s), 2.61 (1H, dd, J=7.1, 11.5 Hz), 2.80 (1H, t, J=8.5 Hz), 3.12 (1H, dd, J=7.1, 8.5 Hz), 3.43 (1H, d, J=11.5 Hz), 3.54 (1H, m), 6.75 (1H, dd, J=2.0 Hz, 8.5 Hz), 6.78 (1H, s), 7.24 (2H, d, J=8.5 Hz), 7.25 (1H, d, J=8.3 Hz), 7.56 (2H, d, J=8.3 Hz), 7.83 (1H, s) Mass spectrum (ESI-MS, m/z): 424 (M$^+$+1)

Example 309

N-(1H-5-Indazolyl)-N-[1-(phenylsulfonyl)tetrahydro-1H-3-pyrrolyl]amine

Benzenesulfonyl chloride (0.2 ml) was added dropwise to a solution (20 ml) of (R)-(–)-3-pyrrolidinol hydrochloride (200 mg) and triethylamine (0.33 ml) in acetonitrile at room temperature, and the reaction mixture was stirred at room temperature for 18 hr. After the completion of the reaction, water was poured into the reaction mixture, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.45 ml) were dissolved in anhydrous dimethyl sulfoxide (10 ml), and a sulfur trioxide-trimethylamine complex (450.5 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (193.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (225.0 mg).

$^1$H-NMR (CDCl$_3$, 400 MHz): 1.75–1.82 (1H, m), 2.00–2.09 (1H, m), 3.15–3.27 (2H, m), 3.30–3.38 (1H, m), 3.43 (1H, dd, J=5.6, 10.5 Hz), 3.85–3.88 (1H, m), 6.51 (1H, dd, J=2.0, 8.8 Hz), 6.56 (1H, d, J=1.5 Hz), 7.19 (1H, t, J=3.9 Hz), 7.43 (2H, t, J=7.6 Hz), 7.52 (1H, t, J=7.3 Hz), 7.73 (2H, d, J=7.6 Hz), 7.80 (1H, s) Mass spectrum (ESI-MS, m/z): 342 (M$^+$+1)

Example 310

N-(1H-5-Indazolyl)-N-{1-[(4-methylphenyl)sulfonyl]tetrahydro-1H-3-pyrrolyl}amine p-toluenesulfonyl chloride (308.5 mg) was added dropwise to a solution (20 ml) of (R)-(–)-3-pyrrolidinol hydrochloride (200 mg) and triethylamine (0.33 ml) in acetonitrile at room temperature, and the reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.45 ml) were dissolved in anhydrous dimethyl sulfoxide (10 ml), and a sulfur trioxide-trimethylamine complex (450.5 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (193.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (125.9 mg).

$^1$H-NMR (CDCl$_3$, 400 MHz): 1.85–1.91 (1H, m), 2.11–2.21 (1H, m), 2.46 (3H, s), 3.27 (1H, dd, J=3.2, 10.7 Hz), 3.31–3.44 (2H, m), 3.52 (1H, dd, J=5.6, 10.5 Hz), 3.96–4.02 (1H, m), 6.60 (1H, dd, J=2.2, 8.8 Hz), 6.65 (1H, d, J=2.0 Hz), 7.30 (1H, d, J=10.7 Hz), 7.32 (2H, d, J=10.5 Hz), 7.71 (2H, d, J=8.3 Hz), 7.88 (1H, s) Mass spectrum (ESI-MS, m/z): 355 (M$^+$+1)

Example 311

N-{1-[(4-Chlorophenyl)sulfonyl]tetrahydro-1H-3-pyrrolyl}-N-(1H-5-indazolyl)amine 4-Chlorobenzenesulfonyl chloride (341.6 mg) was added dropwise to a solution (20 ml) of (R)-(–)-3-pyrrolidinol hydrochloride (200 mg) and triethylamine (0.33 ml) in acetonitrile at room temperature. The reaction mixture was stirred at room temperature for 18 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure to give intermediate A.

This intermediate A and triethylamine (0.45 ml) were dissolved in anhydrous dimethyl sulfoxide (10 ml), and a sulfur trioxide-trimethylamine complex (450.5 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (193.9 mg), and the mixture was stirred at room temperature for 30 min, followed by dissolution in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (143.2 mg).

$^1$H-NMR (CDCl$_3$, 400 MHz): 1.85–1.91 (1H, m), 2.11–2.21 (1H, m), 2.46 (3H, s), 3.27 (1H, dd, J=3.2, 10.7 Hz), 3.31–3.44 (2H, m), 3.52 (1H, dd, J=5.6, 10.5 Hz), 3.96–4.02 (1H, m), 6.60 (1H, dd, J=2.2, 8.8 Hz), 6.65 (1H, d, J=2.0 Hz), 7.30 (1H, d, J=10.7 Hz), 7.32 (2H, d, J=10.5 Hz), 7.71 (2H, d, J=8.3 Hz), 7.88 (1H, s) Mass spectrum (ESI-MS, m/z): 378 (M$^+$+1)

Example 312

N-[1-(2,6-Dichlorobenzyl)-3-piperidyl]-N-(1H-5-indazolyl)amine 2,6-Dichlorobenzyl chloride (425.1 mg) was added dropwise to a solution (10 ml) of 3-hydroxypiperidine (200 mg) and potassium carbonate (327.8 mg) in acetonitrile at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (10 ml), and a sulfur trioxide-trimethylamine complex (550.3 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (254.5 mg).

$^1$H-NMR (CD$_3$OD, 400 MHz): 1.70–1.82 (1H, m), 1.85–2.00 (1H, m), 2.10–2.18 (2H, m), 3.35 (1H, dt, J=2.9, 12.2 Hz), 3.44 (1H, t, J=11.2 Hz), 3.59 (1H, d, J=12.2 Hz), 3.68 (1H, d, J=10.0 Hz), 4.00–4.10 (1H, m), 4.69 (2H, s), 7.36 (1H, dd, J=1.2, 8.8 Hz), 7.40 (1H, d, J=6.6 Hz), 7.46 (1H, d, J=2.0 Hz), 7.59 (1H, d, J=9.0 Hz), 8.16 (1H, d, J=0.7 Hz) Mass spectrum (ESI-MS, m/z): 375 (M$^+$+1)

Example 313

N-[1-(2,5-Dichlorobenzyl)-3-piperidyl]-N-(1H-5-indazolyl)amine 2,5-Dichlorobenzyl chloride (521.8 mg) was added dropwise to a solution (10 ml) of 3-hydroxypiperidine (200 mg) and potassium carbonate (327.8 mg) in acetonitrile at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (1 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (243.8 mg).

Mass spectrum (ESI-MS, m/z): 375 (M$^+$+1)

Example 314

N-[1-(2,4-Dichlorobenzyl)-3-piperidyl]-N-(1H-5-indazolyl)amine 2,4-Dichlorobenzyl bromide (521.8 mg) was added dropwise to a solution (10 ml) of 3-hydroxypiperidine (200 mg) and potassium carbonate (327.8 mg) in acetonitrile at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (10 ml), and a sulfur trioxide-trimethylamine complex (550.3 mg) was added to the solution under an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min. Thereafter, the reaction mixture was dissolved in methanol. Sodium borohydride was added thereto, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (192.0 mg).

$^1$H-NMR (DMSO, 400 MHz): 1.70–1.80 (1H, m), 1.80–1.90 (1H, m), 2.00–2.20 (2H, m), 3.10–3.50 (3H, m), 3.61 (1H, d, J=10.5 Hz), 4.00–4.10 (1H, m), 4.51 (2H, s), 7.35 (1H, dd, J=2.0, 8.8 Hz), 7.41 (1H, dd, J=2.0, 8.3 Hz), 7.51 (1H, d, J=2.0 Hz), 7.63 (1H, dd, J=4.9, 9.0 Hz), 7.72 (1H, d, J=8.3 Hz), 8.21 (1H, s) Mass spectrum (ESI-MS, m/z): 375 (M$^+$+1)

Example 315

N-[1-(2,6-Difluorobenzyl)-3-piperidyl]-N-(1H-5-indazolyl)amine 2,6-Difluorobenzyl chloride (353.5 mg) was added dropwise to a solution (10 ml) of 3-hydroxypiperidine (200 mg) and potassium carbonate (327.8 mg) in acetonitrile at room temperature. The reaction mixture was stirred at room temperature for 18 hr and was then filtered through Celite, and the filtrate was concentrated to give intermediate A.

This intermediate A and triethylamine (0.50 ml) were dissolved in anhydrous dimethyl sulfoxide (10 ml), and a sulfur trioxide-trimethylamine complex (550.2 mg) was added to the solution in an argon atmosphere at room temperature. The reaction mixture was stirred at room temperature for 18 hr. A saturated aqueous sodium hydrogencarbonate solution (10 ml) was then added thereto, and the mixture was extracted with chloroform. The organic layer was dried over anhydrous sodium sulfate and was concentrated to give intermediate B.

Titanium isopropoxide was added to this intermediate B and 5-aminoindazole (236.9 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (237.5 mg).

$^1$H-NMR (CD$_3$OD, 400 MHz): 1.45–1.52 (1H, m), 1.80–1.90 (1H, m), 1.95–2.05 (2H, m), 2.80–3.00 (1H, m), 3.00–3.05 (1H, m), 3.38–3.40 (1H, m), 3.50–3.55 (1H, m), 3.70–3.75 (1H, m), 4.40 (2H, s), 6.96 (1H, dd, J=2.0, 7.3 Hz), 6.97 (1H, s), 7.07 (1H, t, J=8.1 Hz), 7.35 (1H, dd, J=1.0, 9.8 Hz), 7.48–7.55 (1H, m), 7.89 (1H, s) Mass spectrum (ESI-MS, m/z): 342 (M$^+$+1)

Example 316

N-(1H-5-Indazolyl)-N-[1-(2-propynyl)-4-piperidyl]amine

Propargyl bromide (0.19 ml), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoindazole (208.0 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (170.6 mg).

$^1$H-NMR (CDCl$_3$, 400 MHz): 1.55 (2H, dq, J=3.7, 10.5 Hz), 2.13 (2H, d, J=12.2 Hz), 2.26 (1H, t, J=2.5 Hz), 2.41 (2H, dt, J=2.5, 10.5 Hz), 2.89 (2H, d, J=12.2 Hz), 3.28–3.35 (1H, m), 3.34 (2H, d, J=2.4 Hz), 6.79 (1H, dd, J=2.0, 8.5 Hz), 6.81 (1H, s), 7.28 (1H, d, J=8.8 Hz), 7.86 (1H, d, J=1.0 Hz) Mass spectrum (ESI-MS, m/z): 254 (M$^+$+1)

Example 317

N-(1-Butyl-3-piperidyl)-N-(1H-5-indazolyl)amine n-Butyl bromide (0.23 ml), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoindazole (208.0 mg), and the mixture was stirred at room. temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (99.6 mg).

$^1$H-NMR (CDCl$_3$, 400 MHz): 0.85 (3H, t, J=7.3 Hz), 1.25 (2H, q, J=7.3 Hz), 1.43 (4H, t, J=8.1 Hz), 2.03 (2H, d, J=9.3 Hz), 2.08 (2H, d, J=11.2 Hz), 2.29 (2H, t, J=7.3 Hz), 2.85

(2H, d, J=8.6 Hz), 3.15–3.30 (1H, m), 6.72 (1H, dd, J=2.0, 8.3 Hz), 6.74 (1H, s), 7.20 (1H, d, J=8.3 Hz), 7.81 (1H, s) Mass spectrum (ESI-MS, m/z): 272 (M$^+$+1)

Example 318

N-(5-Isoquinolyl)-N-(1-propyl-4-piperidyl)amine n-Propyl bromide (0.2 ml), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoisoquinoline (208.0 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (101.3 mg).

$^1$H-NMR (CDCl$_3$, 400 MHz): 0.85 (3H, t, J=7.3 Hz), 1.47 (2H, q, J=7.6 Hz), 1.57 (2H, dq, J=4.2, 10.7 Hz), 1.92 (1H, s), 2.05–2.18 (4H, m), 2.28 (2H, t, J=7.8 Hz), 2.87 (2H, d, J=12.2 Hz), 3.38–3.50 (1H, m), 4.19 (1H, d, J=5.4 Hz), 6.71 (1H, d, J=7.6 Hz), 7.22 (1H, d, J=8.1 Hz), 7.37 (1H, t, J=7.8 Hz), 7.46 (1H, d, J=6.1 Hz), 8.39 (1H, d, J=5.9 Hz), 9.07 (1H, s) Mass spectrum (ESI-MS, m/z): 269 (M$^+$+1)

Example 319

N-(1-Isobutyl-4-piperidyl)-N-(5-isoquinolyl)amine

1-Bromo-2-methylpropane (0.23 mg), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoisoquinoline (208.0 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (150.3 mg).

$^1$H-NMR (CDCl$_3$, 400 MHz): 0.84 (6H, d, J=6.6 Hz), 1.56 (2H, dq, J=3.2, 10.5 Hz), 1.68–1.77 (1H, m), 2.06 (4H, d, J=7.3 Hz), 2.09 (2H, d, J=10.7 Hz), 2.79 (2H, d, J=11.9 Hz), 3.38–3.45 (1H, m), 6.70 (1H, d, J=7.6 Hz), 7.21 (1H, d, J=8.1 Hz), 7.37 (1H, t, J=7.8 Hz), 7.45 (1H, d, J=5.9 Hz), 8.38 (1H, d, J=5.9 Hz), 9.07 (1H, s) Mass spectrum (ESI-MS, m/z): 283 (M$^+$+1)

Example 320

N-[1-(2-Ethylbutyl)-4-piperidyl]-N-(5-isoquinolyl)amine

1-Bromo-2-ethylbutane (0.3 ml), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoisoquinoline (208 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (203.8 mg).

$^1$H-NMR (CDCl$_3$, 400 MHz): 0.86 (6H, t, J=7.3 Hz), 1.2–1.4 (5H, m), 1.60 (2H, q, J=13.2 Hz), 2.10 (3H, t, J=11.7 Hz), 2.15 (3H, d, J=7.1 Hz), 2.82 (2H, d, J=11.7 Hz), 3.18–3.22 (1H, m), 4.22 (1H, bs), 6.70 (1H, d, J=7.6 Hz), 7.21 (1H, d, J=8.3 Hz), 7.37 (1H, t, J=7.8 Hz), 7.45 (1H, d, J=5.9 Hz), 8.38 (1H, d, J=5.9 Hz), 9.07 (1H, s) Mass spectrum (ESI-MS, m/z): 311 (M$^+$+1)

Example 321

N-[1-(Cyclopropylmethyl)-4-piperidyl]-N-(5-isoquinolyl)amine (Bromomethyl)cyclopropane (0.21 ml), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoisoquinoline (208 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The. solvent was then removed by distillation under the reduced pressure. The residue was purified by column chromatography [silica gel, chloroform-methanol] to give the title compound (183.5 mg).

$^1$H-NMR (CDCl$_3$, 400 MHz): 0.01 (2H, q, J=5.1 Hz), 0.41 (1H, q, J=2.4 Hz), 0.41 (1H, dd, J=1.2, 8.1 Hz), 0.72–0.82 (1H, m), 1.59 (2H, dq, J=3.7, 10.2 Hz), 2.06 (2H, dd, J=2.4, 10.9 Hz), 2.16 (2H, d, J=11.5 Hz), 2.21 (2H, d, J=6.6 Hz), 2.97 (2H, d, J=11.9 Hz), 3.35–3.41 (1H, m), 4.13 (1H, bs), 6.60 (1H, d, J=7.3 Hz), 7.11 (1H, s), 7.14 (1H, d, J=8.3 Hz), 7.29 (1H, t, J=7.8 Hz), 7.39 (1H, d, J=5.9 Hz), 8.31 (1H, d, J=5.9 Hz), 8.99 (1H, s) Mass spectrum (ESI-MS, m/z): 281 (M$^+$+1)

Example 322

N-[1-(3-Fluoropropyl)-4-piperidyl]-N-(5-isoquinolyl)amine

1-Bromo-3-fluoropropane (86 mg), 4-piperidone monohydrate (300 mg), and potassium carbonate (539.8 mg) were dissolved in acetonitrile (10 ml), and the mixture was then stirred at room temperature for 18 hr. The reaction mixture was filtered through Celite, and the filtrate was then concentrated to give an intermediate.

Titanium isopropoxide was added to this intermediate and 5-aminoisoquinoline (225.3 mg), and the mixture was stirred at room temperature for 30 min. Thereafter, the reaction mixture was dissolved in methanol. Sodium borohydride was added to the solution, and the mixture was stirred at room temperature for 3 hr. After the completion of the reaction, the reaction mixture was filtered through Celite, and the filtrate was then concentrated. Water was poured into the concentrate, and the mixture was then extracted with ethyl acetate. The ethyl acetate layer was washed with water and saturated brine and was dried over sodium sulfate. The solvent was then removed by distillation under the reduced pressure. The residue was purified by column chromatography [silica gel, chloroform-methanol] to give the title compound (210.9 mg).

$^1$H-NMR (CDCl$_3$, 400 MHz): 1.56 (2H, dq, J=4.2, 9.8 Hz), 1.82 (1H, dq, J=1.5, 7.1 Hz), 1.88 (1H, dq, J=1.5, 7.1 Hz), 2.10 (2H, d, J=11.2 Hz), 2.45 (2H, t, J=7.6 Hz), 2.48–2.55 (1H, m), 2.85 (2H, d, J=11.7 Hz), 3.43 (1H, s), 4.22 (1H, s), 4.39 (1H, t, J=6.1 Hz), 4.50 (1H, t, J=5.9 Hz), 6.69 (1H, d, J=7.56 Hz), 7.21 (1H, d, J=8.1 Hz), 7.36 (1H, t, J=8.1 Hz), 7.46 (1H, d, J=5.9 Hz), 8.37 (1H, d, J=6.1 Hz), 9.1 (1H, s) Mass spectrum (ESI-MS, m/z): 287 (M$^+$+1)

The compounds prepared in the above examples had the following structures.

| Ex. No. | Structural formula | IC50 (µM) |
|---|---|---|
| 1 | | 0.2 |
| 2 | | 2.21 |
| 3 | | 0.91 |
| 4 | | |
| 5 | | |

-continued

| | | |
|---|---|---|
| 6 | (2,3-dioxoisoindolin-5-yl)-(2,4,6-trichlorophenyl)urea structure | |
| 7 | (E)-3-(2,6-dichlorophenyl)-N-(pyridin-4-yl)acrylamide structure | 2.54 |
| 8 | 1-(2,6-difluorophenyl)-3-(pyridin-4-yl)urea structure | 2 |
| 9 | 1-(2,6-dichlorophenyl)-3-(pyridin-4-yl)urea structure | 0.85 |
| 10 | 1-(2,6-diisopropylphenyl)-3-(pyridin-4-yl)urea structure | |
| 11 | 1-(4-methoxyphenyl)-3-(pyridin-4-yl)urea structure | |
| 12 | 1-(2,4-dichlorophenyl)-3-(pyridin-4-yl)urea structure | |
| 13 | 1-(2,6-dichlorophenyl)-3-(1H-indazol-5-yl)urea structure | 0.98 |
| 14 | 2-(2,6-dichlorophenoxy)-N-(1H-indazol-5-yl)acetamide structure | 1.14 |

-continued

| | | |
|---|---|---|
| 15 | 1H-indazol-5-yl-NH-C(O)-CH₂-O-(2,6-dichloro-4-fluorophenyl) | 0.46 |
| 16 | 1H-indazol-5-yl-NH-C(O)-CH₂-O-(2,4,6-trichlorophenyl) | |
| 17 | pyridin-4-yl-NH-C(O)-CH₂-S-(2,6-dichlorophenyl) | 9.6 |
| 18 | pyridin-4-yl-NH-C(O)-NH-(2-chloro-6-fluorophenyl) | 2.87 |
| 19 | pyridin-4-yl-NH-C(O)-NH-cyclohexyl | 7.26 |
| 20 | (1,3-dioxoisoindolin-5-yl)-NH-C(O)-NH-CH(CH₃)-(4-bromophenyl) | 0.11 |
| 21 | 1H-indazol-5-yl-NH-(1-benzylpiperidin-3-yl) | 0.02 |
| 22 | 1H-indazol-5-yl-NH-(1-(4-bromobenzyl)piperidin-4-yl) | |
| 23 | 1H-indazol-5-yl-NH-(1-(3-bromobenzyl)piperidin-4-yl) | 0.124 |

-continued
| | | |
|---|---|---|
| 24 | 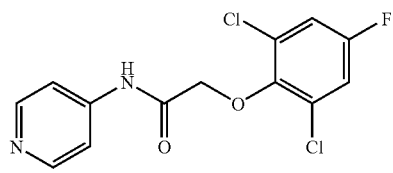 | 0.48 |
| 25 | 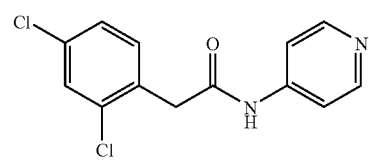 | |
| 26 | 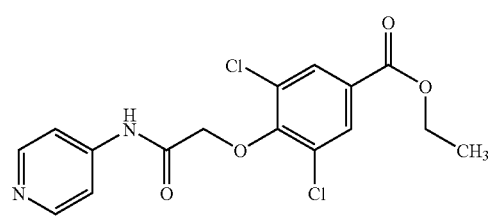 | 1.03 |
| 27 | 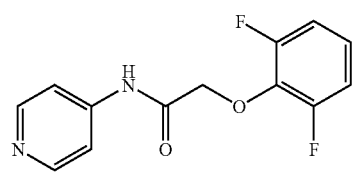 | |
| 28 | 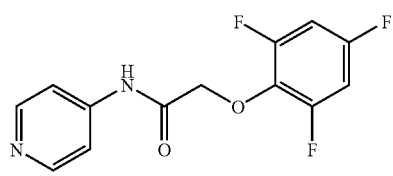 | 8.11 |
| 29 | 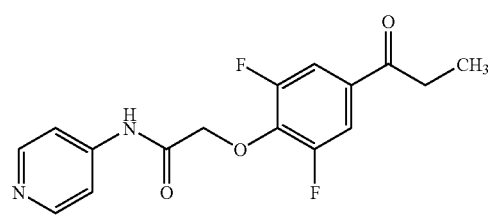 | 8.59 |
| 30 | 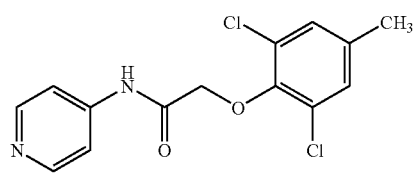 | 1.15 |
| 31 | 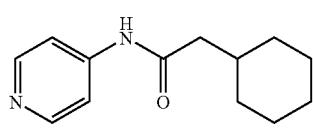 | 5.29 |

-continued
| | | |
|---|---|---|
| 32 | 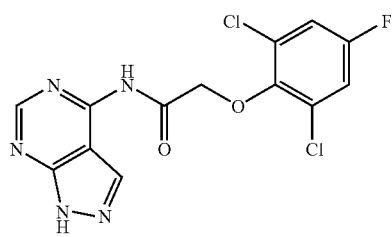 | 1.37 |
| 33 | 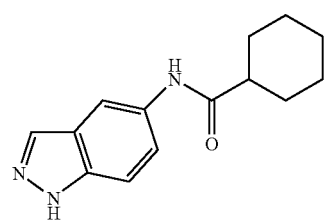 | 0.47 |
| 34 | 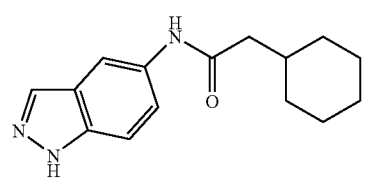 | 0.87 |
| 35 | 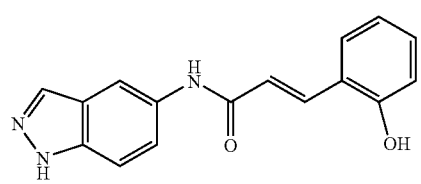 | 1.28 |
| 36 | 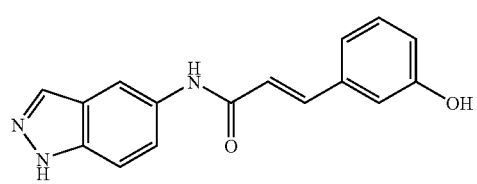 | 0.6 |
| 37 | 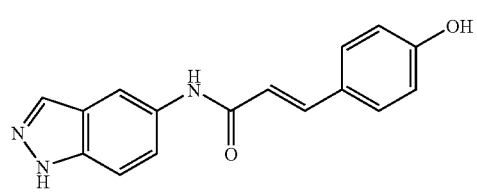 | 0.305 |
| 38 | 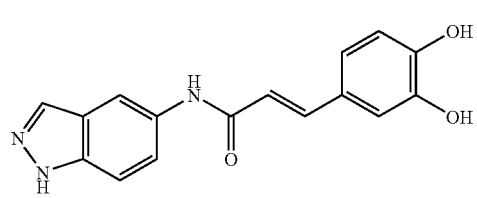 | 0.107 |
| 39 | 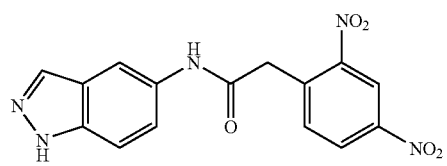 | 0.122 |

-continued
| | | |
|---|---|---|
| 40 | 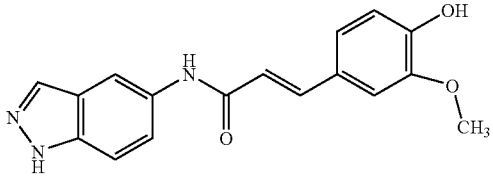 | 0.231 |
| 41 | 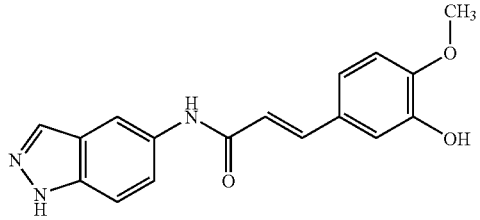 | 0.224 |
| 42 | 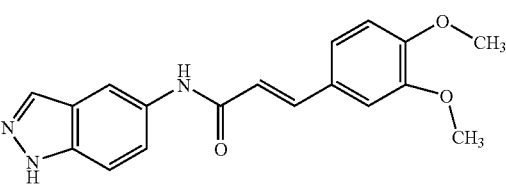 | 0.605 |
| 43 | 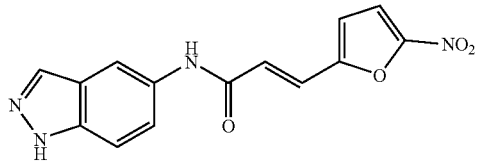 | 0.723 |
| 44 | 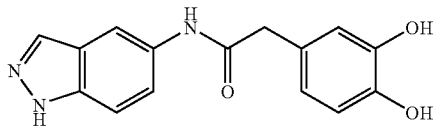 | 0.394 |
| 45 | 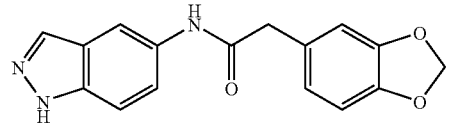 | 0.153 |
| 46 | 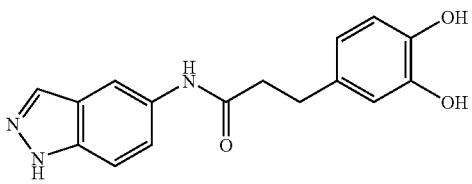 | 0.57 |
| 47 | 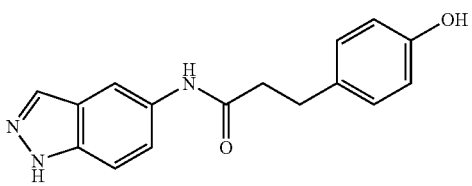 | 0.735 |
| 48 | 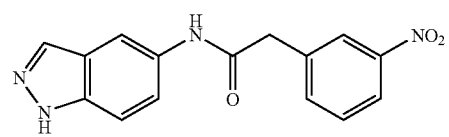 | 0.191 |

-continued

| # | Structure | Value |
|---|---|---|
| 49 | 1H-indazol-5-yl-NH-C(O)-CH2-(4-NO2-phenyl) | 0.513 |
| 50 | 1H-indazol-5-yl-NH-C(O)-CH2-NH-(4-OH-phenyl) | 0.326 |
| 51 | 1H-indazol-5-yl-NH-C(O)-CH2-O-(4-OH-phenyl) | 0.459 |
| 52 | 1H-indazol-5-yl-NH-C(O)-CH2CH2-(benzo[1,3]dioxol-5-yl) | 0.23 |
| 53 | pyridin-4-yl-NH-C(O)-NH-CH2-(2,4-dichlorophenyl) | 4.14 |
| 54 | pyridin-4-yl-NH-C(O)-NH-(2-Cl-4-NO2-phenyl) | — |
| 55 | pyridin-4-yl-NH-C(O)-NH-CH2-(2,3,6-trichlorophenyl) | 1.04 |
| 56 | pyridin-4-yl-NH-C(O)-NH-CH2-(2-Cl-6-F-phenyl) | — |
| 57 | pyridin-4-yl-NH-C(O)-NH-(2-Br-4,6-difluorophenyl) | 1.11 |

-continued
| | | |
|---|---|---|
| 58 | 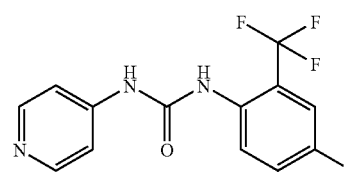 | 13.55 |
| 59 | 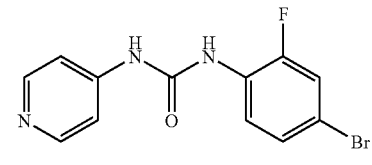 | 7.27 |
| 60 | 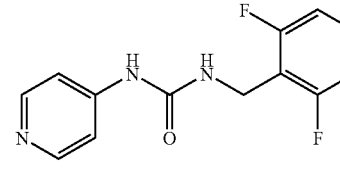 | 10.97 |
| 61 | 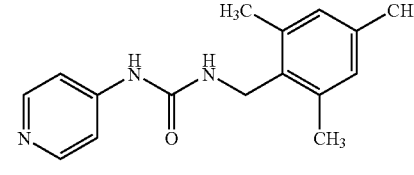 | 6.95 |
| 62 | 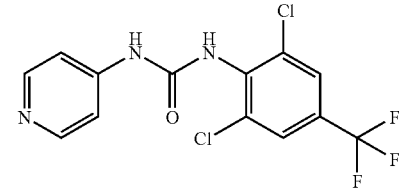 | |
| 63 | 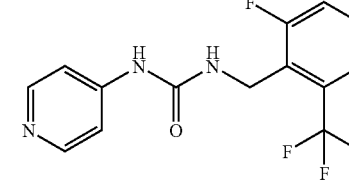 | 2.5 |
| 64 | 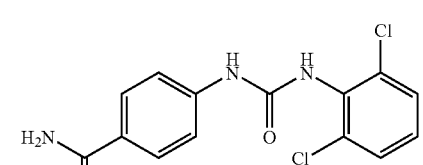 | 2.19 |
| 65 | | 9 |

| | | |
|---|---|---|
| 66 | 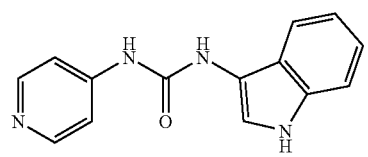 | 6.57 |
| 67 | 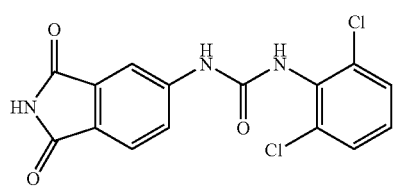 | 1.92 |
| 68 | 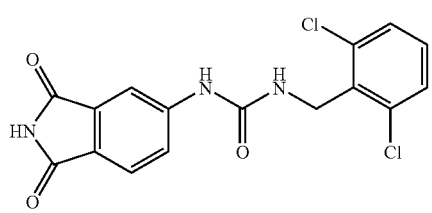 | 0.11 |
| 69 | 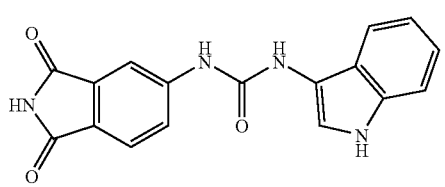 | 2.27 |
| 70 | 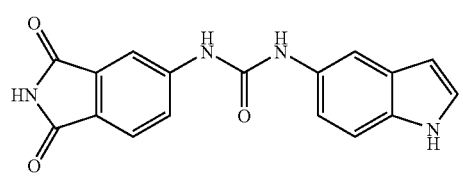 | 0.4 |
| 71 | 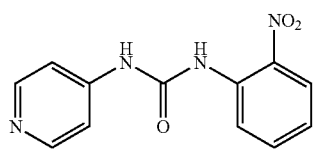 | 3.12 |
| 72 | 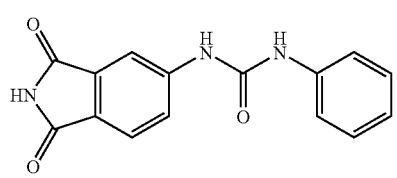 | 0.9 |
| 73 | 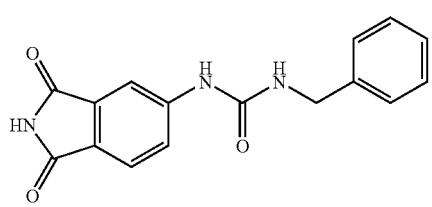 | 0.41 |

-continued
| | | |
|---|---|---|
| 74 | 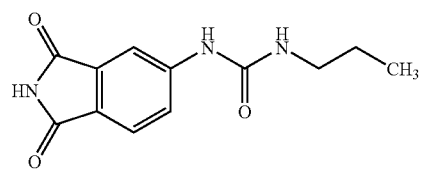 | 8.3 |
| 75 | 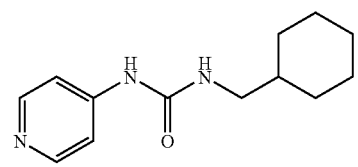 | 6.03 |
| 76 | 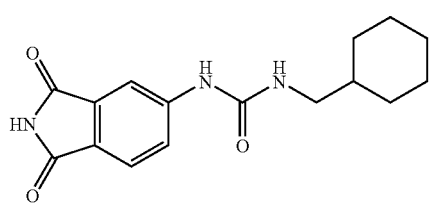 | 1.69 |
| 77 | 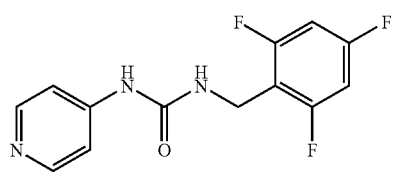 | 4.07 |
| 78 | 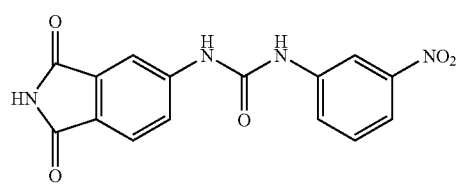 | 10.41 |
| 79 | 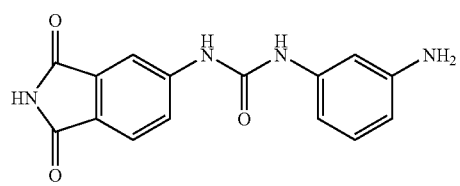 | 8.57 |
| 80 | 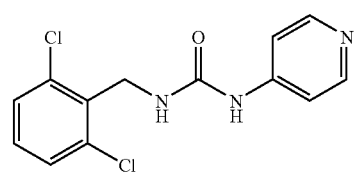 | 0.77 |
| 81 | 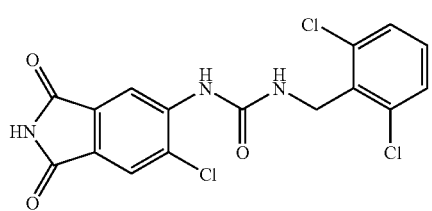 | 0.054 |

-continued
| | | |
|---|---|---|
| 82 | 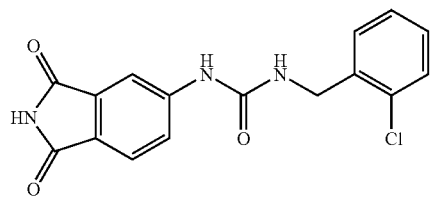 | 0.29 |
| 83 | 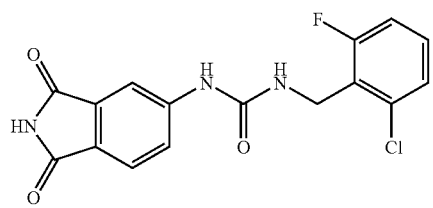 | 0.06 |
| 84 | 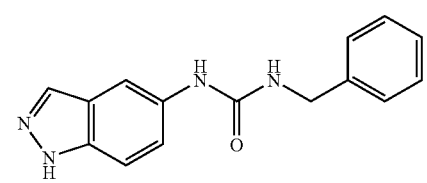 | 0.26 |
| 85 | 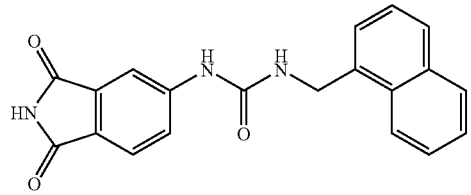 | 0.18 |
| 86 | 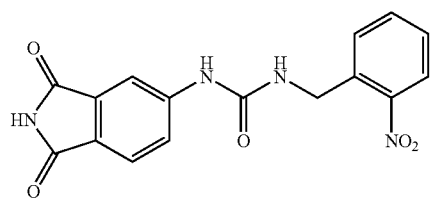 | 0.9 |
| 87 | 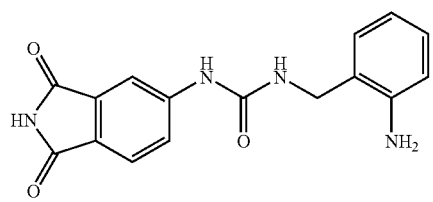 | 0.18 |
| 88 | 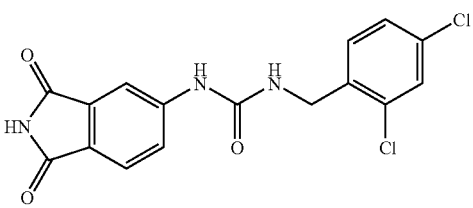 | 0.44 |

-continued
| | | |
|---|---|---|
| 89 | 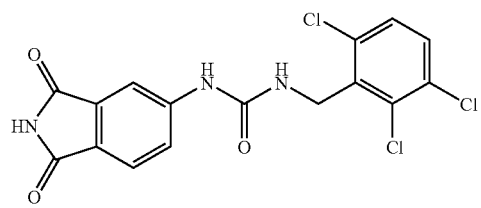 | 0.3 |
| 90 | 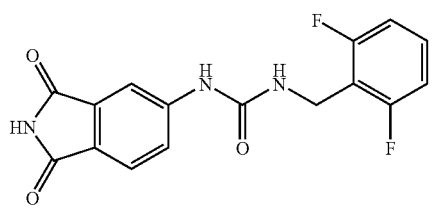 | 0.069 |
| 91 | 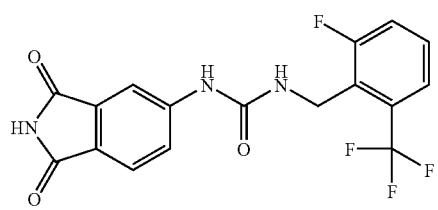 | 0.099 |
| 92 | 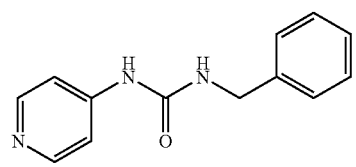 | 10.2 |
| 93 | 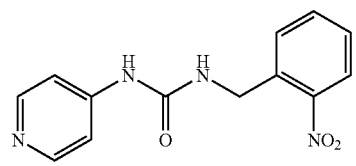 | 12.5 |
| 94 | 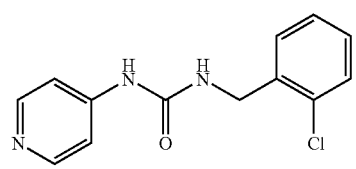 | 7.2 |
| 95 | 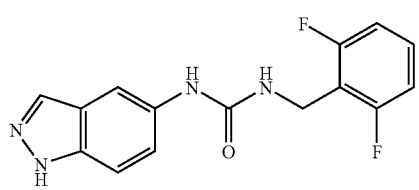 | 0.085 |
| 96 | 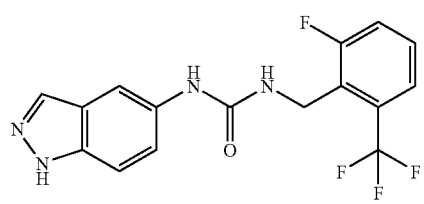 | 0.23 |

| | | |
|---|---|---|
| 97 | 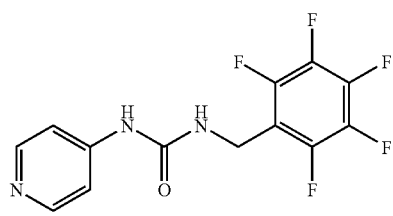 | 2.1 |
| 98 | 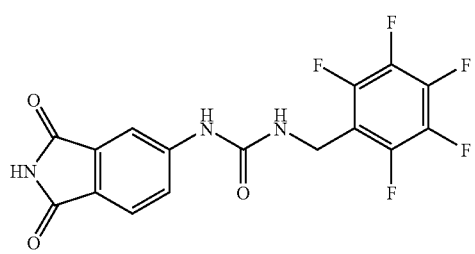 | 0.41 |
| 99 | 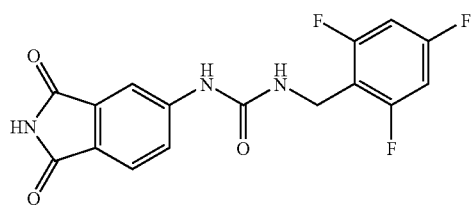 | 0.24 |
| 100 | 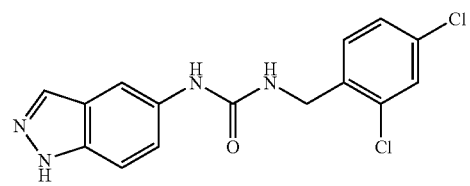 | 0.22 |
| 101 | 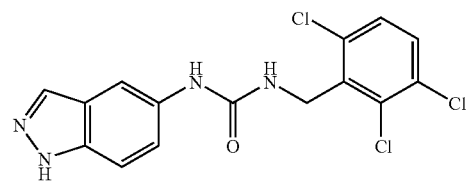 | 1.8 |
| 102 | 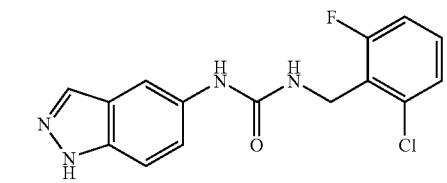 | 0.079 |
| 103 | 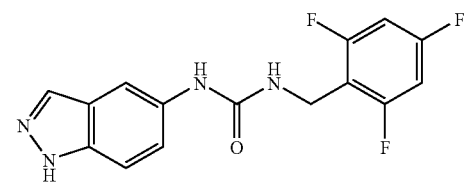 | 0.26 |

-continued
| | | |
|---|---|---|
| 104 | 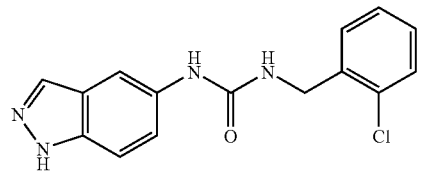 | 0.24 |
| 105 | 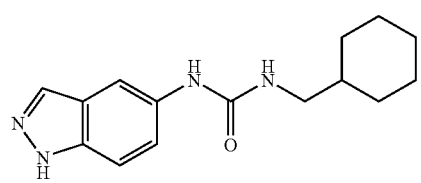 | 0.39 |
| 106 | 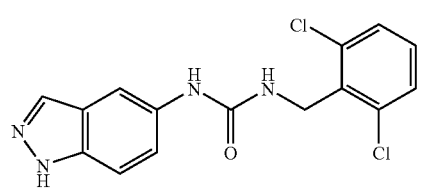 | 1.4 |
| 107 | 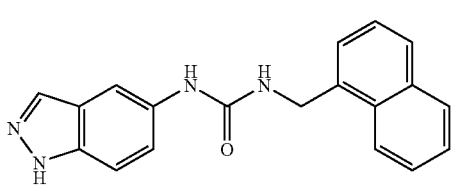 | 0.47 |
| 108 | 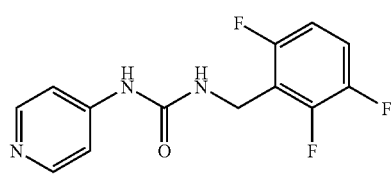 | 3.8 |
| 109 | 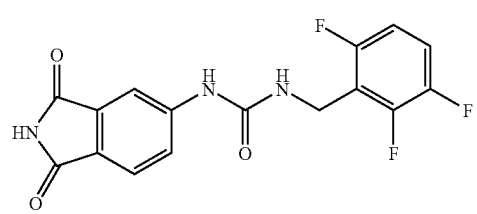 | 0.161 |
| 110 | 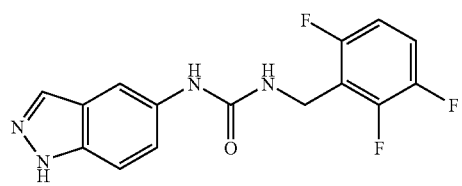 | 0.195 |
| 111 | 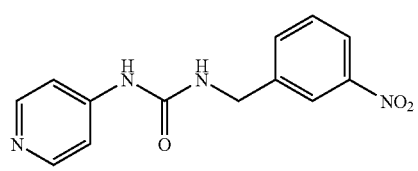 | 1.77 |

-continued
| | | |
|---|---|---|
| 112 | 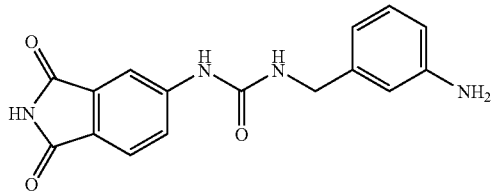 | 0.31 |
| 113 | 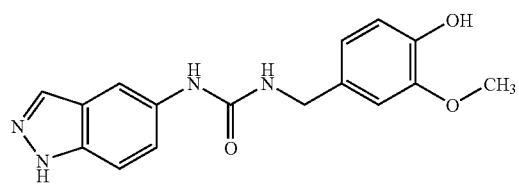 | 0.492 |
| 114 | 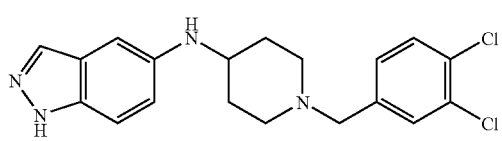 | 0.329 |
| 115 | 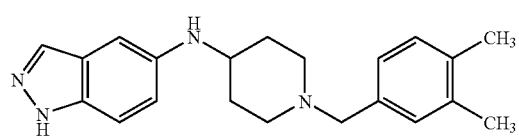 | 0.372 |
| 116 | 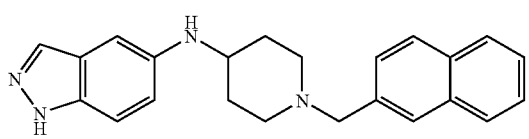 | 0.136 |
| 117 | 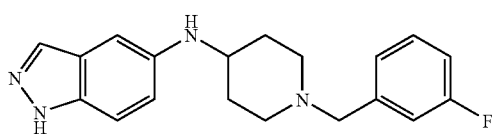 | 0.317 |
| 118 | 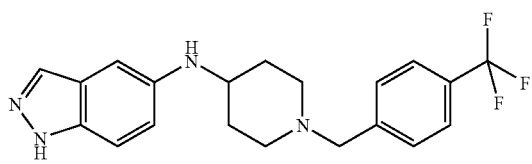 | 0.275 |
| 119 | 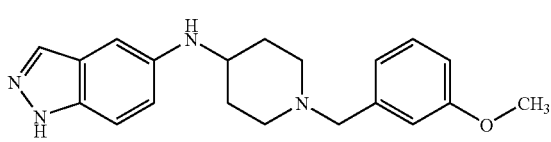 | 0.383 |
| 120 | 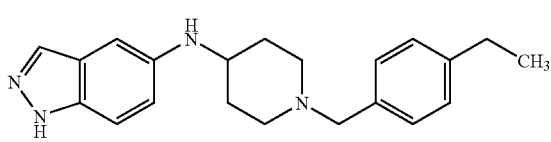 | 0.241 |
| 121 | 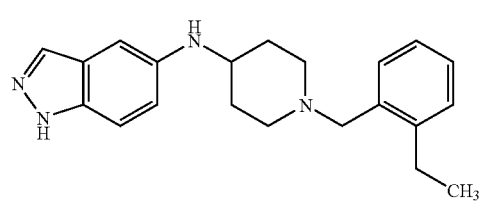 | 0.513 |

-continued
| | | |
|---|---|---|
| 122 | 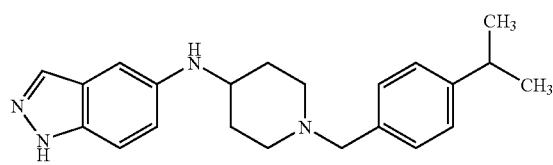 | 0.309 |
| 123 | 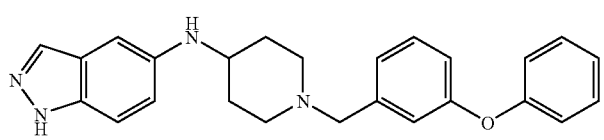 | 0.22 |
| 124 | 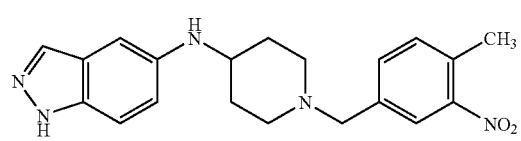 | 0.238 |
| 125 | 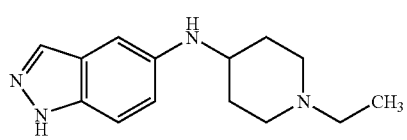 | 0.747 |
| 126 | 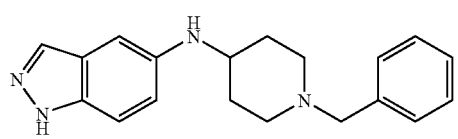<br>HCl | 0.239 |
| 127 | 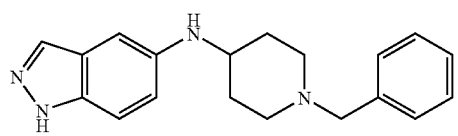<br>HCl | 0.951 |
| 128 | 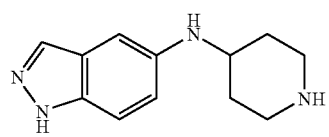 | 0.287 |
| 129 | 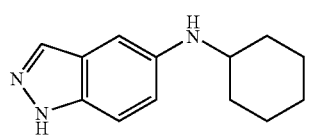 | 0.67 |
| 130 | 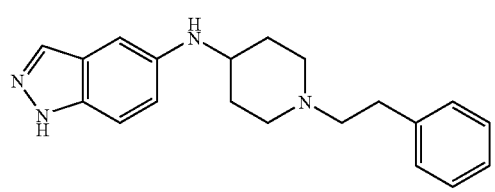 | 0.457 |
| 131 | 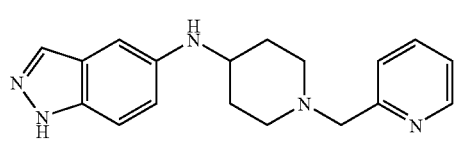 | |

-continued
| | | |
|---|---|---|
| 132 | 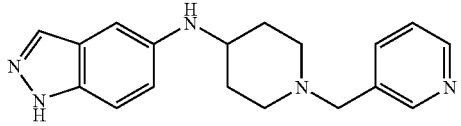 | 0.603 |
| 133 | 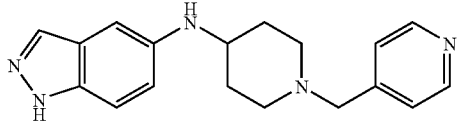 | 0.68 |
| 134 | 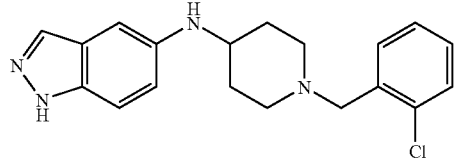 | 0.436 |
| 135 | 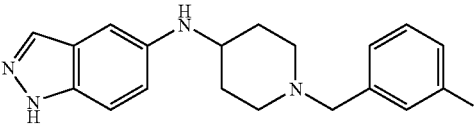 | 0.285 |
| 136 | 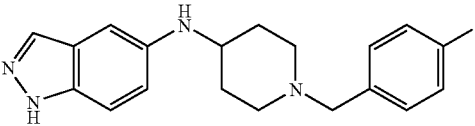 | |
| 137 | 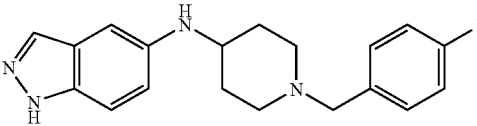 | 0.478 |
| 138 | 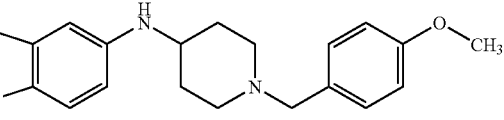 | 0.355 |
| 139 | 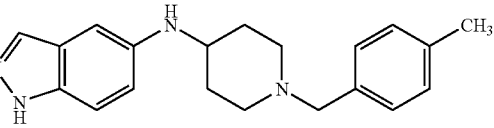 | 0.25 |
| 140 | 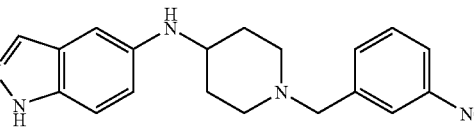 | 0.465 |
| 141 | 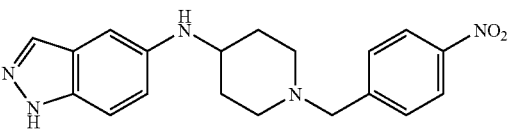 | 0.661 |

-continued
| 142 | 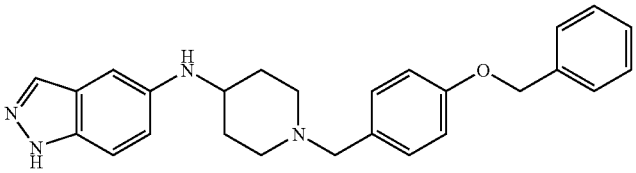 | 0.655 |
| 143 | 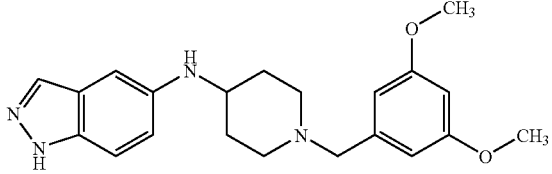 | 0.399 |
| 144 | 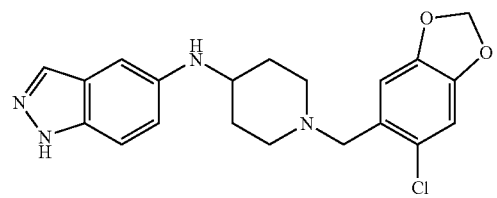 | 0.453 |
| 145 | 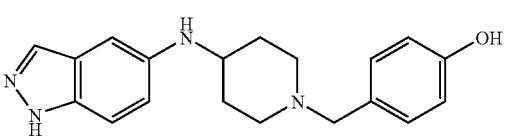 | 0.29 |
| 146 | 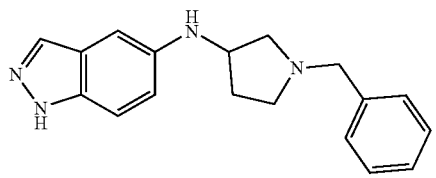 | 0.032 |
| 147 | 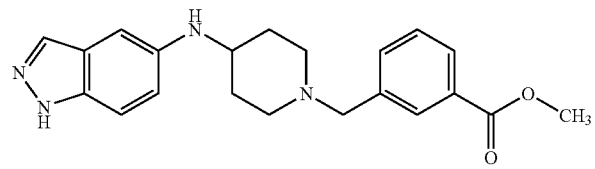 | 0.462 |
| 148 | 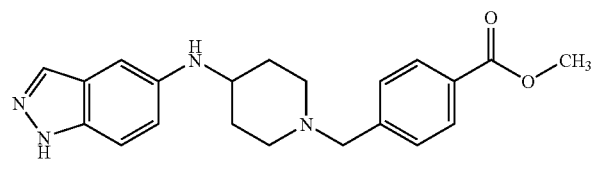 | 0.166 |
| 149 | 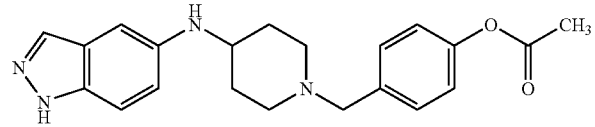 | 0.204 |
| 150 | 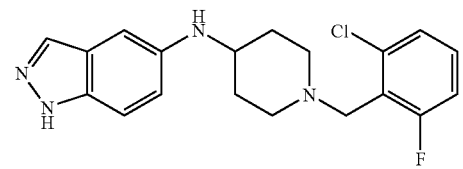 | 0.821 |

-continued
| | | |
|---|---|---|
| 151 | 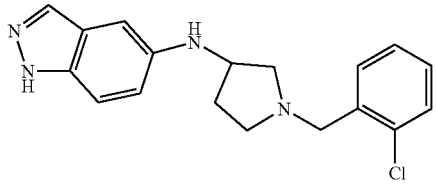 | 0.045 |
| 152 | 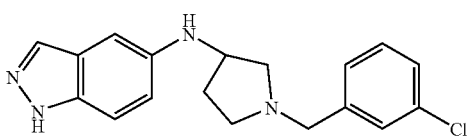 | 0.02 |
| 153 | 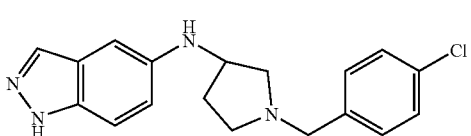 | 0.024 |
| 154 | 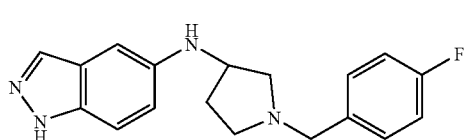 | 0.084 |
| 155 | 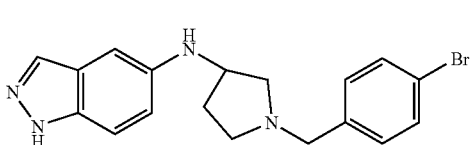 | 0.024 |
| 156 | 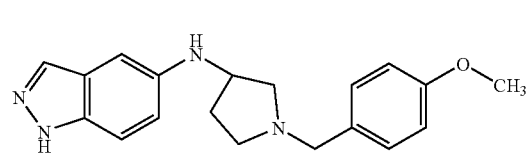 | 0.002 |
| 157 | 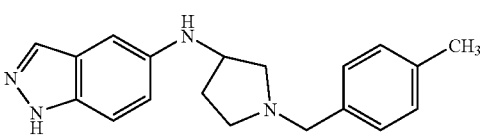 | 0.022 |
| 158 | 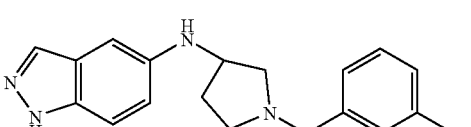 | 0.005 |
| 159 | 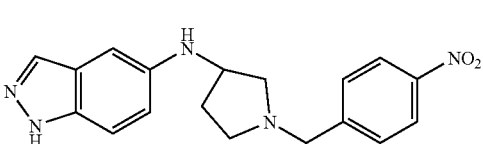 | 0.012 |
| 160 | 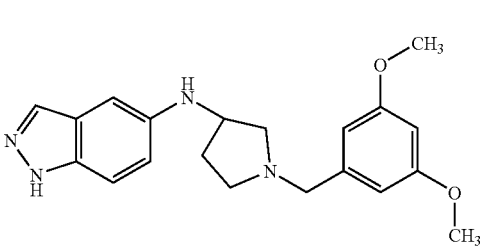 | 0.001 |

-continued
| | | |
|---|---|---|
| 161 | 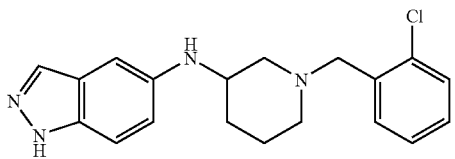 | 0.013 |
| 162 | 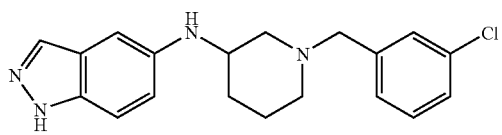 | 0.019 |
| 163 | 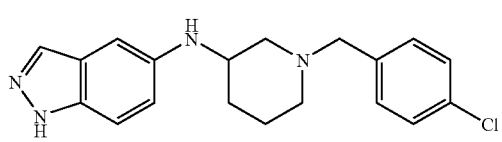 | 0.011 |
| 164 | 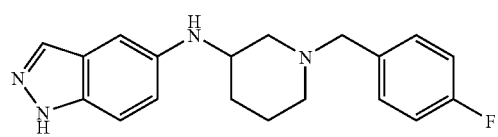 | 0.016 |
| 165 | 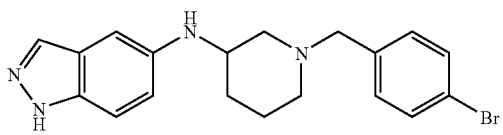 | 0.011 |
| 166 | 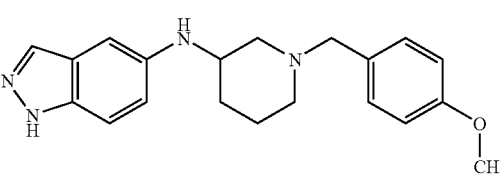 | 0.016 |
| 167 | 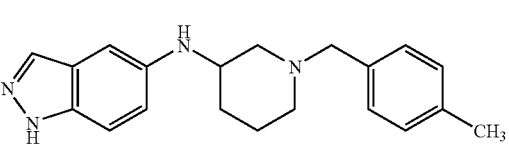 | 0.009 |
| 168 | 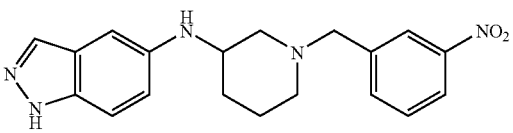 | 0.003 |
| 169 | 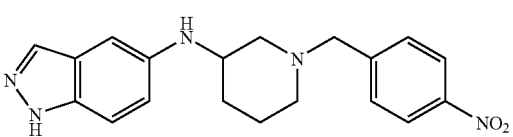 | 0.087 |
| 170 | 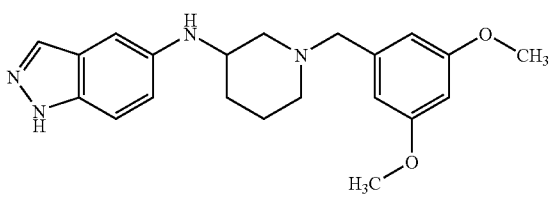 | 0.08 |

-continued
| | | |
|---|---|---|
| 171 | 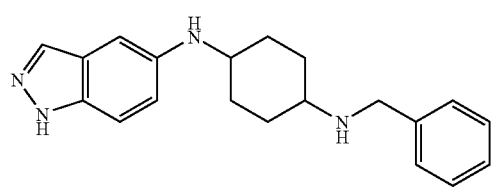 | 0.09 |
| 172 | 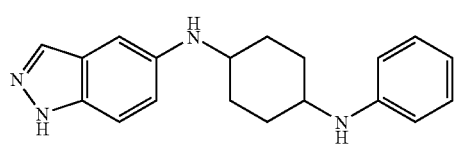 | 0.265 |
| 173 | 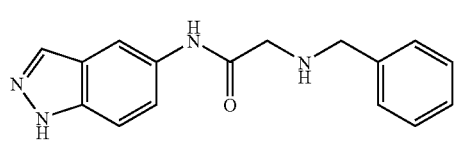 | 0.446 |
| 174 | 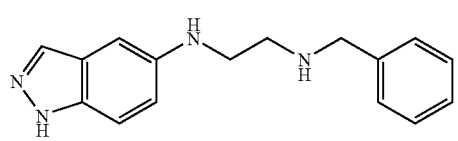 | 0.163 |
| 175 | 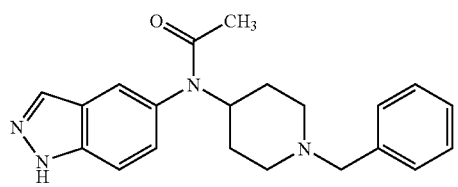 | 15.557 |
| 176 | 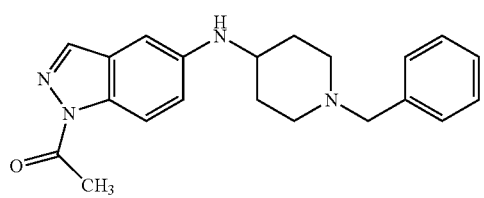 | 0.004 |
| 177 | 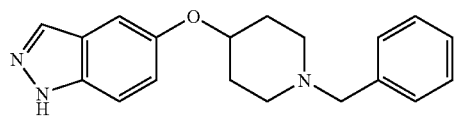 | |
| 178 | 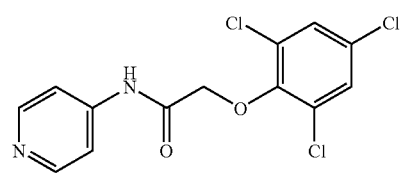 | |
| 179 | 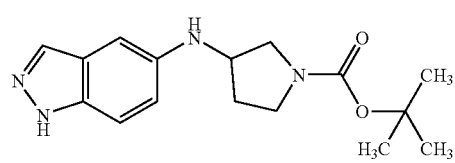 | |

-continued
| | |
|---|---|
| 180 | 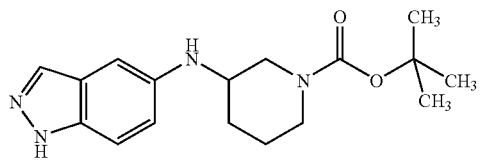 |
| 181 | 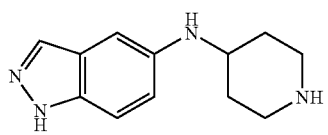<br>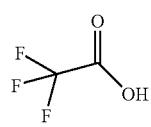 |
| 182 | 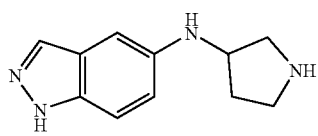<br>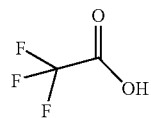 |
| 183 | 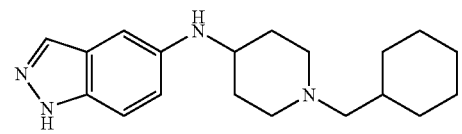 |
| 184 | 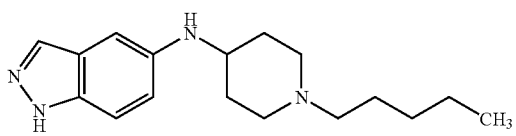 |
| 185 | 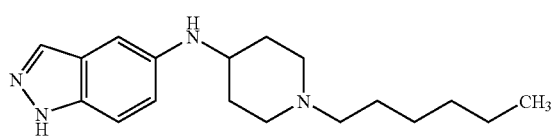 |
| 186 | 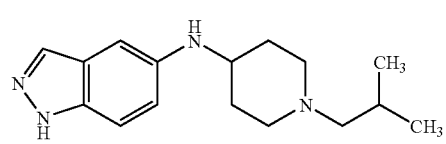 |
| 187 | 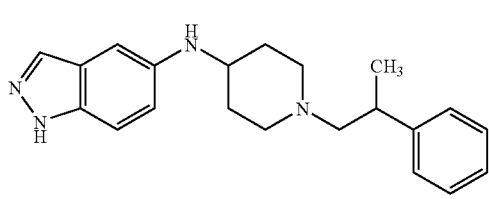 |
| 188 | 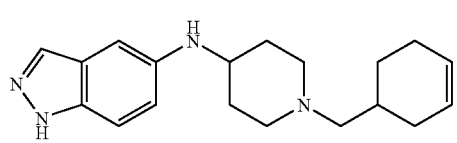 |

-continued
| | |
|---|---|
| 189 | 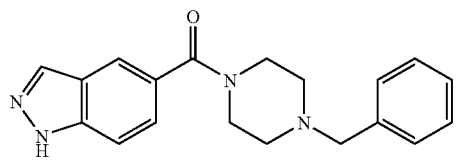 |
| 190 | 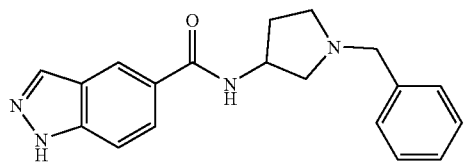 |
| 191 | 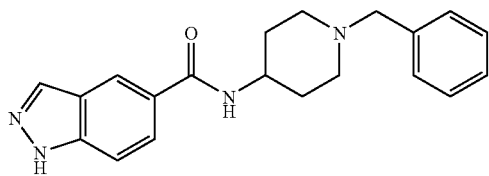 |
| 192 | 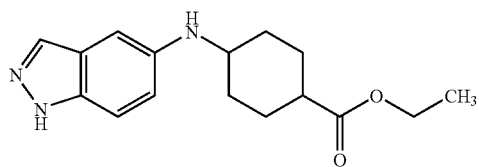 |
| 193 | 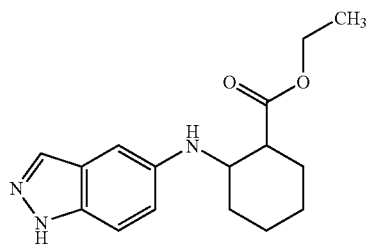 |
| 194 | 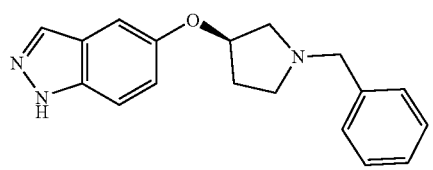 |
| 195 | 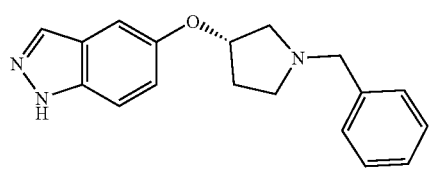 |
| 196 | 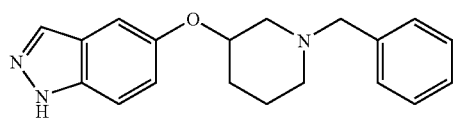 |
| 197 | 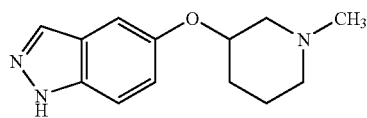 |

-continued
| | | |
|---|---|---|
| 198 | 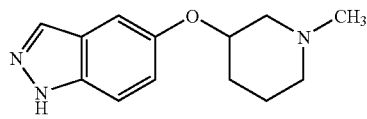 | |
| 199 | 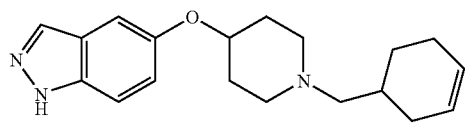 | |
| 200 | 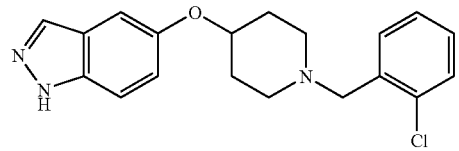  HCl | |
| 201 | 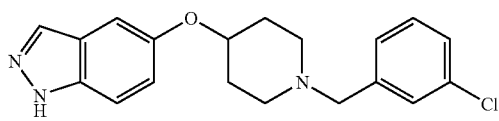  HCl | |
| 202 | 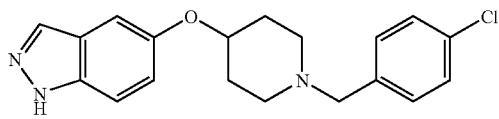  HCl | |
| 203 | 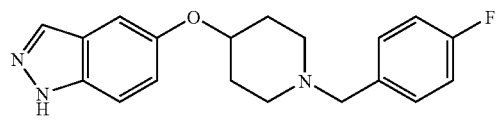  HCl | |
| 204 | 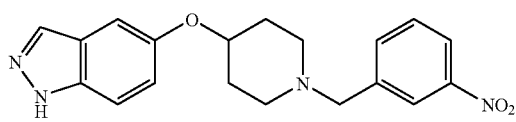  HCl | |
| 205 | 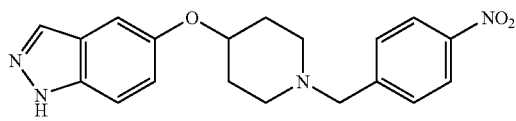  HCl | |

-continued
206
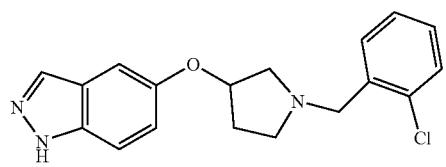
HCl
207
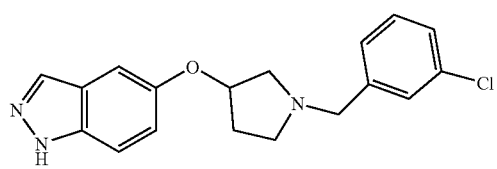
HCl
208
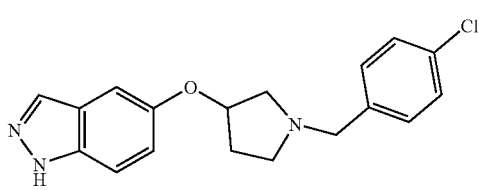
HCl
209
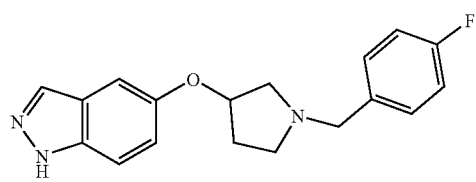
HCl
210
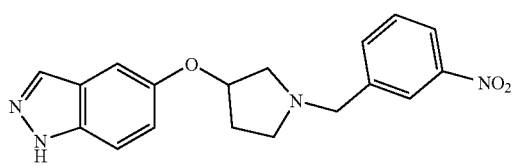
HCl
211
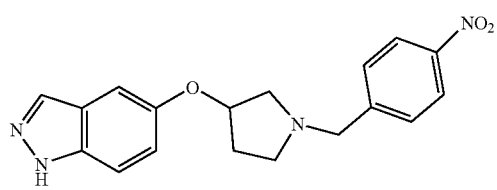
HCl
212
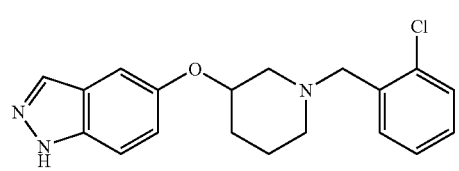
HCl -continued
| | | |
|---|---|---|
| 213 | 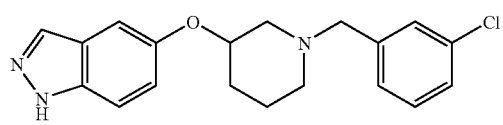 HCl | |
| 214 | 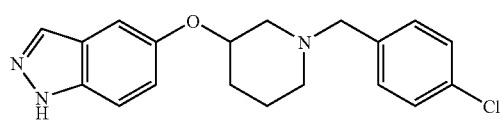 HCl | |
| 215 | 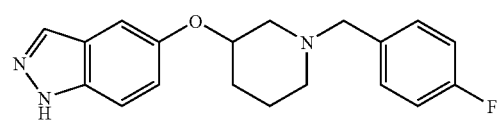 HCl | |
| 216 | 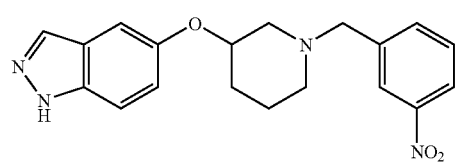 HCl | |
| 217 | 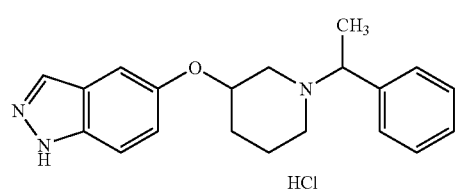 HCl | |
| 218 | 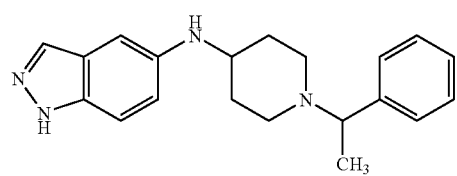 | |
| 219 | 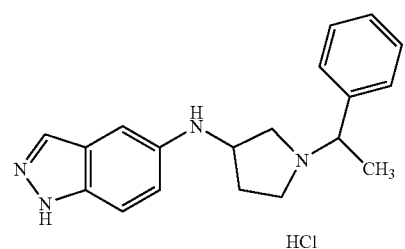 HCl | |
| 220 | 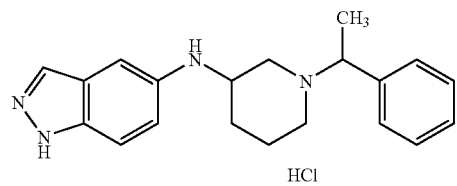 HCl | |

221 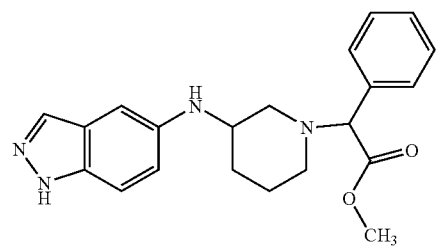
222 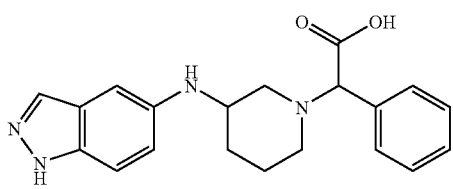
223 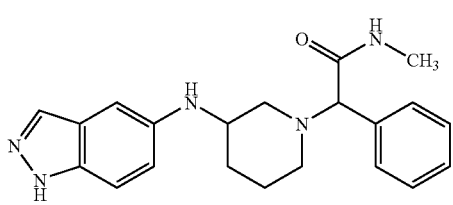
224 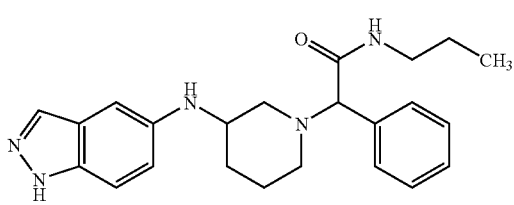
225 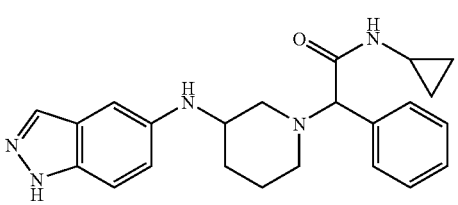
226 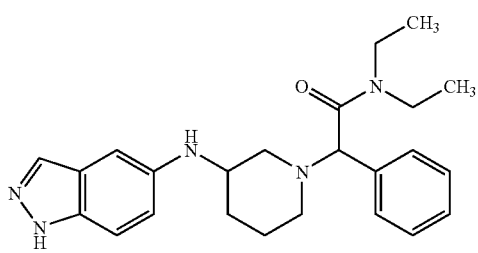
227 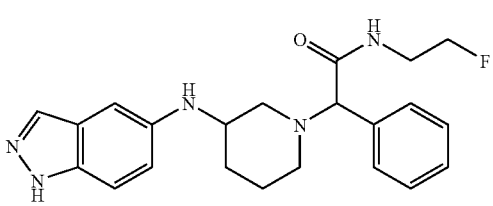

-continued
228 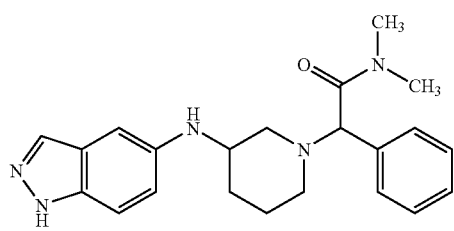
229 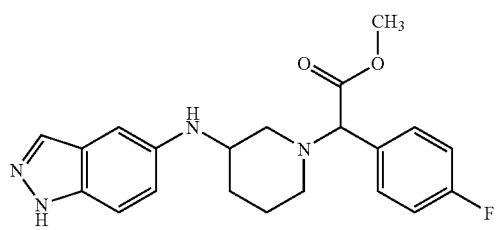
230 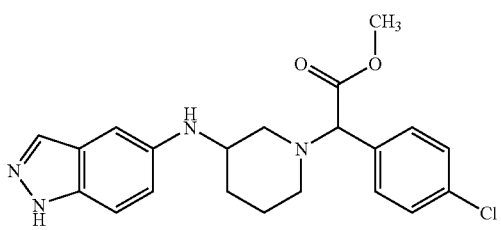
231 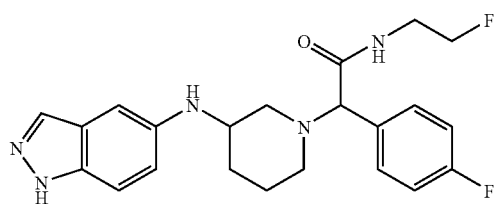
232 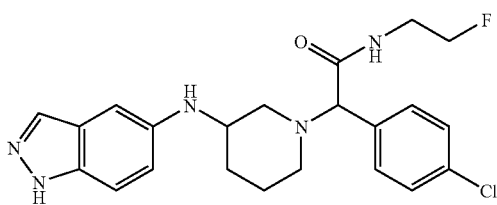
233 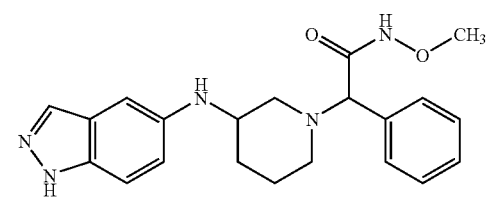
234 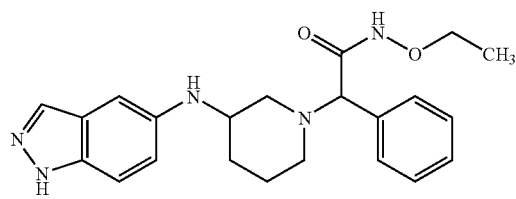

-continued
| | | |
|---|---|---|
| 235 | 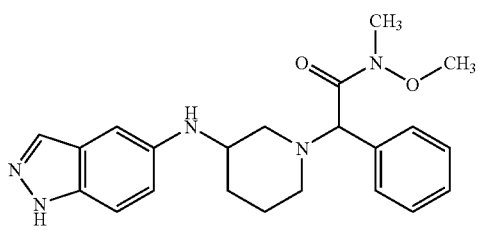 | |
| 236 | 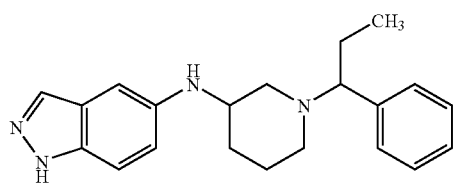 | |
| 237 | 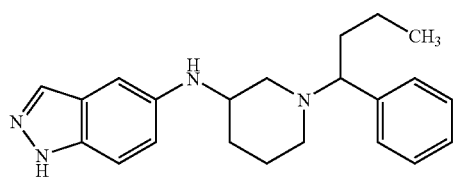 | |
| 238 | 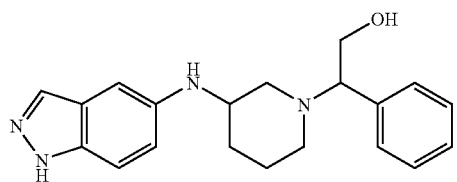 | |
| 239 | 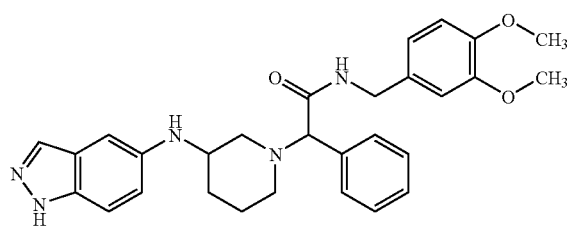 | |
| 240 | 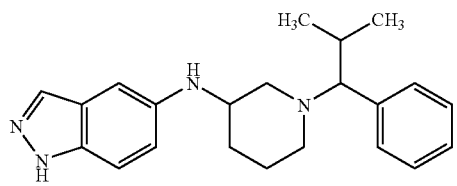 | |
| 241 anti | 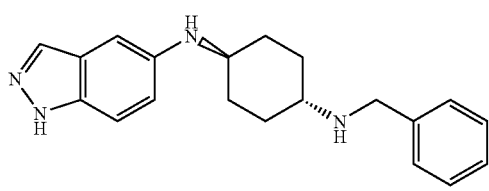 | syn 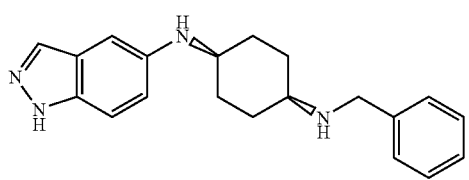 |
| 242 anti | 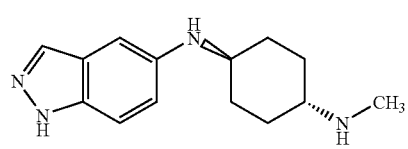 | syn 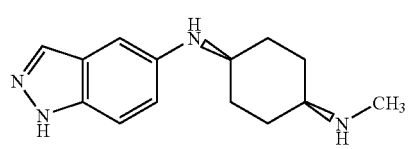 |

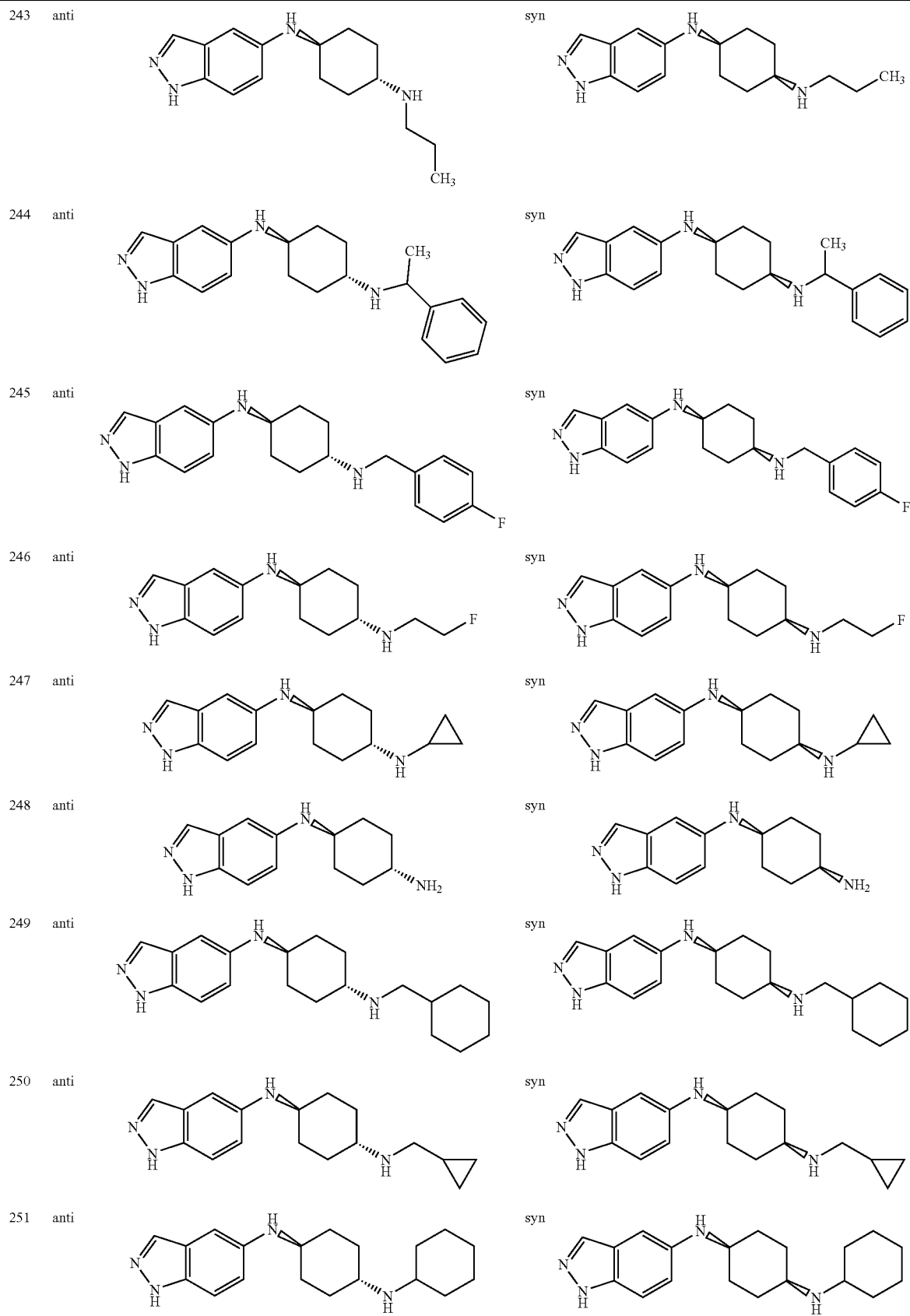

-continued
| | | | | |
|---|---|---|---|---|
| 252 | anti | 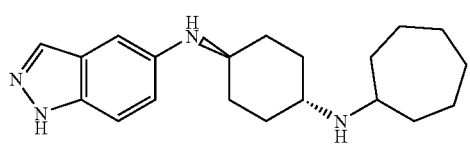 | syn | 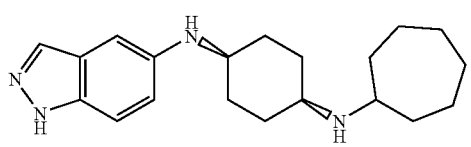 |
| 253 | anti | 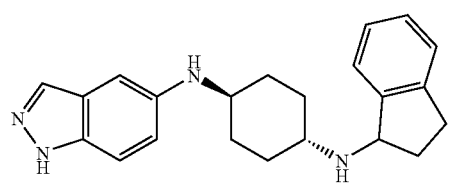 | syn | 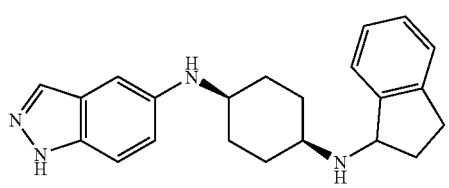 |
| 254 | anti | 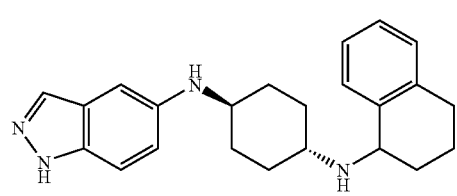 | syn | 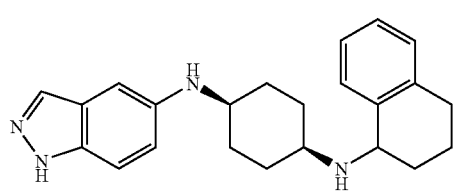 |
| 255 | anti | 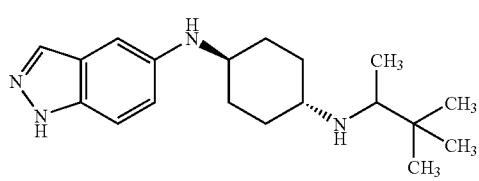 | syn | 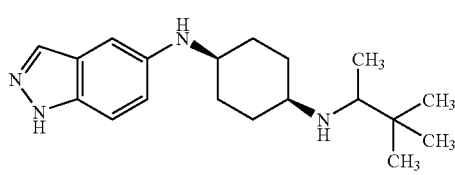 |
| 256 | anti | 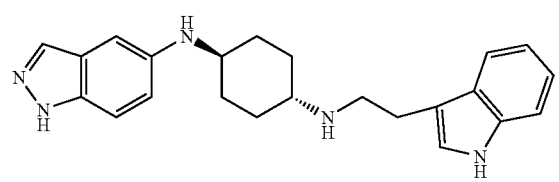 | syn | 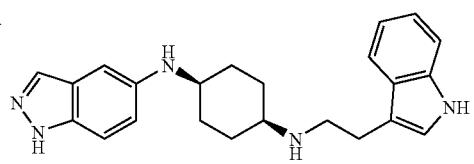 |
| 257 | anti | 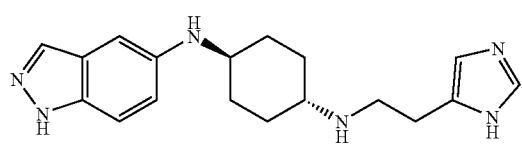 | syn | 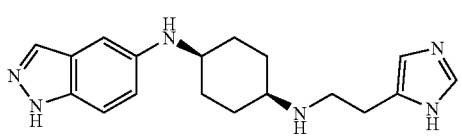 |
| 258 | anti | 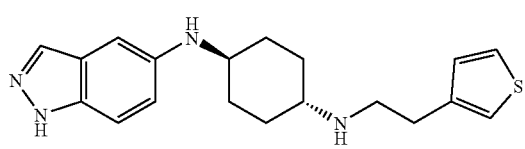 | syn | 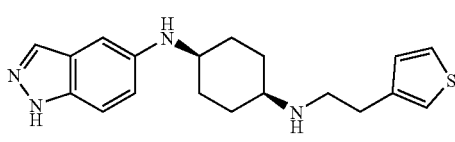 |
| 259 | anti | 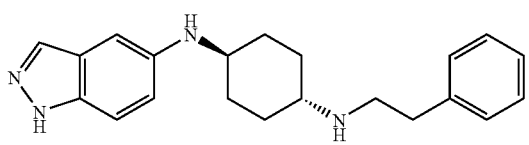 | syn | 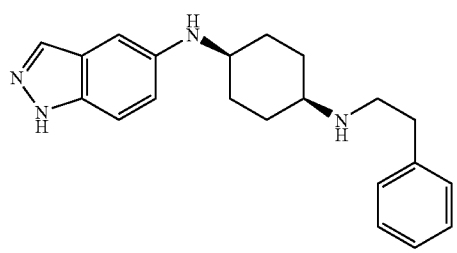 |

-continued
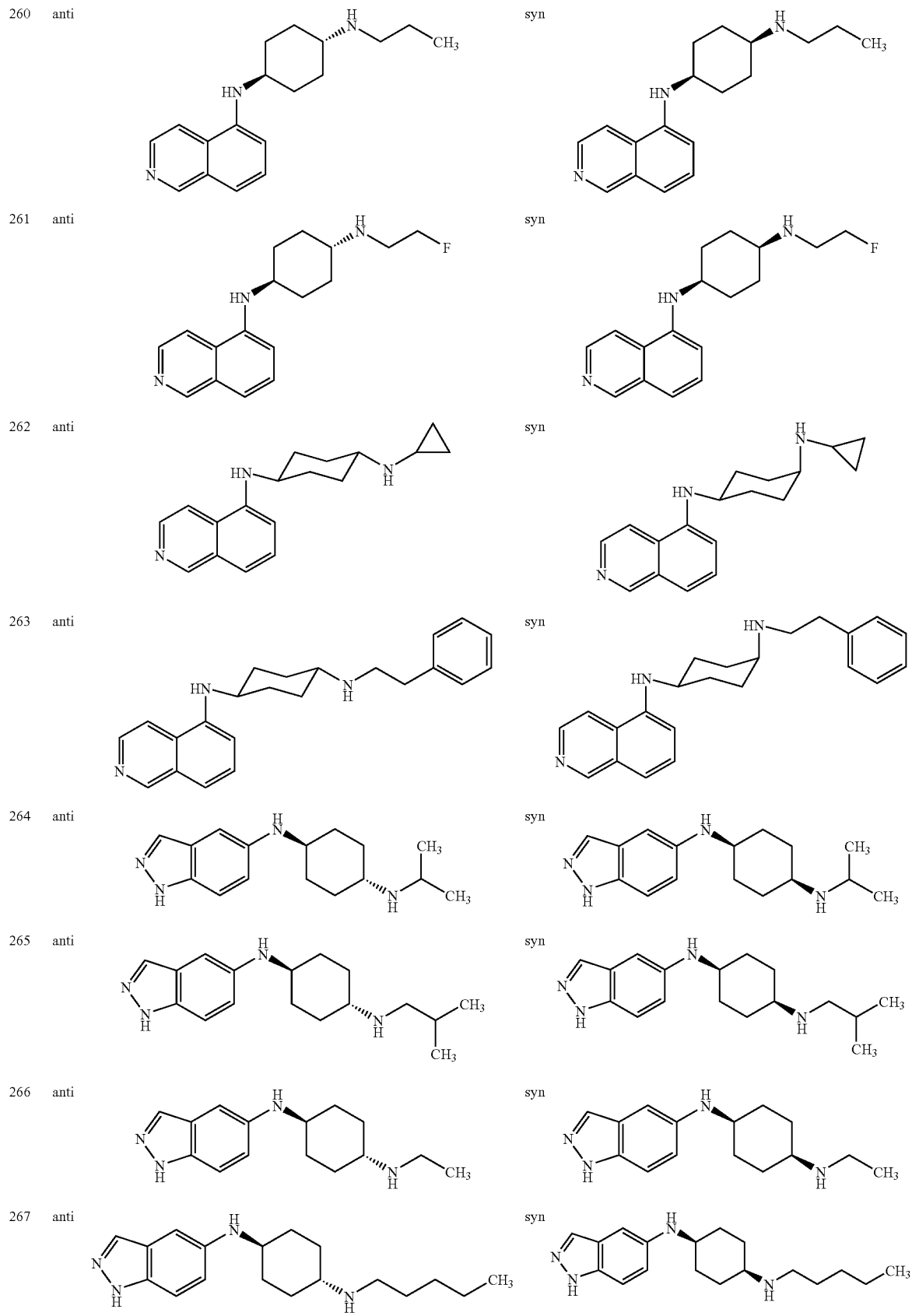

-continued
268 anti 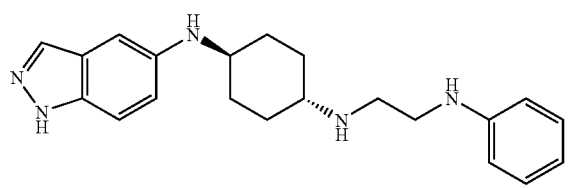 syn 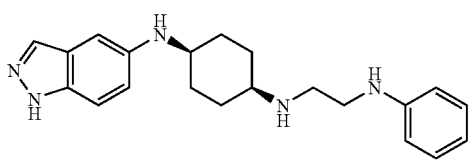
269 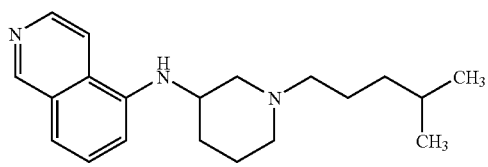
270 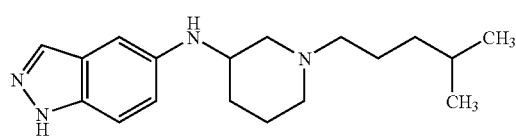
271 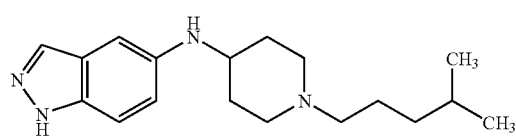
272 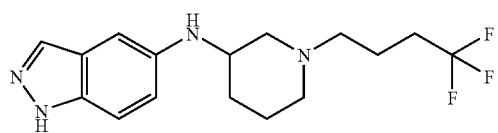
273 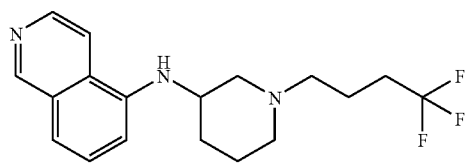
274 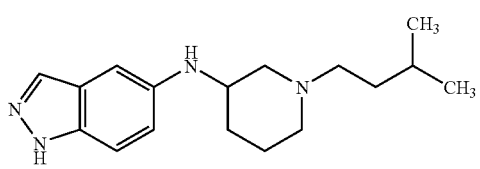
275 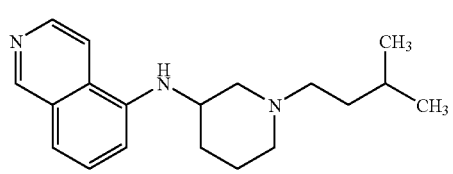
276 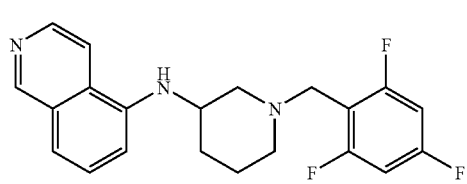

-continued
277 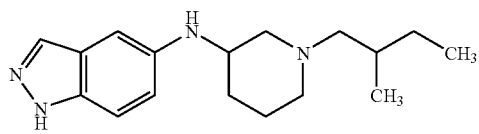
278 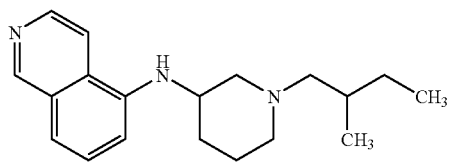
279 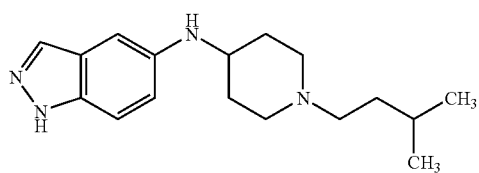
280 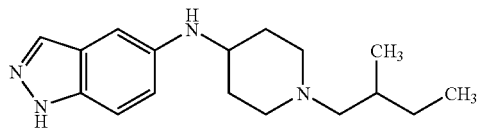
281 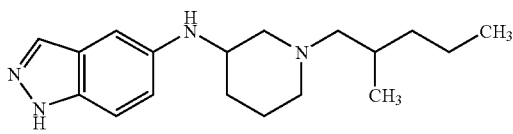
282 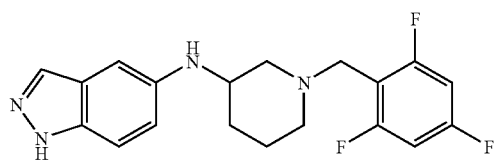
283 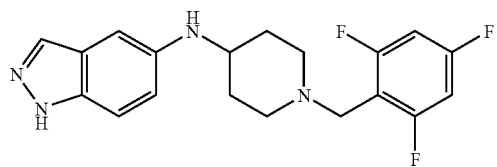
284 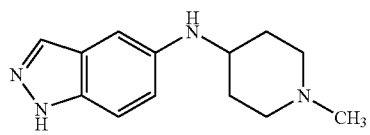
285 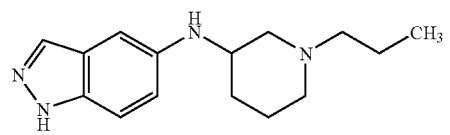
286 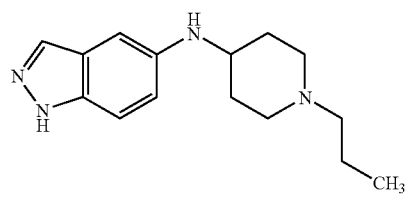

-continued
287 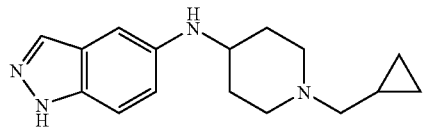
288 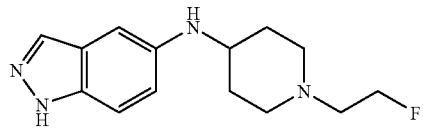
289 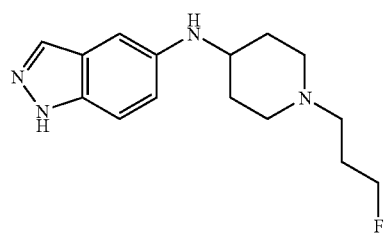
290 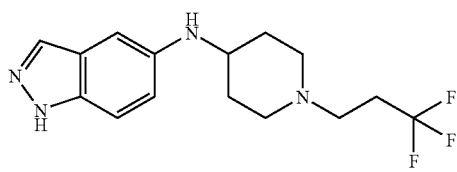
291 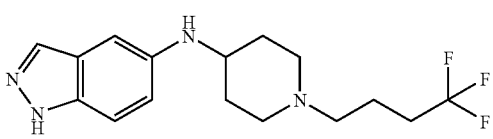
292 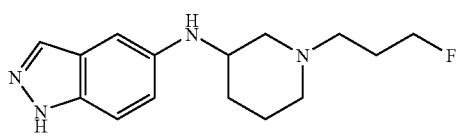
293 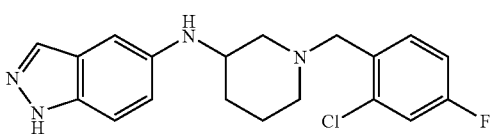
294 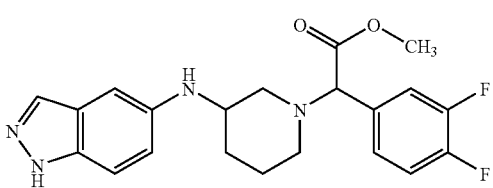
295 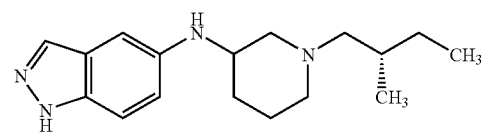

-continued
296 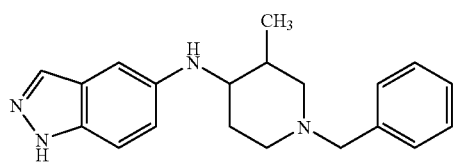
297 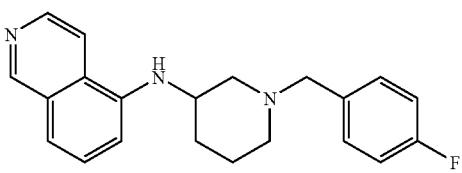
298 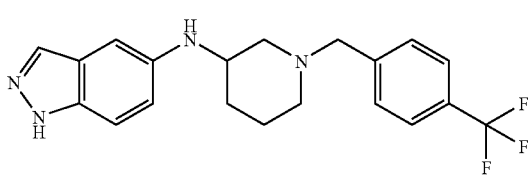
299 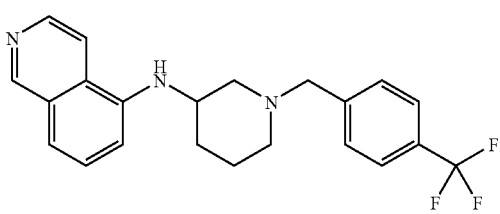
300 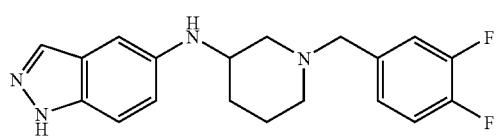
301 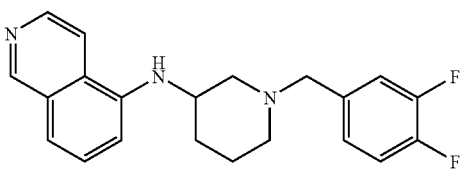
302 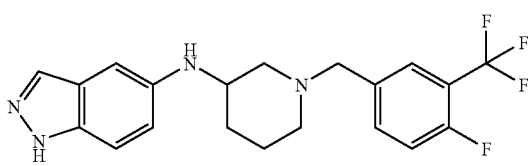
303 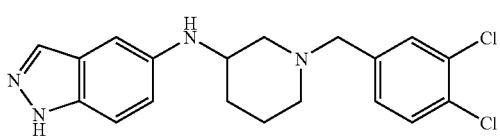
304 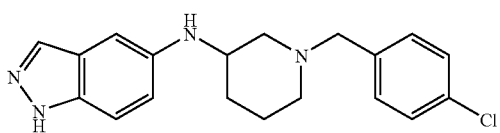

-continued
| | |
|---|---|
| 305 | 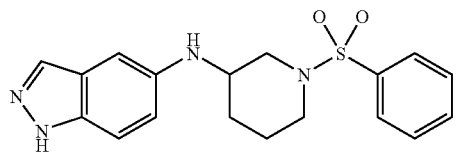 |
| 306 | 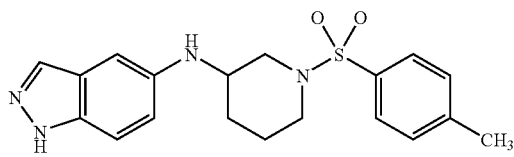 |
| 307 | 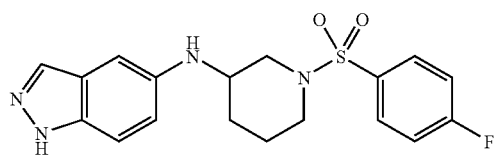 |
| 308 | 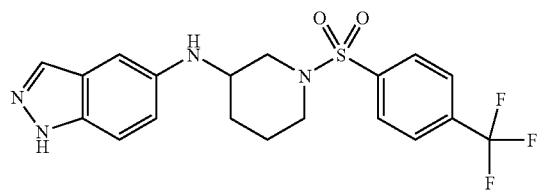 |
| 309 | 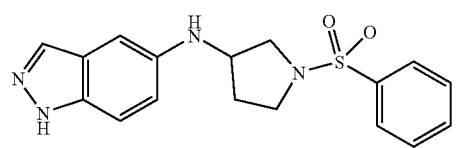 |
| 310 | 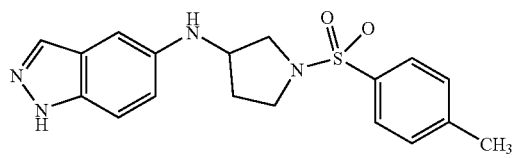 |
| 311 | 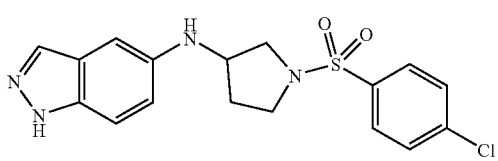 |
| 312 | 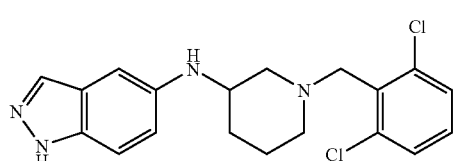 |
| 313 | 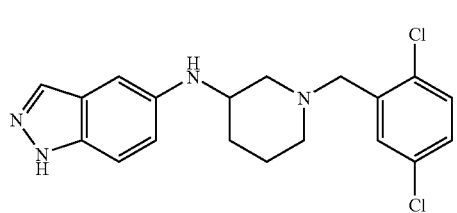 |

-continued
| | |
|---|---|
| 314 | 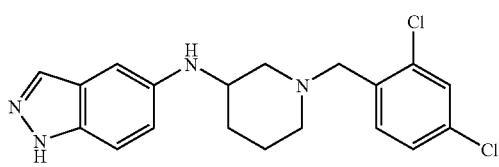 |
| 315 | 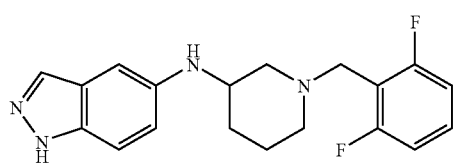 |
| 316 | 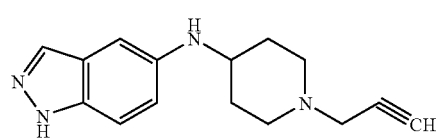 |
| 317 | 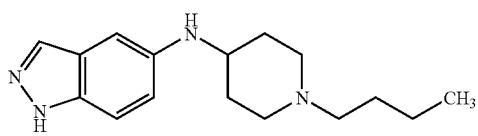 |
| 318 | 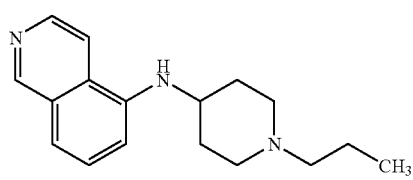 |
| 319 | 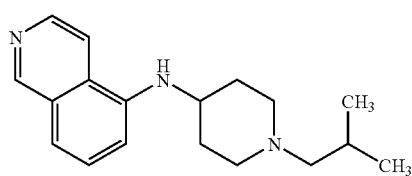 |
| 320 | 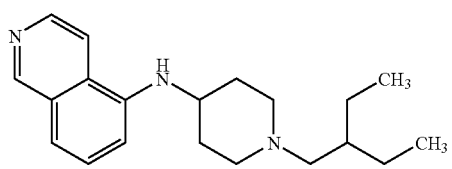 |
| 321 | 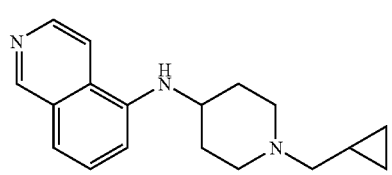 |
| 322 | 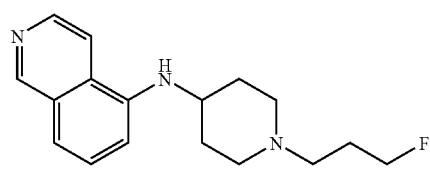 |

Pharmacological Test Example 1

Rho Kinase Inhibitory Activity

Gene recombinant Rho kinase was prepared according to the disclosure of Japanese Patent Laid-Open No. 113187/1998, i.e., by infecting insect cells with baculovirus, into which cDNA coding fused protein composed of bovine Rho kinase catalyst region and glutathione S-transferase had been incorporated, and allowing the insect cells to produce the gene recombinant Rho kinase. A substrate (ribosomal S6 kinase substrate, S6 231–239) was phosphorylated by adding the Rho kinase, together with ATP ($\gamma^{32}$P-ATP) of which phosphorus at the γ-position had been labeled with a radioisotope, to the substrate. This permits the substrate to be labeled with the radioisotope.

Thereafter, the substrate was adsorbed to a filter paper. ATP was washed away with a phosphoric acid solution, and the amount of the phosphorylated substrate was then measured with a liquid scintillation counter.

The antienzymatic activity of a test compound was determined by adding the test sample before the enzymatic reaction, determining the percentage phosphorylation inhibition of the substrate, and determining as $IC_{50}$ the concentration of the test compound necessary for inhibiting the phosphorylation by 50%.

The results were shown in the table described above.

Pharmacological Test Example 2

Leukocyte Migration Inhibitory Activity

Human-derived histiocyte lymphoma (U937/CCR2), in which mouse-derived CCR2 had been highly expressed, was suspended in a 0.1% BSA-containing RPMI 1640 medium, to which a test compound had been added ($5 \times 10^6$/ml), and the suspension was incubated for 20 min. A chemical solution (500 μl) (0.1% BSA-containing RPMI 1640 medium DMSO 1%), to which an MCP-1 ligand (1 μM) and the test compound had been added, was added to a 24-well plate. CHEMOTAXICELL was put thereon, and 200 μl of the cell suspension was added to the top layer, followed by migration under 5% carbon dioxide at 37° C. for one hr. The number of cells, which had migrated to the lower chamber, was counted with a particle count analyzer (CDA-500, SYSMEX CORPORATION), and the percentage migration inhibition was calculated by the following equation;

Migration inhibition (%)={1−(number of migrated cells in the presence of test compound/number of migrated cells in the absence of test compound)}×100

The results are shown in table below.

| Test compound (Ex. No.) | Migration inhibition (%) ± SEM |
|---|---|
| 20 (3 μM) | 46.7 ± 19.4 |
| 20 (30 μM) | 95.4 ± 3.4 |
| 21.HCl (3 μM) | 83.5 ± 3.3 |
| 21.HCl (30 μM) | 99.1 ± 0.4 |
| 22 (3 μM) | 34.8 ± 12.4 |
| 22 (30 μM) | 92.9 ± 1.3 |
| 80 (3 μM) | 26.0 ± 4.7 |
| 80 (30 μM) | 65.1 ± 17.3 |
| 83 (3 μM) | 16.1 ± 9.6 |
| 83 (30 μM) | 92.5 ± 3.3 |
| 90 (30 μM) | 78.3 ± 3.2 |
| 95 (3 μM) | 17.1 ± 11.7 |
| 95 (30 μM) | 77.6 ± 6.4 |
| 102 (3 μM) | 6.8 ± 17.0 |
| 102 (30 μM) | 96.7 ± 1.0 |
| 126 (30 μM) | 49.1 ± 4.6 |
| 126.HCl (3 μM) | 9.9 ± 14.2 |
| 126.HCl (30 μM) | 41.6 ± 4.8 |
| 128 (3 μM) | 2.9 ± 12.3 |
| 128 (30 μM) | 45.9 ± 12.3 |
| 146 (3 μM) | 45.6 ± 9.5 |
| 146 (30 μM) | 93.9 ± 1.7 |
| 146.HCl (3 μM) | 74.5 ± 1.7 |
| 146.HCl (30 μM) | 97.9 ± 1.0 |
| 221 (0.3 μM) | 90.8 ± 11.0 |
| 221 (0.03 μM) | 27.5 ± 33.6 |
| 298 (0.3 μM) | 15.7 ± 9.9 |
| 300 (0.3 μM) | 81.9 ± 11.9 |
| 246 (0.3 μM) | 41.9 ± 15.4 |
| 243 (3 μM) | 82.8 ± 7.1 |
| 227 (3 μM) | 100.3 ± 0.5 |
| 259 (syn) (3 μM) | 85.3 ± 8.5 |
| 293 (3 μM) | 93.5 ± 9.9 |
| 281 (3 μM) | 100.1 ± 8.2 |
| 294 (0.3 μM) | 98.3 ± 1.4 |
| 294 (0.1 μM) | 87.4 ± 6.4 |
| 282 (1 μM) | 29.9 ± 4.1 |
| 260 (anti) (1 μM) | 77.4 ± 14.4 |
| 262 (anti) (1 μM) | 82.5 ± 6.69 |
| 262 (anti) (0.3 μM) | 24.4 ± 8.1 |
| 260 (syn) (1 μM) | 56.5 ± 14.9 |
| 261 (syn) (1 μM) | 59.4 ± 10.4 |
| 261 (syn) (0.3 μM) | 24.2 ± 3.9 |
| 262 (syn) (1 μM) | 69.9 ± 15.1 |
| 320 (1 μM) | 82.9 ± 7.0 |

Pharmacological Test Example 3

Albuminuria Amelioration Activity for anti-GBM Nephritis Model Using S.D. Rats Anti-GBM antibody produced by immunizing domestic rabbits with a rat-derived GBM fraction was caudointravenously administered to S.D. male rats of 8 weeks old to induce nephritis. Immediately after the administration of the antibody and six hr after the administration of the antibody, the compound of Example 300 was orally administered at 30 mg/kg. Urine was collected in a period between immediately after the administration of the antibody and 24 hr after the administration of the antibody, and the protein level of urine was measured to observe albuminuria amelioration activity. The results are shown in the following table.

| Group | Protein level of urine (mg/kg/day) ± SEM |
|---|---|
| Control group | 794.2 ± 113.2 |
| Group of oral administration of the compound of Example 300 at 30 mg/kg twice daily | 437.1 ± 95.9 |

Pharmacological Test Example 4

Albuminuria Amelioration Activity for anti-GBM Nephritis Model Using WKY Rats Anti-GBM antibody produced by immunizing domestic rabbits with a rat-derived GBM fraction was caudointravenously administered to WKY male rats of 9 weeks old to induce nephritis. For two weeks from the day after the administration of the antibody, the compound of Example 300 was orally administered at 30 mg/kg twice daily, and the compound prepared in Example 246 was administered at 25 mg/ml together with drinking water. During 24 hr from two weeks after the administration of the antibody, urine was collected, and the protein level of urine was measured to observe albuminuria amelioration activity. The results are shown in the following table.

| Group | Protein level of urine (mg/kg/day) SEM |
|---|---|
| Control group | 840.4 ± 82.2 |
| Group of oral administration of the compound of Example 300 at 30 mg/kg twice daily | 602.2 ± 47.3 |
| Group of administration of the compound of Example 246 at 25 mg/liter together with drinking water | 220.2 ± 17.7 |

Pharmacological Test Example 5

Antihypertensive Activity

This pharmacological test example demonstrates that the compounds according to the present invention have antihypertensive activity in spontaneously hypertensive male rats (SHR, Charles River Japan, Inc.) of 11 to 18 weeks old by forced oral administration of the compounds. This test was carried out as follows. A test compound was dissolved in purified water, or alternatively the test compound was suspended in a 5% aqueous sodium carboxymethylcellulose solution. The solution or the suspension was forcibly administered into the gaster of SHR through an oral probe. The systolic pressure of SHR was measured with a bloodless sphygmometer (BP-98A, Softron Co.) immediately before the administration of the test compound and 3 to 4 hr after the administration of the test compound or 6 to 7 hr after the administration of the test compound. The percentage of blood pressure depression was calculated by the following equation:

Antihypertensive activity (%)={(blood pressure before administration of test compound−blood pressure after administration of test compound)/blood pressure before administration of test compound}×100

The results were as shown in the following table. Each compound was administered at 30 mg/kg, and the antihypertensive activity (%) was expressed in terms of the mean value of 3 to 4 SHRs and SEM (standard error of the mean).

For data with *, the blood pressure was measured 6 to 7 hr after the administration of the test compound, and, for data with no marks, the blood pressure was measured 3 to 4 hr after the administration of the test compound. The results are shown in the following table.

| Test compound | Blood pressure depression, % |
|---|---|
| Example 126 | 18.0 ± 3.5 |
| Example 127 | 20.4 ± 3.0 |
| Example 21 | 37.0 ± 2.5 |
| Example 164 | 35.0 ± 4.7 |
| Example 298 | 18.9 ± 3.1 * |
| Example 300 | 24.1 ± 3.8 * |
| Example 227 | 22.2 ± 7.4 |
| Example 243 (syn) | 20.4 ± 5.2 |
| Example 246 (syn) | 37.2 ± 11.7 |
| Example 247 (syn) | 43.3 ± 1.2 |
| Example 289 | 30.8 ± 5.7 |
| Example 248 (anti) | 18.8 ± 8.0 |
| Example 243 (syn) | 26.4 ± 5.0 |
| Example 287 | 24.4 ± 6.8 |
| Example 286 | 23.6 ± 8.6 |
| Example 290 | 17.2 ± 2.9 |
| Example 240 | 21.1 ± 6.5 |
| Example 261 (anti) | 47.3 ± 3.6 |
| Example 261 (syn) | 46.4 ± 4.8 |
| Example 260 (syn) | 19.6 ± 10.5 |
| Example 322 | 41.4 ± 7.4 |
| Example 318 | 22.7 ± 5.1 |
| Example 246 (anti) | 51.4 ± 0.9 |
| Example 273 | 30.4 ± 7.3 |

The invention claimed is:

1. A compound represented by formula (I) or a pharmaceutically acceptable salt or solvate thereof:

Het—X—Z  (I)

wherein
Het represents

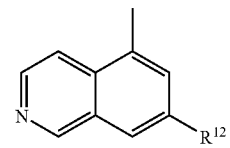

wherein $R^{12}$ represents a hydrogen atom or a halogen atom;
X is —N(—$R^1$)—Q6-Q7-
wherein
$R^1$ represents a hydrogen atom,
Q6 represents a five- to seven-membered saturated heterocyclic group and the heterocyclic groups are optionally substituted by an oxygen atom, hydroxyl, or $C_{1-4}$alkyl,
Q7 represents
—$(CH_2)$n1-$CR^{2a}R^{2b}$—$(CH_2)$n2-
wherein
n1 and n2 are each an integer of 0 to 3,
when n2 is 2 or 3, —$CH_2$—$CH_2$— in —$(CH_2)$n2- may represent —CH=CH— or —C≡C—,
$R^{2a}$ and $R^{2b}$, which may be the same or different, represent
a hydrogen atom,
a halogen atom,
$C_{1-6}$ alkyl optionally substituted by hydroxyl, carboxyl,
$C_{1-4}$ alkoxycarbonyl,
cyano,
Z represents
a hydrogen atom,
a halogen atom, a three- to seven-membered saturated or unsaturated monocyclic carbocyclic or heterocyclic group, a nine- to twelve-membered bicyclic saturated or unsaturated carbocyclic or heterocyclic group, or a thirteen- to fifteen-membered tricyclic saturated or unsaturated carbocyclic or heterocyclic group, wherein the carbocyclic and heterocyclic groups are optionally substituted by a halogen atom; hydroxyl; nitro; amino; $C_{1-4}$ alkyl optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy of which the phenyl portion is optionally substituted by a halogen atom.

2. The compound according to claim 1, wherein Q6 represents a five- to seven-membered saturated Q6 represents a five- to seven-membered saturated heterocyclic group containing one nitrogen atom and the heterocyclic groups are optionally substituted by an oxygen atom; and Q7 represents —(CH$_2$)n1-CR$^{2a}$R$^{2b}$—(CH$_2$)n2-, wherein n1 is an integer of 0 or 1, n2 is 0, R$^{2a}$ represents a hydrogen atom, and R$^{2b}$ represents a hydrogen atom, $C_{1-4}$ alkyl, or optionally substituted phenyl.

3. The compound according to claim 1 wherein Q6 represents a five- to seven-membered saturated heterocyclic group containing one nitrogen atom and the heterocyclic groups are optionally substituted by an oxygen atom; and Q7 represents —(CH$_2$)n1-CR R$^{2b}$R$^{2b}$(CH$_2$)n2-, wherein n1 and n2 are each an integer of 0 to 3, R$^{2a}$ represents a hydrogen atom, and R$^{2b}$ represents a hydrogen atom, optionally substituted $C_{1-6}$ alkyl, carboxyl, $C_{1-4}$ alkoxycarbonyl, cyano.

4. The compound according to claim 2, wherein Q6 represents a five- to seven-membered saturated heterocyclic group which is optionally substituted by an oxygen atom and contains one nitrogen atom.

5. The compound according to claim 3, wherein Q6 represents a five- to seven-membered saturated heterocyclic group containing one nitrogen atom and the heterocyclic groups are optionally substituted by an oxygen atom; and Q7 represents —(CH$_2$)n1-CR$^{2a}$R$^{2b}$—(CH$_2$)n2- wherein n1 and n2, which may be the same or different, are each an integer of 0 to 3, R$^{2a}$ represents a hydrogen atom, and R$^{2b}$ represents a hydrogen atom or optionally substituted $C_{1-4}$ alkyl.

6. The compound according to claim 3, wherein Q6 represents a five- to seven-membered saturated heterocyclic group containing one nitrogen atom and the heterocyclic groups are optionally substituted by an oxygen atom; and Q7 represents —(CH$_2$)n1-CR$^{2a}$R$^{2b}$—(CH$_2$)n2-wherein n1 and n2 are each 0, R$^{2a}$ represents a hydrogen atom, and R$^{2b}$ represents optionally substituted $C_{1-6}$ alkyl, carboxyl, $C_{1-4}$ alkoxycarbonyl, cyano.

7. The compound according to claim 3, wherein Q6 represents a five- to seven-membered saturated heterocyclic group containing one nitrogen atom and the heterocyclic groups are optionally substituted by an oxygen atom; and Q7 represents —(CH$_2$)n1-CR$^{2a}$R$^{2b}$—(CH$_2$)n2- wherein n1 is an integer of 0 to 3, n2 is 0, and R$^{2a}$ and R$^{2b}$ represent a halogen atom.

8. The compound according to claim 1, wherein Q6 represents any one of the following groups:

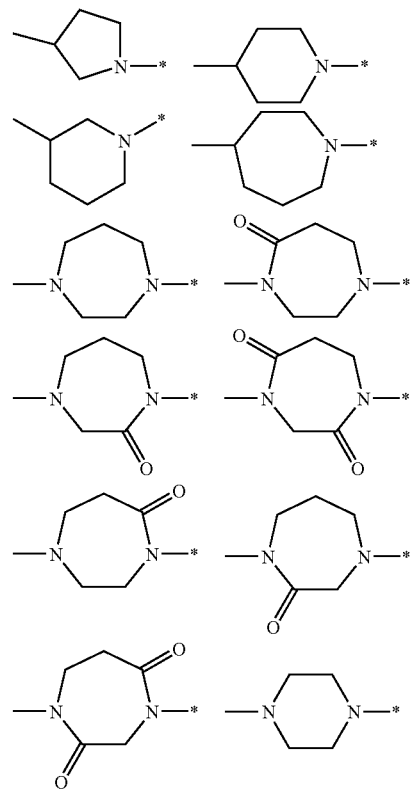

wherein the bond with * represents a bond to Q7 and the bond without * represents a bond to group —N(—R$^1$)—.

9. The compound according to claim 1, wherein Z represents a hydrogen atom, a halogen atom, a three- to seven-membered saturated or unsaturated carbocyclic group, a five- to seven-membered saturated or unsaturated heterocyclic group containing one nitrogen atom and/or one oxygen atom, a nine- or ten-membered unsaturated bicyclic carbocyclic group, a nine- or ten-membered unsaturated bicyclic heterocyclic group containing one nitrogen atom and/or one or two oxygen atoms, or a thirteen- to fifteen-membered unsaturated tricyclic carbocyclic group or heterocyclic group.

10. The compound according to claim 9, wherein Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted by a halogen atom; hydroxyl; nitro; amino; $C_{1-4}$ alkyl which is optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy of which the phenyl portion is optionally substituted by a halogen atom.

11. The compound according to claim 1, wherein
Z represents a hydrogen atom, a halogen atom, phenyl, cyclopropyl, cyclohexyl, furanyl, pyridyl, piperidyl, naphthyl, naphthalenyl, indenyl, indolyl, imidazolyl, thienyl, 1,3-benzodioxole, fluorenyl, or carbazolyl and these groups are optionally substituted by a halogen atom; hydroxyl; nitro; amino; $C_{1-4}$ alkyl which is optionally substituted by a halogen atom; $C_{1-4}$ alkoxy of which the alkyl portion is optionally substituted by a halogen atom; $C_{1-4}$ alkoxycarbonyl of which the alkyl portion is optionally substituted by a halogen atom; $C_{1-4}$ alkylcarbonyl of which the alkyl portion is optionally substituted by a halogen atom; $C_{1-4}$ alkylcarbonyloxy of which the alkyl portion is optionally substituted by a halogen atom; or benzyloxy of which the phenyl portion is optionally substituted by a halogen atom.

12. A compound selected from the group consisting of the following compounds:
   (269) N-(5-isoquinolyl)-N-[1-(4-methylpentyl)-3-piperidyl]amine;
   (273) N-(5-isoquinolyl)-N-[1-(4,4,4-trifluoro-butyl)-3-piperidyl]amine;
   (276) N-(5-isoquinolyl)-N-[1-(2,4,6-trifluorobenzyl)-3-piperidyl]amine;
   (278) N-(5-isoquinolyl)-N-[1-(2-methylbutyl)-3-piperidyl]amine;
   (297) N-[1-(4-fluorobenzyl)-3-piperidyl]-N-(5-isoquinolyl)amine;
   (299) N-(5-isoquinolyl)-N-{1-[4-(trifluoromethyl)benzyl]-3-piperidyl}amine;
   (301) N-[1-(3,4-difluorobenzyl)-3-piperidyl]-N-(5-isoquinolyl)amine;
   (318) N-(5-isoquinolyl)-N-(1-propyl-4-piperidyl)-amine;
   (319) N-(1-isobutyl-4-piperidyl)-N-(5-isoquinolyl)amine;
   (320) N-[1-(2-ethylbutyl)-4-piperidyl]-N-(5-isoquinolyl)amine;
   (321) N-[1-(cyclopropylmethyl)-4-piperidyl]-N-(5-isoquinolyl)amine; and
   (322) N-[1-(3-fluoropropyl)-4-piperidyl]-N-(5-isoquinolyl)amine.

13. A compound selected from the group consisting of the following compounds,
   N-(1-Isopentyl-3-piperidyl)-N-(5-isoquinolyl)amine and
   N-(5-Isoquinolyl)-N-[1-(2,4,6-trifluorobenzyl)-3-piperidyl]amine.

14. A pharmaceutical composition comprising a pharmaceutically effective amount of the compound according to claim 1, a pharmaceutically acceptable salt or solvate thereof.

15. A pharmaceutical composition comprising a pharmaceutically effective amount of the compound according to claim 12.

16. A method for treating hypertension comprising the step of administering a pharmaceutically effective amount of the compound of claim 1 or a pharmaceutically acceptable salt or solvate thereof together with a pharmaceutically acceptable carrier, to a mammal in need thereof.

17. The method of claim 16, wherein the mammal is a human.

* * * * *